United States Patent
Zion et al.

(10) Patent No.: US 9,265,838 B2
(45) Date of Patent: *Feb. 23, 2016

(54) CONJUGATE BASED SYSTEMS FOR CONTROLLED DRUG DELIVERY

(71) Applicant: SmartCells, Inc., Whitehouse Station, NJ (US)

(72) Inventors: Todd C. Zion, Marblehead, MA (US); Thomas M. Lancaster, Stoneham, MA (US)

(73) Assignee: Smart Cells, Inc., Kenilworth, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/291,021

(22) Filed: May 30, 2014

(65) Prior Publication Data

US 2014/0274888 A1    Sep. 18, 2014

Related U.S. Application Data

(63) Continuation of application No. 13/145,532, filed as application No. PCT/US2010/022268 on Jan. 27, 2010.

(60) Provisional application No. 61/159,643, filed on Mar. 12, 2009, provisional application No. 61/219,897, filed on Jun. 24, 2009, provisional application No. 61/147,878, filed on Jan. 28, 2009, provisional application No. 61/162,107, filed on Mar. 20, 2009, provisional application No. 61/223,572, filed on Jul. 7, 2009, provisional application No. 61/252,857, filed on Oct. 19, 2009, provisional application No. 61/163,084, filed on Mar. 25, 2009.

(51) Int. Cl.
*A61K 38/28* (2006.01)
*C07K 14/62* (2006.01)
*A61K 47/48* (2006.01)

(52) U.S. Cl.
CPC .............. *A61K 47/4823* (2013.01); *A61K 38/28* (2013.01); *A61K 47/48015* (2013.01); *A61K 47/48092* (2013.01)

(58) Field of Classification Search
CPC .................. A61K 47/48015; A61K 47/48092; A61K 47/4823
See application file for complete search history.

(56) References Cited

U.S. PATENT DOCUMENTS

| 5,563,056 | A |   | 10/1996 | Swan et al. | |
|---|---|---|---|---|---|
| 5,994,517 | A |   | 11/1999 | Ts'o et al. | |
| 8,603,529 | B2 | * | 12/2013 | Zion et al. | 424/486 |
| 8,623,345 | B2 | * | 1/2014 | Zion et al. | 424/78.29 |
| 8,846,103 | B2 | * | 9/2014 | Zion et al. | 424/493 |
| 8,906,850 | B2 | * | 12/2014 | Zion et al. | 514/5.9 |
| 8,940,690 | B2 | * | 1/2015 | Zion et al. | 514/5.9 |
| 2002/0068295 | A1 |   | 6/2002 | Madou et al. | |
| 2007/0099820 | A1 |   | 5/2007 | Lancaster et al. | |
| 2011/0281792 | A1 | * | 11/2011 | Zion et al. | 514/5.9 |
| 2011/0301083 | A1 | * | 12/2011 | Zion et al. | 514/6.6 |
| 2014/0121159 | A1 | * | 5/2014 | Zion et al. | 514/5.9 |
| 2014/0275476 | A1 | * | 9/2014 | Lancaster et al. | 530/303 |
| 2014/0342980 | A1 | * | 11/2014 | Zion et al. | 514/5.9 |

FOREIGN PATENT DOCUMENTS

CN           101273961           10/2008

OTHER PUBLICATIONS

Sardzik et al. Preparation of aminoethyl glycosides for glycoconjugation. Beilstein J. Org. Chem. 2010, vol. 6, pp. 699-703.*
Disney et al. Detection of Bacteria with Carbohydrate-Functionalized Fluorescent Polymers. JACS Articles. Published on Web Sep. 25, 2004. vol. 126, pp. 13343-13346.*
Drug—definition of drug by Medical dictionary. accessed online at http://medical-dictionary.thefreedictionary.com/drug on May 8, 2015, 8 pages.*
Cheshev et al. Synthesis of Aminoethyl Glycosides of the Ganglioside GM1 and Asialo-GM1 Oligosaccharide Chains. Russian Journal of Bioorganic chemistry. 2004. vol. 30, No. 1, pp. 60-70.*
International Search Report and Written Opinion for PCT/US10/22225, mailed on Mar. 9, 2010.
Lindhorst et al. Trivalent alpha-D-mannoside clusters as inhibitors of type-1 fimbriae-mediated adhesion of *Escherichia coli*: structural variation and biotinylation. J. Chem. Soc. Perkin Trans 1:823-831 (2001).

* cited by examiner

*Primary Examiner* — Marcela M Cordero Garcia
(74) *Attorney, Agent, or Firm* — John David Reilly

(57) ABSTRACT

Conjugates which comprise a drug and a ligand which includes a first saccharide; wherein the conjugate is characterized in that, when the conjugate is administered to a mammal, at least one pharmacokinetic or pharmacodynamic property of the conjugate is sensitive to serum concentration of a second saccharide. Exemplary conjugates and sustained release formulations are provided in addition to methods of use and preparation.

20 Claims, 87 Drawing Sheets

(a) IPC Peak Retention Times, %Free Insulin, and %Desamido Insulin

| Sample | Peak 1 RT[1] (min) | Peak 2 RT (min) | Peak 3 RT (min) | % Purity IPC | % Free Insulin | % Desamido Insulin |
|---|---|---|---|---|---|---|
| HS-1-60-1 (fresh) | 20.62 | - | - | >99 | <0.1 | <0.1 |
| HS-1-60-1 (AST, PBS) | 20.61 | 19.19 | - | 85 | <0.1 | <0.1 |
| HS-1-60-1 (AST, HEPES) | 20.65 | - | - | >99 | <0.1 | <0.1 |
| TL-13-85 (fresh) | 20.46 | - | - | >99 | <0.1 | <0.1 |
| TL-13-85 (AST, PBS) | 20.40 | 19.84 | 18.91 | 30 | <0.1 | <0.1 |
| TL-13-85 (AST, HEPES) | 20.46 | - | - | >99 | <0.1 | <0.1 |

[1] C8 reverse phase column, water:acetonitrile (0.1% TFA) elution gradient, RT = Retention Time

(b) Mass Spectroscopy Data on IPC's and IPC Breakdown Products

| Sample | Peak 1 MW (Da) | Peak 2 MW (Da) | Peak 3 MW (Da) |
|---|---|---|---|
| HS-1-60-1 (fresh) | 6730[2] | - | - |
| HS-1-60-1 (AST, PBS) | 6730 | 5947 | - |
| HS-1-60-1 (AST, HEPES) | 6730 | - | - |
| TL-13-85 (fresh) | 6829[2] | - | - |
| TL-13-85 (AST, PBS) | 6829 | 5944 | 7928 |
| TL-13-85 (AST, HEPES) | 6829 | - | - |

[2] The two IPC's shown here have different structures and, therefore, different MW's

Figure 3

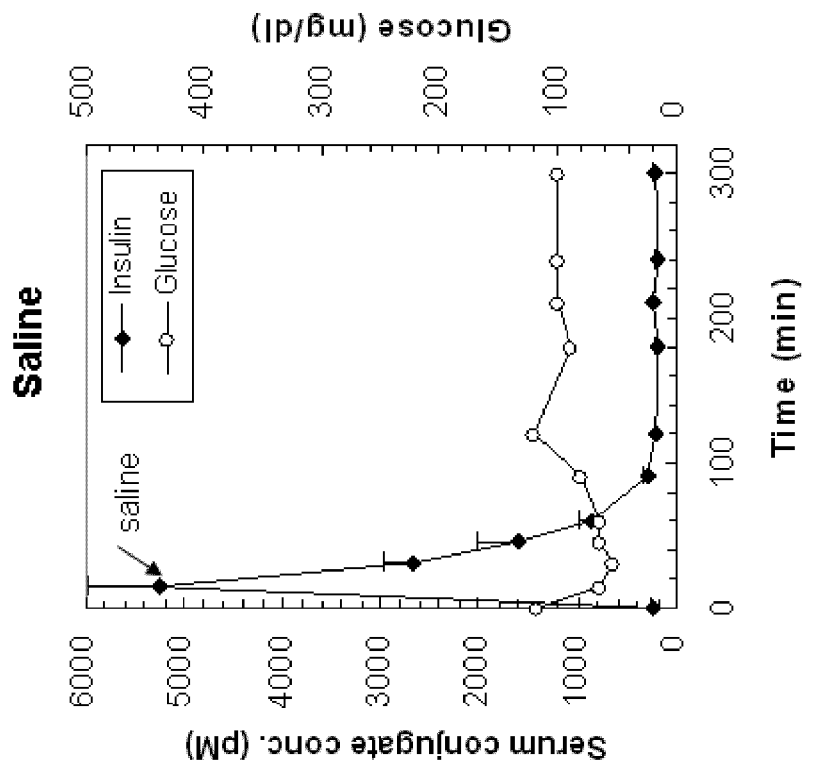
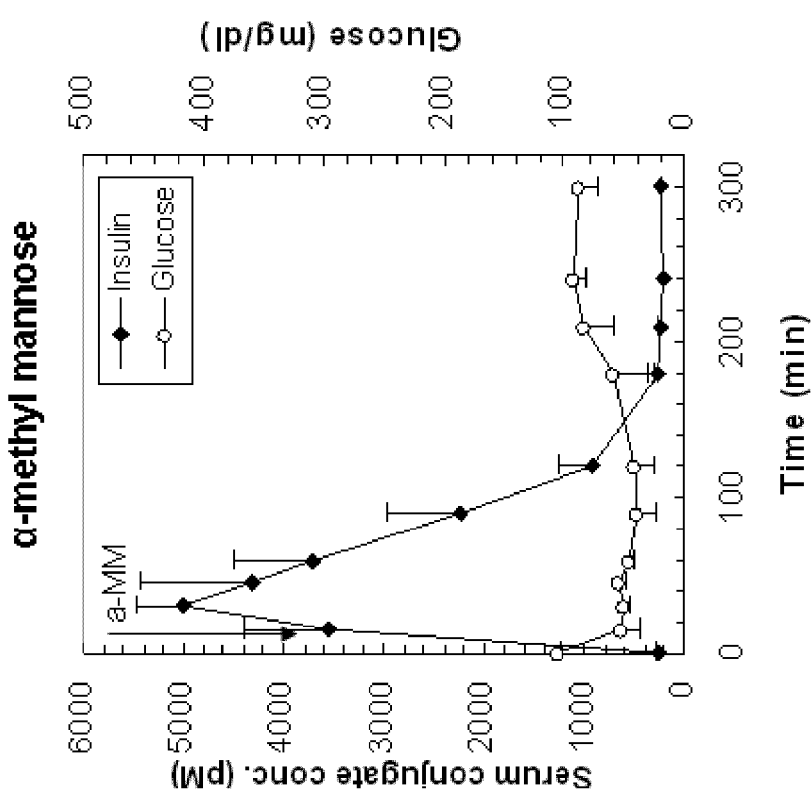
Figure 27

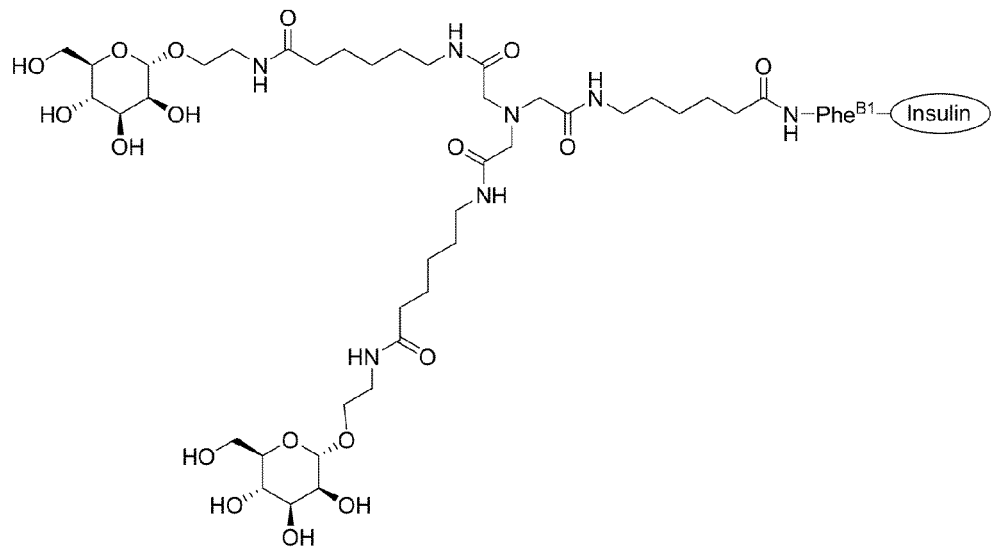
Conjugate I-1
TSAT-C6-AEM-2 (B1)
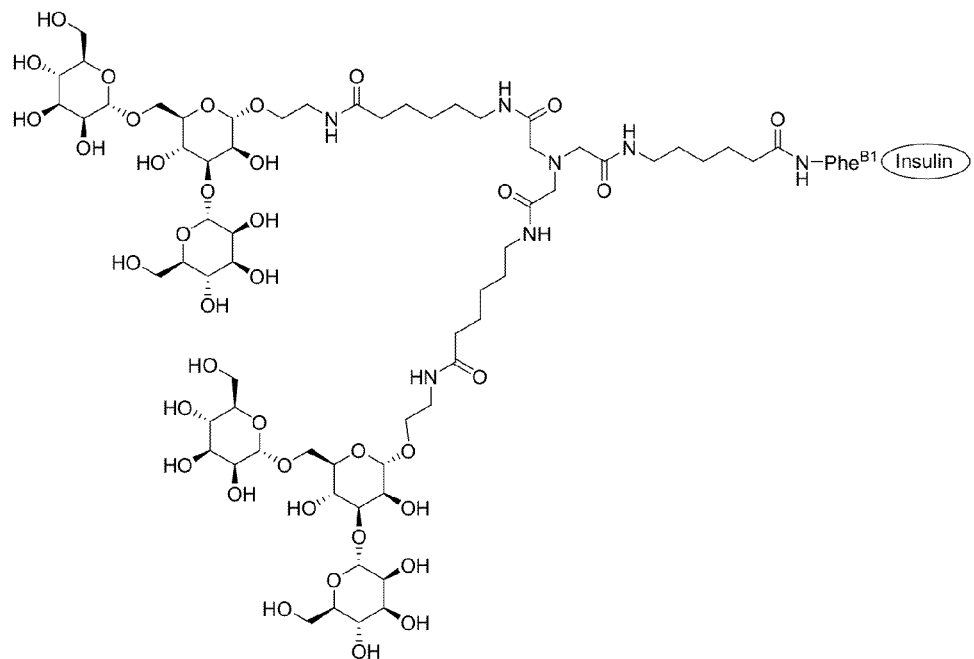
Conjugate I-2
TSAT-C6-AETM-2 (B1)
Figure 45

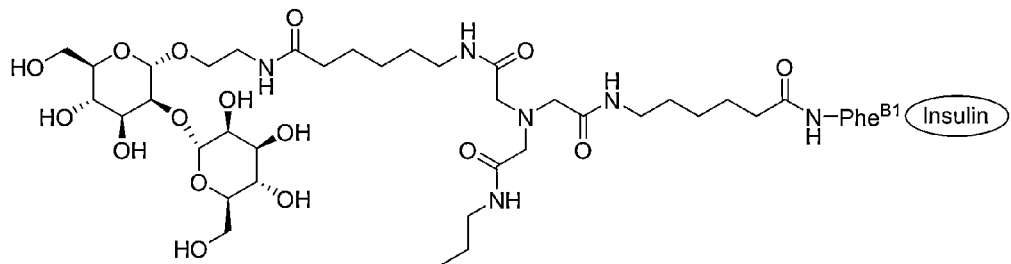
Conjugate I-3
TSAT-C6-AEBM-2 (B1)
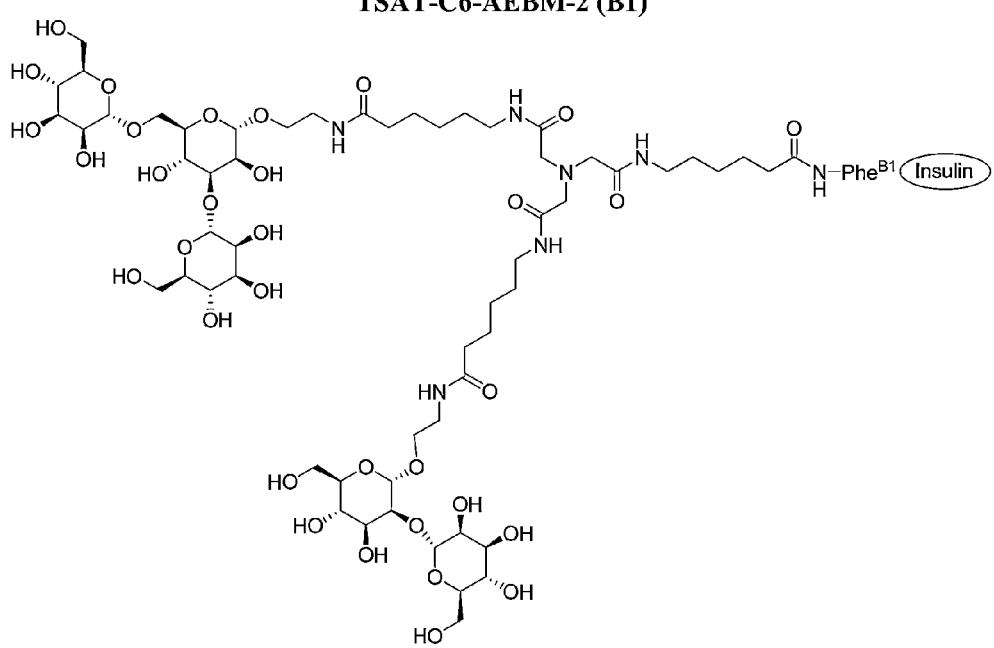
Conjugate I-4
TSAT-C6-AEBM-1-AETM-1 (B1)
Figure 45 (continued)

Conjugate I-5
TSAT-C6-GA-2 (B29)

Conjugate I-6
TSAT-C6-AETM-2 (B29)

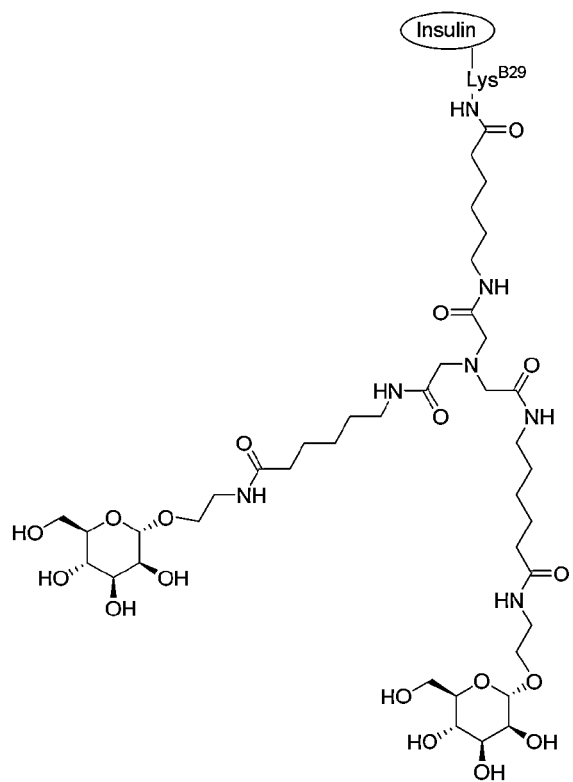
Conjugate I-7
TSAT-C6-AEM-2 (B29)
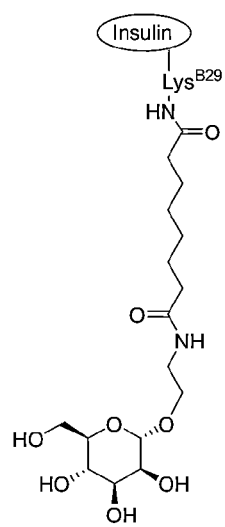
Conjugate I-8
DSS-AEM-1 (B29)
Figure 45 (continued)

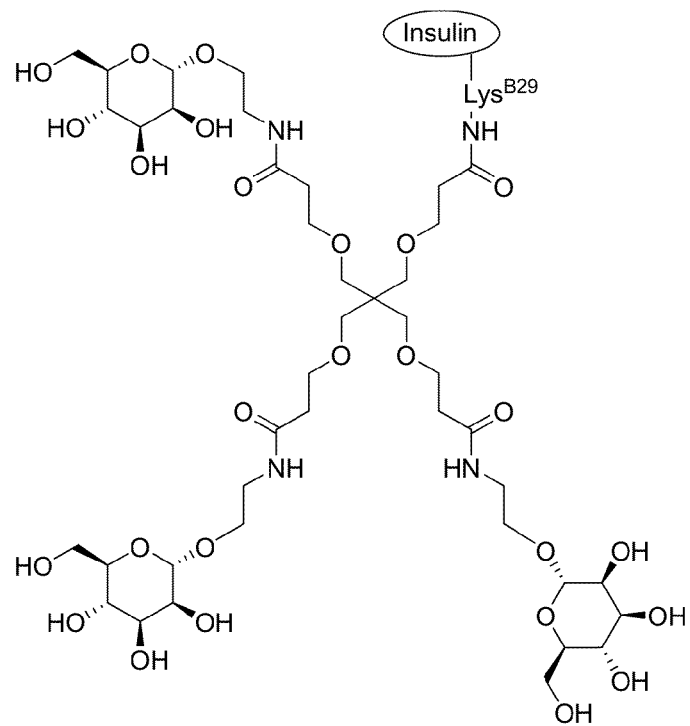
Conjugate I-9
TSPE-AEM-3 (B29)
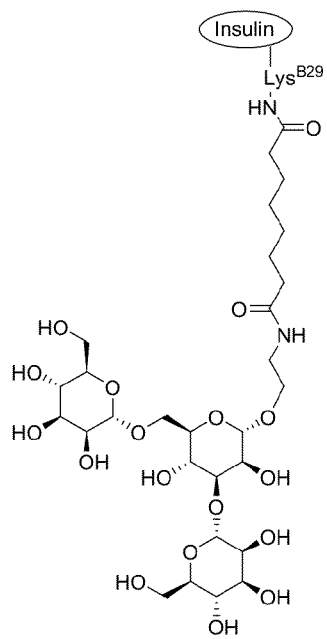
Conjugate I-10
DSS-AETM-1 (B29)
Figure 45 (continued)

Conjugate I-11
TSPE-AETM-3 (B29)

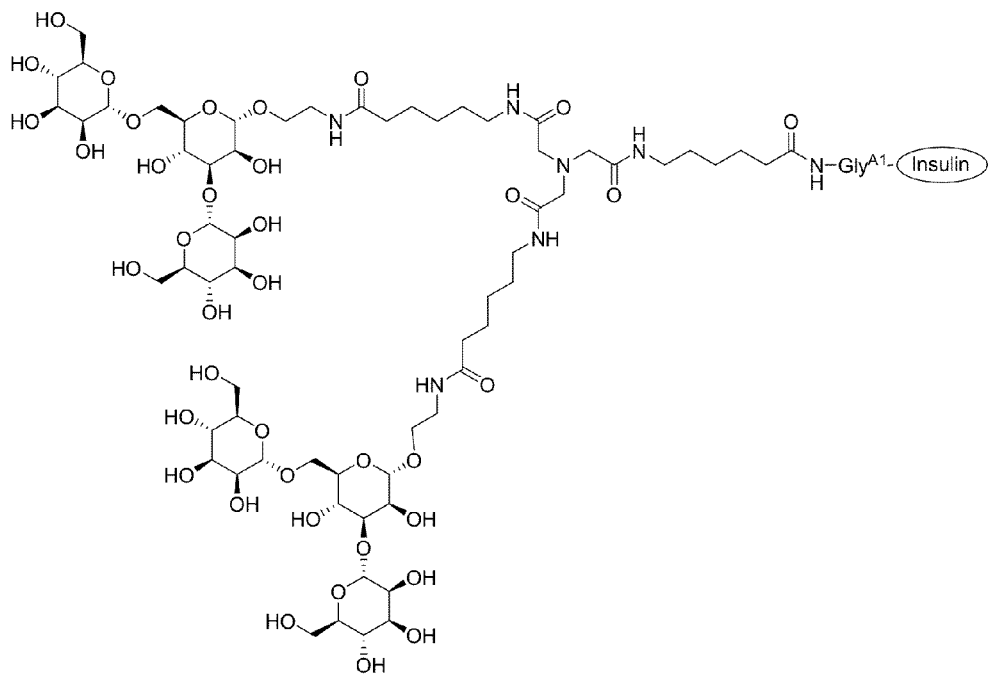
Conjugate I-12
TSAT-C6-AETM-2 (A1)
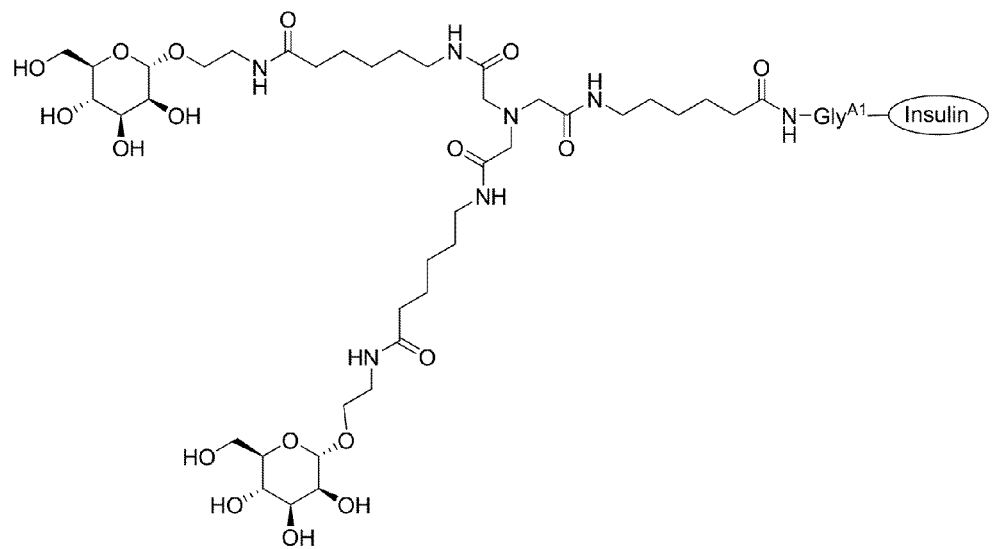
Conjugate I-13
TSAT-C6-AEM-2 (A1)
Figure 45 (continued)

Conjugate I-14
TSPE-AETM-3 (A1)

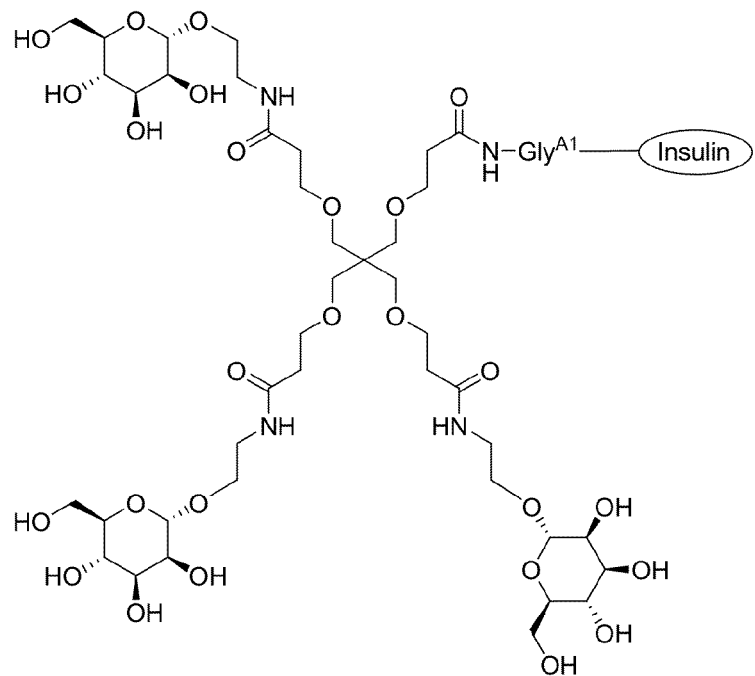
Conjugate I-15
TSPE-AEM-3 (A1)
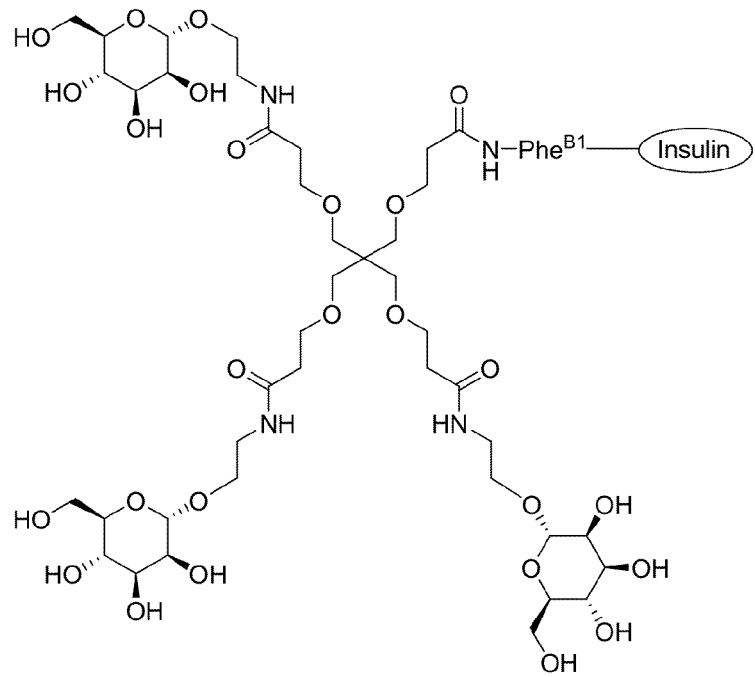
Conjugate I-16
TSPE-AEM-3 (B1)
Figure 45 (continued)

Conjugate I-17

C6-Amide-AEM-2 (B29)

Conjugate II-1
TSAT-C6-Di-sub-AEM-2 (A1,B29)

Conjugate II-2
TSAT-C6-Di-sub-AETM-2 (A1,B29)

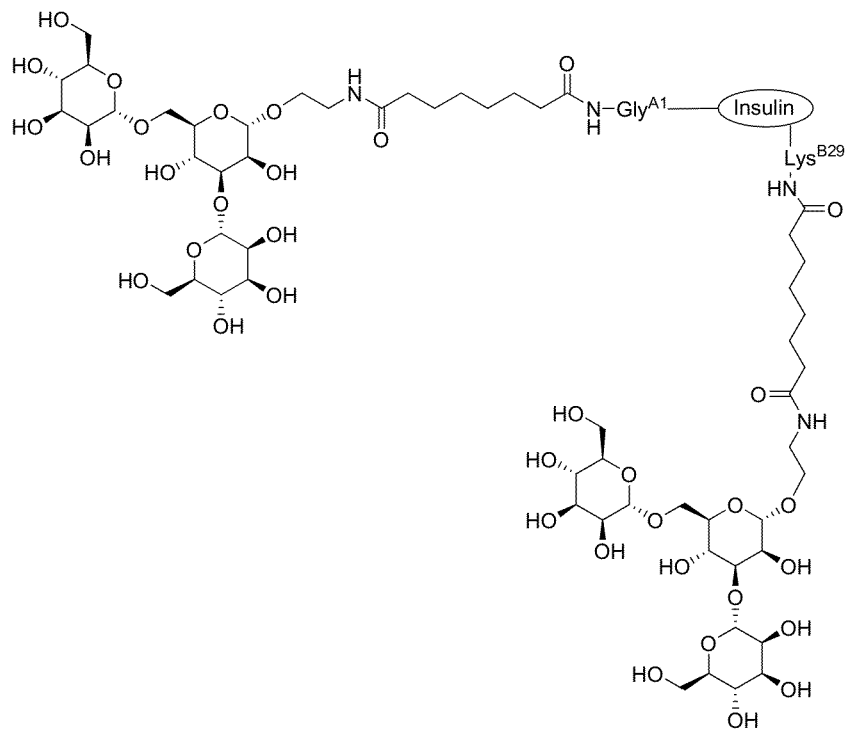
Conjugate II-3
DSS-Di-sub-AETM-1 (A1,B29)
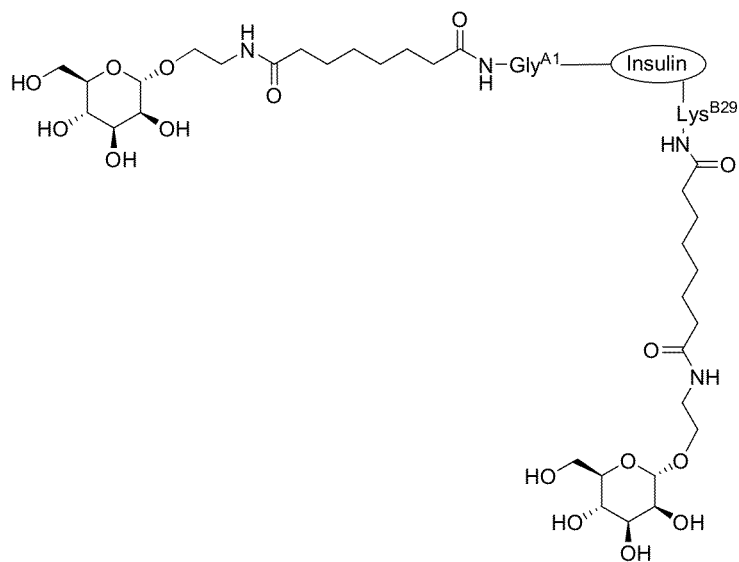
Conjugate II-4
DSS-Di-sub-AEM-1 (A1,B29)
Figure 45 (continued)

Conjugate II-5
TSAT-C6-Di-sub-AETM-2 (A1,B1)

Conjugate II-6
TSAT-C6-Di-sub-AETM-2 (B1,B29)

Conjugate II-7
DSS-Di-sub-AETM-2 (B1,B29)

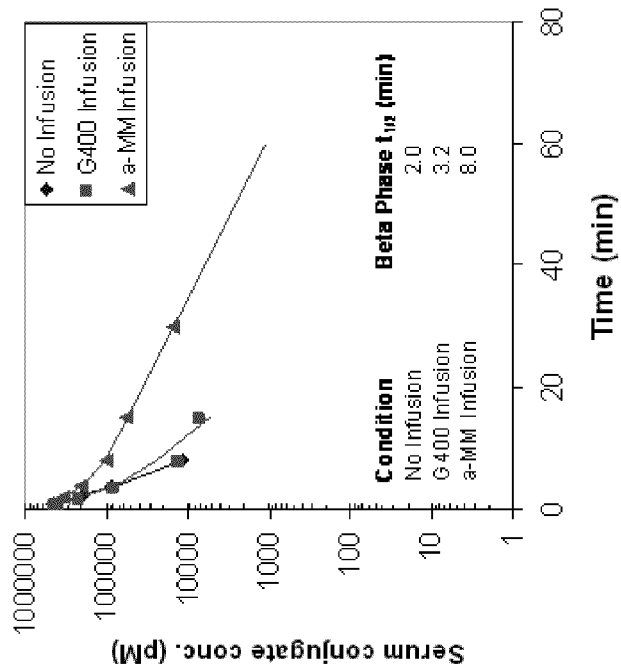
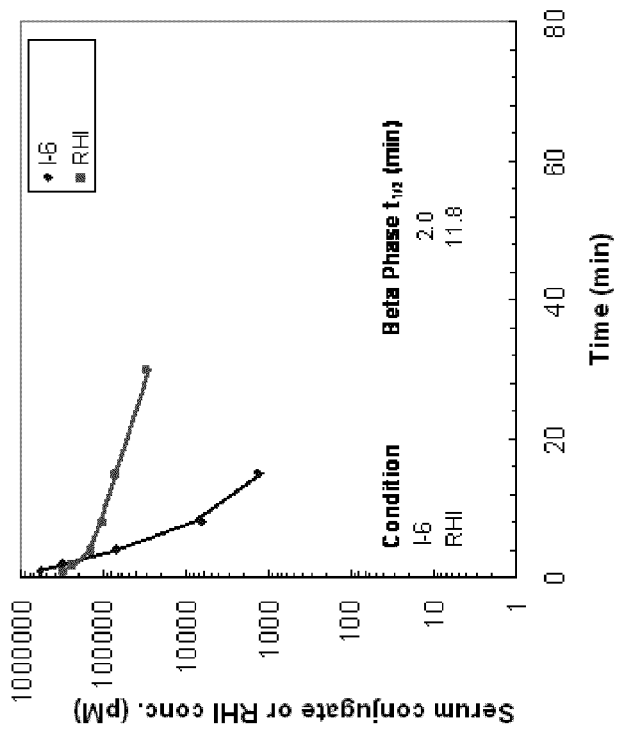
Figure 46

| Formulation | Scaffold – X | Scaffold – Y | Sugar (n) |
|---|---|---|---|
| RHI | n/a | n/a | n/a |
| I-7: AEM-2 | n/a | TSAT-C$_6$ | AEM (2) |
| I-6: AETM-2 | n/a | TSAT-C$_6$ | AETM (2) |
| I-11: AETM-3 | n/a | TSPE | AETM (3) |
| II-2: Di-sub-AETM-2 | TSAT-C$_6$ | TSAT-C$_6$ | AETM (2x2) |

| Formulation | β-phase half-life (min) for each type of infusion | | |
| --- | --- | --- | --- |
| | Saline | Glucose | α-methyl mannose |
| RHI | 2.7 | 2.3 | 3.3 |
| I-7: AEM-2 | 5.5 | 5.8 | 5.4 |
| I-6: AETM-2 | 4.8 | 3.3 | 8.1 |
| I-11: AETM-3 | 6.7 | 3.7 | 10.8 |
| II-2: Di-sub-AETM-2 | 2.5 | n/a | 20.3 |

Figure 50

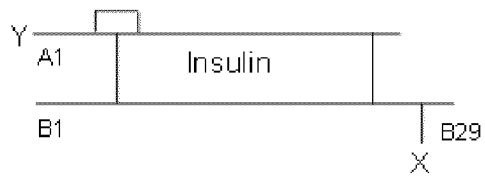
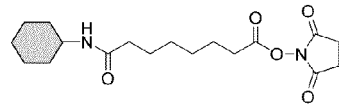
DSS
| Formulation | Scaffold – X | Scaffold – Y | Sugar (n) |
|---|---|---|---|
| I-12: AETM-2 | n/a | TSAT-C$_6$ | AETM (2) |
| I-13: AEM-2 | n/a | TSAT-C$_6$ | AEM (2) |
| I-15: AEM-3 | n/a | TSPE | AEM (3) |
| I-14: AETM-3 | n/a | TSPE | AETM (3) |
| II-1: Di-sub-AEM-2 | TSAT-C$_6$ | TSAT-C$_6$ | AEM (2x2) |
| II-3: Di-sub-AETM-1 | DSS | DSS | AETM (2x1) |
| II-4: Di-sub-AEM-1 | DSS | DSS | AEM (2x1) |
Figure 55

| Insulin-conjugate | Sugar Composition | $t_{1/2,\beta}$ (a-MM)/ $t_{1/2,\beta}$ (No Inf) |
|---|---|---|
| II-2 | B29: AETMx2, A1: AETMx2 | 8.1 |
| I-12 | A1: AETMx2 | 2.3 |
| I-6 | B29: AETMx2 | 1.7 |
| I-11 | B29: AETMx3 | 1.6 |
| I-9 | B29: AEMx3 | 1.6 |
| II-1 | B29: AEMx2, A1: AEMx2 | 1.5 |
| II-3 | B29: AETMx1, A1: AETMx1 | 1.3 |
| RHI | n/a | 1.2 |
| I-7 | B29: AEMx2 | 1.0 |
| II-4 | B29: AEMx1, A1: AEMx1 | 0.9 |

Figure 57

CONJUGATE BASED SYSTEMS FOR CONTROLLED DRUG DELIVERY

CROSS REFERENCE TO RELATED APPLICATIONS

This application is a continuation of U.S. application Ser. No. 13/145,532, filed Jul. 20, 2011, which is a U.S. National Phase application under 35 U.S.C. 371 of International Application No. PCT/US10/22268, filed on Jan. 27, 2010, which claims benefit of U.S. Provisional Application No. 61/147,878 filed Jan. 28, 2009, U.S. Provisional Application No. 61/159,643 filed Mar. 12, 2009, U.S. Provisional Application No. 61/162,107 filed Mar. 20, 2009, U.S. Provisional Application No. 61/163,084 filed Mar. 25, 2009, U.S. Provisional Application No. 61/219,897 filed Jun. 24, 2009, U.S. Provisional Application No. 61/223,572 filed Jul. 7, 2009, and U.S. Provisional Application No. 61/252,857 filed Oct. 19, 2009, the content of each of which is hereby incorporated by reference in its entirety.

REFERENCE TO SEQUENCE LISTING SUBMITTED ELECTRONICALLY

The sequence listing of the present application is submitted electronically via EFS-Web as an ASCII formatted sequence listing with a file name "23028-US-CNT-SEQLIST.txt", creation date of May 21, 2014 and a size of 2 KB. This sequence listing submitted via EFS-Web is part of the specification and is herein incorporated by reference in its entirety.

BACKGROUND

The majority of "controlled-release" drug delivery systems known in the prior art (e.g., U.S. Pat. No. 4,145,410 to Sears which describes drug release from capsules which are enzymatically labile) are incapable of providing drugs to a patient at intervals and concentrations which are in direct proportion to the amount of a molecular indicator (e.g., a metabolite) present in the human body. The drugs in these prior art systems are thus not literally "controlled," but simply provided in a slow release format which is independent of external or internal factors.

The treatment of diabetes mellitus with injectable insulin is a well-known and studied example where uncontrolled, slow release of insulin is undesirable. In fact, it is apparent that the simple replacement of the hormone is not sufficient to prevent the pathological sequelae associated with this disease. The development of these sequelae is believed to reflect an inability to provide exogenous insulin proportional to varying blood glucose concentrations experienced by the patient. To solve this problem several biological and bioengineering approaches to develop a more physiological insulin delivery system have been suggested (e.g., see U.S. Pat. No. 4,348,387 to Brownlee et al.; U.S. Pat. Nos. 5,830,506, 5,902,603, and U.S. Pat. No. 6,410,053 to Taylor et al. and U.S. Patent Application Publication No. 2004-0202719 to Zion et al.).

Each of these systems relies on the combination of a multivalent glucose binding molecule (e.g., the lectin Con A) and a sugar based component that is reversibly bound by the multivalent glucose binding molecule. Unfortunately, Con A and many of the other readily available lectins have the potential to stimulate lymphocyte proliferation. By binding to carbohydrate receptors on the surfaces of certain types of lymphocytes, these so-called "mitogenic" lectins can potentially induce the mitosis of lymphocytes and thereby cause them to proliferate. Most mitogenic lectins including Con A are selective T-cell mitogens. A few lectins are less selective and stimulate both T-cells and B-cells. Local or systemic in vivo exposure to mitogenic lectins can result in inflammation, cytotoxicity, macrophage digestion, and allergic reactions including anaphylaxis. In addition, plant lectins are known to be particularly immunogenic, giving rise to the production of high titers of anti-lectin specific antibodies. It will be appreciated that mitogenic lectins cannot therefore be used in their native form for in vivo methods and devices unless great care is taken to prevent their release. For example, in U.S. Pat. No. 5,830,506, Taylor highlights the toxic risks that are involved in using Con A and emphasizes the importance and difficulty of containing Con A within a drug delivery device that also requires glucose and insulin molecules to diffuse freely in and out of the device.

The risks and difficulties that are involved with these and other in vivo uses of lectins could be significantly diminished if an alternative controlled drug delivery system could be provided that did not require lectins.

SUMMARY

In one aspect, the disclosure provides methods for controlling the pharmacokinetic (PK) and/or pharmacodynamic (PD) profiles of a drug such as insulin in a manner that is responsive to the systemic concentrations of a saccharide such as glucose. As discussed in the Examples, the methods are based in part on the discovery that when certain insulin-conjugates were modified to include high affinity saccharide ligands they could be made to exhibit PK/PD profiles that responded to saccharide concentration changes even in the absence of an exogenous multivalent saccharide-binding molecule such as Con A. This finding was unexpected and provides an unprecedented opportunity to generate simple lectin-free saccharide-responsive drug systems. In another aspect, the disclosure provides exemplary conjugates and methods for making these. In general, these conjugates include a drug and one or more separate ligands that each includes a saccharide. In certain embodiments, the ligands are capable of competing with a saccharide (e.g., glucose or mannose) for binding to an endogenous saccharide-binding molecule. In certain embodiments, the ligands are capable of competing with glucose or mannose for binding to Con A. As discussed in more detail below, in certain embodiments, the ligands and drug may be covalently or non-covalently attached to a conjugate framework. In certain embodiments, the framework is non-polymeric. In certain embodiments, a conjugate may have a polydispersity index of one and a MW of less than about 20,000 Da. In certain embodiments, the conjugate is long acting (i.e., exhibits a PK profile that is more sustained than soluble recombinant human insulin or RHI).

As discussed in more detail below, it is to be understood that the methods, conjugates and formulations that are described herein are in no way limited to the delivery of insulin and that they can be used to deliver any drug. It is also to be understood that the methods may be used to deliver drugs in response to saccharides other than glucose. In particular, as discussed in the Examples, exemplary conjugates have been shown to respond to exogenous saccharides such as alpha-methyl mannose and L-fucose. In certain embodiments, this can be used to prepare conjugates that can be controlled by administration of one of these exogenous saccharides (i.e., instead of or in addition to being controlled by fluctuations in endogenous glucose).

DEFINITIONS

Definitions of specific functional groups, chemical terms, and general terms used throughout the specification are described in more detail below. For purposes of this invention, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito, 1999; Smith and March March's Advanced Organic Chemistry, 5$^{th}$ Edition, John Wiley & Sons, Inc., New York, 2001; Larock, Comprehensive Organic Transformations, VCH Publishers, Inc., New York, 1989; Carruthers, Some Modern Methods of Organic Synthesis, 3$^{rd}$ Edition, Cambridge University Press, Cambridge, 1987.

Acyl—As used herein, the term "acyl," refers to a group having the general formula —C(=O)R$^{X1}$, —C(=O)OR$^{X1}$, —C(=O)—O—C(=O)R$^{X1}$, —C(=O)SR$^{X1}$, —C(=O)N(R$^{X1}$)$_2$, —C(=S)R$^{X1}$, —C(=S)N(R$^{X1}$)$_2$, and —C(=S)S(R$^{X1}$), —C(=NR$^{X1}$)R$^{X1}$, —C(=NR$^{X1}$)OR$^{X1}$, —C(=NR$^{X1}$)SR$^{X1}$, and —C(=NR$^{X1}$)N(R$^{X1}$)$_2$, wherein R$^{X1}$ is hydrogen; halogen; substituted or unsubstituted hydroxyl; substituted or unsubstituted thiol; substituted or unsubstituted amino; substituted or unsubstituted acyl; cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl, substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two R$^{X1}$ groups taken together form a 5- to 6-membered heterocyclic ring. Exemplary acyl groups include aldehydes (—CHO), carboxylic acids (—CO$_2$H), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

Aliphatic—As used herein, the term "aliphatic" or "aliphatic group" denotes an optionally substituted hydrocarbon moiety that may be straight-chain (i.e., unbranched), branched, or cyclic ("carbocyclic") and may be completely saturated or may contain one or more units of unsaturation, but which is not aromatic. Unless otherwise specified, aliphatic groups contain 1-12 carbon atoms. In some embodiments, aliphatic groups contain 1-6 carbon atoms. In some embodiments, aliphatic groups contain 1-4 carbon atoms, and in yet other embodiments aliphatic groups contain 1-3 carbon atoms. Suitable aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

Alkenyl—As used herein, the term "alkenyl" denotes an optionally substituted monovalent group derived from a straight- or branched-chain aliphatic moiety having at least one carbon-carbon double bond by the removal of a single hydrogen atom. In certain embodiments, the alkenyl group employed in the invention contains 2-6 carbon atoms. In certain embodiments, the alkenyl group employed in the invention contains 2-5 carbon atoms. In some embodiments, the alkenyl group employed in the invention contains 2-4 carbon atoms. In another embodiment, the alkenyl group employed contains 2-3 carbon atoms. Alkenyl groups include, for example, ethenyl, propenyl, butenyl, 1-methyl-2-buten-1-yl, and the like.

Alkyl—As used herein, the term "alkyl" refers to optionally substituted saturated, straight- or branched-chain hydrocarbon radicals derived from an aliphatic moiety containing between 1-6 carbon atoms by removal of a single hydrogen atom. In some embodiments, the alkyl group employed in the invention contains 1-5 carbon atoms. In another embodiment, the alkyl group employed contains 1-4 carbon atoms. In still other embodiments, the alkyl group contains 1-3 carbon atoms. In yet another embodiment, the alkyl group contains 1-2 carbons. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like.

Alkynyl—As used herein, the term "alkynyl" refers to an optionally substituted monovalent group derived from a straight- or branched-chain aliphatic moiety having at least one carbon-carbon triple bond by the removal of a single hydrogen atom. In certain embodiments, the alkynyl group employed in the invention contains 2-6 carbon atoms. In certain embodiments, the alkynyl group employed in the invention contains 2-5 carbon atoms. In some embodiments, the alkynyl group employed in the invention contains 2-4 carbon atoms. In another embodiment, the alkynyl group employed contains 2-3 carbon atoms. Representative alkynyl groups include, but are not limited to, ethynyl, 2-propynyl (propargyl), 1-propynyl, and the like.

Aryl—As used herein, the term "aryl" used alone or as part of a larger moiety as in "aralkyl", "aralkoxy", or "aryloxyalkyl", refers to an optionally substituted monocyclic and bicyclic ring systems having a total of five to 10 ring members, wherein at least one ring in the system is aromatic and wherein each ring in the system contains three to seven ring members. The term "aryl" may be used interchangeably with the term "aryl ring". In certain embodiments of the present invention, "aryl" refers to an aromatic ring system which includes, but not limited to, phenyl, biphenyl, naphthyl, anthracyl and the like, which may bear one or more substituents.

Arylalkyl—As used herein, the term "arylalkyl" refers to an alkyl group substituted with an aryl group (e.g., an aromatic or heteroaromatic group).

Bivalent hydrocarbon chain—As used herein, the term "bivalent hydrocarbon chain" (also referred to as a "bivalent alkylene group") is a polymethylene group, i.e., —(CH$_2$)$_z$—, wherein z is a positive integer from 1 to 30, from 1 to 20, from 1 to 12, from 1 to 8, from 1 to 6, from 1 to 4, from 1 to 3, from 1 to 2, from 2 to 30, from 2 to 20, from 2 to 10, from 2 to 8, from 2 to 6, from 2 to 4, or from 2 to 3. A substituted bivalent hydrocarbon chain is a polymethylene group in which one or more methylene hydrogen atoms are replaced with a substituent. Suitable substituents include those described below for a substituted aliphatic group.

Carbonyl—As used herein, the term "carbonyl" refers to a monovalent or bivalent moiety containing a carbon-oxygen double bond. Non-limiting examples of carbonyl groups include aldehydes, ketones, carboxylic acids, ester, amide, enones, acyl halides, anhydrides, ureas, carbamates, carbonates, thioesters, lactones, lactams, hydroxamates, isocyanates, and chloroformates.

Cycloaliphatic—As used herein, the terms "cycloaliphatic", "carbocycle", or "carbocyclic", used alone or as part of a larger moiety, refer to an optionally substituted saturated or partially unsaturated cyclic aliphatic monocyclic or bicyclic ring systems, as described herein, having from 3 to 10 members. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, and cyclooctadienyl. In some embodiments, the cycloalkyl has 3-6 carbons.

Halogen—As used herein, the terms "halo" and "halogen" refer to an atom selected from fluorine (fluoro, —F), chlorine (chloro, —Cl), bromine (bromo, —Br), and iodine (iodo, —I).

Heteroaliphatic—As used herein, the terms "heteroaliphatic" or "heteroaliphatic group", denote an optionally substituted hydrocarbon moiety having, in addition to carbon atoms, from one to five heteroatoms, that may be straight-chain (i.e., unbranched), branched, or cyclic ("heterocyclic") and may be completely saturated or may contain one or more units of unsaturation, but which is not aromatic. Unless otherwise specified, heteroaliphatic groups contain 1-6 carbon atoms wherein 1-3 carbon atoms are optionally and independently replaced with heteroatoms selected from oxygen, nitrogen and sulfur. In some embodiments, heteroaliphatic groups contain 1-4 carbon atoms, wherein 1-2 carbon atoms are optionally and independently replaced with heteroatoms selected from oxygen, nitrogen and sulfur. In yet other embodiments, heteroaliphatic groups contain 1-3 carbon atoms, wherein 1 carbon atom is optionally and independently replaced with a heteroatom selected from oxygen, nitrogen and sulfur. Suitable heteroaliphatic groups include, but are not limited to, linear or branched, heteroalkyl, heteroalkenyl, and heteroalkynyl groups.

Heteroaralkyl—As used herein, the term "heteroaralkyl" refers to an alkyl group substituted by a heteroaryl, wherein the alkyl and heteroaryl portions independently are optionally substituted.

Heteroaryl—As used herein, the term "heteroaryl" used alone or as part of a larger moiety, e.g., "heteroaralkyl", or "heteroaralkoxy", refers to an optionally substituted group having 5 to 10 ring atoms, preferably 5, 6, or 9 ring atoms; having 6, 10, or 14π electrons shared in a cyclic array; and having, in addition to carbon atoms, from one to five heteroatoms. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, carbocyclic, or heterocyclic rings, where the radical or point of attachment is on the heteroaromatic ring. Non limiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, and tetrahydroisoquinolinyl. A heteroaryl group may be mono- or bicyclic. The term "heteroaryl" may be used interchangeably with the terms "heteroaryl ring", "heteroaryl group", or "heteroaromatic", any of which terms include rings that are optionally substituted.

Heteroatom—As used herein, the term "heteroatom" refers to nitrogen, oxygen, or sulfur, and includes any oxidized form of nitrogen or sulfur, and any quaternized form of a basic nitrogen. The term "nitrogen" also includes a substituted nitrogen.

Heterocyclic—As used herein, the terms "heterocycle", "heterocyclyl", "heterocyclic radical", and "heterocyclic ring" are used interchangeably and refer to a stable optionally substituted 5- to 7-membered monocyclic or 7- to 10-membered bicyclic heterocyclic moiety that is either saturated or partially unsaturated, and having, in addition to carbon atoms, one or more heteroatoms, as defined above. A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or carbocyclic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

Unsaturated—As used herein, the term "unsaturated", means that a moiety has one or more double or triple bonds.

Partially unsaturated—As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

Optionally substituted—As described herein, compounds of the invention may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —$(CH_2)_{0-4}R^\circ$; —$(CH_2)_{0-4}OR^\circ$; —O—$(CH_2)_{0-4}C(O)OR^\circ$; —$(CH_2)_{0-4}CH(OR^\circ)_2$; —$(CH_2)_{0-4}SR^\circ$;

—(CH$_2$)$_{0-4}$Ph, which may be substituted with R°; —(CH$_2$)$_{0-4}$(CH$_2$)$_{0-1}$Ph which may be substituted with R°; —CH=CHPh, which may be substituted with R°; —NO$_2$; —CN; —N$_3$; —(CH$_2$)$_{0-4}$N(R°)$_2$; —(CH$_2$)$_{0-4}$N(R°)C(O)R; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR—, SC(S)SR°; —(CH$_2$)$_{0-4}$SC(O)R°; —(CH$_2$)$_{0-4}$C(O)NR°$_2$; —C(S)NR°$_2$; —C(S)SR°; —SC(S)SR°, —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; SiR°$_3$; —(C$_{1-4}$ straight or branched alkylene)O—N(R°)$_2$; or —(C$_{1-4}$ straight or branched alkylene)C(O)O—N(R°)$_2$, wherein each R° may be substituted as defined below and is independently hydrogen, C$_{1-6}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R•, -(haloR•), —(CH$_2$)$_{0-2}$OH, —(CH$_2$)$_{0-2}$OR•, —(CH$_2$)$_{0-2}$CH(OR•)$_2$; —O(haloR•), —CN, —N$_3$, —(CH$_2$)$_{0-2}$C(O)R•, —(CH$_2$)$_{0-2}$C(O)OH, —(CH$_2$)$_{0-2}$C(O)OR•, —(CH$_2$)$_{0-2}$SR•, —(CH$_2$)$_{0-2}$SH, —(CH$_2$)$_{0-2}$NH$_2$, —(CH$_2$)$_{0-2}$NHR•, —(CH$_2$)$_{0-2}$NR•$_2$, —NO$_2$, —SiR•$_3$, —OSiR•$_3$, —C(O)SR•, —(C$_{1-4}$ straight or branched alkylene)C(O)OR•, or —SSR• wherein each R• is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R•, -(haloR•), —OH, —OR•, —R•), —CN, —C(O)OH, —C(O)OR•, —NH$_2$, —NHR•, —NR•$_2$, or —NO$_2$, wherein each R• is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R†, —NR†$_2$, —C(O)R†, —C(O)OR†, —C(O)C(O)R†, —C(O)CH$_2$C(O)R†, —S(O)$_2$R†, —S(O)$_2$NR†$_2$, —C(S)NR†$_2$, —C(NH)NR†$_2$, or —N(R†)S(O)$_2$R†; wherein each R† is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R†, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R• are independently halogen, —R•, -(haloR•), —OH, —OR•, —R•), —CN, —C(O)OH, —C(O)OR•, —NH$_2$, —NHR•, —NR•$_2$, or —NO$_2$, wherein each R• is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable protecting group—As used herein, the term "suitable protecting group," refers to amino protecting groups or hydroxyl protecting groups depending on its location within the compound and includes those described in detail in *Protecting Groups in Organic Synthesis*, T. W. Greene and P. G. M. Wuts, 3$^{rd}$ edition, John Wiley & Sons, 1999.

Suitable amino-protecting groups include methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, i-methyl-1-(p-phenylazophenyl)ethyl carbamate, i-methyl-1-phenylethyl carbamate, i-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxycarbonylamino)acetamide, 3-(p-hydroxyphenyl)propanamide, 3-(o-nitrophenyl) propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentacarbonylchromium- or tungsten) carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Suitable hydroxyl protecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxide, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl) diphenylmethyl, 4,4',4"-tris(4,5-dichlorophthalimidophenyl) methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl)ethyl carbonate (Psec), 2-(triphenylphosphonio)ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N,N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl)ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N, N-dimethylamino)ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate.

In any case where a chemical variable (e.g., an R group) is shown attached to a bond that crosses a bond of ring, this means that one or more such variables are optionally attached to the ring having the crossed bond. Each R group on such a ring can be attached at any suitable position, this is generally understood to mean that the group is attached in place of a hydrogen atom on the parent ring. This includes the possibility that two R groups can be attached to the same ring atom. Furthermore, when more than one R group is present on a ring, each may be the same or different than other R groups attached thereto, and each group is defined independently of other groups that may be attached elsewhere on the same molecule, even though they may be represented by the same identifier.

Biodegradable—As used herein, the term "biodegradable" refers to molecules that degrade (i.e., lose at least some of their covalent structure) under physiological or endosomal conditions. Biodegradable molecules are not necessarily hydrolytically degradable and may require enzymatic action to degrade.

Biomolecule—As used herein, the term "biomolecule" refers to molecules (e.g., polypeptides, amino acids, polynucleotides, nucleotides, polysaccharides, sugars, lipids, nucleoproteins, glycoproteins, lipoproteins, steroids, metabolites, etc.) whether naturally-occurring or artificially created (e.g., by synthetic or recombinant methods) that are commonly found in cells and tissues. Specific classes of biomolecules include, but are not limited to, enzymes, receptors, neurotransmitters, hormones, cytokines, cell response modifiers such as growth factors and chemotactic factors, antibodies, vaccines, haptens, toxins, interferons, ribozymes, anti-sense agents, plasmids, DNA, and RNA.

Drug—As used herein, the term "drug" refers to small molecules or biomolecules that alter, inhibit, activate, or otherwise affect a biological event. For example, drugs may include, but are not limited to, anti-AIDS substances, anti-cancer substances, antibiotics, anti-diabetic substances, immunosuppressants, anti-viral substances, enzyme inhibitors, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and anti-adhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, anti-secretory factors, anti-coagulants and/or anti-thrombotic agents, local anesthetics, ophthalmics, prostaglandins, anti-depressants, anti-psychotic substances, anti-emetics, and imaging agents. A more complete listing of exemplary drugs suitable for use in the present invention may be found in "Pharmaceutical Substances: Syntheses, Patents, Applications" by Axel Kleemann and Jurgen Engel, Thieme Medical Publishing, 1999; the "Merck Index: An Encyclopedia of Chemicals, Drugs, and Biologicals", edited by Susan Budavari et al., CRC Press, 1996, and the United States Pharmacopeia-25/National Formulary-20, published by the United States Pharmcopeial Convention, Inc., Rockville Md., 2001.

Exogenous—As used herein, an "exogenous" molecule is one which is not present at significant levels in a patient unless administered to the patient. In certain embodiments the patient is a mammal, e.g., a human, a dog, a cat, a rat, a minipig, etc. As used herein, a molecule is not present at significant levels in a patient if normal serum for that type of patient includes less than 0.1 mM of the molecule. In certain embodiments normal serum for the patient may include less than 0.08 mM, less than 0.06 mM, or less than 0.04 mM of the molecule.

Hyperbranched—As used herein, a "hyperbranched" structure is a covalent structure that includes at least one branched branch (e.g., a dendrimeric structure). A hyperbranched structure may include polymeric and/or non-polymeric substructures.

Normal serum—As used herein, "normal serum" is serum obtained by pooling approximately equal amounts of the liquid portion of coagulated whole blood from five or more non-diabetic patients. A non-diabetic human patient is a randomly selected 18-30 year old who presents with no diabetic symptoms at the time blood is drawn.

Polymer—As used herein, a "polymer" or "polymeric structure" is a structure that includes a string of covalently bound monomers. A polymer can be made from one type of monomer or more than one type of monomer. The term "polymer" therefore encompasses copolymers, including block-copolymers in which different types of monomer are grouped separately within the overall polymer. A polymer can be linear or branched.

Polynucleotide—As used herein, a "polynucleotide" is a polymer of nucleotides. The terms "polynucleotide", "nucleic acid", and "oligonucleotide" may be used interchangeably. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, 5-methylcytidine, C5-bromouridine, C5-fluorouridine, C5-iodouridine, C5-propynyl-uridine, C5-propynyl-cytidine, C5-methylcytidine, 7-deazaadenosine, 7-deazaguanosine, 8-oxoadenosine, 8-oxoguanosine, O(6)-methylguanine, 4-acetylcytidine, 5-(carboxyhydroxymethyl) uridine, dihydrouridine, methylpseudouridine, 1-methyl adenosine, 1-methyl guanosine, N6-methyl adenosine, and 2-thiocytidine), chemically modified bases, biologically modified bases (e.g., methylated bases), intercalated bases, modified sugars (e.g., 2'-fluororibose, ribose, 2'-deoxyribose, 2'-O-methylcytidine, arabinose, and hexose), or modified phosphate groups (e.g., phosphorothioates and 5'-N-phosphoramidite linkages).

Polypeptide—As used herein, a "polypeptide" is a polymer of amino acids. The terms "polypeptide", "protein", "oligopeptide", and "peptide" may be used interchangeably. Polypeptides may contain natural amino acids, non-natural amino acids (i.e., compounds that do not occur in nature but that can be incorporated into a polypeptide chain) and/or amino acid analogs as are known in the art. Also, one or more of the amino acid residues in a polypeptide may be modified, for example, by the addition of a chemical entity such as a carbohydrate group, a phosphate group, a farnesyl group, an isofarnesyl group, a fatty acid group, a linker for conjugation, functionalization, or other modification, etc. These modifications may include cyclization of the peptide, the incorporation of D-amino acids, etc.

Polysaccharide—As used herein, a "polysaccharide" is a polymer of saccharides. The terms "polysaccharide", "carbohydrate", and "oligosaccharide", may be used interchangeably. The polymer may include natural saccharides (e.g., arabinose, lyxose, ribose, xylose, ribulose, xylulose, allose, altrose, galactose, glucose, gulose, idose, mannose, talose, fructose, psicose, sorbose, tagatose, mannoheptulose, sedoheptulose, octolose, and sialose) and/or modified saccharides (e.g., 2'-fluororibose, 2'-deoxyribose, and hexose). Exemplary disaccharides include sucrose, lactose, maltose, trehalose, gentiobiose, isomaltose, kojibiose, laminaribiose, mannobiose, melibiose, nigerose, rutinose, and xylobiose.

Small molecule—As used herein, the term "small molecule" refers to molecules, whether naturally-occurring or artificially created (e.g., via chemical synthesis), that have a relatively low molecular weight. Typically, small molecules are monomeric and have a molecular weight of less than about 1500 Da. Preferred small molecules are biologically active in that they produce a local or systemic effect in animals, preferably mammals, more preferably humans. In certain preferred embodiments, the small molecule is a drug. Preferably, though not necessarily, the drug is one that has already been deemed safe and effective for use by the appropriate governmental agency or body. For example, drugs for human use listed by the FDA under 21 C.F.R. §§330.5, 331 through 361, and 440 through 460; drugs for veterinary use listed by the FDA under 21 C.F.R. §§500 through 589, are all considered acceptable for use in accordance with the present invention.

Treat—As used herein, the term "treat" (or "treating", "treated", "treatment", etc.) refers to the administration of a conjugate of the present disclosure to a subject in need thereof with the purpose to alleviate, relieve, alter, ameliorate, improve or affect a condition (e.g., diabetes), a symptom or symptoms of a condition (e.g., hyperglycemia), or the predisposition toward a condition.

BRIEF DESCRIPTION OF THE DRAWINGS

FIG. 3: Accelerated stability testing (AST) chemical stability results: (a) RP-HPLC AST conjugate stability and (b) LC/MS data on AST conjugates.

FIG. 27: Plot of serum insulin and blood glucose levels following subcutaneous injection in non-diabetic, male SD rats (n=3) at time 0 with TSPE-AEM-3 conjugate I-9 followed by IP injection of alpha-methyl mannose (left) or saline (right) after 15 minutes. Alpha-methyl mannose is a very high affinity saccharide which is capable of competing with AEM for binding to lectins such as Con A. As shown, the change in PK/PD profile that results from injection of alpha-methyl mannose is significant ($p<0.05$).

FIG. 46: Plots of serum insulin concentration as a function of time following injection of conjugate I-6 or RHI (left) and conjugate I-6 with and without glucose or α-methyl mannose (right).

FIG. 50: β-phase elimination half-life results in non-diabetic minipigs during glucose, α-methyl mannose or saline infusion.

Figure 52:
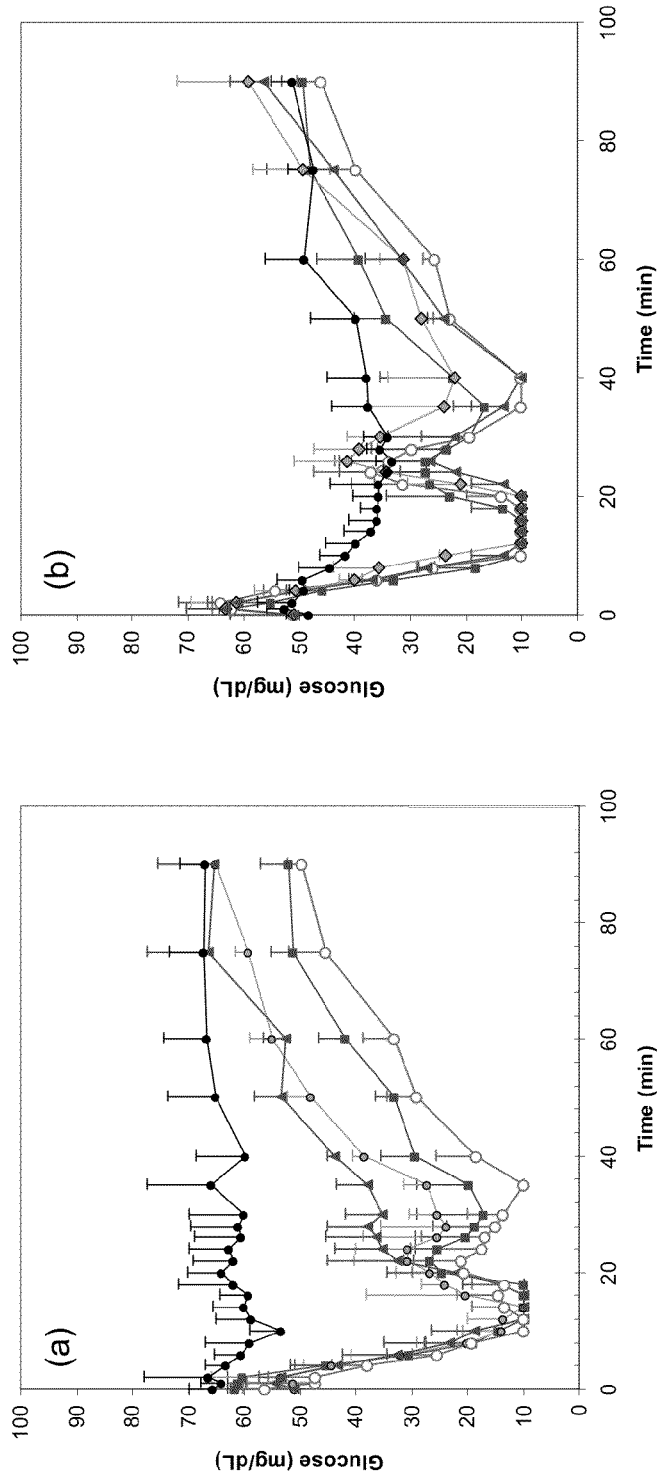

FIG. 52: Blood glucose depression curves in non-diabetic male Yucatan minipigs equipped with dual vascular access ports (n=3 per study) following i.v. injection of conjugates at 0.1 U/kg under conditions of (a) no i.v. sugar infusion or (b) i.v. alpha methyl mannose (a-MM) infusion (25% w/v infused at constant rate of 80 ml/h). (■)RHI, (○) I-7, (✳) I-6, (▲) I-11, and (●) II-2.

Figure 53:
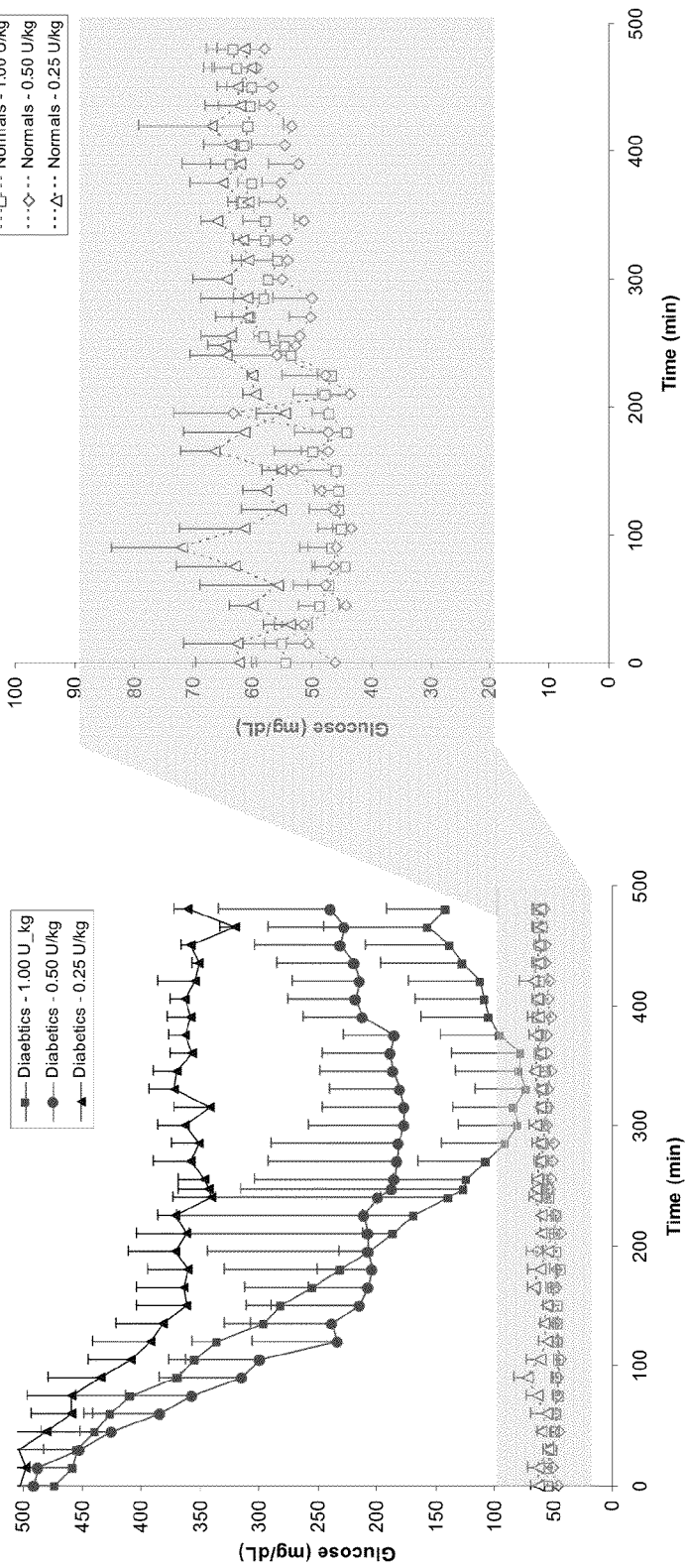

FIG. 53: Blood glucose levels in (a, -, closed symbols) alloxan-diabetic Yucatan minipigs (n=3 per dose) and (b, - - - -, open symbols) non-diabetic Yucatan minipigs (n=3 per dose) under fasting conditions after a sub-Q injection at time 0 with soluble Di-Sub-AETM-2 insulin conjugate II-2 at doses of 0.25, 0.50, and 1.00 U/kg. Data are plotted as the average values±one standard deviation. NOTE: FIG. 53(b) scale is enlarged for clarity.

Figure 54:
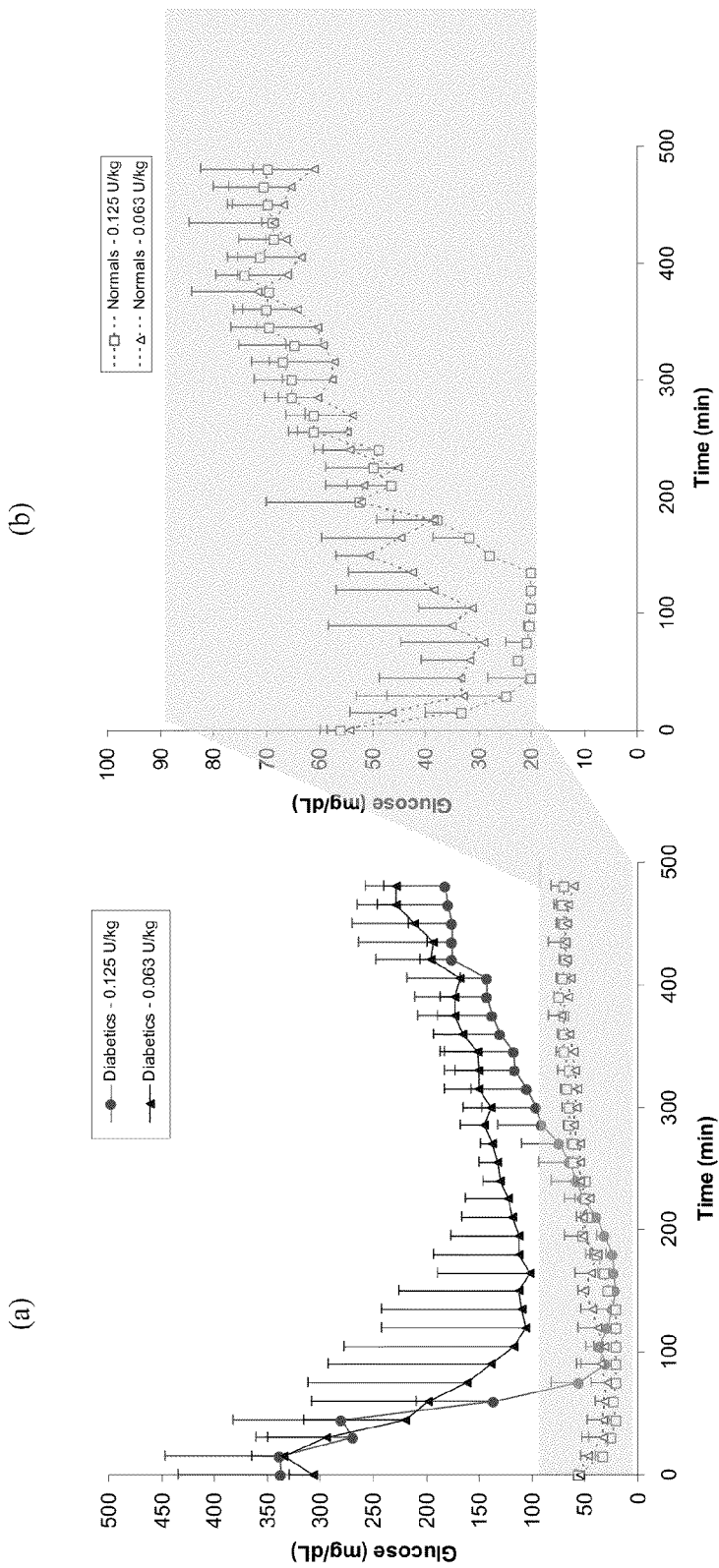

FIG. 54: Blood glucose levels in (a, -, closed symbols) alloxan-diabetic Yucatan minipigs (n=3 per dose) and (b, - - - -, open symbols) non-diabetic Yucatan minipigs (n=3 per dose) under fasting conditions after a sub-Q injection at time 0 with soluble recombinant human insulin (RHI) at doses of (▲,△) 0.063 and (■,□) 0.125 U/g. Data are plotted as the average values±one standard deviation. NOTE: FIG. 54(b) scale is enlarged for clarity.

FIG. 55: Additional insulin conjugates for use in non-diabetic minipig sugar-dependent elimination half-life studies. As described in the Examples, these conjugates were each prepared with recombinant wild-type human insulin (see FIG. 63 for the structure of wild-type human insulin). The schematic in FIG. 55 is therefore primarily intended to represent a wild-type human insulin. As discussed herein, it is to be understood that the present disclosure also encompasses inter alia versions of these and other conjugates that include an insulin molecule other than wild-type human insulin.

Figure 56:
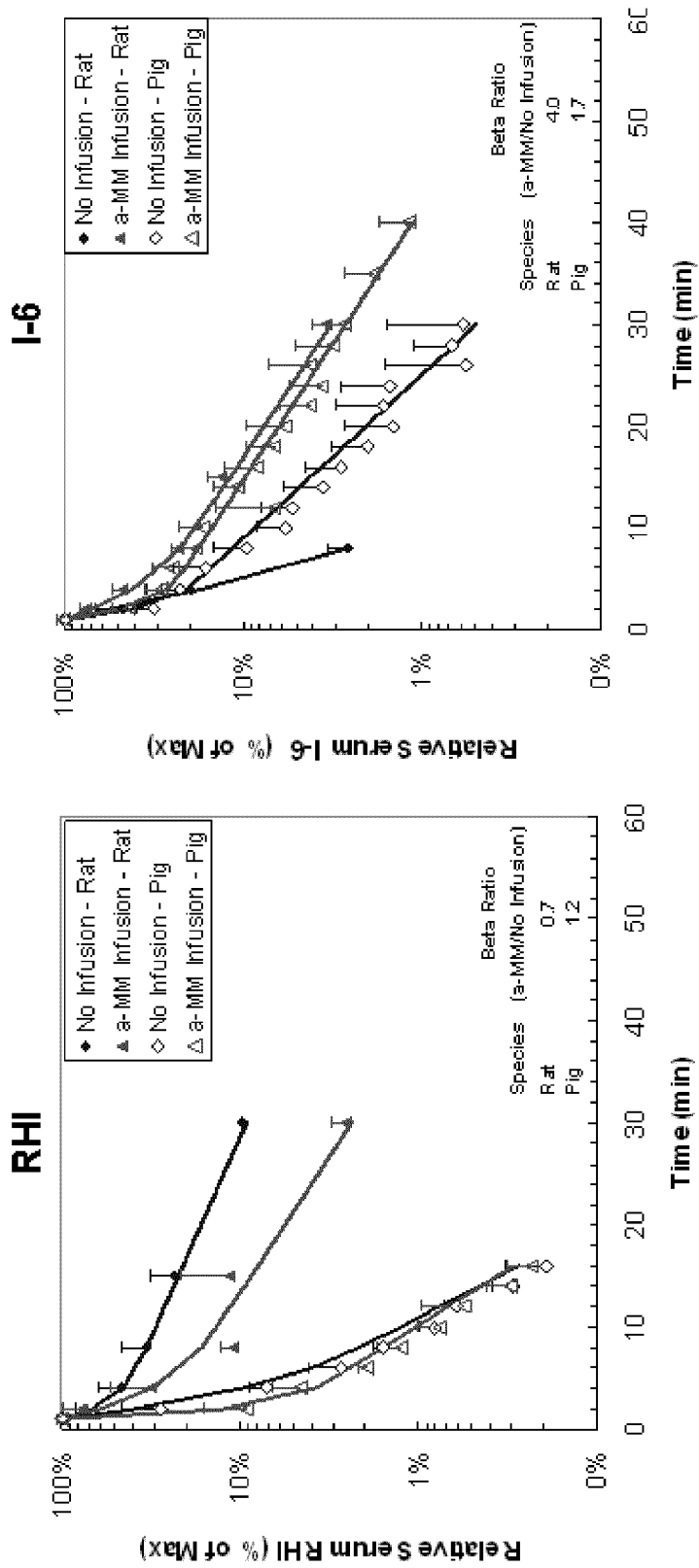

FIG. 56: Plots of serum insulin concentration as a function of time following administration of RHI or conjugate I-6 in rats and minipigs.

FIG. 57: Summary of i.v. half-life results in minipigs for additional insulin-conjugates.

Figure 58:
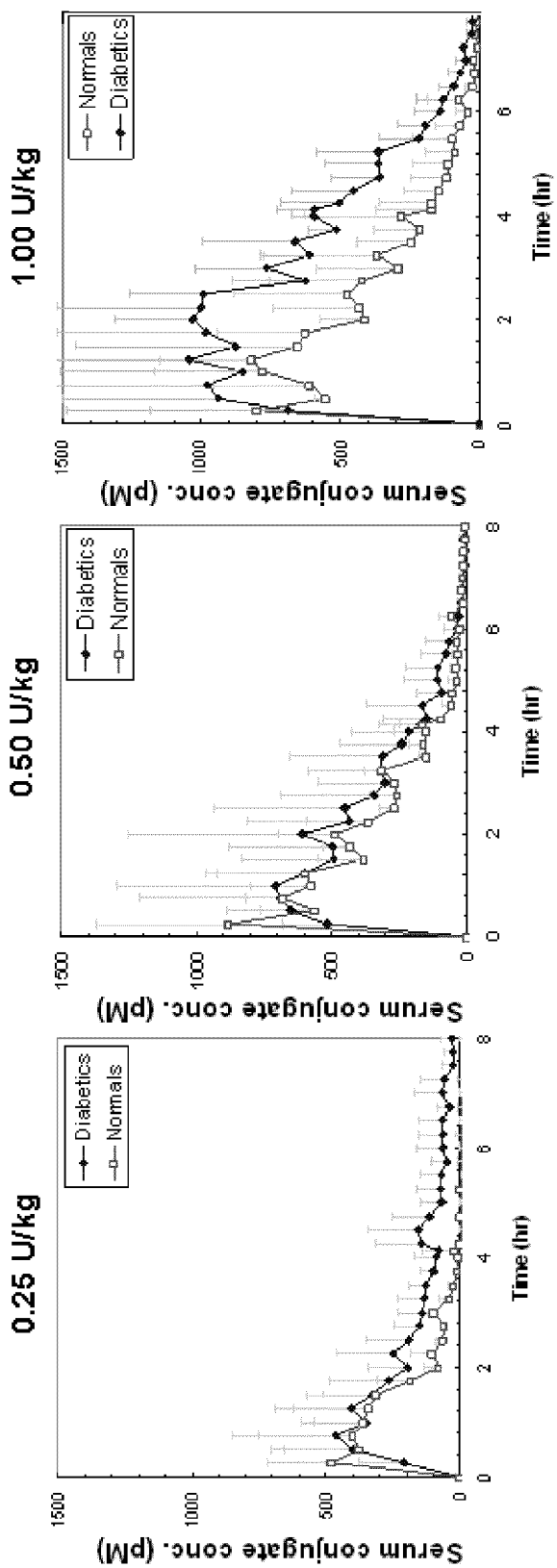

FIG. 58: Plot of serum insulin levels after a single subcutaneous injection of 0.25, 0.5 and 1 U/kg insulin conjugate II-2 in diabetic and normal minipigs.

Figure 59:
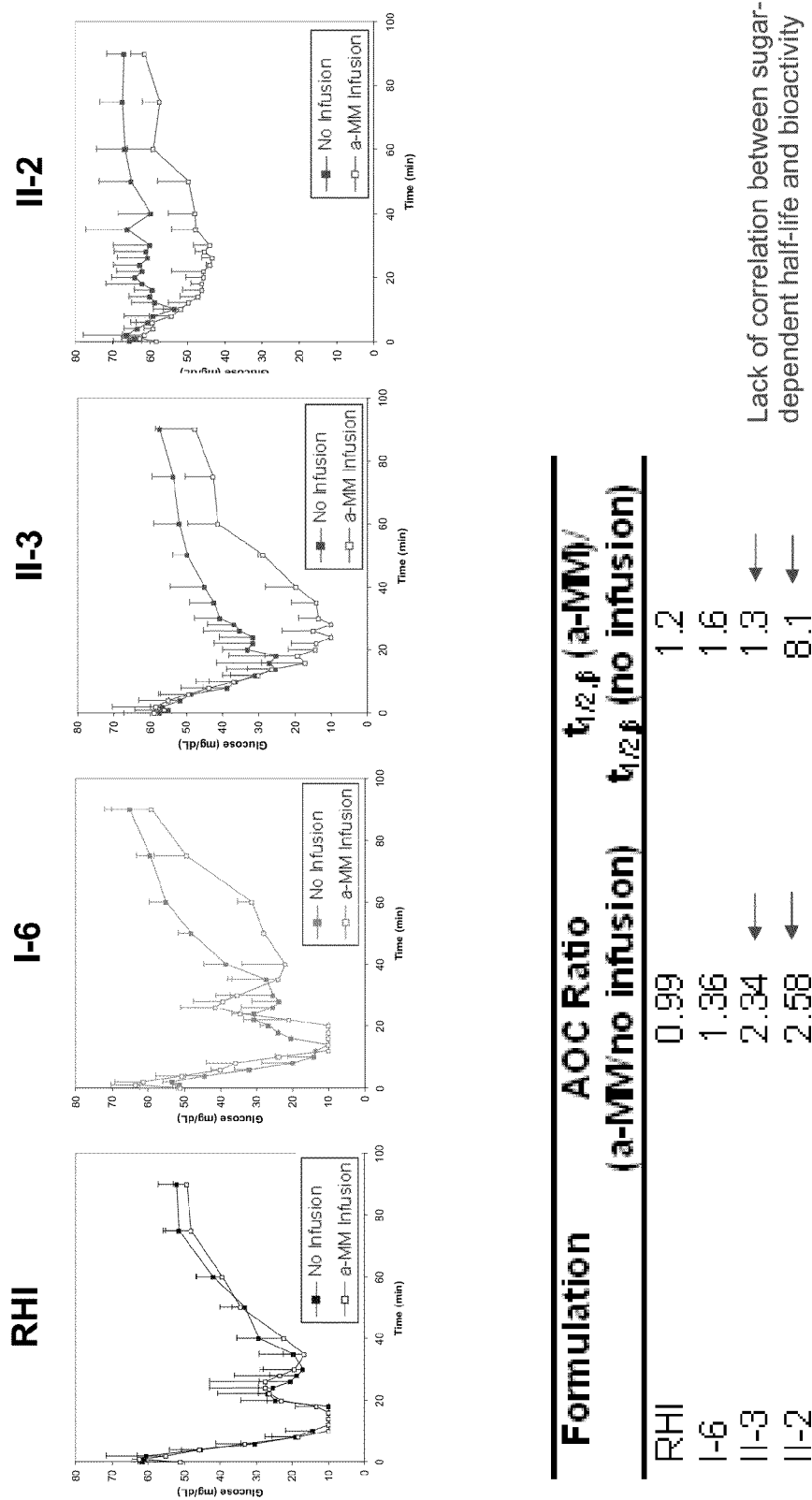

FIG. 59: Plots of serum glucose levels after i.v. injections of RHI and conjugates I-6, II-3 and II-2 in minipigs with and without a-MM infusion.

Figure 60:
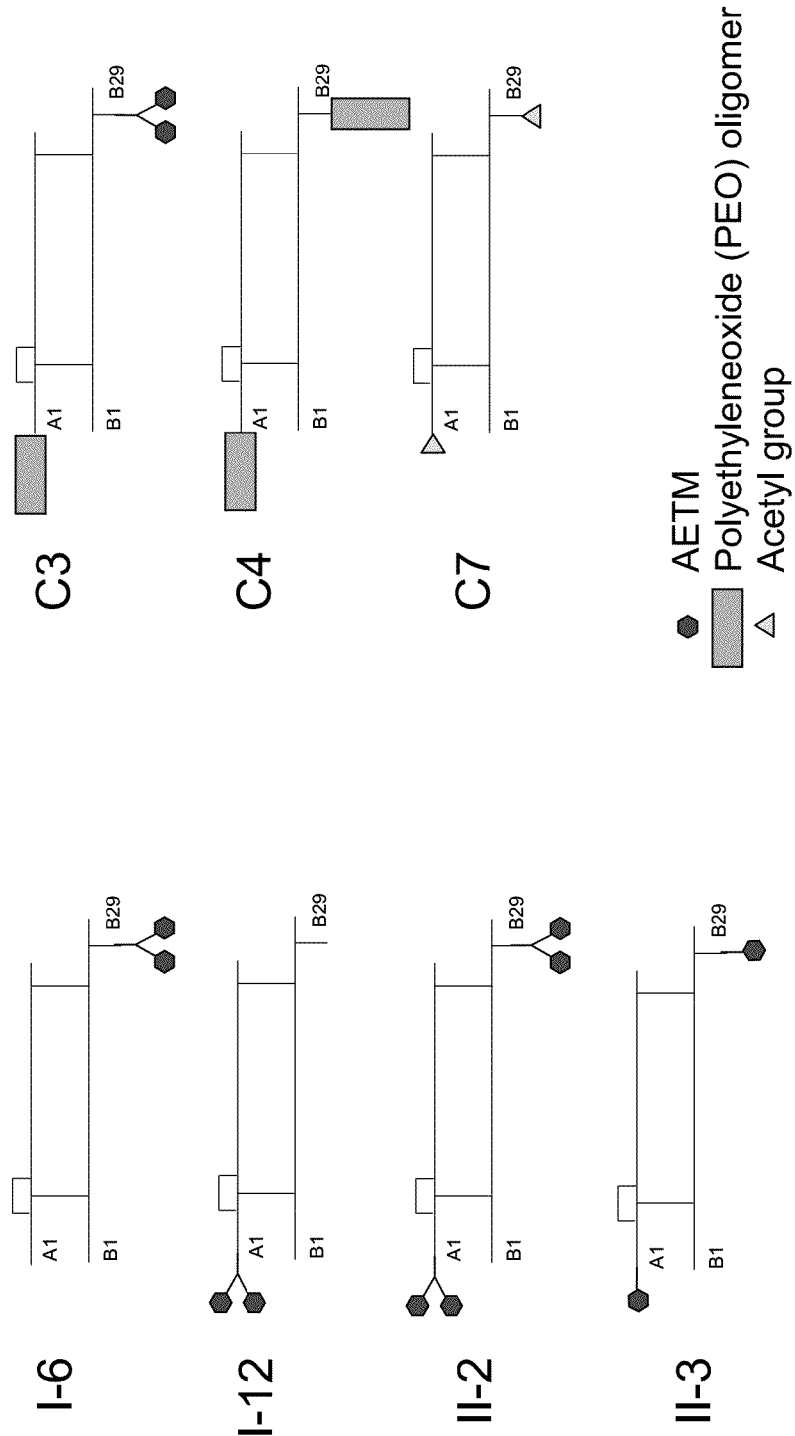

FIG. 60: Structures of selected insulin conjugates (C3, C4, and C7) tested in minipigs as controls, along with insulin conjugates I-6, I-12, II-2, and II-3. As described in the Examples, these conjugates were each prepared with recombinant wild-type human insulin (see FIG. 63 for the structure of wild-type human insulin). The schematic in FIG. 60 is therefore primarily intended to represent a wild-type human insulin. As discussed herein, it is to be understood that the present disclosure also encompasses inter alia versions of these and other conjugates that include an insulin molecule other than wild-type human insulin.

Figure 61:
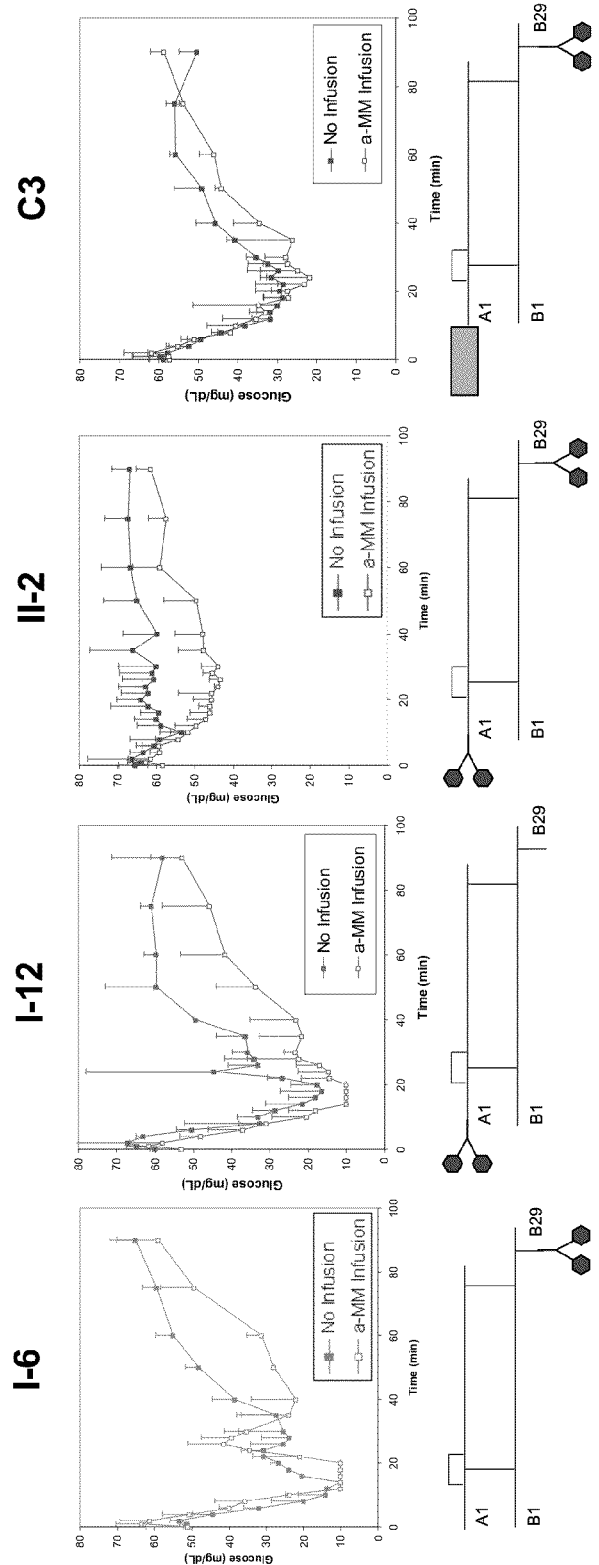

FIG. 61: Plots of serum glucose levels after i.v. injections of RHI and insulin conjugates I-6, I-12, II-2 and C3 in minipigs with and without a-MM infusion.

Figure 62:
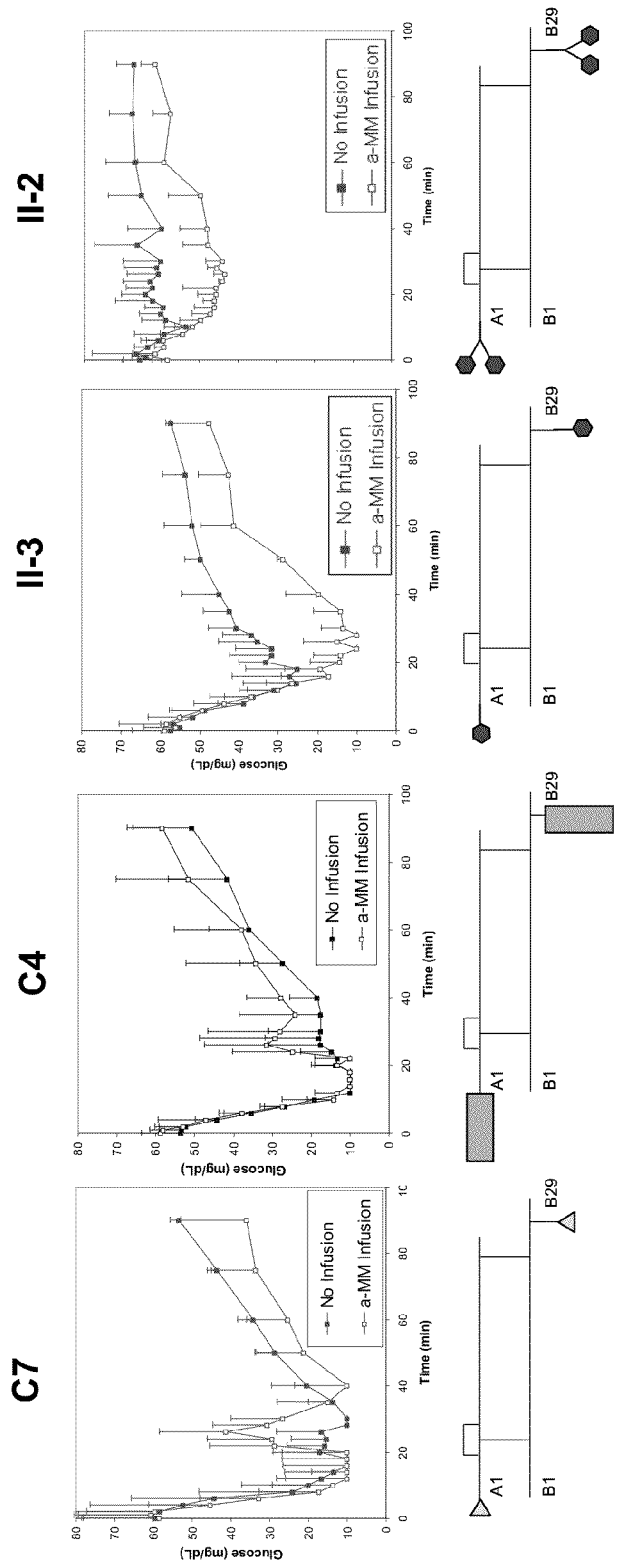

FIG. 62: Plots of serum glucose levels after i.v. injections of RHI and insulin conjugates C7, C4, II-3 and II-2 in minipigs with and without a-MM infusion.

Figure 63:
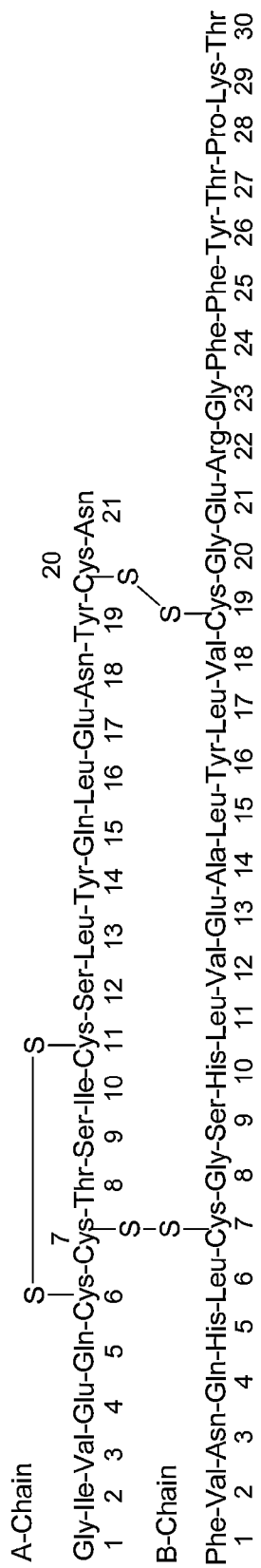

FIG. 63: Structure of wild-type human insulin.

DETAILED DESCRIPTION OF VARIOUS EMBODIMENTS

This application refers to a number of documents including patent and non-patent documents. The entirety of each of these documents is incorporated herein by reference.

In one aspect, the disclosure provides methods for controlling the pharmacokinetic (PK) and/or pharmacodynamic (PD) profiles of a drug such as insulin in a manner that is responsive to the systemic concentrations of a saccharide such as glucose. As discussed in the Examples, the methods are based in part on the discovery that when certain insulin-conjugates were modified to include high affinity saccharide ligands they could be made to exhibit PK/PD profiles that responded to saccharide concentration changes even in the absence of an exogenous multivalent saccharide-binding molecule such as Con A. This finding was unexpected and provides an unprecedented opportunity to generate simple lectin-free saccharide-responsive drug systems. In another aspect, the disclosure provides exemplary conjugates and methods for making these. In general, these conjugates include a drug and one or more separate ligands that each include a saccharide. In certain embodiments, the ligands are capable of competing with a saccharide (e.g., glucose or mannose) for binding to an endogenous saccharide-binding molecule. In certain embodiments, the ligands are capable of competing with glucose or mannose for binding to Con A. As discussed in more detail below, in certain embodiments, the ligands and drug may be covalently or non-covalently attached to a conjugate framework. In certain embodiments, the framework is non-polymeric. In certain embodiments, a conjugate may have a polydispersity index of one and a MW of less than about 20,000 Da. In certain embodiments, the conjugate is of formula (I) or (II) as defined and described herein. In certain embodiments, the conjugate is long acting (i.e., exhibits a PK profile that is more sustained than soluble recombinant human insulin or RHI).

As discussed in more detail below, it is to be understood that the methods, conjugates and formulations that are described herein are in no way limited to the delivery of insulin and that they can be used to deliver any drug. It is also to be understood that the methods may be used to deliver drugs in response to saccharides other than glucose. In particular, as discussed in the Examples, exemplary conjugates have been shown to respond to exogenous saccharides such as alpha-methyl mannose and L-fucose. In certain embodiments, this can be used to prepare conjugates that can be controlled by administration of one of these exogenous saccharides (i.e., instead of or in addition to being controlled by fluctuations in endogenous glucose).

Conjugates

In one aspect, the disclosure provides conjugates that comprise a drug and a ligand that includes a first saccharide. The ligand (or ligands when the conjugates include more than one ligand) are such that when the conjugate is administered to a mammal at least one pharmacokinetic or pharmacodynamic property of the conjugate is sensitive to the serum concentration of a second saccharide. In certain embodiments, the PK and/or PD properties of the conjugate are sensitive to the serum concentration of an endogenous saccharide such as glucose. In certain embodiments, the PK and/or PD properties of the conjugate are sensitive to the serum concentration of an exogenous saccharide, e.g., without limitation, mannose, L-fucose, N-acetyl glucosamine and/or alpha-methyl mannose.

As discussed in more detail below, in certain embodiments, the ligand(s) and drug may be covalently or non-covalently attached to a conjugate framework.

In certain embodiments, the molecular weight of the conjugate absent the drug is less than about 10,000 Da. For example, the molecular weight of the conjugate absent the drug may be in the range of about 250 to about 5,000 Da, about 450 to about 3,500 Da, about 750 to about 2,500 Da, or about 900 to about 2,000 Da.

In certain embodiments, the molecular weight of the conjugate including the drug is less than about 20,000 Da. For example, the molecular weight of the conjugate including the drug may be in the range of about 2,000 to about 18,000 Da, about 4,000 to about 15,000 Da, about 5,000 to about 10000 Da, or about 6,500 to about 8,000 Da.

In certain embodiments, the conjugate has a unique molecular weight (i.e., has a polydispersity index of one).

PK and PD Properties

In various embodiments, the pharmacokinetic and/or pharmacodynamic behavior of a conjugate (i.e., conjugated drug and/or drug which has been released from a conjugate by chemical or enzymatic degradation) may be modified by variations in the serum concentration of a saccharide.

For example, from a pharmacokinetic (PK) perspective, the serum concentration curve may shift upward when the serum concentration of the saccharide (e.g., glucose) increases or when the serum concentration of the saccharide crosses a threshold (e.g., is higher than normal glucose levels).

In certain embodiments, the serum concentration curve of a conjugate is substantially different when administered to the mammal under fasted and hyperglycemic conditions. As used herein, the term "substantially different" means that the two curves are statistically different as determined by a student t-test (p<0.05). As used herein, the term "fasted conditions" means that the serum concentration curve was obtained by combining data from five or more fasted non-diabetic individuals. In certain embodiments, a fasted non-diabetic individual is a randomly selected 18-30 year old human who presents with no diabetic symptoms at the time blood is drawn and who has not eaten within 12 hours of the time blood is drawn. As used herein, the term "hyperglycemic conditions" means that the serum concentration curve was obtained by combining data from five or more fasted non-diabetic individuals in which hyperglycemic conditions (glucose $C_{max}$ at least 100 mg/dL above the mean glucose concentration observed under fasted conditions) were induced by concurrent administration of conjugate and glucose. Concurrent administration of conjugate and glucose simply requires that the glucose $C_{max}$ occur during the period when the conjugate is present at a detectable level in the serum. For example, a glucose injection (or ingestion) could be timed to occur shortly before, at the same time or shortly after the conjugate is administered. In certain embodiments, the conjugate and glucose are administered by different routes or at different locations. For example, in certain embodiments, the conjugate is administered subcutaneously while glucose is administered orally or intravenously.

In certain embodiments, the serum $C_{max}$ of the conjugate is higher under hyperglycemic conditions as compared to fasted conditions. Additionally or alternatively, in certain embodiments, the serum area under the curve (AUC) of the conjugate is higher under hyperglycemic conditions as compared to fasted conditions. In various embodiments, the serum elimination rate of the conjugate is slower under hyperglycemic conditions as compared to fasted conditions. As discussed in the Examples, we have found that in certain embodiments, the serum concentration curve of the conjugates can be fit using a two-compartment bi-exponential model with one short and one long half-life. The long half-life appears to be particularly sensitive to glucose concentration. Thus, in certain embodiments, the long half-life is longer under hyperglycemic conditions as compared to fasted conditions. In certain embodiments, the fasted conditions involve a glucose $C_{max}$ of less than 100 mg/dL (e.g., 80 mg/dL, 70 mg/dL, 60 mg/dL, 50 mg/dL, etc.). In certain embodiments, the hyperglycemic conditions involve a glucose $C_{max}$ in excess of 200 mg/dL (e.g., 300 mg/dL, 400 mg/dL, 500 mg/dL, 600 mg/dL, etc.). It will be appreciated that other PK parameters such as mean serum residence time (MRT), mean serum absorption time (MAT), etc. could be used instead of or in conjunction with any of the aforementioned parameters.

The normal range of glucose concentrations in humans, dogs, cats, and rats is 60 to 200 mg/dL. One skilled in the art will be able to extrapolate the following values for species with different normal ranges (e.g., the normal range of glucose concentrations in miniature pigs is 40 to 150 mg/dl). Glucose concentrations below 60 mg/dL are considered hypoglycemic. Glucose concentrations above 200 mg/dL are considered hyperglycemic. In certain embodiments, the PK properties of the conjugate may be tested using a glucose clamp method (see Examples) and the serum concentration curve of the conjugate may be substantially different when administered at glucose concentrations of 50 and 200 mg/dL, 50 and 300 mg/dL, 50 and 400 mg/dL, 50 and 500 mg/dL, 50 and 600 mg/dL, 100 and 200 mg/dL, 100 and 300 mg/dL, 100 and 400 mg/dL, 100 and 500 mg/dL, 100 and 600 mg/dL, 200 and 300 mg/dL, 200 and 400 mg/dL, 200 and 500 mg/dL, 200 and 600 mg/dL, etc. Additionally or alternatively, the serum $T_{max}$, serum $C_{max}$, mean serum residence time (MRT), mean serum absorption time (MAT) and/or serum half-life may be substantially different at the two glucose concentrations. As discussed below, in certain embodiments, 100 mg/dL and 300 mg/dL may be used as comparative glucose concentrations. It is to be understood however that the present disclosure encompasses each of these embodiments with an alternative pair of comparative glucose concentrations including, without limitation, any one of the following pairs: 50 and 200 mg/dL, 50 and 300 mg/dL, 50 and 400 mg/dL, 50 and 500 mg/dL, 50 and 600 mg/dL, 100 and 200 mg/dL, 100 and 400 mg/dL, 100 and 500 mg/dL, 100 and 600 mg/dL, 200 and 300 mg/dL, 200 and 400 mg/dL, 200 and 500 mg/dL, 200 and 600 mg/dL, etc.

Thus, in certain embodiments, the $C_{max}$ of the conjugate is higher when administered to the mammal at the higher of the two glucose concentrations (e.g., 300 vs. 100 mg/dL glucose). In certain embodiments, the $C_{max}$ of the conjugate is at least 50% (e.g., at least 100%, at least 200% or at least 400%) higher when administered to the mammal at the higher of the two glucose concentrations (e.g., 300 vs. 100 mg/dL glucose).

In certain embodiments, the AUC of the conjugate is higher when administered to the mammal at the higher of the two glucose concentrations (e.g., 300 vs. 100 mg/dL glucose). In certain embodiments, the AUC of the conjugate is at least 50% (e.g., at least e.g., at least 100%, at least 200% or at least 400%) higher when administered to the mammal at the higher of the two glucose concentrations (e.g., 300 vs. 100 mg/dL glucose).

In certain embodiments, the serum elimination rate of the conjugate is slower when administered to the mammal at the higher of the two glucose concentrations (e.g., 300 vs. 100 mg/dL glucose). In certain embodiments, the serum elimination rate of the conjugate is at least 25% (e.g., at least 50%, at least 100%, at least 200%, or at least 400%) faster when administered to the mammal at the lower of the two glucose concentrations (e.g., 100 vs. 300 mg/dL glucose).

As discussed in the Examples, we have found that in certain embodiments the serum concentration curve of conjugates can be fit using a two-compartment bi-exponential model with one short and one long half-life. The long half-life appears to be particularly sensitive to glucose concentration. Thus, in certain embodiments, the long half-life is longer when administered to the mammal at the higher of the two glucose concentrations (e.g., 300 vs. 100 mg/dL glucose).

In certain embodiments, the long half-life is at least 50% (e.g., at least 100%, at least 200% or at least 400%) longer when administered to the mammal at the higher of the two glucose concentrations (e.g., 300 vs. 100 mg/dL glucose).

In certain embodiments, the present disclosure provides a method in which the serum concentration curve of a conjugate is obtained at two different glucose concentrations (e.g., 300 vs. 100 mg/dL glucose); the two curves are fit using a two-compartment bi-exponential model with one short and one long half-life; and the long half-lives obtained under the two glucose concentrations are compared. In certain embodiments, this method may be used as an assay for testing or comparing the glucose sensitivity of one or more conjugates.

In certain embodiments, the present disclosure provides a method in which the serum concentration curves of a conjugated drug (e.g., an insulin conjugate of the present disclosure) and an unconjugated version of the drug (e.g., RHI) are obtained under the same conditions (e.g., fasted conditions); the two curves are fit using a two-compartment bi-exponential model with one short and one long half-life; and the long half-lives obtained for the conjugated and unconjugated drug are compared. In certain embodiments, this method may be used as an assay for identifying conjugates that are cleared more rapidly than the unconjugated drug.

In certain embodiments, the serum concentration curve of a conjugate is substantially the same as the serum concentration curve of an unconjugated version of the drug when administered to the mammal under hyperglycemic conditions. As used herein, the term "substantially the same" means that there is no statistical difference between the two curves as determined by a student t-test (p>0.05). In certain embodiments, the serum concentration curve of the conjugate is substantially different from the serum concentration curve of an unconjugated version of the drug when administered under fasted conditions. In certain embodiments, the serum concentration curve of the conjugate is substantially the same as the serum concentration curve of an unconjugated version of the drug when administered under hyperglycemic conditions and substantially different when administered under fasted conditions. In certain embodiments, the hyperglycemic conditions involve a glucose $C_{max}$ in excess of 200 mg/dL (e.g., 300 mg/dL, 400 mg/dL, 500 mg/dL, 600 mg/dL, etc.). In certain embodiments, the fasted conditions involve a glucose $C_{max}$ of less than 100 mg/dL (e.g., 80 mg/dL, 70 mg/dL, 60 mg/dL, 50 mg/dL, etc.). It will be appreciated that any of the aforementioned PK parameters such as serum $T_{max}$, serum $C_{max}$, AUC, mean serum residence time (MRT), mean serum absorption time (MAT) and/or serum half-life could be compared.

From a pharmacodynamic (PD) perspective, the bioactivity of the conjugate may increase when the glucose concentration increases or when the glucose concentration crosses a threshold, e.g., is higher than normal glucose levels. In certain embodiments, the bioactivity of a conjugate is lower when administered under fasted conditions as compared to hyperglycemic conditions. In certain embodiments, the fasted conditions involve a glucose $C_{max}$ of less than 100 mg/dL (e.g., 80 mg/dL, 70 mg/dL, 60 mg/dL, 50 mg/dL, etc.). In certain embodiments, the hyperglycemic conditions involve a glucose $C_{max}$ in excess of 200 mg/dL (e.g., 300 mg/dL, 400 mg/dL, 500 mg/dL, 600 mg/dL, etc.).

In certain embodiments, the PD properties of the conjugate may be tested by measuring the glucose infusion rate (GIR) required to maintain a steady glucose concentration. According to such embodiments, the bioactivity of the conjugate may be substantially different when administered at glucose concentrations of 50 and 200 mg/dL, 50 and 300 mg/dL, 50 and 400 mg/dL, 50 and 500 mg/dL, 50 and 600 mg/dL, 100 and 200 mg/dL, 100 and 300 mg/dL, 100 and 400 mg/dL, 100 and 500 mg/dL, 100 and 600 mg/dL, 200 and 300 mg/dL, 200 and 400 mg/dL, 200 and 500 mg/dL, 200 and 600 mg/dL, etc. Thus, in certain embodiments, the bioactivity of the conjugate is higher when administered to the mammal at the higher of the two glucose concentrations (e.g., 300 vs. 100 mg/dL glucose). In certain embodiments, the bioactivity of the conjugate is at least 25% (e.g., at least 50% or at least 100%) higher when administered to the mammal at the higher of the two glucose concentrations (e.g., 300 vs. 100 mg/dL glucose).

In certain embodiments, the conjugate includes an insulin molecule as the drug. According to such embodiments, the PD behavior for insulin can be observed by comparing the time to reach minimum blood glucose concentration ($T_{nadir}$), the duration over which the blood glucose level remains below a certain percentage of the initial value (e.g., 70% of initial value or $T_{70\% \, BGL}$), etc.

In general, it will be appreciated that any of the PK and PD characteristics discussed in this section can be determined according to any of a variety of published pharmacokinetic and pharmacodynamic methods (e.g., see Baudys et al., *Bioconjugate Chem.* 9:176-183, 1998 for methods suitable for subcutaneous delivery). It is also to be understood that the PK and/or PD properties may be measured in any mammal (e.g., a human, a rat, a cat, a minipig, a dog, etc.). In certain embodiments, PK and/or PD properties are measured in a human. In certain embodiments, PK and/or PD properties are measured in a rat. In certain embodiments, PK and/or PD properties are measured in a minipig. In certain embodiments, PK and/or PD properties are measured in a dog.

It will also be appreciated that while the foregoing was described in the context of glucose-responsive conjugates, the same properties and assays apply to conjugates that are responsive to other saccharides including exogenous saccharides, e.g., mannose, L-fucose, N-acetyl glucosamine, alpha-methyl mannose, etc. As discussed in more detail below and in the Examples, instead of comparing PK and/or PD properties under fasted and hyperglycemic conditions, the PK and/or PD properties may be compared under fasted conditions with and without administration of the exogenous saccharide. It is to be understood that conjugates can be designed that respond to different $C_{max}$ values of a given exogenous saccharide.

Ligand(s)

In general, the conjugates include at least one ligand. In certain embodiments, the conjugates include a single ligand. In certain embodiments, the conjugates include at least two separate ligands, e.g., 2, 3, 4, 5 or more ligands. When more than one ligand is present the ligands may have the same or different chemical structures.

In certain embodiments, the ligands are capable of competing with a saccharide (e.g., glucose or mannose) for binding to an endogenous saccharide-binding molecule (e.g., without limitation surfactant proteins A and D or members of the selectin family). In certain embodiments, the ligands are capable of competing with a saccharide (e.g., glucose or mannose) for binding to cell-surface sugar receptor (e.g., without limitation macrophage mannose receptor, glucose transporter ligands, endothelial cell sugar receptors, or hepatocyte sugar receptors). In certain embodiments, the ligands are capable of competing with glucose for binding to an endogenous glucose-binding molecule (e.g., without limitation surfactant proteins A and D or members of the selectin family). In certain embodiments, the ligands are capable of competing with a saccharide for binding to a non-human lectin (e.g., Con A). In certain embodiments, the ligands are capable of competing with glucose or mannose for binding to a non-human lectin (e.g., Con A). Exemplary glucose-binding lectins include calnexin, calreticulin, N-acetylglucosamine receptor, selectin, asialoglycoprotein receptor, collectin (mannose-binding lectin), mannose receptor, aggrecan, versican, *pisum sativum* agglutinin (PSA), *vicia faba* lectin, *lens culinaris* lectin, soybean lectin, peanut lectin, lathyrus ochrus lectin, sainfoin lectin, *sophora japonica* lectin, *bowringia milbraedii* lectin, concanavalin A (Con A), and pokeweed mitogen.

In certain embodiments, the ligand is of formula (IIIa) or (IIIb):

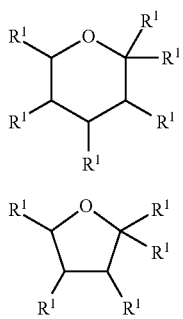

wherein:
each $R^1$ is independently hydrogen, $-OR^y$, $-N(R^y)_2$, $-SR^y$, $-O-Y$, -G-Z, or $-CH_2R^x$;
each $R^x$ is independently hydrogen, $-OR^y$, $-N(R^y)_2$, $-SR^y$, or $-O-Y$;
each $R^y$ is independently $-R^2$, $-SO_2R^2$, $-S(O)R^2$, $-P(O)(OR^2)_2$, $-C(O)R^2$, $-CO_2R^2$, or $-C(O)N(R^2)_2$;
each Y is independently a monosaccharide, disaccharide, or trisaccharide;
each G is independently a covalent bond or an optionally substituted $C_{1-9}$ alkylene, wherein one or more methylene units of G is optionally replaced by $-O-$, $-S-$, $-N(R^2)-$, $-C(O)-$, $-OC(O)-$, $-C(O)O-$, $-C(O)N(R^2)-$, $-N(R^2)C(O)-$, $-N(R^2)C(O)N(R^2)-$, $-SO_2-$, $-SO_2N(R^2)-$, $-N(R^2)SO_2-$, or $-N(R^2)SO_2N(R^2)-$;
each Z is independently halogen, $-N(R^2)_2$, $-OR^2$, $-SR^2$, $-N_3$, $-C\equiv CR^2$, $-CO_2R^2$, $-C(O)R^2$, or $-OSO_2R^2$; and
each $R^2$ is independently hydrogen or an optionally substituted group selected from $C_{1-6}$ aliphatic, phenyl, a 4-7 membered heterocyclic ring having 1-2 heteroatoms selected from nitrogen, oxygen, or sulfur, or a 5-6 membered monocyclic heteroaryl ring having 1-4 heteroatoms selected from nitrogen, oxygen, or sulfur.

In certain embodiments, the ligand of formula (IIIa) or (IIIb) is a monosaccharide. In certain embodiments, the ligand is a disaccharide. In certain embodiments, the ligand is a trisaccharide. In certain embodiments, the ligand is a tetrasaccharide. In certain embodiments, the ligand comprises no more than a total of four monosaccharide moieties.

As defined generally above, each $R^1$ is independently hydrogen, $-OR^y$, $-N(R^y)_2$, $-SR^y$, $-O-Y$, -G-Z, or $-CH_2R^x$. In certain embodiments, $R^1$ is hydrogen. In certain embodiments, $R^1$ is $-OH$. In other embodiments, $R^1$ is $-NHC(O)CH_3$. In certain embodiments, $R^1$ is $-O-Y$. In certain other embodiments, $R^1$ is -G-Z. In some embodiments, $R^1$ is $-CH_2OH$. In other embodiments, $R^1$ is $-CH_2-O-Y$. In yet other embodiments, $R^1$ is $-NH_2$. One of ordinary skill in the art will appreciate that each $R^1$ substituent in formula (IIIa) or (IIIb) may be of (R) or (S) stereochemistry.

As defined generally above, each $R^x$ is independently hydrogen, $-OR^y$, $-N(R^y)_2$, $-SR^y$, or $-O-Y$. In some embodiments, $R^x$ is hydrogen. In certain embodiments, $R^x$ is $-OH$. In other embodiments, $R^x$ is $-O-Y$.

As defined generally above, each $R^y$ is independently $-R^2$, $-SO_2R^2$, $-S(O)R^2$, $-P(O)(OR^2)_2$, $-C(O)R^2$, $-CO_2R^2$, or $-C(O)N(R^2)_2$. In some embodiments, $R^y$ is hydrogen. In other embodiments, $R^y$ is $-R^2$. In some embodiments, $R^y$ is $-C(O)R^2$. In certain embodiments, $R^y$ is acetyl. In other embodiments, $R^y$ is $-SO_2R^2$, $-S(O)R^2$, $-P(O)(OR^2)_2$, $-CO_2R^2$, or $-C(O)N(R^2)_2$.

As defined generally above, Y is a monosaccharide, disaccharide, or trisaccharide. In certain embodiments, Y is a monosaccharide. In some embodiments, Y is a disaccharide. In other embodiments, Y is a trisaccharide. In some embodiments, Y is mannose, glucose, fructose, galactose, rhamnose, or xylopyranose. In some embodiments, Y is sucrose, maltose, turanose, trehalose, cellobiose, or lactose. In certain embodiments, Y is mannose. In certain embodiments, Y is D-mannose. One of ordinary skill in the art will appreciate that the saccharide Y is attached to the oxygen group of $-O-Y$ through anomeric carbon to form a glycosidic bond. The glycosidic bond may be of an alpha or beta configuration.

As defined generally above, each G is independently a covalent bond or an optionally substituted $C_{1-9}$ alkylene, wherein one or more methylene units of G is optionally replaced by $-O-$, $-S-$, $-N(R^2)-$, $-C(O)-$, $-OC(O)-$, $-C(O)O-$, $-C(O)N(R^2)-$, $-N(R^2)C(O)-$, $-N(R^2)C(O)N(R^2)-$, $-SO_2-$, $-SO_2N(R^2)-$, $-N(R^2)SO_2-$, or $-N(R^2)SO_2N(R^2)-$. In some embodiments, G is a covalent bond. In certain embodiments, G is $-O-C_{1-8}$ alkylene. In certain embodiments, G is $-OCH_2CH_2-$.

As defined generally above, each Z is independently halogen, $-N(R^2)_2$, $-OR^2$, $-SR^2$, $-N_3$, $-C\equiv CR^2$, $-CO_2R^2$, $-C(O)R^2$, or $-OSO_2R^2$. In some embodiments, Z is a halogen or $-OSO_2R^2$. In other embodiments, Z is $-N_3$ or $-C\equiv CR^2$. In certain embodiments, Z is $-N(R^2)_2$, $-OR^2$, or $-SR^2$. In certain embodiments, Z is $-SH$. In certain embodiments, Z is $-NH_2$. In certain embodiments, -G-Z is $-OCH_2CH_2NH_2$.

In some embodiments, the $R^1$ substituent on the C1 carbon of formula (IIIa) is -G-Z to give a compound of formula (IIIa-i):

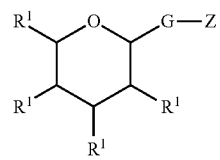

wherein $R^1$, G, and Z are as defined and described herein.

In some embodiments, the ligand is of formula (IIIa-ii):

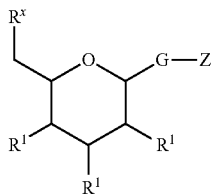

IIIa-ii wherein $R^1$, $R^x$, G, and Z are as defined and described herein.

In certain embodiments, the ligand(s) may have the same chemical structure as glucose or may be a chemically related species of glucose. In various embodiments it may be advantageous for the ligand(s) to have a different chemical structure from glucose, e.g., in order to fine tune the glucose response of the conjugate. For example, in certain embodiments, one might use a ligand that includes glucose, mannose, L-fucose or derivatives of these (e.g., alpha-L-fucopyranoside, mannosamine, beta-linked N-acetyl mannosamine, methylglucose, methylmannose, ethylglucose, ethylmannose, propylglucose, propylmannose, etc.) and/or higher order combinations of these (e.g., a bimannose, linear and/or branched trimannose, etc.).

In certain embodiments, the ligand includes a monosaccharide. In certain embodiments, the ligand includes a disaccharide. In certain embodiments, the ligand is includes a trisaccharide. In some embodiments, the ligand comprises a saccharide and one or more amine groups. In certain embodiments the saccharide and amine group are separated by a $C_1$-$C_6$ alkyl group, e.g., a $C_1$-$C_3$ alkyl group. In some embodiments, the ligand is aminoethylglucose (AEG). In some embodiments, the ligand is aminoethylmannose (AEM). In some embodiments, the ligand is aminoethylbimannose (AEBM). In some embodiments, the ligand is aminoethyltrimannose (AETM). In some embodiments, the ligand is P3-aminoethyl-N-acetylglucosamine (AEGA). In some embodiments, the ligand is aminoethylfucose (AEF). In certain embodiments, a saccharide ligand is of the "D" configuration. In other embodiments, a saccharide ligand is of the "L" configuration. Below we show the structures of these exemplary ligands. Other exemplary ligands will be recognized by those skilled in the art.

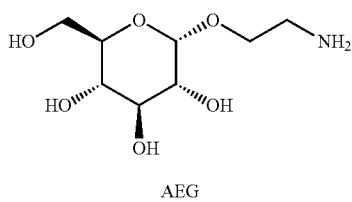

AEG

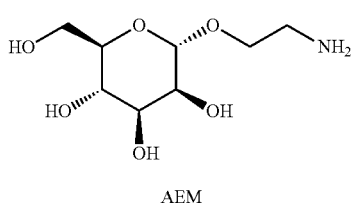

AEM

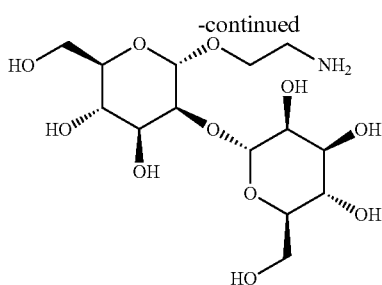

AEBM

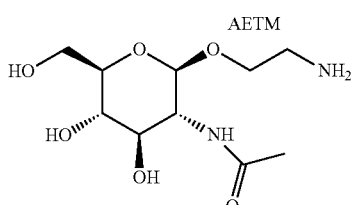

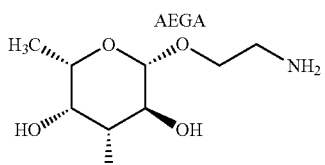

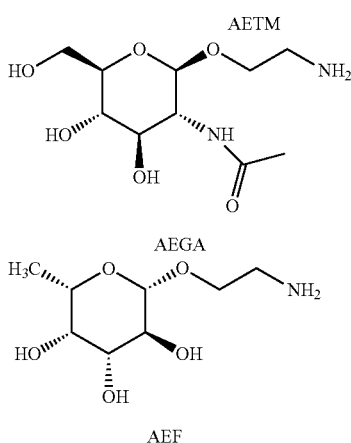

AETM

AEGA

AEF

In general, ligands may be directly or indirectly conjugated (i.e., via a linker or framework) to the drug. As discussed in more detail below, the ligands may be naturally present within a conjugate framework (e.g., as part of a polymer backbone or as a side group of a monomer). Alternatively (or additionally) ligands may be artificially incorporated into a conjugate framework (e.g., in the form of a chemical group that is synthetically added to a conjugate framework). In certain embodiments, a conjugate may include a framework which comprises 5 or more, 10 or more, or 20 or more ligands. In certain embodiments, a conjugate may comprise as few as 1, 2, 3, 4 or 5 separate ligands.

In certain embodiments, at least two separate ligands are conjugated to the drug via different conjugation points. In certain embodiments, at least two separate ligands are conjugated to a single conjugate framework that is also conjugated to the drug. In some embodiments, at least one ligand, such as AETM, AEG, AEM, AEBM, AEGA, or AEF, is conjugated to one insulin molecule. In certain embodiments, at least one AETM ligand is conjugated to one insulin molecule. In some embodiments, at least two ligands, such as AETM, AEG, AEM, AEBM, AEGA, or AEF, are conjugated to one insulin molecule, either through one conjugation point or multiple conjugation points. In certain embodiments, the at least two ligands are not the same ligand. In certain embodiments, the at least two ligands are the same ligand. In certain embodiments, at least two AETM ligands are conjugated to one insulin molecule, either through one conjugation point or multiple conjugation points. As discussed in more detail below in the context of certain exemplary conjugate frameworks, in certain embodiments the separate ligands and drug (e.g., an insulin molecule) may each be located on a separate branch of a branched conjugate framework. For example, the ligands and drug may be located on termini of these branches. In certain embodiments a hyperbranched conjugate framework may be used. Both polymeric and non-polymeric conjugate frameworks are encompassed.

Methods for conjugating ligands to a conjugate framework are discussed in more detail below. In certain embodiments, the saccharide within the one or more ligands is conjugated (directly or indirectly by way of a linker) via the C1, C2 or C6 position. In certain embodiments, the conjugation involves the C1 position. The C1 position of a saccharide is also referred to as the anomeric carbon and may be connected to the drug or conjugate framework in the alpha or beta conformation. In certain embodiments, the C1 position is configured as the alpha anomer. In other embodiments, the C1 position is configured as the beta anomer.

Drug

It is to be understood that a conjugate can comprise any drug. A conjugate can comprise more than one copy of the same drug and/or can comprise more than one type of drug. The conjugates are not limited to any particular drug and may include small molecule drugs or biomolecular drugs. In general, the drug(s) used will depend on the disease or disorder to be treated. As used herein, the term "drug" encompasses salt and non-salt forms of the drug. For example, the term "insulin molecule" encompasses all salt and non-salt forms of the insulin molecule. It will be appreciated that the salt form may be anionic or cationic depending on the drug.

For example, without limitation, in various embodiments a conjugate can comprise any one of the following drugs: diclofenac, nifedipine, rivastigmine, methylphenidate, fluoroxetine, rosiglitazone, prednison, prednisolone, codeine, ethylmorphine, dextromethorphan, noscapine, pentoxiverine, acetylcysteine, bromhexine, epinephrine, isoprenaline, orciprenaline, ephedrine, fenoterol, rimiterol, ipratropium, cholinetheophyllinate, proxiphylline, bechlomethasone, budesonide, deslanoside, digoxine, digitoxin, disopyramide, proscillaridin, chinidine, procainamide, mexiletin, flecainide, alprenolol, proproanolol, nadolol, pindolol, oxprenolol, labetalol, tirnolol, atenolol, pentaeritrityltetranitrate, isosorbiddinitrate, isosorbidmononitrate, niphedipin, phenylamine, verapamil, diltiazem, cyclandelar, nicotinylalcholhol, inositolnicotinate, alprostatdil, etilephrine, prenalterol, dobutamine, dopamine, dihydroergotamine, guanetidine, betanidine, methyldopa, reserpine, guanfacine, trimethaphan, hydralazine, dihydralazine, prazosine, diazoxid, captopril, nifedipine, enalapril, nitroprusside, bendroflumethiazide, hydrochlorthiazide, metychlothiazide, polythiazide, chlorthalidon, cinetazon, clopamide, mefruside, metholazone, bumetanide, ethacrynacide, spironolactone, amiloride, chlofibrate, nicotinic acid, nicheritrol, brompheniramine, cinnarizine, dexchlorpheniramine, clemastine, antazoline, cyproheptadine, proethazine, cimetidine, ranitidine, sucralfat, papaverine, moxaverine, atropin, butylscopolamin, emepron, glucopyrron, hyoscyamine, mepensolar, methylscopolamine, oxiphencyclimine, probanteline, terodilin, sennaglycosides, sagradaextract, dantron, bisachodyl, sodiumpicosulfat, etulos, diphenolxylate, loperamide, salazosulfapyridine, pyrvin, mebendazol, dimeticon, ferrofumarate, ferrosuccinate, ferritetrasemisodium, cyanochobalamine, folid acid heparin, heparin co-factor, diculmarole, warfarin, streptokinase, urokinase, factor VIII, factor IX, vitamin K, thiopeta, busulfan, chlorambucil, cyclophosphamid, melfalan, carmustin, mercatopurin, thioguanin, azathioprin, cytarabin, vinblastin, vinchristin, vindesin, procarbazine, dacarbazine, lomustin, estramustin, teniposide, etoposide, cisplatin, amsachrin, aminogluthetimid, phosphestrol, medroxiprogresterone, hydroxiprogesterone, megesterol, noretisteron, tamoxiphen, ciclosporin, sulfosomidine, bensylpenicillin, phenoxymethylpenicillin, dicloxacillin, cloxacillin, flucoxacillin, ampicillin, amoxicillin, pivampicillin, bacampicillin, piperacillin, meziocillin, mecillinam, pivmecillinam, cephalotin, cephalexin, cephradin, cephadroxil, cephaclor, cefuroxim, cefotaxim, ceftazidim, cefoxitin, aztreonam, imipenem, cilastatin, tetracycline, lymecycline, demeclocycline, metacycline, oxitetracycline, doxycycline, chloramphenicol, spiramycin, fusidic acid, lincomycin, clindamycin, spectinomycin, rifampicin, amphotericin B, griseofulvin, nystatin, vancomycin, metronidazole, tinidazole, trimethoprim, norfloxacin, salazosulfapyridin, aminosalyl, isoniazid, etambutol, nitrofurantoin, nalidixic acid, metanamine, chloroquin, hydroxichloroquin, tinidazol, ketokonazol, acyclovir, interferon idoxuridin, retinal, tiamin, dexpantenol, pyridoxin, folic acid, ascorbic acid, tokoferol, phytominadion, phenfluramin, corticotropin, tetracosactid, tyrotropin, somatotoprin, somatrem, vasopressin, lypressin, desmopressin, oxytocin, chloriongonadotropin, cortison, hydrocortisone, fluodrocortison, prednison, prednisolon, fluoximesteron, mesterolon, nandrolon, stanozolol, oximetolon, cyproteron, levotyroxin, liotyronin, propylthiouracil, carbimazol, tiamazol, dihydrotachysterol, alfacalcidol, calcitirol, insulin, tolbutamid, chlorpropamid, tolazamid, glipizid, glibenclamid, phenobarbital, methyprylon, pyrityidion, meprobamat, chlordiazepoxid, diazepam, nitrazepam, baclofen, oxazepam, dikaliumclorazepat, lorazepam, flunitrazepam, alprazolam, midazolam, hydroxizin, dantrolene, chlometiazol, propionmazine, alimemazine, chlorpromazine, levomepromazine, acetophenazine, fluphenazine, perphenazine, prochlorperazine, trifluoperazine, dixyrazine, thiodirazine, periciazin, chloprothixene, tizanidine, zaleplon, zuclopentizol, flupentizol, thithixen, haloperidol, trimipramin, opipramol, chlomipramin, desipramin, lofepramin, amitriptylin, nortriptylin, protriptylin, maptrotilin, caffeine, cinnarizine, cyclizine, dimenhydinate, meclozine, prometazine, thiethylperazine, metoclopramide, scopolamine, phenobarbital, phenytoine, ethosuximide, primidone, carbamazepine, chlonazepam, orphenadrine, atropine, bensatropine, biperiden, metixene, procylidine, levodopa, bromocriptin, amantadine, ambenon, pyridostigmine, synstigmine, disulfiram, morphine, codeine, pentazocine, buprenorphine, pethidine, phenoperidine, phentanyl, methadone, piritramide, dextropropoxyphene, ketobemidone, acetylsalicylic acid, celecoxib, phenazone, phenylbutazone, azapropazone, piroxicam, ergotamine, dihydroergotamine, cyproheptadine, pizitifen, flumedroxon, allopurinol, probenecid, sodiummaurothiomalate auronofin, penicillamine, estradiol, estradiolvalerianate, estriol, ethinylestradiol, dihydrogesteron, lynestrenol, medroxiprogresterone, noretisterone, cyclophenile, clomiphene, levonorgestrel, mestranol, ornidazol, tinidazol, ekonazol, chlotrimazol, natamycine, miconazole, sulbentin, methylergotamine, dinoprost, dinoproston, gemeprost, bromocriptine, phenylpropanolamine, sodiumchromoglicate, azetasolamide, dichlophenamide, betacarotene, naloxone, calciumfolinate, in particular clonidine, thephylline, dipyradamol, hydrochlothiazade, scopolamine, indomethacine, furosemide, potassium chloride, morphine, ibuprofen, salbutamol, terbutalin, calcitonin, etc. It is to be understood that this list is intended to be exemplary and that any drug, whether known or later discovered, may be used in a conjugate of the present disclosure.

In various embodiments, a conjugate may include a hormonal drug which may be peptidic or non-peptidic, e.g., adrenaline, noradrenaline, angiotensin, atriopeptin, aldosterone, dehydroepiandrosterone, androstenedione, testosterone, dihydrotestosterone, calcitonin, calcitriol, calcidiol, corticotropin, cortisol, dopamine, estradiol, estrone, estriol, erythropoietin, follicle-stimulating hormone, gastrin, ghrelin, glucagon, gonadotropin-releasing hormone, growth hormone, growth hormone-releasing hormone, human chorionic gonadotropin, histamine, human placental lactogen, insulin, insulin-like growth factor, inhibin, leptin, a leukotriene, lipotropin, melatonin, orexin, oxytocin, parathyroid hormone, progesterone, prolactin, prolactin-releasing hormone, a prostglandin, renin, serotonin, secretin, somatostatin, thrombopoietin, thyroid-stimulating hormone, thyrotropin-releasing hormone (or thyrotropin), thyrotropin-releasing hormone, thyroxine, triiodothyronine, vasopressin, etc. In certain embodiments, the hormone may be selected from glucagon, insulin, insulin-like growth factor, leptin, thyroid-stimulating hormone, thyrotropin-releasing hormone (or thyrotropin), thyrotropin-releasing hormone, thyroxine, and triiodothyronine. In certain embodiments, the drug is insulin-like growth factor 1 (IGF-1). It is to be understood that this list is intended to be exemplary and that any hormonal drug, whether known or later discovered, may be used in a conjugate of the present disclosure.

In various embodiments, a conjugate may include a thyroid hormone.

In various embodiments, a conjugate may include an antidiabetic drug (i.e., a drug which has a beneficial effect on patients suffering from diabetes).

In various embodiments, a conjugate may include an insulin molecule. As used herein, the term "insulin" or "insulin molecule" encompasses all salt and non-salt forms of the insulin molecule. It will be appreciated that the salt form may be anionic or cationic depending on the insulin molecule. By "insulin" or "an insulin molecule" we intend to encompass both wild-type and modified forms of insulin as long as they are bioactive (i.e., capable of causing a detectable reduction in glucose when administered in vivo). Wild-type insulin includes insulin from any species whether in purified, synthetic or recombinant form (e.g., human insulin, porcine insulin, bovine insulin, rabbit insulin, sheep insulin, etc.). A number of these are available commercially, e.g., from Sigma-Aldrich (St. Louis, Mo.). A variety of modified forms of insulin are known in the art (e.g. see Crotty and Reynolds, *Pediatr. Emerg. Care.* 23:903-905, 2007 and Gerich, *Am. J. Med.* 113:308-16, 2002 and references cited therein). Modified forms of insulin may be chemically modified (e.g., by addition of a chemical moiety such as a PEG group or a fatty acyl chain as described below) and/or mutated (i.e., by addition, deletion or substitution of one or more amino acids).

In certain embodiments, an insulin molecule of the present disclosure will differ from a wild-type insulin by 1-10 (e.g., 1-9, 1-8, 1-7, 1-6, 1-5, 1-4, 1-3, 1-2, 2-9, 2-8, 2-7, 2-6, 2-5, 2-4, 2-3, 3-9, 3-8, 3-7, 3-6, 3-5, 3-4, 4-9, 4-8, 4-7, 4-6, 4-5, 5-9, 5-8, 5-7, 5-6, 6-9, 6-8, 6-7, 7-9, 7-8, 8-9, 9, 8, 7, 6, 5, 4, 3, 2 or 1) amino acid substitutions, additions and/or deletions. In certain embodiments, an insulin molecule of the present disclosure will differ from a wild-type insulin by amino acid substitutions only. In certain embodiments, an insulin molecule of the present disclosure will differ from a wild-type insulin by amino acid additions only. In certain embodiments, an insulin molecule of the present disclosure will differ from a wild-type insulin by both amino acid substitutions and additions. In certain embodiments, an insulin molecule of the present disclosure will differ from a wild-type insulin by both amino acid substitutions and deletions.

In certain embodiments, amino acid substitutions may be made on the basis of similarity in polarity, charge, solubility, hydrophobicity, hydrophilicity, and/or the amphipathic nature of the residues involved. In certain embodiments, a substitution may be conservative, that is, one amino acid is replaced with one of similar shape and charge. Conservative substitutions are well known in the art and typically include substitutions within the following groups: glycine, alanine; valine, isoleucine, leucine; aspartic acid, glutamic acid; asparagine, glutamine; serine, threonine; lysine, arginine; and tyrosine, phenylalanine. In certain embodiments, the hydrophobic index of amino acids may be considered in choosing suitable mutations. The importance of the hydrophobic amino acid index in conferring interactive biological function on a polypeptide is generally understood in the art. Alternatively, the substitution of like amino acids can be made effectively on the basis of hydrophilicity. The importance of hydrophilicity in conferring interactive biological function of a polypeptide is generally understood in the art. The use of the hydrophobic index or hydrophilicity in designing polypeptides is further discussed in U.S. Pat. No. 5,691,198.

The wild-type sequence of human insulin (A-chain and B-chain) is shown below and in FIG. 63.

A-Chain (SEQ ID NO: 1): GIVEQCCTSICSLYQLENYCN
B-Chain (SEQ ID NO:2): FVNQHLCGSHLVEALYLVCGERGFFYTPKT Human insulin differs from rabbit, porcine, bovine, and sheep insulin only in amino acids A8, A9, A10, and B30 (see table below).

|  | Amino Acid Position | | | |
|---|---|---|---|---|
| Insulin | A8 | A9 | A10 | B30 |
| human | Thr | Ser | Ile | Thr |
| rabbit | Thr | Ser | Ile | Ser |
| porcine | Thr | Ser | Ile | Ala |
| bovine | Ala | Ser | Val | Ala |
| sheep | Ala | Gly | Val | Ala |

In various embodiments, an insulin molecule of the present disclosure is mutated at the B28 and/or B29 positions of the B-peptide sequence. For example, insulin lispro (HUMALOG®) is a rapid acting insulin mutant in which the penultimate lysine and proline residues on the C-terminal end of the B-peptide have been reversed ($Lys^{B28}Pro^{B29}$-human insulin). This modification blocks the formation of insulin multimers. Insulin as part (NOVOLOG®) is another rapid acting insulin mutant in which proline at position B28 has been substituted with aspartic acid ($Asp^{B28}$-human insulin). This mutant also prevents the formation of multimers. In some embodiments, mutation at positions B28 and/or B29 is accompanied by one or more mutations elsewhere in the insulin polypeptide. For example, insulin glulisine (APIDRA®) is yet another rapid acting insulin mutant in which aspartic acid at position B3 has been replaced by a lysine residue and lysine at position B29 has been replaced with a glutamic acid residue (Lys$^{B3}$Glu$^{B29}$-human insulin).

In various embodiments, an insulin molecule of the present disclosure has an isoelectric point that is shifted relative to human insulin. In some embodiments, the shift in isoelectric point is achieved by adding one or more arginine residues to the N-terminus of the insulin A-peptide and/or the C-terminus of the insulin B-peptide. Examples of such insulin polypeptides include Arg$^{A0}$-human insulin, Arg$^{B31}$Arg$^{B32}$-human insulin, Gly$^{A21}$Arg$^{B31}$Arg$^{B32}$-human insulin, Arg$^{A0}$Arg$^{B31}$Arg$^{B32}$-human insulin, and Arg$^{A0}$Gly$^{A21}$Arg$^{B31}$Arg$^{B32}$-human insulin. By way of further example, insulin glargine (LANTUS®) is an exemplary long acting insulin mutant in which Asp$^{A21}$ has been replaced by glycine, and two arginine residues have been added to the C-terminus of the B-peptide. The effect of these changes is to shift the isoelectric point, producing a solution that is completely soluble at pH 4. Thus, in some embodiments, an insulin molecule of the present disclosure comprises an A-peptide sequence wherein A21 is Gly and B-peptide sequence wherein B31 and B32 are Arg-Arg. It is to be understood that the present disclosure encompasses all single and multiple combinations of these mutations and any other mutations that are described herein (e.g., Gly$^{A21}$-human insulin, Gly$^{A21}$Arg$^{B31}$-human insulin, Arg$^{B31}$Arg$^{B32}$-human insulin, Arg$^{B31}$-human insulin).

In various embodiments, an insulin molecule of the present disclosure is truncated. For example, in certain embodiments, a B-peptide sequence of an insulin polypeptide of the present disclosure is missing B1, B2, B3, B26, B27, B28, B29 and/or B30. In certain embodiments, combinations of residues are missing from the B-peptide sequence of an insulin polypeptide of the present disclosure. For example, the B-peptide sequence may be missing residues B(1-2), B(1-3), B(29-30), B(28-30), B(27-30) and/or B(26-30). In some embodiments, these deletions and/or truncations apply to any of the aforementioned insulin molecules (e.g., without limitation to produce des(B30)-insulin lispro, des(B30)-insulin as part, des (B30)-insulin glulisine, des(B30)-insulin glargine, etc.).

In some embodiments, an insulin molecule contains additional amino acid residues on the N- or C-terminus of the A or B-peptide sequences. In some embodiments, one or more amino acid residues are located at positions A0, A21, B0 and/or B31. In some embodiments, one or more amino acid residues are located at position A0. In some embodiments, one or more amino acid residues are located at position A21. In some embodiments, one or more amino acid residues are located at position B0. In some embodiments, one or more amino acid residues are located at position B31. In certain embodiments, an insulin molecule does not include any additional amino acid residues at positions A0, A21, B0 or B31.

In certain embodiments, an insulin molecule of the present disclosure is mutated such that one or more amidated amino acids are replaced with acidic forms. For example, asparagine may be replaced with aspartic acid or glutamic acid. Likewise, glutamine may be replaced with aspartic acid or glutamic acid. In particular, Asn$^{A18}$, Asn$^{A21}$, or Asn$^{B3}$, or any combination of those residues, may be replaced by aspartic acid or glutamic acid. Gln$^{A15}$ or Gln$^{B4}$, or both, may be replaced by aspartic acid or glutamic acid. In certain embodiments, an insulin molecule has aspartic acid at position A21 or aspartic acid at position B3, or both.

One skilled in the art will recognize that it is possible to mutate yet other amino acids in the insulin molecule while retaining biological activity. For example, without limitation, the following modifications are also widely accepted in the art: replacement of the histidine residue of position B10 with aspartic acid (His$^{B10}$→Asp$^{B10}$); replacement of the phenylalanine residue at position B1 with aspartic acid (Phe$^{B1}$→Asp$^{B1}$); replacement of the threonine residue at position B30 with alanine (Thr$^{B30}$→Ala$^{B30}$); replacement of the tyrosine residue at position B26 with alanine (Tyr$^{B26}$→Ala$^{B26}$); and replacement of the serine residue at position B9 with aspartic acid (Ser$^{B9}$→Asp$^{B9}$).

In various embodiments, an insulin molecule of the present disclosure has a protracted profile of action. Thus, in certain embodiments, an insulin molecule of the present disclosure may be acylated with a fatty acid. That is, an amide bond is formed between an amino group on the insulin molecule and the carboxylic acid group of the fatty acid. The amino group may be the alpha-amino group of an N-terminal amino acid of the insulin molecule, or may be the epsilon-amino group of a lysine residue of the insulin molecule. An insulin molecule of the present disclosure may be acylated at one or more of the three amino groups that are present in wild-type human insulin or may be acylated on lysine residue that has been introduced into the wild-type human insulin sequence. In certain embodiments, an insulin molecule may be acylated at position B1. In certain embodiments, an insulin molecule may be acylated at position B29. In certain embodiments, the fatty acid is selected from myristic acid (C14), pentadecylic acid (C15), palmitic acid (C16), heptadecylic acid (C17) and stearic acid (C18). For example, insulin detemir (LEVEMIR®) is a long acting insulin mutant in which Thr$^{B30}$ has been deleted, and a C14 fatty acid chain (myristic acid) has been attached to Lys$^{B29}$.

In some embodiments, the N-terminus of the A-peptide, the N-terminus of the B-peptide, the epsilon-amino group of Lys at position B29 or any other available amino group in an insulin molecule of the present disclosure is covalently linked to a fatty acid moiety of general formula:

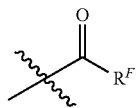

wherein R$^F$ is hydrogen or a C$_{1-30}$ alkyl group. In some embodiments, R$^F$ is a C$_{1-20}$ alkyl group, a C$_{3-19}$ alkyl group, a C$_{5-18}$ alkyl group, a C$_{6-17}$ alkyl group, a C$_{8-16}$ alkyl group, a C$_{10-15}$ alkyl group, or a C$_{12-14}$ alkyl group. In certain embodiments, the insulin polypeptide is conjugated to the moiety at the A1 position. In certain embodiments, the insulin polypeptide is conjugated to the moiety at the B1 position. In certain embodiments, the insulin polypeptide is conjugated to the moiety at the epsilon-amino group of Lys at position B29. In certain embodiments, position B28 of the insulin molecule is Lys and the epsilon-amino group of Lys$^{B28}$ is conjugated to the fatty acid moiety. In certain embodiments, position B3 of the insulin molecule is Lys and the epsilon-amino group of Lys$^{B3}$ is conjugated to the fatty acid moiety. In some embodiments, the fatty acid chain is 8-20 carbons long. In some embodiments, the fatty acid is octanoic acid (C8), nonanoic acid (C9), decanoic acid (C10), undecanoic acid (C11), dodecanoic acid (C12), or tridecanoic acid (C13). In certain embodiments, the fatty acid is myristic acid (C14), pentadecanoic acid (C15), palmitic acid (C16), heptadecanoic acid (C17), stearic acid (C18), nonadecanoic acid (C19), or arachidic acid (C20).

In certain embodiments, an insulin molecule of the present disclosure comprises the mutations and/or chemical modifications of one of the following insulin molecules: Lys$^{B28}$Pro$^{B29}$-human insulin (insulin lispro), Asp$^{B28}$-human insulin (insulin as part), Lys$^{B3}$Glu$^{B29}$-human insulin (insulin glulisine), Arg$^{B31}$Arg$^{B32}$-human insulin (insulin glargine), N$^{\epsilon B29}$ myristoyl-des(B30)-human insulin (insulin detemir), Ala$^{B26}$-human insulin, Asp$^{B1}$-human insulin, Arg$^{A0}$-human insulin, Asp$^{B1}$Glu$^{B13}$-human insulin, Gly$^{A21}$-human insulin, Gly$^{A21}$Arg B3Arg$^{B32}$-human insulin, Arg$^{A0}$Arg B3Arg$^{B32}$-human insulin, Arg$^{A0}$Gly$^{A21}$Arg$^{B31}$Arg$^{B32}$-human insulin, des(B30)-human insulin, des(B27)-human insulin, des(B28-B30)-human insulin, des(B1)-human insulin, des(B1-B3)-human insulin.

In certain embodiments, an insulin molecule of the present disclosure comprises the mutations and/or chemical modifications of one of the following insulin molecules: N$^{\epsilon B29}$-palmitoyl-human insulin, N$^{\epsilon B29}$-myrisotyl-human insulin, N$^{\epsilon B28}$-palmitoyl-Lys$^{B28}$Pro$^{B29}$-human insulin, N$^{\epsilon B28}$-myristoyl-Lys$^{B28}$Pro$^{B29}$-human insulin.

In certain embodiments, an insulin molecule of the present disclosure comprises the mutations and/or chemical modifications of one of the following insulin molecules: N$^{\epsilon B29}$-palmitoyl-des(B30)-human insulin, N$^{\epsilon B30}$-myristoyl-Thr$^{B29}$ Lys$^{B30}$-human insulin, N$^{B30}$-palmitoyl-Thr$^{B29}$ Lys$^{B30}$-human insulin, N$^{\epsilon B29}$-(N-palmitoyl-γ-glutamyl)-des(B30)-human insulin, N$^{\epsilon B29}$-(N-lithocolyl-γ-glutamyl)-des(B30)-human insulin, N$^{\epsilon B29}$-(ω-carboxyheptadecanoyl)-des(B30)-human insulin, N$^{\epsilon B29}$-(ω-carboxyheptadecanoyl)-human insulin.

In certain embodiments, an insulin molecule of the present disclosure comprises the mutations and/or chemical modifications of one of the following insulin molecules: N$^{\epsilon B29}$-octanoyl-human insulin, N$^{\epsilon B29}$-myristoyl-Gly$^{A21}$Arg$^{B31}$Arg B3-human insulin, N$^{\epsilon B29}$-myristoyl-Gly$^{A21}$Gln$^{B3}$Arg$^{B31}$Arg$^{B32}$-human insulin, N$^{\epsilon B29}$-myristoyl-Arg$^{A0}$Gly$^{A21}$Arg$^{B31}$Arg$^{B3}$2-human insulin, N$^{\epsilon B29}$-Arg$^{A0}$Gly$^{A21}$Gln$^{B3}$Arg$^{B31}$Arg$^{B32}$-human insulin, N$^{\epsilon B29}$-myristoyl-Arg$^{A0}$Gly$^{A21}$Asp$^{B3}$Arg$^{B31}$Arg$^{B32}$-human insulin, N$^{\epsilon B29}$-myristoyl-Arg$^{B31}$Arg$^{B32}$-human insulin, N$^{\epsilon B29}$-myristoyl-Arg$^{A0}$Arg$^{B31}$Arg$^{B32}$-human insulin, N$^{\epsilon B29}$-octanoyl-Gly$^{A21}$Arg$^{B31}$Arg$^{B32}$-human insulin, N$^{\epsilon B29}$-octanoyl-Gly$^{A21}$Gln$^{B3}$Arg$^{B31}$Arg$^{B32}$-human insulin, N$^{\epsilon B29}$-octanoyl-Arg$^{A0}$Gly$^{A21}$Arg$^{B31}$Arg$^{B32}$-human insulin, N$^{\epsilon B29}$-octanoyl-Arg$^{A0}$Gly$^{A21}$Gln$^{B3}$Arg$^{B31}$Arg$^{B32}$-human insulin, N$^{\epsilon B29}$-octanoyl-Arg$^{B0}$Gly$^{A21}$Asp$^{B3}$Arg$^{B31}$Arg$^{B32}$-human insulin, N$^{\epsilon B29}$-octanoyl-Arg$^{B31}$Arg$^{B32}$-human insulin, N$^{\epsilon B29}$-octanoyl-Arg$^{A0}$Arg$^{B31}$Arg$^{B32}$-human insulin.

In certain embodiments, an insulin molecule of the present disclosure comprises the mutations and/or chemical modifications of one of the following insulin polypeptides: N$^{\epsilon B28}$-myristoyl-Gly$^{A21}$Lys$^{B28}$Pro$^{B29}$Arg$^{B31}$Arg$^{B32}$-human insulin, N$^{\epsilon B28}$-myristoyl-Gly$^{A21}$Gln$^{B3}$Lys$^{B28}$Pro$^{B30}$Arg$^{B31}$Arg$^{B32}$-human insulin, N$^{\epsilon B28}$-myristoyl-Arg$^{A0}$Gly$^{A21}$Lys$^{B28}$Pro$^{B29}$Arg$^{B31}$Arg$^{B32}$-human insulin, N$^{\epsilon B28}$-myristoyl-Arg$^{A0}$Gly$^{A21}$Gln$^{B3}$Lys$^{B28}$Pro$^{B29}$Arg$^{B31}$Arg$^{B32}$-human insulin, N$^{\epsilon B28}$-myristoyl-Arg$^{A0}$Gly$^{A21}$Asp$^{B3}$Lys$^{B28}$Pro$^{B29}$Arg$^{B31}$Arg$^{B32}$-human insulin, N$^{\epsilon B28}$-myristoyl-Lys$^{B28}$Pro$^{B29}$Arg$^{B31}$Arg$^{B32}$-human insulin, N$^{\epsilon B28}$-myristoyl-arg$^{A0}$Lys$^{B28}$Pro$^{B29}$Arg$^{B3}$Arg$^{32}$-human insulin, N$^{\epsilon B28}$-octanoyl-Gly$^{A21}$Lys$^{B28}$Pro$^{B29}$Arg$^{B31}$Arg$^{B32}$-human insulin.

In certain embodiments, an insulin molecule of the present disclosure comprises the mutations and/or chemical modifications of one of the following insulin molecules: N$^{\epsilon B28}$-octanoyl-Gly$^{A21}$Gln$^{B3}$Lys$^{B28}$Pro$^{B29}$Arg$^{B31}$Arg$^{B32}$-human insulin, N$^{\epsilon B28}$-octanoyl-Arg$^{A0}$Gly$^{A21}$Lys$^{B28}$Pro$^{B29}$Arg$^{B31}$Arg$^{B32}$-human insulin, N$^{\epsilon B28}$-octanoyl-Arg$^{A0}$Gly$^{A21}$Gln$^{B3}$Lys$^{B28}$Pro$^{B29}$Arg$^{B31}$Arg$^{B32}$-human insulin, N$^{\epsilon B28}$-octanoyl-Arg$^{A0}$Gly$^{A21}$Asp$^{B3}$Lys$^{B28}$Pro$^{B29}$Arg$^{B31}$Arg$^{B32}$-human insulin, N$^{\epsilon B28}$-octanoyl-Lys$^{B28}$Pro$^{B29}$Arg$^{B31}$Arg$^{B32}$-human insulin, N$^{\epsilon B28}$-octanoyl-Arg$^{A0}$Lys$^{B28}$Pro$^{B29}$Arg$^{B31}$Arg$^{B32}$-human insulin.

In certain embodiments, an insulin molecule of the present disclosure comprises the mutations and/or chemical modifications of one of the following insulin molecules: N$^{\epsilon B29}$-tridecanoyl-des(B30)-human insulin, N$^{\epsilon B29}$-tetradecanoyl-des(B30)-human insulin, N$^{\epsilon B29}$-decanoyl-des(B30)-human insulin, N$^{\epsilon B29}$-dodecanoyl-des(B30)-human insulin, N$^{\epsilon B29}$-tridecanoyl-Gly$^{A21}$-des(B30)-human insulin, N$^{\epsilon B29}$-tetradecanoyl-Gly$^{A21}$-des(B30)-human insulin, N$^{\epsilon B29}$-decanoyl-Gly$^{A21}$-des(B30)-human insulin, N$^{\epsilon B29}$-dodecanoyl-Gly$^{A21}$-des(B30)-human insulin, N$^{\epsilon B29}$-tridecanoyl-Gly$^{A21}$Gln$^{B3}$-des(B30)-human insulin, N$^{\epsilon B29}$-tetradecanoyl-Gly$^{A21}$Gln$^{B3}$-des(B30)-human insulin, N$^{\epsilon B29}$-decanoyl-Gly$^{A21}$-Gln$^{B3}$-des(B30)-human insulin, N$^{\epsilon B29}$-dodecanoyl-Gly$^{A21}$-Gln$^{B3}$-des(B30)-human insulin, N$^{\epsilon B29}$-tridecanoyl-Ala$^{A21}$-des(B30)-human insulin, N$^{\epsilon B29}$-tetradecanoyl-Ala$^{A21}$-des(B30)-human insulin, N$^{\epsilon B29}$-decanoyl-Ala$^{A21}$-des(B30)-human insulin, N$^{\epsilon B29}$-dodecanoyl-Ala$^{A21}$-des(B30)-human insulin, N$^{\epsilon B29}$-tridecanoyl-Ala$^{A21}$-Gln$^{B3}$-des(B30)-human insulin, N$^{\epsilon B29}$-tetradecanoyl-Ala$^{A21}$ Gln$^{B3}$-des(B30)-human insulin, N$^{\epsilon B29}$-decanoyl-Ala$^{A21}$Gln$^{B3}$-des(B30)-human insulin, N$^{\epsilon B29}$-dodecanoyl-Ala$^{A21}$Gln$^{B3}$-des(B30)-human insulin, N$^{\epsilon B29}$-tridecanoyl-Gln$^{B3}$-des(B30)-human insulin, N$^{\epsilon B29}$-tetradecanoyl-Gln$^{B3}$-des(B30)-human insulin, N$^{\epsilon B29}$-decanoyl-Gln$^{B3}$-des(B30)-human insulin, N$^{\epsilon B29}$-dodecanoyl-Gln$^{B3}$-des(B30)-human insulin.

In certain embodiments, an insulin molecule of the present disclosure comprises the mutations and/or chemical modifications of one of the following insulin molecules: N$^{\epsilon B29}$-tridecanoyl-Gly$^{A21}$-human insulin, N$^{\epsilon B29}$-tetradecanoyl-Gly$^{A21}$-human insulin, N$^{\epsilon B29}$-decanoyl-Gly$^{A21}$-human insulin, N$^{\epsilon B29}$-dodecanoyl-Gly$^{A21}$-human insulin, N$^{\epsilon B29}$-tridecanoyl-Ala$^{A21}$-human insulin, N$^{\epsilon B29}$-tetradecanoyl-Ala$^{A21}$-human insulin, N$^{\epsilon B29}$-decanoyl-Ala$^{A21}$-human insulin, N$^{\epsilon B29}$-dodecanoyl-Ala$^{A21}$-human insulin.

In certain embodiments, an insulin molecule of the present disclosure comprises the mutations and/or chemical modifications of one of the following insulin molecules: N$^{\epsilon B29}$-tridecanoyl-Gly$^{A21}$Gln$^{B3}$-human insulin, N$^{\epsilon B29}$-tetradecanoyl-Gly$^{A21}$Gln$^{B3}$-human insulin, N$^{\epsilon B29}$-decanoyl-Gly$^{A21}$Gln$^{B3}$-human insulin, N$^{\epsilon B29}$-dodecanoyl-Gly$^{A21}$Gln$^{B3}$-human insulin, N$^{\epsilon B29}$-tridecanoyl-Ala$^{A21}$Gln$^{B3}$-human insulin, N$^{\epsilon B29}$-tetradecanoyl-Ala$^{A21}$ Gln$^{B3}$-human insulin, N$^{\epsilon B29}$-decanoyl-Ala$^{A21}$Gln$^{B3}$-human insulin, N$^{\epsilon B29}$-dodecanoyl-Ala$^{A21}$Gln$^{B3}$-human insulin.

In certain embodiments, an insulin molecule of the present disclosure comprises the mutations and/or chemical modifications of one of the following insulin molecules: N$^{\epsilon B29}$-tridecanoyl-Gln$^{B3}$-human insulin, N$^{\epsilon B29}$-tetradecanoyl-Gln$^{B3}$-human insulin, N$^{\epsilon B29}$-decanoyl-Gln$^{B3}$-human insulin, N$^{\epsilon B29}$-dodecanoyl-Gln$^{B3}$-human insulin.

In certain embodiments, an insulin molecule of the present disclosure comprises the mutations and/or chemical modifications of one of the following insulin molecules: N$^{\epsilon B29}$-tridecanoyl-Glu$^{B30}$-human insulin, N$^{\epsilon B29}$-tetradecanoyl-Glu$^{B30}$-human insulin, N$^{\epsilon B29}$-decanoyl-Glu$^{B30}$-human insulin, N$^{\epsilon B29}$-dodecanoyl-Glu$^{B30}$-human insulin.

In certain embodiments, an insulin molecule of the present disclosure comprises the mutations and/or chemical modifications of one of the following insulin molecules: N$^{\epsilon B29}$-tridecanoyl-Gly$^{A21}$Glu$^{B30}$-human insulin, N$^{\epsilon B29}$-tetradecanoyl-Gly$^{A21}$Glu$^{B30}$-human insulin, N$^{\epsilon B29}$-decanoyl-Gly$^{A21}$Glu$^{B30}$-human insulin, N$^{\epsilon B29}$-dodecanoyl-Gly$^{A21}$Glu$^{B30}$-human insulin.

In certain embodiments, an insulin molecule of the present disclosure comprises the mutations and/or chemical modifications of one of the following insulin molecules: N$^{\epsilon B29}$-tridecanoyl-Gly$^{A21}$Gln$^{B3}$Glu$^{B30}$-human insulin, N$^{\epsilon B29}$-tetradecanoyl-Gly$^{A21}$Gln$^{B3}$Glu$^{B30}$-human insulin, N$^{\epsilon B29}$-decanoyl-Gly$^{A21}$Gln$^{B3}$Glu$^{B30}$-human insulin, N$^{\epsilon B29}$-dodecanoyl-Gly$^{A21}$Gln$^{B3}$Glu$^{B30}$-human insulin, N$^{\epsilon B29}$-tridecanoyl-Ala$^{A21}$Glu$^{B30}$-human insulin, N$^{\epsilon B29}$-tetradecanoyl-Ala$^{A21}$Glu$^{B30}$-human insulin, N$^{\epsilon B29}$-decanoyl-Ala$^{A21}$Glu$^{B30}$-human insulin, N$^{\epsilon B29}$-dodecanoyl-Ala$^{A21}$Glu$^{B30}$-human insulin, N$^{\epsilon B29}$-tridecanoyl-Ala$^{A21}$Gln$^{B3}$Glu$^{B30}$-human insulin, N$^{\epsilon B29}$-tetradecanoyl-Ala$^{A21}$Gln$^{B3}$Glu$^{B30}$-human insulin, N$^{\epsilon B29}$-decanoyl-Ala$^{A21}$Gln$^{B3}$Glu$^{B30}$-human insulin, N$^{\epsilon B29}$-dodecanoyl-Ala$^{A21}$Gln$^{B3}$Glu$^{B30}$-human insulin.

In certain embodiments, an insulin molecule of the present disclosure comprises the mutations and/or chemical modifications of one of the following insulin molecules: N$^{\epsilon B29}$-tridecanoyl-Gln$^{B3}$Glu$^{B30}$-human insulin, N$^{\epsilon B29}$-tetradecanoyl-Gln$^{B3}$Glu$^{B30}$-human insulin, N$^{\epsilon B29}$-decanoyl-Gln$^{B3}$Glu$^{B30}$-human insulin, N$^{\epsilon B29}$-dodecanoyl-Gln$^{B3}$Glu$^{B30}$-human insulin.

In certain embodiments, an insulin molecule of the present disclosure comprises the mutations and/or chemical modifications of one of the following insulin molecules: N$^{\epsilon B29}$-formyl-human insulin, N$^{\alpha B1}$-formyl-human insulin, N$^{\alpha A1}$-formyl-human insulin, N$^{\epsilon B29}$-formyl-N$^{\alpha B1}$-formyl-human insulin, N$^{\epsilon B29}$-formyl-N$^{\alpha A1}$-formyl-human insulin, N$^{\alpha A1}$-formyl-N$^{\alpha B1}$-formyl-human insulin, N$^{\epsilon B29}$-formyl-N$^{\alpha A1}$-formyl-N$^{\alpha B1}$-formyl-human insulin.

In certain embodiments, an insulin molecule of the present disclosure comprises the mutations and/or chemical modifications of one of the following insulin molecules: N$^{\epsilon B29}$-acetyl-human insulin, N$^{\alpha B1}$-acetyl-human insulin, N$^{\alpha A1}$-acetyl-human insulin, N$^{\epsilon B29}$-acetyl-N$^{\alpha B1}$-acetyl-human insulin, N$^{\epsilon B29}$-acetyl-N$^{\alpha A1}$-acetyl-human insulin, N$^{\alpha A1}$-acetyl-N$^{\alpha B1}$-acetyl-human insulin, N$^{\epsilon B29}$-acetyl-N$^{\alpha A1}$-acetyl-N$^{\alpha B1}$-acetyl-human insulin.

In certain embodiments, an insulin molecule of the present disclosure comprises the mutations and/or chemical modifications of one of the following insulin molecules: N$^{\epsilon B29}$-propionyl-human insulin, N$^{\alpha B1}$-propionyl-human insulin, N$^{\alpha A1}$-propionyl-human insulin, N$^{\epsilon B29}$-acetyl-N$^{\alpha B1}$-propionyl-human insulin, N$^{\epsilon B29}$-propionyl-N$^{\alpha A1}$-propionyl-human insulin, N$^{\alpha A1}$-propionyl-N$^{\alpha B1}$-propionyl-human insulin, N$^{\epsilon B29}$-propionyl-N$^{\alpha A1}$-propionyl-N$^{\alpha B1}$-propionyl-human insulin.

In certain embodiments, an insulin molecule of the present disclosure comprises the mutations and/or chemical modifications of one of the following insulin molecules: N$^{\epsilon B29}$-butyryl-human insulin, N$^{\alpha B1}$-butyryl-human insulin, N$^{\alpha A1}$-butyryl-human insulin, N$^{\epsilon B29}$-butyryl-N$^{\alpha B1}$-butyryl-human insulin, N$^{\epsilon B29}$-butyryl-N$^{\alpha A1}$-butyryl-human insulin, N$^{\alpha A1}$-butyryl-N$^{\alpha B1}$-butyryl-human insulin, N$^{\epsilon B29}$-butyryl-N$^{\alpha A1}$-butyryl-N$^{\alpha B1}$-butyryl-human insulin.

In certain embodiments, an insulin molecule of the present disclosure comprises the mutations and/or chemical modifications of one of the following insulin molecules: N$^{\epsilon B29}$-pentanoyl-human insulin, N$^{\alpha B1}$-pentanoyl-human insulin, N$^{\alpha A1}$-pentanoyl-human insulin, N$^{\epsilon B29}$-pentanoyl-N$^{\alpha B1}$-pentanoyl-human insulin, N$^{\epsilon B29}$-pentanoyl-N$^{\alpha A1}$-pentanoyl-human insulin, N$^{\alpha A1}$-pentanoyl-N$^{\alpha B1}$-pentanoyl-human insulin, N$^{\epsilon B29}$-pentanoyl-N$^{\alpha A1}$-pentanoyl-N$^{\alpha B1}$-pentanoyl-human insulin.

In certain embodiments, an insulin molecule of the present disclosure comprises the mutations and/or chemical modifications of one of the following insulin molecules: N$^{\epsilon B29}$-hexanoyl-human insulin, N$^{\alpha B1}$-hexanoyl-human insulin, N$^{\alpha A1}$-hexanoyl-human insulin, N$^{\epsilon B29}$-hexanoyl-N$^{\alpha B1}$-hexanoyl-human insulin, N$^{\epsilon B29}$-hexanoyl-N$^{\alpha A1}$-hexanoyl-human insulin, N$^{\alpha A1}$-hexanoyl-N$^{\alpha B1}$-hexanoyl-human insulin, N$^{\epsilon B29}$-hexanoyl-N$^{\alpha A1}$-hexanoyl-N$^{\alpha B1}$-hexanoyl-human insulin.

In certain embodiments, an insulin molecule of the present disclosure comprises the mutations and/or chemical modifications of one of the following insulin molecules: N$^{\epsilon B29}$-heptanoyl-human insulin, N$^{\alpha B1}$-heptanoyl-human insulin, N$^{\alpha A1}$-heptanoyl-human insulin, N$^{\epsilon B29}$-heptanoyl-N$^{\alpha B1}$-heptanoyl-human insulin, N$^{\epsilon B29}$-heptanoyl-N$^{\alpha A1}$-heptanoyl-human insulin, N$^{\alpha A1}$-heptanoyl-N$^{\alpha B1}$-heptanoyl-human insulin, N$^{\epsilon B29}$-heptanoyl-N$^{\alpha A1}$-heptanoyl-N$^{\alpha B1}$-heptanoyl-human insulin.

In certain embodiments, an insulin molecule of the present disclosure comprises the mutations and/or chemical modifications of one of the following insulin molecules: N$^{\alpha B1}$-octanoyl-human insulin, N$^{\alpha A1}$-octanoyl-human insulin, N$^{\epsilon B29}$-Octanoyl-N$^{\alpha B1}$-octanoyl-human insulin, N$^{\epsilon B29}$-octanoyl-N$^{\alpha A1}$-octanoyl-human insulin, N$^{\alpha A1}$-octanoyl-N$^{\alpha B1}$-octanoyl-human insulin, N$^{\epsilon B29}$-Octanoyl-N$^{\alpha A1}$-octanoyl-N$^{\alpha B1}$-octanoyl-human insulin.

In certain embodiments, an insulin molecule of the present disclosure comprises the mutations and/or chemical modifications of one of the following insulin molecules: N$^{\epsilon B29}$-nonanoyl-human insulin, N$^{\alpha B1}$-nonanoyl-human insulin, N$^{\alpha A1}$-nonanoyl-human insulin, N$^{\epsilon B29}$-nonanoyl-N$^{\alpha B1}$-nonanoyl-human insulin, N$^{\epsilon B29}$-nonanoyl-N$^{\alpha A1}$-nonanoyl-human insulin, N$^{\alpha A1}$-nonanoyl-N$^{\alpha B1}$-nonanoyl-human insulin, N$^{\epsilon B29}$-nonanoyl-N$^{\alpha A1}$-nonanoyl-N$^{\alpha B1}$-nonanoyl-human insulin.

In certain embodiments, an insulin molecule of the present disclosure comprises the mutations and/or chemical modifications of one of the following insulin molecules: N$^{\epsilon B29}$-decanoyl-human insulin, N$^{\alpha B1}$-decanoyl-human insulin, N$^{\alpha A1}$-decanoyl-human insulin, N$^{\epsilon B29}$-decanoyl-N$^{\alpha B1}$-decanoyl-human insulin, N$^{\epsilon B29}$-decanoyl-N$^{\alpha A1}$-decanoyl-human insulin, N$^{\alpha A1}$-decanoyl-N$^{\alpha B1}$-decanoyl-human insulin, N$^{\epsilon B29}$-decanoyl-N$^{\alpha A1}$-decanoyl-N$^{\alpha B1}$-decanoyl-human insulin.

In certain embodiments, an insulin molecule of the present disclosure comprises the mutations and/or chemical modifications of one of the following insulin molecules: N$^{\epsilon B28}$-formyl-Lys$^{B28}$Pro$^{B29}$-human insulin, N$^{\alpha B1}$-formyl-Lys$^{B28}$Pro$^{B29}$-human insulin, N$^{\alpha A1}$-formyl-Lys$^{B28}$Pro$^{B29}$-human insulin, N$^{\epsilon B28}$-formyl-N-formyl-Lys$^{B28}$Pro$^{B29}$-human insulin, N$^{\epsilon B28}$ formyl-N$^{\alpha A1}$-formyl-Lys$^{B28}$Pro$^{B29}$-human insulin, N$^{\alpha A1}$-formyl-N$^{\alpha B1}$-formyl-Lys$^{B28}$Pro$^{B29}$-human insulin, N$^{\epsilon B28}$-formyl-N$^{\alpha A1}$-formyl-N$^{\alpha B1}$-formyl-Lys Pro$^{B29}$-human insulin, N$^{\epsilon B29}$-acetyl-Lys$^{B28}$Pro$^{B29}$-human insulin, Nm-acetyl-Lys$^{B28}$Pro$^{B29}$-human insulin, N$^{\alpha A1}$-acetyl-Lys$^{B28}$Pro$^{B29}$-human insulin, N$^{\epsilon B28}$-acetyl-N$^{\alpha B1}$-acetyl-Lys$^{B28}$Pro$^{B29}$-human insulin.

In certain embodiments, an insulin molecule of the present disclosure comprises the mutations and/or chemical modifications of one of the following insulin molecules: N$^{\epsilon B28}$-acetyl-N$^{\alpha A1}$-acetyl-Lys$^{B28}$Pro$^{B29}$-human insulin, N$^{\alpha A1}$-acetyl-N$^{\alpha B1}$-acetyl-Lys$^{B28}$Pro$^{B29}$-human insulin, N$^{\epsilon B28}$-acetyl-N$^{\alpha A1}$-acetyl-N$^{\alpha B1}$-acetyl-Lys$^{B28}$Pro$^{B29}$-human insulin.

In certain embodiments, an insulin molecule of the present disclosure comprises the mutations and/or chemical modifications of one of the following insulin molecules: N$^{\epsilon B28}$- propionyl-Lys$^{B28}$Pro$^{B29}$-human insulin, Nm-propionyl-Lys$^{B28}$Pro$^{B29}$-human insulin, N$^{\alpha A1}$-propionyl-Lys$^{B28}$Pro$^{B29}$-human insulin, N$^{\epsilon B28}$-propionyl-N$^{\alpha B1}$-propionyl-Lys$^{B28}$Pro$^{B29}$-human insulin, N$^{\epsilon B28}$-propionyl-N$^{\alpha A1}$-propionyl-Lys$^{B28}$Pro$^{B29}$-human insulin, N$^{\alpha A1}$-propionyl-N$^{\alpha B1}$-propionyl-Lys$^{B28}$Pro$^{B29}$-human insulin, N$^{\epsilon B28}$-propionyl-N$^{\alpha A1}$-propionyl-N$^{\alpha B1}$-propionyl-Lys$^{B28}$Pro$^{B29}$-human insulin.

In certain embodiments, an insulin molecule of the present disclosure comprises the mutations and/or chemical modifications of one of the following insulin molecules: N$^{\epsilon B28}$-butyryl-Lys$^{B28}$Pro$^{B29}$-human insulin, Nm-butyryl-Lys$^{B28}$Pro$^{B29}$-human insulin, N$^{\alpha A1}$-butyryl-Lys$^{B28}$Pro$^{B29}$-human insulin, N$^{\epsilon B28}$-butyryl-N$^{\alpha B1}$-butyryl-Lys$^{B28}$Pro$^{B29}$-human insulin, N$^{\epsilon B28}$-butyryl-N$^{\alpha A1}$-butyryl-Lys$^{B28}$Pro$^{B29}$-human insulin, N$^{\alpha A1}$-butyryl-N-butyryl-Lys$^{B28}$Pro$^{B29}$-human insulin, N$^{\epsilon B28}$-butyryl-N$^{\alpha A1}$-butyryl-N$^{\alpha B1}$-butyryl-Lys$^{B28}$Pro$^{B29}$-human insulin.

In certain embodiments, an insulin molecule of the present disclosure comprises the mutations and/or chemical modifications of one of the following insulin molecules: N$^{\epsilon B28}$ pentanoyl-Lys$^{B28}$Pro$^{B29}$-human insulin, N$^{\alpha B1}$-pentanoyl-Lys$^{B28}$Pro$^{B29}$-human insulin, N$^{\alpha A1}$-pentanoyl-Lys$^{B28}$Pro$^{B29}$-human insulin, N$^{\epsilon B28}$-pentanoyl-N$^{\alpha B1}$-pentanoyl-Lys$^{B28}$Pro$^{B29}$-human insulin, N$^{\epsilon B28}$-pentanoyl-N$^{\alpha A1}$-pentanoyl-Lys$^{B28}$Pro$^{B29}$-human insulin, N$^{\alpha A1}$-pentanoyl-N$^{\alpha B1}$-pentanoyl-Lys$^{B28}$Pro$^{B29}$-human insulin, N$^{\epsilon B28}$-pentanoyl-N$^{\alpha A1}$-pentanoyl-N$^{\alpha B1}$-pentanoyl-Lys$^{B28}$Pro$^{B29}$-human insulin.

In certain embodiments, an insulin molecule of the present disclosure comprises the mutations and/or chemical modifications of one of the following insulin molecules: N$^{\epsilon B28}$-hexanoyl-Lys$^{B28}$Pro$^{B29}$-human insulin, Nm-hexanoyl-Lys$^{B28}$Pro$^{B29}$-human insulin, N$^{\alpha A1}$-hexanoyl-Lys$^{B28}$Pro$^{B29}$-human insulin, N$^{\epsilon B28}$-hexanoyl-N$^{\alpha B1}$-hexanoyl-Lys$^{B28}$Pro$^{B29}$-human insulin, N$^{\epsilon B28}$-hexanoyl-N$^{\alpha A1}$-hexanoyl-Lys$^{B28}$Pro$^{B29}$-human insulin, N$^{\alpha A1}$-hexanoyl-N$^{\alpha B1}$-hexanoyl-Lys$^{B28}$Pro$^{B29}$-human insulin, N$^{\epsilon B28}$-hexanoyl-N$^{\alpha A1}$-hexanoyl-N$^{\alpha B1}$-hexanoyl-Lys$^{B28}$Pro$^{B29}$-human insulin.

In certain embodiments, an insulin molecule of the present disclosure comprises the mutations and/or chemical modifications of one of the following insulin molecules: N$^{\epsilon B28}$-heptanoyl-Lys$^{B28}$Pro$^{B29}$-human insulin, N$^{\alpha B1}$-heptanoyl-Lys$^{B28}$Pro$^{B29}$-human insulin, N$^{\alpha A1}$-heptanoyl-Lys$^{B28}$Pro$^{B29}$-human insulin, N$^{\epsilon B28}$-heptanoyl-N$^{\alpha B1}$-heptanoyl-Lys$^{B28}$Pro$^{B29}$-human insulin, N$^{\epsilon B28}$-heptanoyl-N$^{\alpha A1}$-heptanoyl-Lys$^{B28}$Pro$^{B29}$-human insulin, N$^{\alpha A1}$-heptanoyl-N$^{\alpha B1}$-heptanoyl-Lys$^{B28}$Pro$^{B29}$-human insulin, N$^{\epsilon B28}$-heptanoyl-N$^{\alpha A1}$-heptanoyl-NB-heptanoyl-Lys$^{B28}$Pro$^{B29}$-human insulin.

In certain embodiments, an insulin molecule of the present disclosure comprises the mutations and/or chemical modifications of one of the following insulin molecules: N$^{\epsilon B28}$-octanoyl-Lys$^{B28}$Pro$^{B29}$-human insulin, N$^{\alpha B1}$-octanoyl-Lys$^{B28}$Pro$^{B29}$-human insulin, N$^{\alpha A1}$-octanoyl-Lys$^{B28}$Pro$^{B29}$-human insulin, N$^{\epsilon B28}$-octanoyl-N$^{\alpha B1}$-octanoyl-Lys$^{B28}$Pro$^{B29}$-human insulin, N$^{\epsilon B28}$-octanoyl-N$^{\alpha A1}$-octanoyl-Lys$^{B28}$Pro$^{B29}$-human insulin, N$^{\alpha A1}$-octanoyl-N$^{\alpha B1}$-octanoyl-Lys$^{B28}$Pro$^{B29}$-human insulin, N$^{\epsilon B28}$-octanoyl-N$^{\alpha A1}$-octanoyl-N$^{\alpha B1}$-octanoyl-Lys$^{B28}$Pro$^{B29}$-human insulin.

In certain embodiments, an insulin molecule of the present disclosure comprises the mutations and/or chemical modifications of one of the following insulin molecules: N$^{\epsilon B28}$-nonanoyl-Lys$^{B28}$Pro$^{B29}$-human insulin, N$^{\alpha B1}$-nonanoyl-Lys$^{B28}$Pro$^{B29}$-human insulin, N$^{\alpha A1}$-nonanoyl-Lys$^{B28}$Pro$^{B29}$-human insulin, N$^{\epsilon B28}$-nonanoyl-N$^{\alpha B1}$-nonanoyl-Lys$^{B28}$Pro$^{B29}$-human insulin, N$^{\epsilon B28}$-nonanoyl-N$^{\alpha A1}$-nonanoyl-Lys$^{B28}$Pro$^{B29}$-human insulin, N$^{\alpha A1}$-nonanoyl-N$^{\alpha B1}$-nonanoyl-Lys$^{B28}$Pro$^{B29}$-human insulin, N$^{\epsilon B28}$-nonanoyl-N$^{\alpha A1}$-nonanoyl-N$^{\alpha B1}$-nonanoyl-Lys$^{B28}$Pro$^{B29}$-human insulin.

In certain embodiments, an insulin molecule of the present disclosure comprises the mutations and/or chemical modifications of one of the following insulin molecules: N$^{\epsilon B28}$-decanoyl-Lys$^{B28}$Pro$^{B29}$-human insulin, N$^{\alpha B1}$-decanoyl-Lys$^{B28}$Pro$^{B29}$-human insulin, N$^{\alpha A1}$-decanoyl-Lys$^{B28}$Pro$^{B29}$-human insulin, N$^{\epsilon B28}$-decanoyl-N$^{\alpha B1}$-decanoyl-Lys$^{B28}$Pro$^{B29}$-human insulin, N$^{\epsilon B28}$-decanoyl-N$^{\alpha A1}$-decanoyl-Lys$^{B28}$Pro$^{B29}$-human insulin, N$^{\alpha A1}$-decanoyl-N$^{\alpha B1}$-decanoyl-Lys$^{B28}$Pro$^{B29}$-human insulin, N$^{\epsilon B28}$-decanoyl-N$^{\alpha A1}$-decanoyl-N$^{\alpha B1}$-decanoyl-Lys$^{B28}$Pro$^{B29}$-human insulin.

In certain embodiments, an insulin molecule of the present disclosure comprises the mutations and/or chemical modifications of one of the following insulin molecules: N$^{\epsilon B29}$-pentanoyl-Gly$^{A21}$Arg$^{B31}$Arg$^{B32}$-human insulin, N$^{\alpha B1}$-hexanoyl-Gly$^{A21}$Arg$^{B31}$Arg$^{B32}$-human insulin, N$^{\alpha A1}$-heptanoyl-Gly$^{A21}$Arg$^{B31}$Arg$^{B32}$-human insulin, N$^{\epsilon B29}$-octanoyl-N$^{\alpha B1}$-octanoyl-Gly$^{A21}$Arg$^{B31}$Arg$^{B32}$-human insulin, N$^{\epsilon B29}$-propionyl-N$^{\alpha A1}$-propionyl-Gly$^{A21}$Arg 1Arg$^{B32}$-human insulin, N$^{\alpha A1}$-acetyl-N$^{\alpha B1}$-acetyl-Gly$^{A21}$Arg$^{B31}$Arg$^{B32}$-human insulin, N$^{\epsilon B29}$-formyl-N$^{\alpha A1}$-formyl-N$^{\alpha B1}$-formyl-Gly$^{A21}$Arg$^{B31}$Arg$^{B32}$-human insulin, N$^{\epsilon B29}$-formyl-des (B26)-human insulin, N$^{\alpha B1}$-acetyl-Asp$^{B28}$-human insulin, N$^{\epsilon B29}$-propionyl-N$^{\alpha A1}$-propionyl-N$^{\alpha B1}$-propionyl-Asp$^{B1}$Asp$^{B3}$Asp$^{B21}$-human insulin, N$^{\epsilon B29}$-pentanoyl-Gly$^{A21}$-human insulin, N$^{\alpha B1}$-hexanoyl-Gly$^{A21}$-human insulin, N$^{\alpha A1}$-heptanoyl-Gly$^{A21}$-human insulin, N$^{\epsilon B29}$-octanoyl-N$^{\alpha B1}$-octanoyl-Gly$^{A21}$-human insulin, N$^{\epsilon B29}$-propionyl-N$^{\alpha A1}$-propionyl-Gly$^{A21}$-human insulin, N$^{\alpha A1}$-acetyl-N$^{\alpha B1}$-acetyl-Gly$^{A21}$-human insulin, N$^{\epsilon B29}$-formyl-N$^{\alpha A1}$-formyl-N$^{\alpha B1}$-formyl-Gly$^{A21}$-human insulin, N$^{\epsilon B29}$-butyryl-des(B30)-human insulin, N$^{\alpha B1}$-butyryl-des(B30)-human insulin, N$^{\alpha A1}$-butyryl-des(B30)-human insulin, N$^{\epsilon B29}$-butyryl-N$^{\alpha B1}$-butyryl-des(B30)-human insulin, N$^{\epsilon B29}$-butyryl-N$^{\alpha A1}$-butyryl-des(B30)-human insulin, N$^{\alpha A1}$-butyryl-N$^{\alpha B1}$-butyryl-des(B30)-human insulin, N$^{\epsilon B29}$-butyryl-N$^{\alpha A1}$-butyryl-N$^{\alpha B1}$-butyryl-des(B30)-human insulin.

The present disclosure also encompasses modified forms of non-human insulins (e.g., porcine insulin, bovine insulin, rabbit insulin, sheep insulin, etc.) that comprise any one of the aforementioned mutations and/or chemical modifications.

These and other modified insulin molecules are described in detail in U.S. Pat. Nos. 6,906,028; 6,551,992; 6,465,426; 6,444,641; 6,335,316; 6,268,335; 6,051,551; 6,034,054; 5,952,297; 5,922,675; 5,747,642; 5,693,609; 5,650,486; 5,547,929; 5,504,188; 5,474,978; 5,461,031; and 4,421,685; and in U.S. Pat. Nos. 7,387,996; 6,869,930; 6,174,856; 6,011,007; 5,866,538; and 5,750,497, the entire disclosures of which are hereby incorporated by reference.

In various embodiments, an insulin molecule of the present disclosure includes the three wild-type disulfide bridges (i.e., one between position 7 of the A-chain and position 7 of the B-chain, a second between position 20 of the A-chain and position 19 of the B-chain, and a third between positions 6 and 11 of the A-chain).

In some embodiments, an insulin molecule is modified and/or mutated to reduce its affinity for the insulin receptor. Without wishing to be bound to a particular theory, it is believed that attenuating the receptor affinity of an insulin molecule through modification (e.g., acylation) or mutation may decrease the rate at which the insulin molecule is eliminated from serum. In some embodiments, a decreased insulin receptor affinity in vitro translates into a superior in vivo activity for an insulin conjugate. In certain embodiments, an insulin molecule is mutated such that the site of mutation is used as a conjugation point, and conjugation at the mutated site reduces binding to the insulin receptor (e.g., $Lys^{A3}$). In certain other embodiments, conjugation at an existing wild-type amino acid or terminus reduces binding to the insulin receptor (e.g., $Gly^{A1}$). In some embodiments, an insulin molecule is conjugated at position A4, A5, A8, A9, or B30. In certain embodiments, the conjugation at position A4, A5, A8, A9, or B30 takes place via a wild-type amino acid side chain (e.g., $Glu^{A4}$). In certain other embodiments, an insulin molecule is mutated at position A4, A5, A8, A9, or B30 to provide a site for conjugation (e.g., $Lys^{A4}$, $Lys^{A5}$, $Lys^{A8}$, $Lys^{A9}$, or $Lys^{B30}$).

Methods for conjugating drugs including insulin molecules are described below. In certain embodiments, an insulin molecule is conjugated to a ligand or conjugate framework via the A1 amino acid residue. In certain embodiments the A1 amino acid residue is glycine. It is to be understood however, that the present disclosure is not limited to N-terminal conjugation and that in certain embodiments an insulin molecule may be conjugated via a non-terminal A-chain amino acid residue. In particular, the present disclosure encompasses conjugation via the epsilon-amine group of a lysine residue present at any position in the A-chain (wild-type or introduced by site-directed mutagenesis). It will be appreciated that different conjugation positions on the A-chain may lead to different reductions in insulin activity. In certain embodiments, an insulin molecule is conjugated to the conjugate framework via the B1 amino acid residue. In certain embodiments the B1 amino acid residue is phenylalanine. It is to be understood however, that the present disclosure is not limited to N-terminal conjugation and that in certain embodiments an insulin molecule may be conjugated via a non-terminal B-chain amino acid residue. In particular, the present disclosure encompasses conjugation via the epsilon-amine group of a lysine residue present at any position in the B-chain (wild-type or introduced by site-directed mutagenesis). For example, in certain embodiments an insulin molecule may be conjugated via the B29 lysine residue. In the case of insulin glulisine, conjugation to the at least one ligand via the B3 lysine residue may be employed. It will be appreciated that different conjugation positions on the B-chain may lead to different reductions in insulin activity.

In certain embodiments, the ligands are conjugated to more than one conjugation point on a drug such as an insulin molecule. For example, an insulin molecule can be conjugated at both the A1 N-terminus and the B29 lysine. In some embodiments, amide conjugation takes place in carbonate buffer to conjugate at the B29 and A1 positions, but not at the B1 position. In other embodiments, an insulin molecule can be conjugated at the A1 N-terminus, the B1 N-terminus, and the B29 lysine. In yet other embodiments, protecting groups are used such that conjugation takes place at the B1 and B29 or B1 and A1 positions. It will be appreciated that any combination of conjugation points on an insulin molecule may be employed. In some embodiments, at least one of the conjugation points is a mutated lysine residue, e.g., $Lys^{A3}$.

In various embodiments, a conjugate may include an insulin sensitizer (i.e., a drug which potentiates the action of insulin). Drugs which potentiate the effects of insulin include biguanides (e.g., metformin) and glitazones. The first glitazone drug was troglitazone which turned out to have severe side effects. Second generation glitazones include pioglitazone and rosiglitazone which are better tolerated although rosiglitazone has been associated with adverse cardiovascular events in certain trials.

In various embodiments, a conjugate may include an insulin secretagogue (i.e., a drug which stimulates insulin secretion by beta cells of the pancreas). For example, in various embodiments, a conjugate may include a sulfonylurea. Sulfonylureas stimulate insulin secretion by beta cells of the pancreas by sensitizing them to the action of glucose. Sulfonylureas can, moreover, inhibit glucagon secretion and sensitize target tissues to the action of insulin. First generation sulfonylureas include tolbutamide, chlorpropamide and carbutamide. Second generation sulfonylureas which are active at lower doses include glipizide, glibenclamide, gliclazide, glibornuride and glimepiride. In various embodiments, a conjugate may include a meglitinide. Suitable meglitinides include nateglinide, mitiglinide and repaglinide. Their hypoglycemic action is faster and shorter than that of sulfonylureas. Other insulin secretagogues include glucagon-like peptide 1 (GLP-1) and GLP-1 analogs (i.e., a peptide with GLP-1 like bioactivity that differs from GLP-1 by 1-10 amino acid substitutions, additions or deletions and/or by a chemical modification). GLP-1 reduces food intake by inhibiting gastric emptying, increasing satiety through central actions and by suppressing glucagon release. GLP-1 lowers plasma glucose levels by increasing pancreas islet cell proliferation and increases insulin production following food consumption. GLP-1 may be chemically modified, e.g., by lipid conjugation as in liraglutide to extend its in vivo half-life. Yet other insulin secretagogues include exendin-4 and exendin-4 analogs (i.e., a peptide with exendin-4 like bioactivity that differs from exendin-4 by 1-10 amino acid substitutions, additions or deletions and/or by a chemical modification). Exendin-4, found in the venom of the Gila Monster, exhibits GLP-1 like bioactivity. It has a much longer half-life than GLP-1 and, unlike GLP-1, it can be truncated by 8 amino acid residues at its N-terminus without losing bioactivity. The N-terminal region of GLP-1 and exendin-4 are almost identical, a significant difference being the second amino acid residue, alanine in GLP-1 and glycine in exendin-4, which gives exendin-4 its resistance to in vivo digestion. Exendin-4 also has an extra 9 amino acid residues at its C-terminus as compared to GLP-1. Mann et al. *Biochem. Soc. Trans.* 35:713-716, 2007 and Runge et al., *Biochemistry* 46:5830-5840, 2007 describe a variety of GLP-1 and exendin-4 analogs which may be used in a conjugate of the present disclosure. The short half-life of GLP-1 results from enzymatic digestion by dipeptidyl peptidase IV (DPP-IV). In certain embodiments, the effects of endogenous GLP-1 may be enhanced by administration of a DPP-IV inhibitor (e.g., vildagliptin, sitagliptin, saxagliptin, linagliptin or alogliptin).

In various embodiments, a conjugate may include amylin or an amylin analog (i.e., a peptide with amylin like bioactivity that differs from amylin by 1-10 amino acid substitutions, additions or deletions and/or by a chemical modification). Amylin plays an important role in glucose regulation (e.g., see Edelman and Weyer, *Diabetes Technol. Ther.* 4:175-189, 2002). Amylin is a neuroendocrine hormone that is co-secreted with insulin by the beta cells of the pancreas in response to food intake. While insulin works to regulate glucose disappearance from the bloodstream, amylin works to help regulate glucose appearance in the bloodstream from the stomach and liver. Pramlintide acetate (SYMLIN®) is an exemplary amylin analog. Since native human amylin is amyloidogenic, the strategy for designing pramlintide involved substituting certain residues with those from rat amylin, which is not amyloidogenic. In particular, proline residues are known to be structure-breaking residues, so these were directly grafted from the rat sequence into the human sequence. Glu-10 was also substituted with an asparagine.

In various embodiments, a pre-conjugated drug may contain one or more reactive moieties (e.g., carboxyl or reactive ester, amine, hydroxyl, aldehyde, sulfhydryl, maleimidyl, alkynyl, azido, etc. moieties). As discussed below, these reactive moieties may, in certain embodiments, facilitate the conjugation process. Specific examples include peptidic drugs bearing alpha-terminal amine and/or epsilon-amine lysine groups. It will be appreciated that any of these reactive moieties may be artificially added to a known drug if not already present. For example, in the case of peptidic drugs a suitable amino acid (e.g., a lysine) may be added or substituted into the amino acid sequence. In addition, as discussed in more detail below, it will be appreciated that the conjugation process may be controlled by selectively blocking certain reactive moieties prior to conjugation.

In various embodiments, a conjugate of the present disclosure may be exploited to manipulate a natural feedback mechanism between glucose and insulin (where the level of insulin increases as the level of glucose increases and the level of glucose decreases as the level of insulin increases). Alternatively, in various embodiments, the drug can be a molecule that (a) has the same function as insulin (e.g., reduces glucose levels), (b) stimulates the production of the insulin and/or (c) potentiates the effect(s) of insulin. For example, as discussed above one could use an insulin secretagogue or an insulin sensitizer instead of insulin as the drug.

In various embodiments, a conjugate can be used which includes a drug with a function that is not directly related to glucose. Without limitation, a conjugate which responds to glucose may be used to provide long-term, mealtime dosing of a drug. Any drug which needs to be dosed periodically and/or with food would benefit from such a delivery system. As is well known in the art, many traditional drugs need to be administered with food or at mealtimes. For example, drugs which inhibit the absorption of fats (e.g., orlistat) are advantageously present during mealtime. Similarly, drugs which lower lipid levels, e.g., lovastatin, atorvastatin, or simvastatin, or triglyceride levels, e.g., gemfibrozil, may also be advantageously released at mealtimes.

Exemplary Insulin Conjugates

In various embodiments, a conjugate of the present disclosure comprises an insulin molecule conjugated to one or more ligands that are independently selected from the group consisting of aminoethylglucose (AEG), aminoethylmannose (AEM), aminoethylbimannose (AEBM), aminoethyltrimannose (AETM), β-aminoethyl-N-acetylglucosamine (AEGA), and aminoethylfucose (AEF). In certain embodiments, the insulin molecule is conjugated via the A1 amino acid residue. In certain embodiments, the insulin molecule is conjugated via the B1 amino acid residue. In certain embodiments, the insulin molecule is conjugated via the epsilon-amino group of $Lys^{B29}$. In certain embodiments, the insulin molecule is insulin glulisine conjugated via the epsilon-amino group of $Lys^{B3}$.

In certain embodiments, a conjugate of the present disclosure comprises an insulin molecule conjugated to one or more aminoethylglucose (AEG) ligands. In certain embodiments, a conjugate of the present disclosure comprises an insulin molecule conjugated to one or more aminoethylmannose (AEM) ligands. In certain embodiments, a conjugate of the present disclosure comprises an insulin molecule conjugated to one or more aminoethylbimannose (AEBM) ligands. In certain embodiments, a conjugate of the present disclosure comprises an insulin molecule conjugated to one or more aminoethyltrimannose (AETM) ligands. In certain embodiments, a conjugate of the present disclosure comprises an insulin molecule conjugated to one or more β-aminoethyl-N-acetylglucosamine (AEGA) ligands. In certain embodiments, a conjugate of the present disclosure comprises an insulin molecule conjugated to one or more aminoethylfucose (AEF) ligands.

In various embodiments, a conjugate of the present disclosure comprises an insulin molecule conjugated to two or more separate ligands. In some embodiments, a conjugate of the present disclosure comprises an insulin molecule conjugated to two separate ligands. In other embodiments, a conjugate of the present disclosure comprises an insulin molecule conjugated to three separate ligands. In certain embodiments, a conjugate of the present disclosure comprises an insulin molecule conjugated to four separate ligands. In certain embodiments, the two or more separate ligands of such a conjugate are aminoethylglucose (AEG). In certain embodiments, the two or more separate ligands of such a conjugate are aminoethylmannose (AEM). In certain embodiments, the two or more separate ligands of such a conjugate are aminoethylbimannose (AEBM). In certain embodiments, the two or more separate ligands of such a conjugate are aminoethyltrimannose (AETM). In certain embodiments, the two or more separate ligands of such a conjugate are β-aminoethyl-N-acetylglucosamine (AEGA). In certain embodiments, the two or more separate ligands of such a conjugate are aminoethylfucose (AEF).

In various embodiments, a conjugate of the present disclosure comprises two or more separate ligands conjugated to a single conjugate framework that is also conjugated to an insulin molecule. In some embodiments, the two or more separate ligands and insulin molecule of such a conjugate are each located on a separate branch of a single branched conjugate framework. In some embodiments, the two or more separate ligands and insulin molecule of such a conjugate are each located on termini of separate branches of a single branched conjugate framework. In some embodiments, the two or more separate ligands of such a conjugate are conjugated to the insulin molecule via two or more different conjugation points. In certain such embodiments, the insulin molecule is conjugated via the A1 amino acid residue and the epsilon-amino group of $Lys^{B29}$. In certain such embodiments, the insulin molecule is conjugated to two separate conjugate frameworks that are each conjugated to one or more separate ligands. In other such embodiments, the insulin molecule is conjugated to two separate conjugate frameworks that are each conjugated to one ligand. In yet other such embodiments, the insulin molecule is conjugated to two separate branched conjugate frameworks that are each conjugated to two ligands. In certain such embodiments, the ligands are located on separate branches of the branched conjugate frameworks. In other such embodiments, the ligands are located on termini of separate branches of the branched conjugate frameworks.

In various embodiments, a conjugate of the present disclosure comprises an insulin molecule conjugated to aminoethylglucose (AEG). In certain such embodiments, the insulin molecule is conjugated via the A1 amino acid residue. In certain such embodiments, the insulin molecule is conjugated via the B1 amino acid residue. In certain such embodiments, the insulin molecule is conjugated via the epsilon-amino group of $Lys^{B29}$. In certain such embodiments, the insulin molecule is insulin glulisine conjugated via the epsilon-amino group of $Lys^{B3}$. In certain such embodiments, the insulin molecule is conjugated via the A1 amino acid residue and the epsilon-amino group of $Lys^{B29}$.

In various embodiments, a conjugate of the present disclosure comprises an insulin molecule conjugated to aminoethylmannose (AEM). In certain such embodiments, the insulin molecule is conjugated via the A1 amino acid residue. In certain such embodiments, the insulin molecule is conjugated via the B1 amino acid residue. In certain such embodiments, the insulin molecule is conjugated via the epsilon-amino group of $Lys^{B29}$. In certain such embodiments, the insulin molecule is insulin glulisine conjugated via the epsilon-amino group of $Lys^{B3}$. In certain such embodiments, the insulin molecule is conjugated via the A1 amino acid residue and the epsilon-amino group of $Lys^{B29}$.

In various embodiments, a conjugate of the present disclosure comprises an insulin molecule conjugated to aminoethylbimannose (AEBM). In certain such embodiments, the insulin molecule is conjugated via the A1 amino acid residue. In certain such embodiments, the insulin molecule is conjugated via the B1 amino acid residue. In certain such embodiments, the insulin molecule is conjugated via the epsilon-amino group of $Lys^{B29}$. In certain such embodiments, the insulin molecule is insulin glulisine conjugated via the epsilon-amino group of $Lys^{B3}$. In certain such embodiments, the insulin molecule is conjugated via the A1 amino acid residue and the epsilon-amino group of $Lys^{B29}$.

In various embodiments, a conjugate of the present disclosure comprises an insulin molecule conjugated to aminoethyltrimannose (AETM). In certain such embodiments, the insulin molecule is conjugated via the A1 amino acid residue. In certain such embodiments, the insulin molecule is conjugated via the B1 amino acid residue. In certain such embodiments, the insulin molecule is conjugated via the epsilon-amino group of $Lys^{B29}$. In certain such embodiments, the insulin molecule is insulin glulisine conjugated via the epsilon-amino group of $Lys^{B3}$. In certain such embodiments, the insulin molecule is conjugated via the A1 amino acid residue and the epsilon-amino group of $Lys^{B29}$.

In various embodiments, a conjugate of the present disclosure comprises an insulin molecule conjugated to β-aminoethyl-N-acetylglucosamine (AEGA). In certain such embodiments, the insulin molecule is conjugated via the A1 amino acid residue. In certain such embodiments, the insulin molecule is conjugated via the B1 amino acid residue. In certain such embodiments, the insulin molecule is conjugated via the epsilon-amino group of $Lys^{B29}$ In certain such embodiments, the insulin molecule is insulin glulisine conjugated via the epsilon-amino group of $Lys^{B3}$. In certain such embodiments, the insulin molecule is conjugated via the A1 amino acid residue and the epsilon-amino group of $Lys^{B29}$.

In various embodiments, a conjugate of the present disclosure comprises an insulin molecule conjugated to aminoethylfucose (AEF). In certain such embodiments, the insulin molecule is conjugated via the A1 amino acid residue. In certain such embodiments, the insulin molecule is conjugated via the B1 amino acid residue. In certain such embodiments, the insulin molecule is conjugated via the epsilon-amino group of $Lys^{B29}$. In certain such embodiments, the insulin molecule is insulin glulisine conjugated via the epsilon-amino group of $Lys^{B3}$. In certain such embodiments, the insulin molecule is conjugated via the A1 amino acid residue and the epsilon-amino group of $Lys^{B29}$.

Conjugate Frameworks

This section describes some exemplary conjugate frameworks. In various embodiments, a conjugate of the present disclosure may have the general formula (I):

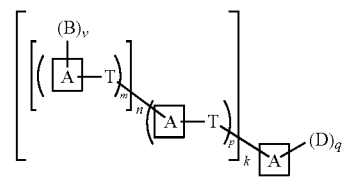

wherein:
each occurrence of

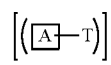

represents a potential branch within the conjugate;
each occurrence of

represents a potential repeat within a branch of the conjugate;

each occurrence of Ⓐ is independently a covalent bond, a carbon atom, a heteroatom, or an optionally substituted group selected from the group consisting of acyl, aliphatic, heteroaliphatic, aryl, heteroaryl, and heterocyclic;

each occurrence of T is independently a covalent bond or a bivalent, straight or branched, saturated or unsaturated, optionally substituted $C_{1-30}$ hydrocarbon chain wherein one or more methylene units of T are optionally and independently replaced by —O—, —S—, —N(R)—, —C(O)—, —C(O)O—, —OC(O)—, —N(R)C(O)—, —C(O)N(R)—, —S(O)—, —S(O)$_2$—, —N(R)SO$_2$—, —SO$_2$N(R)—, a heterocyclic group, an aryl group, or a heteroaryl group;

each occurrence of R is independently hydrogen, a suitable protecting group, or an acyl moiety, arylalkyl moiety, aliphatic moiety, aryl moiety, heteroaryl moiety, or heteroaliphatic moiety;

—B is -T-$L^B$-X;

each occurrence of X is independently a ligand;

each occurrence of $L^B$ is independently a covalent bond or a group derived from the covalent conjugation of a T with an X;

-D is -T-$L^D$-W;

each occurrence of W is independently a drug;

each occurrence of $L^D$ is independently a covalent bond or a group derived from the covalent conjugation of a T with a W;

k is an integer from 1 to 12, inclusive;

q is an integer from 1 to 4, inclusive;

each occurrence of p is independently an integer from 1 to 5, inclusive; and each occurrence of n is independently an integer from 0 to 5, inclusive; and each occurrence of m is independently an integer from 1 to 5, inclusive; and each occurrence of v is independently an integer from 0 to 5, inclusive, with the proviso that within each k-branch at least one occurrence of n is ≥1 and at least one occurrence of v is ≥1.

It is to be understood that general formula (I) (and other formulas herein) does not expressly list every hydrogen. For example, if the central [A] is a $C_6$ aryl group and k+q<6 it will be appreciated that the open position(s) on the $C_6$ aryl ring include a hydrogen.

In general, it will be appreciated that each occurrence of [A] represents a potential branching node and that the number of branches at each node are determined by the values of k for the central [A] and n for non-central occurrences of [A]. One of ordinary skill will appreciate that because each occurrence of n may be an integer from 0 to 5, the present disclosure contemplates linear, branched, and hyperbranched (e.g., dendrimer-like) embodiments of these conjugates. The proviso which requires that within each k-branch at least one occurrence of n is ≥1 and at least one occurrence of v is ≥1 ensures that every conjugate includes at least one occurrence of B (i.e., a ligand).

In certain embodiments, each occurrence of [A] in a p-bracketed moiety is substituted by a number of n-bracketed moieties corresponding to a value of n≥1. For example, when k=2 and p=2 in both k-branches, the conjugate may be of the formula (Ia):

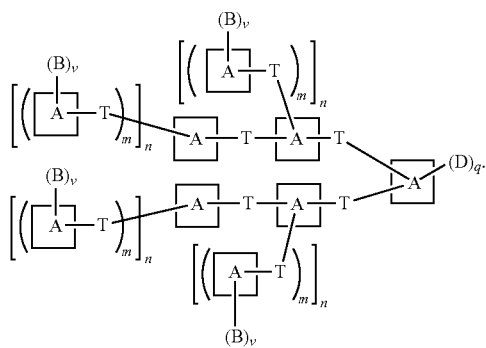

Ia

In other embodiments, only terminal occurrences of [A] in a p-bracketed moiety are substituted by a number of n-bracketed moieties corresponding to a value of n≥1. For example, when k=2 and p=2 in both k-branches (and n=0 for the first p-bracketed moiety in both k-branches), the conjugate may be of the formula (Ib):

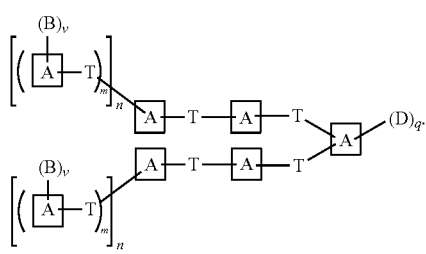

Ib

In certain embodiments, each occurrence of [A] in an m-bracketed moiety is substituted by a number of B moieties corresponding to the value of v≥1. For example, when k=2, each occurrence of p=1, and each occurrence of m=2, the conjugate may be of the formula (Ic):

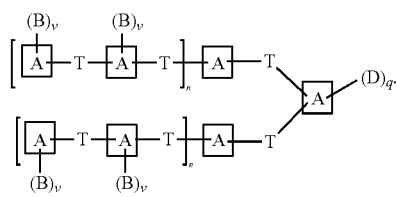

Ic

In other embodiments, only terminal occurrences of [A] in an m-bracketed moiety are substituted by a number of B moieties corresponding to a value of v≥1. For example, when k=2, each occurrence of p=1, and each occurrence of m=2 (and v=0 for the first m-bracketed moiety in each n-branch), the conjugate may be of the formula (Id):

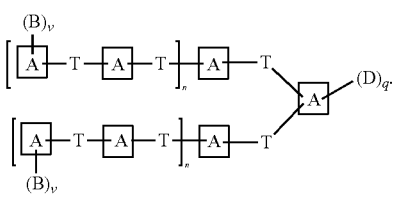

Id

By way of further example, when q=1 and n=1 in both k-branches of the previous formula, the conjugate may be of the formula (Ie):

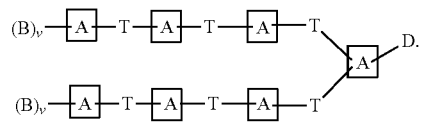

Ie

Alternatively, when q=1 and n=2 in both k-branches of the previous formula, the conjugate may be of the formula (If):

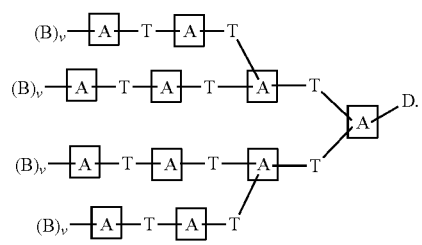

If

In various embodiments, the present disclosure also provides conjugates which include ligands and/or a drug which is non-covalently bound to a conjugate framework.

For example, in some embodiments, the present disclosure provides conjugates of any of the foregoing formulas, wherein:

each of [A], T, D, k, q, p, n, m and v is defined as described above and herein;
—B is -T-LRP$^B$—X;
each occurrence of X is independently a ligand; and
each occurrence of LRP$^B$ is independently a ligand-receptor pair which forms a non-covalent bond between T and X with a dissociation constant in human serum of less than 1 pmol/L.

In yet other embodiments, the present disclosure provides conjugates of any of the foregoing formulas, wherein:

each of Ⓐ, T, B, k, q, p, n, m and v is defined as described above and herein;
-D is -T-LRP$^D$—W;
each occurrence of W is independently a drug; and
each occurrence of LRP$^D$ is independently a ligand-receptor pair which forms a non-covalent bond between T and W with a dissociation constant in human serum of less than 1 pmol/L.

In other embodiments, the present disclosure provides conjugates of any of the foregoing formulas wherein:

each of Ⓐ, T, k, q, p, n, m and v is defined as described above and herein;
—B is -T-LRP$^B$—X;
each occurrence of X is independently a ligand;
each occurrence of LRP$^B$ is independently a ligand-receptor pair which forms a non-covalent bond between T and X with a dissociation constant in human serum of less than 1 pmol/L;
-D is -T-LRP$^D$—W;
each occurrence of W is independently a drug; and
each occurrence of LRP$^D$ is independently a ligand-receptor pair which forms a non-covalent bond between T and W with a dissociation constant in human serum of less than 1 pmol/L.

In another aspect, a conjugate of the present disclosure may have the general formula (II):

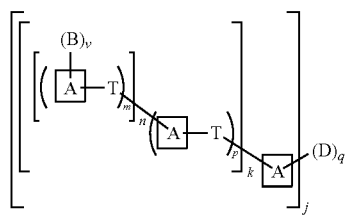

II wherein Ⓐ, B, T, D, v, m, n, p, and k are as defined and described herein, and j is an integer from 1 to 4 inclusive. Conjugates of formula (II) may have multiple sites of conjugation of ligand to drug (i.e., where two or more ligands are conjugated to a single drug molecule via different sites on the drug, e.g., different amino acids in a biomolecular drug). It will be appreciated that, when q is 1, the subgenera described above (i.e., formulae (Ia)-(If)) apply to conjugates of formula (II) when j is 1. Likewise, similar subgenera can be contemplated by one skilled in the art for conjugates wherein j is 2, 3, or 4.

For purposes of exemplification and for the avoidance of confusion it is to be understood that an occurrence of: -Ⓐ-D-Ⓐ- in a conjugate of formula (II) (i.e., when j is 2) could be represented as: -Ⓐ-T-L$^D$-W-L$^D$-T-Ⓐ- (when the drug is covalently bound to the conjugate framework) or -Ⓐ-T-LRP$^D$—W-LRP$^D$-T-Ⓐ- (when the drug is non-covalently bound to the conjugate framework).

Description of Exemplary Groups

Ⓐ (node)

In certain embodiments, each occurrence of Ⓐ is independently an optionally substituted group selected from the group consisting of acyl, aliphatic, heteroaliphatic, aryl, heteroaryl, and heterocyclic. In some embodiments, each occurrence of Ⓐ is the same. In some embodiments, the central Ⓐ is different from all other occurrences of Ⓐ. In certain embodiments, all occurrences of Ⓐ are the same except for the central Ⓐ.

In some embodiments, Ⓐ is an optionally substituted aryl or heteroaryl group. In some embodiments, Ⓐ is 6-membered aryl. In certain embodiments, Ⓐ is phenyl.

In certain embodiments, Ⓐ is a heteroatom selected from N, O, or S. In some embodiments, Ⓐ is nitrogen atom. In some embodiments, Ⓐ is an oxygen atom. In some embodiments, Ⓐ is sulfur atom. In some embodiments, Ⓐ is a carbon atom.

T (Spacer)

In certain embodiments, each occurrence of T is independently a bivalent, straight or branched, saturated or unsaturated, optionally substituted $C_{1-20}$ hydrocarbon chain wherein one or more methylene units of T are optionally and independently replaced by —O—, —S—, —N(R)—, —C(O)—, —C(O)O—, —OC(O)—, —N(R)C(O)—, —C(O)N(R)—, —S(O)—, —S(O)$_2$—, —N(R)SO$_2$—, —SO$_2$N(R)—, a heterocyclic group, an aryl group, or a heteroaryl group. In certain embodiments, one, two, three, four, or five methylene units of T are optionally and independently replaced. In certain embodiments, T is constructed from a $C_{1-10}$, $C_{1-8}$, $C_{1-6}$, $C_{1-4}$, $C_{2-12}$, $C_{4-12}$, $C_{6-12}$, $C_{8-12}$, or $C_{10-12}$ hydrocarbon chain wherein one or more methylene units of T are optionally and independently replaced by —O—, —S—, —N(R)—, —C(O)—, —C(O)O—, —OC(O)—, —N(R)C(O)—, —C(O)N(R)—, —S(O)—, —S(O)$_2$—, —N(R)SO$_2$—, —SO$_2$N(R)—, a heterocyclic group, an aryl group, or a heteroaryl group. In some embodiments, one or more methylene units of T is replaced by a heterocyclic group. In some embodiments, one or more methylene units of T is replaced by a triazole moiety. In certain embodiments, one or more methylene units of T is replaced by —C(O)—. In certain embodiments, one or more methylene units of T is replaced by —C(O)N(R)—. In certain embodiments, one or more methylene units of T is replaced by —O—.

In some embodiments, T is

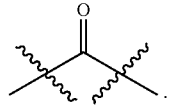

.

In some embodiments, T is

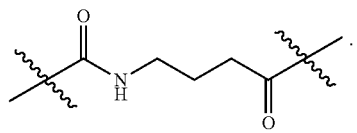 [SMILES: *C(=O)CCCNC(*)=O]

.

In some embodiments, T is

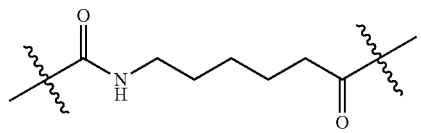

.

In some embodiments, T is

[structure: short chain with ketone C=O]

In some embodiments, T is

[structure: -C(=O)-NH-(CH2)5-C(=O)-]

In some embodiments, T is

[structure: -CH2-O-CH2CH2-C(=O)-]

In certain embodiments, each occurrence of T is the same.

In certain embodiments, each occurrence of T (outside groups B and D) is a covalent bond and the conjugate is of the general formula (IV) or (V):

$$\left[ \left( \left( \underset{(B)_v}{\boxed{A}} \right)_m \boxed{A} \right)_n \boxed{A} \right)_p \boxed{A} \right]_k \boxed{A} -(D)_q \quad \text{IV}$$

or $$\left[ \left( \left( \underset{(B)_v}{\boxed{A}} \right)_m \boxed{A} \right)_n \boxed{A} \right)_p \boxed{A} \right]_k \boxed{A} \bigg]_j - D, \quad \text{V}$$

wherein $\boxed{A}$, B, D, v, m, n, p, k, and j are as defined and described herein.

In certain embodiments of general formulae (IV) and (V), each occurrence of $\boxed{A}$ except for the central $\boxed{A}$ is a covalent bond, each occurrence of v=1, and the conjugate is of the formula (VI) or (VII):

$$(B)_k - \boxed{A} - (D)_q \quad \text{VI}$$

or $$\left[ (B)_k - \boxed{A} \right]_j - D, \quad \text{VII}$$

wherein $\boxed{A}$, B, D, q, k, and j are as defined and described herein.

In certain such embodiments for formula (VI), k=1 and q=1.
In other embodiments, k=2 and q=1.
In other embodiments, k=3 and q=1.
In other embodiments, k=1 and q=2.
In other embodiments, k=2 and q=2.
In certain such embodiments for formula (VII), k=1 and j=2.
In other embodiments, k=2 and j=2.
In other embodiments, k=3 and j=2.
In other embodiments, k=1 and j=1.
In other embodiments, k=2 and j=1.
In other embodiments, k=3 and j=1.
In other embodiments, k=1 and j=3.
In other embodiments, k=2 and j=3.
In other embodiments, k=3 and j=3.

In some embodiments, the present disclosure provides conjugates of general formula (VIa):

[structure: 1,3,5-trisubstituted benzene with B, B, D substituents] VIa wherein B and D are as defined and described herein.

For example, in some embodiments, the present disclosure provides conjugates of formula:

[structure: 1,3,5-benzenetricarboxamide with three X-NH- groups] ;

[structure: 1,3,5-benzene with two X-NH-C(=O)-CH2CH2CH2-NH-C(=O)- arms ending in W and one X-NH-C(=O)-CH2CH2CH2-NH-C(=O)- arm] ; or

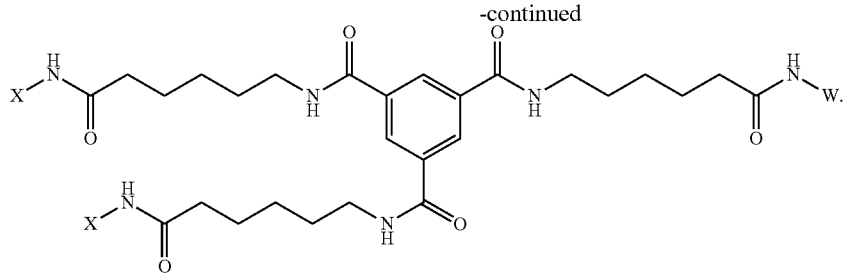
wherein W and X are as defined and described herein.
In some embodiments, the present disclosure provides conjugates of general formula (VIb):
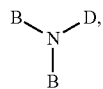
VIb
wherein B and D are as defined and described herein.
For example, in some embodiments, the present disclosure provides conjugates of formula:
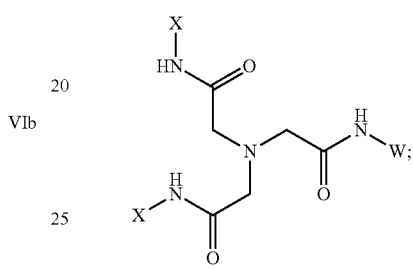
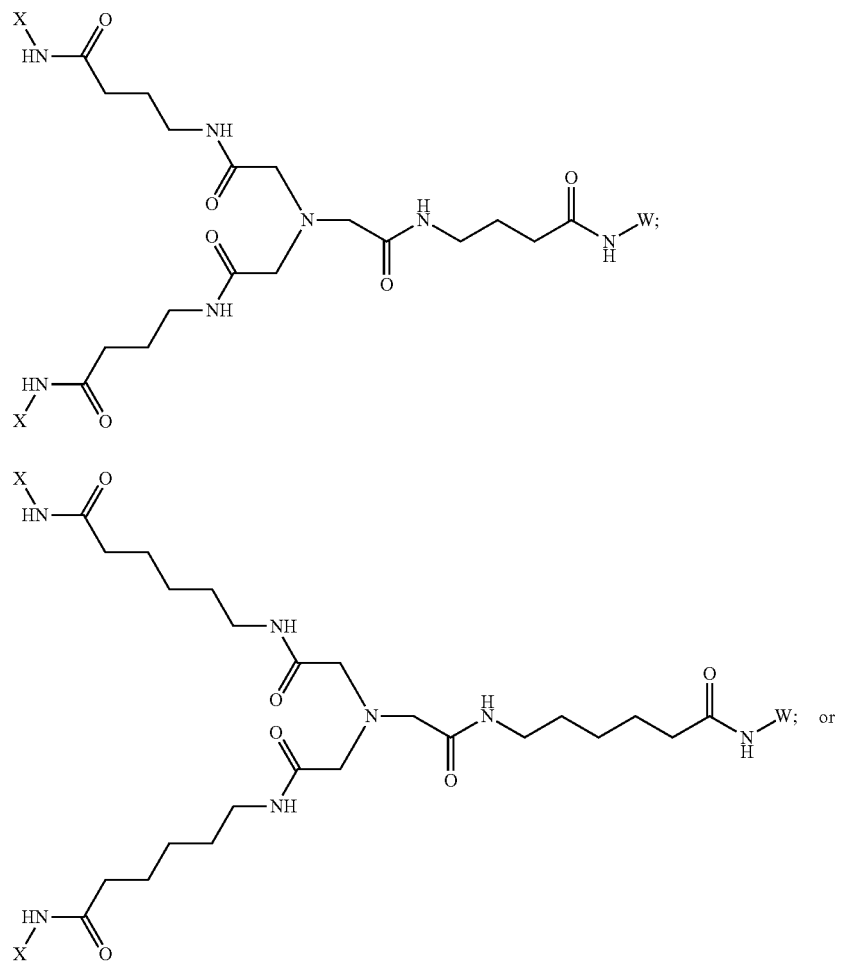

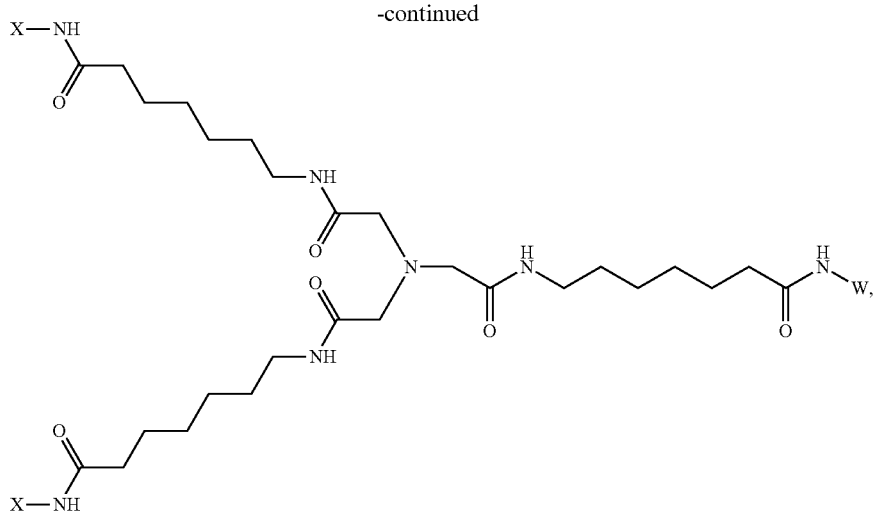

wherein W and X are as defined and described herein.

For example, in some embodiments, the present disclosure provides conjugates of formula:

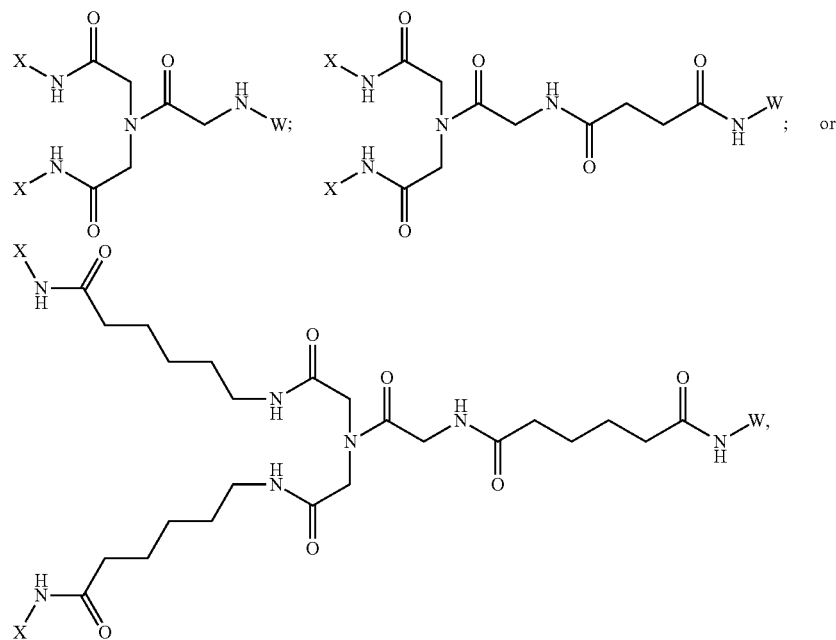

wherein W and X are as defined and described herein.

In some embodiments, the present disclosure provides conjugates of general formula (VIc):

VIc wherein B and D are as defined and described herein.

For example, in some embodiments, the present disclosure provides conjugates of formula:

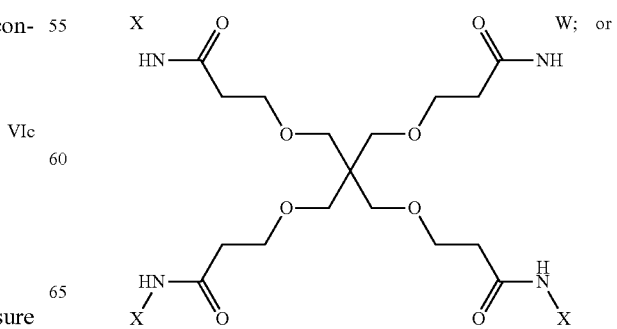

-continued

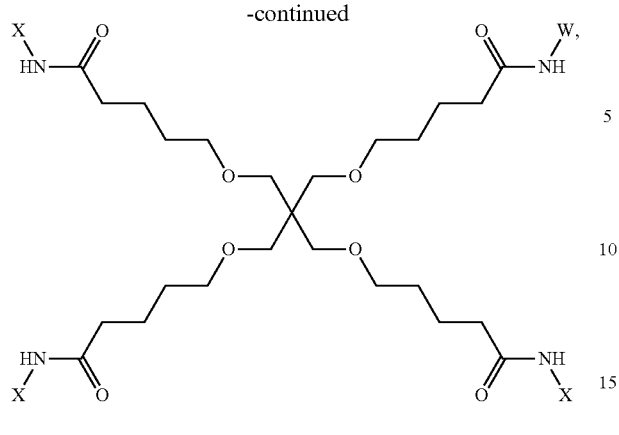

wherein W and X are as defined and described herein.

In some embodiments, the present disclosure provides conjugates of general formula (VId) or (VIe):

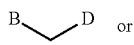   VId

   VIe wherein B and D are as defined and described herein.

For example, in some embodiments, the present disclosure provides conjugates of formula:

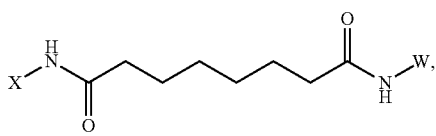

wherein W and X are as defined and described herein.

It will be appreciated that subgenera of formulae (VIa), (VIb), (VIc), (VId), and (VIe) and species thereof, apply to conjugates of formula (VII) wherein j is 1. Likewise, similar subgenera and species can be contemplated by one skilled in the art for conjugates of formula (VII) wherein j is 2, 3, or 4. For example, when j is 2, the present disclosure provides conjugates of formula:

   VIIb-i

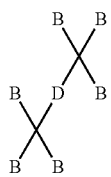   VIIc-i

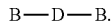   VIIe-i wherein B and D are as defined and described herein.

In certain embodiments, the present disclosure provides conjugates of formula:

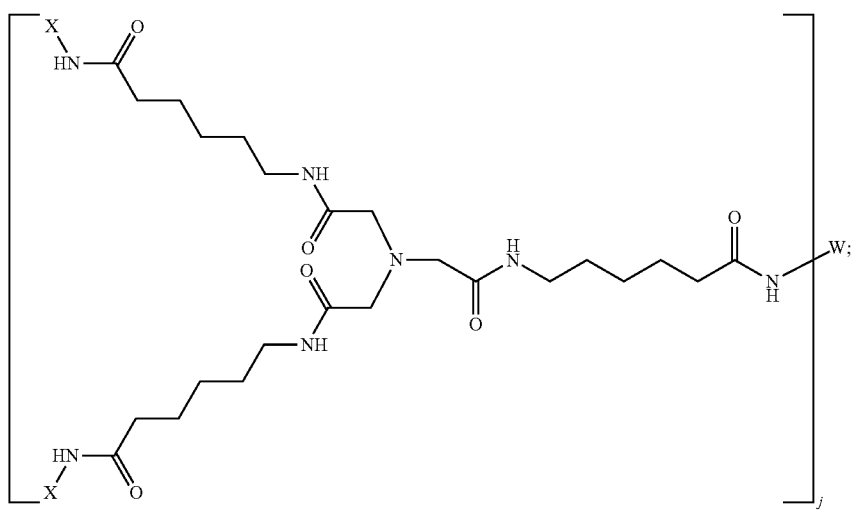

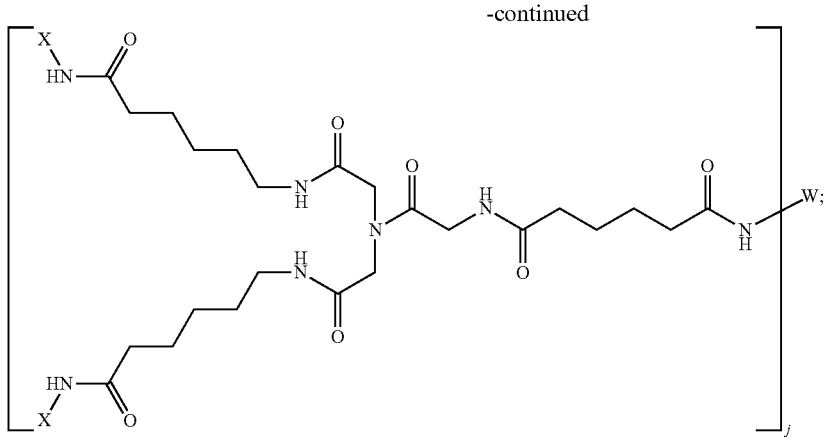

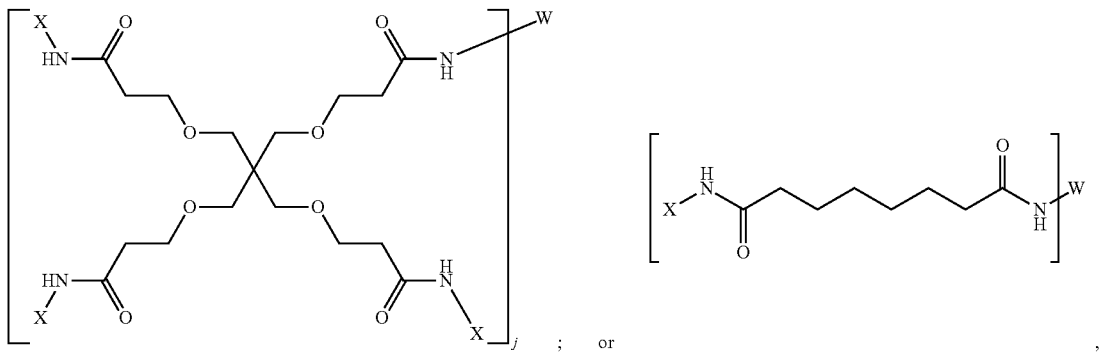

wherein W, X, and j are as defined and described herein.

In another aspect, a conjugate of the present disclosure may have the general formula (VIII):

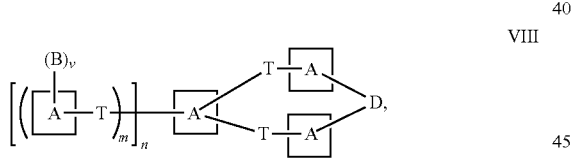

(VIII)

wherein [A], T, D, v, m, and n are as defined and described for conjugates of formula (I), and B is -T-L$^B$-X, wherein each occurrence of X is independently a ligand that includes a saccharide.

For example, in some embodiments, the present disclosure provides conjugates of formula:

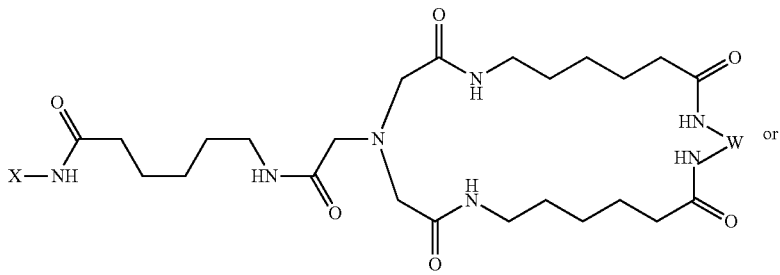

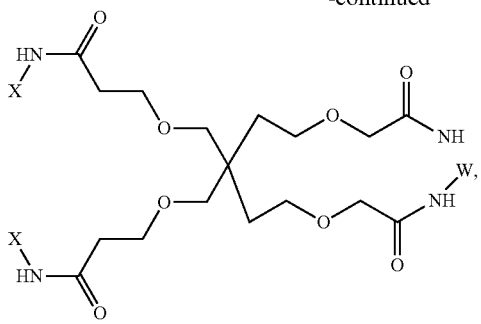

wherein W and X are as defined and described for conjugates of formula (I).

In yet another aspect, the conjugate scaffold is not of formula (I) or (II), but instead is a macrocycle. In some embodiments, the macrocycle is a polyamine macrocycle. For example, in various embodiments, a conjugate of the present disclosure may have the general formula (IX):

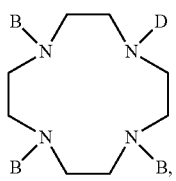

IX wherein D is as defined and described for conjugates of formula (I), and B is -T-$L^B$-X, wherein each occurrence of X is independently a ligand that includes a saccharide.

B (Ligand)

In certain embodiments, —B is -T-$L^B$-X where X is a ligand and $L^B$ is a covalent bond or a group derived from the covalent conjugation of an X with a T. Exemplary ligands and their saccharide components were described above.

D (Drug)

In certain embodiments, -D is -T-$L^D$-W where W is a drug and $L^D$ is a covalent bond or a group derived from the covalent conjugation of a W with a T. Exemplary drugs were described above.

$L^B$ and $L^D$ (Covalent Conjugation)

One of ordinary skill will appreciate that a variety of conjugation chemistries may be used to covalently conjugate an X with a T and/or a W with a T (generally "components"). Such techniques are widely known in the art, and exemplary techniques are discussed below. Components can be directly bonded (i.e., with no intervening chemical groups) or indirectly bonded through a spacer (e.g., a coupling agent or covalent chain that provides some physical separation between the conjugated element and the remainder of the conjugate framework). It is to be understood that components may be covalently bound to a conjugate framework through any number of chemical bonds, including but not limited to amide, amine, ester, ether, thioether, isourea, imine, etc. bonds. In certain embodiments, $L^B$ and/or $L^D$ (generally "L" for the purposes of this section) is a covalent bond. In some embodiments, L is an optionally substituted moiety derived from conjugating an optionally substituted carbonyl-reactive, thiol-reactive, amine-reactive, or hydroxyl-reactive moiety of T with a carboxyl, thiol, amine, or hydroxyl group of X or W. In some embodiments, L is an optionally substituted moiety derived from conjugating an optionally substituted carboxyl-reactive, thiol-reactive, amine-reactive, or hydroxyl-reactive moiety of X or W with a carboxyl, thiol, amine, or hydroxyl group of T. In some embodiments, L is

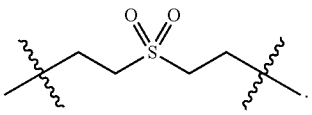 [SMILES: *CCS(=O)(=O)CC*]

In some embodiments, L is a succinimide moiety.

In various embodiments, components may be covalently bound to a conjugate framework using "click chemistry" reactions as is known in the art. These include, for example, cycloaddition reactions, nucleophilic ring-opening reactions, and additions to carbon-carbon multiple bonds (e.g., see Kolb and Sharpless, Drug Discovery Today 8:1128-1137, 2003 and references cited therein as well as Dondoni, Chem. Asian J. 2:700-708, 2007 and references cited therein). As discussed above, in various embodiments, the components may be bound to a conjugate framework via natural or chemically added pendant groups. In general, it will be appreciated that the first and second members of a pair of reactive groups (e.g., a carboxyl group and an amine group which react to produce an amide bond) can be present on either one of the component and framework (i.e., the relative location of the two members is irrelevant as long as they react to produce a conjugate). Exemplary linkages are discussed in more detail below.

In various embodiments, carboxyl (or reactive ester) bearing components can be conjugated to —OH bearing frameworks (OBFs) using the procedure outlined by Kim et al., Biomaterials 24:4843-4851 (2003). Briefly, the OBF is dissolved in DMSO along with the carboxyl bearing component and reacted by means of N',N'-dicyclohexylcarbodiimide (DCC) and 4-dimethylaminopyridine (DMAP) as catalysts under a dry atmosphere. Carboxyl bearing components can be conjugated to —$NH_2$ bearing frameworks (NBFs) using a carbodiimide (EDAC) coupling procedure. Using this procedure, the carboxyl bearing component is functionalized by reaction with EDAC in a pH 5 buffer followed by the addition of the NBF. In either of these cases (and in any of the following cases), the resulting products may be purified by any number of means available to those skilled in the art including, but not limited to, size exclusion chromatography, reversed phase chromatography, silica gel chromatography, ion exchange chromatography, ultrafiltration, and selective precipitation.

In various embodiments, amine bearing components can be coupled to —COOH bearing frameworks (CBFs). CBFs using activated ester moieties (e.g., see Hermanson in Bio-

*conjugate Techniques, 2nd edition*, Academic Press, 2008 and references cited therein). Briefly, a CBF with terminal activated carboxylic acid esters such as —NHS, —SSC, —NPC, etc. is dissolved in an anhydrous organic solvent such as DMSO or DMF. The desired number of equivalents of amine bearing component are then added and mixed for several hours at room temperature. Amine bearing components can also be conjugated to CBFs to produce a stable amide bond as described by Baudys et al., *Bioconj. Chem.* 9:176-183, 1998. This reaction can be achieved by adding tributylamine (TBA) and isobutylchloroformate to a solution of the CBF and an amine bearing component in dimethylsulfoxide (DMSO) under anhydrous conditions. Amine bearing components can alternatively be coupled to OBFs through cyanalation using reagents including, but not limited to, cyanogen bromide (CNBr), N-cyanotriethylammonium tetrafluoroborate (CTEA), 1-Cyano-4-(Dimethylamino)-pyridinium tetrafluorborate (CDAP), and p-nitrophenylcyanate (pNPC). CNBr reactions can be carried out at mildly basic pH in aqueous solution. CDAP reactions are carried out in a mixture of DMSO and water at mildly basic pH using triethylamine (TEA) as a catalyst. In certain embodiments, amine bearing components can be conjugated to NBFs, e.g., through glutaraldehyde coupling in aqueous buffered solutions containing pyridine followed by quenching with glycine. In certain embodiments, amine bearing components can be conjugated to aldehyde bearing frameworks using a Schiff Base coupling procedure followed by reduction (e.g., see Hermanson in *Bioconjugate Techniques, 2nd edition*, Academic Press, 2008 and references cited therein as well as Mei et al. in *Pharm. Res.* 16: 1680-1686, 1999 and references cited therein). Briefly, a framework with terminal activated aldehydes (e.g., acetaldehyde, propionaldehyde, butyraldehyde, etc.) is dissolved in an aqueous buffer with the pH at or below neutral to prevent unwanted aldehyde hydrolysis. The desired number of equivalents of an amine bearing component are then added and mixed at room temperature followed by addition of an excess of suitable reducing agent (e.g., sodium borohydride, sodium cyanobrohydride, sodium triacetoxyborohydride pyridine borane, triethylamine borane, etc.).

In various embodiments, hydroxyl bearing components can be conjugated to OBFs according to the divinylsulfone (DVS) procedure. Using this procedure, the OBF is added to a pH 11.4 bicarbonate buffer and activated with DVS followed by addition of a hydroxyl bearing component after which glycine is added to neutralize and quench the reaction. Hydroxyl bearing components may also be coupled to OBFs using activated ester moieties as described above to produce ester bonds.

In various embodiments, sulfhydryl bearing components can be coupled to maleimide bearing frameworks (MBFs) using a relatively mild procedure to produce thioether bonds (e.g., see Hermanson in *Bioconjugate Techniques, 2nd edition*, Academic Press, 2008 and references cited therein). Because the maleimide group is much less susceptible to hydrolysis than activated esters, the reaction can be carried out under aqueous conditions. Briefly, an MBF is dissolved in a buffered aqueous solution at pH 6.5-7.5 followed by the desired number of equivalents of sulfhydryl bearing component. After mixing at room temperature for several hours, the thioether coupled conjugate may be purified. Sulfhydryl bearing components can also be conjugated to NBFs according to a method described by Thoma et al., *J. Am. Chem. Soc.* 121:5919-5929, 1999. This reaction involves suspending the NBF in anhydrous dimethylformamide (DMF) followed by the addition of 2,6-lutidine and acid anhydride and subsequent purification of the reactive intermediate. A sulfhydryl bearing component is then added to a solution of the intermediate in DMF with triethylamine.

In various embodiments, azide bearing components can be coupled to an alkyne bearing framework (ABF) using the copper(I)-catalyzed modern version of the Huisgen-type azide-alkyne cycloaddition to give a 1,4-di-substituted 1,2,3-triazole (e.g., see Dondoni, *Chem. Asian J.* 2:700-708, 2007 and references cited therein as well as Dedola et al., *Org. Biomol. Chem.* 5: 1006-1017, 2007). This reaction, commonly referred to as a "click" reaction, may be carried out for example in neat THF using N,N-diisopropylethylamine and $Cu(PPh_3)_3Br$ as the catalyst system (e.g., see Wu et al., *Chem. Commun.* 5775-5777, 2005). The reaction may also be carried out in a 3:1 (THF:water) mixture using sodium ascorbate and $CuSO_4.5H_2O$ as the catalyst system (e.g., see Wu et al., supra). In either case, the azide bearing component is added to the ABF at the desired number of equivalents followed by mixing for 12-48 hours at room temperature. Alternatively, alkyne bearing components may be conjugated to an azide bearing framework using exactly the same conditions described above.

Certain components may naturally possess more than one of the same chemically reactive moiety. In some examples, it is possible to choose the chemical reaction type and conditions to selectively react the component at only one of those sites. For example, in the case where insulin is conjugated through reactive amines, in certain embodiments, the N-terminal α-Phe-B1 is a preferred site of attachment over the N-terminal α-Gly-A1 and ε-Lys-B29 to preserve insulin bioactivity (e.g., see Mei et al., *Pharm. Res.* 16: 1680-1686, 1999 and references cited therein as well as Tsai et al., *J. Pharm. Sci.* 86: 1264-1268, 1997). In an exemplary reaction between insulin with hexadecenal (an aldehyde-terminated molecule), researchers found that mixing the two components overnight in a 1.5M pH 6.8 sodium salicylate aqueous solution containing 54% isopropanol at a ratio of 1:6 (insulin:aldehyde mol/mol) in the presence of sodium cyanoborohydride resulted in over 80% conversion to the single-substituted Phe-B1 secondary amine-conjugated product (Mei et al., *Pharm. Res.* 16:1680-1686, 1999). Their studies showed that the choice of solvent, pH, and insulin:aldehyde ratio all affected the selectivity and yield of the reaction. In most cases, however, achieving selectivity through choice of chemical reaction conditions is difficult. Therefore, in certain embodiments it may be advantageous to selectively protect the component (e.g., insulin) at all sites other than the one desired for reaction followed by a deprotection step after the material has been reacted and purified. For example, there are numerous examples of selective protection of insulin amine groups available in the literature including those that may be deprotected under acidic (BOC), slightly acidic (citraconic anhydride), and basic (MSC) conditions (e.g., see Tsai et al., *J. Pharm. Sci.* 86: 1264-1268, 1997; Dixon et al., *Biochem. J.* 109: 312-314, 1968; and Schuettler et al., *D. Brandenburg Hoppe Seyler's Z. Physiol. Chem.* 360: 1721, 1979). In one example, the Gly-A1 and Lys-B29 amines may be selectively protected with tert-butoxycarbonyl (BOC) groups which are then removed after conjugation by incubation for one hour at 4 C in a 90% trifluoroacetic acid (TFA)/10% anisole solution. In one embodiment, a dry powder of insulin is dissolved in anhydrous DMSO followed by an excess of triethylamine. To this solution, approximately two equivalents of di-tert-butyl dicarbonate solution in THF are added slowly and the solution allowed to mix for 30-60 minutes. After reaction, the crude solution is poured in an excess of acetone followed by dropwise addition of dilute HCl to precipitate the reacted insulin. The precipitated material is centrifuged, washed with acetone and dried completely under vacuum. The desired di-BOC protected product may be separated from unreacted insulin, undesired di-BOC isomers, and mono-BOC and tri-BOC byproducts using preparative reverse phase HPLC or ion exchange chromatography (e.g., see Tsai et al., *J. Pharm. Sci.* 86: 1264-1268, 1997). In the case of reverse phase HPLC, a solution of the crude product in 70% water/30% acetonitrile containing 0.1% TFA is loaded onto a C8 column and eluted with an increasing acetonitrile gradient. The desired di-BOC peak is collected, rotovapped to remove acetonitrile, and lyophilized to obtain the pure product.

$LRP^B$ and $LRP^D$ (Non-Covalent Conjugation)

One of ordinary skill will appreciate that a variety of conjugation chemistries may be used to non-covalently conjugate an X with a T and/or W with a T (generally "components"). Such techniques are widely known in the art, and exemplary techniques are discussed below. In certain embodiments, the dissociation constant ($K_d$) of the non-covalent linkage in human serum is less than 1 pmol/L. For example, a component may be non-covalently bound to a conjugate framework via a non-covalent ligand-receptor pair as is well known in the art (e.g., without limitation a biotin-avidin based pair). In such an embodiment, one member of the ligand receptor-pair is covalently bound to the component while the other member of the pair is covalently bound to the conjugate framework. When the component and conjugate framework are combined, the strong non-covalent interaction between the ligand and its receptor causes the component to become non-covalently bound to the conjugate framework. Typical ligand/receptor pairs include protein/co-factor and enzyme/substrate pairs. Besides the commonly used biotin/avidin pair, these include without limitation, biotin/streptavidin, digoxigenin/anti-digoxigenin, FK506/FK506-binding protein (FKBP), rapamycin/FKBP, cyclophilin/cyclosporin and glutathione/glutathione transferase pairs. Other suitable ligand/receptor pairs would be recognized by those skilled in the art, e.g., monoclonal antibodies paired with a epitope tag such as, without limitation, glutathione-S-transferase (GST), c-myc, FLAG® and further those described in Kessler pp. 105-152 of *Advances in Mutagenesis*" Ed. by Kessler, Springer-Verlag, 1990; *"Affinity Chromatography: Methods and Protocols (Methods in Molecular Biology)*" Ed. by Pascal Baillon, Humana Press, 2000; and *"Immobilized Affinity Ligand Techniques"* by Hermanson et al., Academic Press, 1992.

k and q k is an integer from 1 to 12, inclusive. In certain embodiments, k=1 to 6, e.g., 1, 2, or 3. q is an integer from 1 to 4, inclusive, and defines the number of D groups which are bound to the central Ⓐ group. In certain embodiments, q=1. In some embodiments, q=2. In certain embodiments, k+q is an integer from 2 to 6, inclusive. In certain embodiments, k+q=2, 3 or 4.

p and m

Each occurrence of p is independently an integer from 1 to 5, inclusive. In certain embodiments, each occurrence of p is the same. In certain embodiments, p=1, 2 or 3. In certain embodiments, p=1.

Each occurrence of m is independently an integer from 1 to 5, inclusive. In certain embodiments, each occurrence of m is the same. In certain embodiments, m=1, 2 or 3. In certain embodiments, m=1.

n and v

Each occurrence of n is independently an integer from 0 to 5, inclusive, with the proviso that within each k-branch at least one occurrence of n is ≥1. Branches within a given k-branch are referred to herein as n-branches.

In certain embodiments, each occurrence of Ⓐ in a p-bracketed moiety is substituted by a number of n-bracketed moieties corresponding to a value of n≥1, e.g., see formula (Ia) above. In some such embodiments, each occurrence of n in the conjugate is the same. In some of these embodiments, n=1 or 2.

In other embodiments, only terminal occurrences of Ⓐ in a p-bracketed moiety are substituted by a number of n-bracketed moieties corresponding to a value of n≥1, e.g., see formula (Ib) above. In certain embodiments, each k-branch includes just one occurrence of n≥1 (i.e., all other occurrences of n=0). In some such embodiments, each occurrence of n in the conjugate is the same. In some of these embodiments, n=1 or 2.

Each occurrence of v is independently an integer from 0 to 5, inclusive, with the proviso that within each k-branch at least one occurrence of v is ≥1.

In certain embodiments, each occurrence of Ⓐ in an m-bracketed moiety is substituted by a number of B moieties corresponding to the value of v≥1, e.g., see formula (Ic) above. In some such embodiments, each occurrence of v in the conjugate is the same. In some of these embodiments, v=1 or 2.

In other embodiments, only terminal occurrences of Ⓐ in an m-bracketed moiety are substituted by a number of B moieties corresponding to a value of v≥1, e.g., see formula (Id) above. In certain embodiments, each k-branch includes just one occurrence of v≥1 (i.e., all other occurrences of v=0). In some such embodiments, each occurrence of v in the conjugate is the same. In some of these embodiments, v=1 or 2. In certain embodiments, each n-branch includes at least one occurrence of v≥1. In certain embodiment, each n-branch includes just one occurrence of v≥1 (i.e., all other occurrences of v=0). In some such embodiments, each occurrence of v in the conjugate is the same. In some of these embodiments, v=1 or 2.

j j of formula (II) is an integer from 1 to 4, inclusive, and defines the number of conjugations to the D group. In certain embodiments, j=1. In certain embodiments, j=2. In some embodiments, j=3. In other embodiments, j=4.

Drug Loading

In general, the amount of drug that is loaded onto a conjugate can be controlled by adjusting the molecular weight of the conjugate framework and/or the level of chemical activation (i.e., when pendant groups are added to the framework). In various embodiments, the drug loading level may be in the range of 5 to 99% w/w of drug to conjugate. In various embodiments, loading levels within the narrower range of 50 to 99% may be used, e.g., in the range of 80 to 99%.

Other

It is to be understood that while the preceding sections describe components of the conjugates (e.g., ligand, drug, framework) under separate headings, the present disclosure encompasses conjugates that are comprised of any and all of the disclosed ligands, drugs and frameworks.

Intermediates for Preparing Conjugates

In one aspect, the present disclosure provides reagents for preparing conjugates. Thus, in various embodiments, a compound of general formula (I) is provided wherein:

each of Ⓐ, T, D, k, q, k+q, p, n, m and v is defined as described above and herein;

—B is -T-$L^{B'}$; and each occurrence of $L^B$ is independently hydrogen, an alkyne-containing moiety, an azide-containing moiety, or an optionally substituted carbonyl-reactive, thiol-reactive, amine-reactive, or hydroxyl-reactive moiety.

In other embodiments, a compound of general formula (I) is provided wherein:

each of $\boxed{A}$, T, B, k, q, k+q, p, n, m and v is defined as described above and herein;

-D is -T-$L^{D'}$; and each occurrence of $L^D$ is independently hydrogen, an alkyne-containing moiety, an azide-containing moiety, or an optionally substituted carbonyl-reactive, thiol-reactive, amine-reactive, or hydroxyl-reactive moiety.

Methods for Preparing Conjugates

As described in the Examples, we have exemplified methods for preparing the aforementioned conjugates using insulin as an exemplary drug and aminoethylglucose (AEG), aminoethylmannose (AEM), aminoethylbimannose (AEBM), aminoethyltrimannose (AETM), aminoethylfucose (AEF), and/or β-aminoethyl-N-acetylglucosamine (AEGA) as exemplary ligands. Without limitation, conjugates with two ligands per conjugation site and with short distances between all framework components may be prepared using tris(hydroxymethyl)aminomethane (Tris), tris-succinimidyl aminotriacetate (TSAT), tris-succinimidyl-1,3,5-benzenetricarboxylate (TSB), and benzene-1,3,5-tricarboxy-(N-4-butyric-NHS-ester)amide (TSB-C4) as conjugate frameworks. If more space between framework components is desired, then succinimidyl (6-aminocaproyl)aminotriacetate (TSAT-C6), succinimidyl (6-amino(PEO-6))aminotriacetate (TSAT-PEO-6), benzene-1,3,5-tricarboxy-(N-6-aminocaproic-NHS ester)amide (TSB-C6), and benzene-1,3,5-tricarboxy-(N-10-aminodecanoic-NHS ester)amide (TSB-C10) may be used. The TSAT-C6 spacer arm chemistry imparts more hydrophobic character to the conjugate as compared to TSAT-PEO-6.

For example, for purposes of illustration, in one embodiment, both the ligand (e.g., AEG, AEM, AEMB and AETM) and insulin may be reacted to a TSAT-C6 framework through the terminal activated esters to produce insulin-TSAT-C6-AEG-2, insulin-TSAT-C6-AEM-2, insulin-TSAT-C6-AEMB-2, and insulin-TSAT-C6-AETM-2 conjugates. The various ligands are synthesized ahead of time as discussed in the Examples. In some embodiments, the A1 and B29 amino groups of insulin are BOC-protected as described in the Examples so that each insulin can only react at the Phe-B1 α-amino group. In some embodiments, the B1 and B29 amino groups of insulin are BOC-protected as described in the Examples so that each insulin can only react at the Gly-A1 α-amino group. Approximately one equivalent of BOC-insulin as a 40-50 mg/ml solution in DMSO is added at room temperature to a 50 mg/ml solution of TSAT-C6 in DMSO containing excess triethylamine and allowed to react for approximately one hour. Next, an excess of AEG, AEM, AEBM, and/or AETM (2-10 equivalents) as a 100 mg/ml solution in DMSO is added and allowed to react for an additional 2 hours. After reaction, the DMSO solution is superdiluted by 10× into a pH 5 saline buffer after which the pH is adjusted to 8.0 and the solution passed through a Biogel P2 column to remove low molecular reactants and salts. The material eluting in the void fraction is concentrated using a 3K ultrafiltration apparatus after which it is injected on a prep scale reverse phase HPLC column (C8, acetonitrile/water mobile phase containing 0.1% TFA) to purify the desired product from unreacted BOC2-insulin. The desired elution peak is collected pooled and rotovapped to remove acetonitrile followed by lyophilization to obtain a dry powder. Finally, the BOC protecting groups are removed by dissolving the lyophilized powder in 90% TFA/10% anisole for one hour at 4 C followed by 10× superdilution in HEPES pH 8.2 buffer containing 0.150 M NaCl. The pH is adjusted to between 7.0 and 8.0 using NaOH solution after which the material is passed through a Biogel P2 column to remove anisole, BOC, and any other contaminating salts. The deprotected, purified aqueous conjugate solution is then concentrated to the desired level and stored at 4 C until needed.

In another aspect, reaction may take place at the B29 epsilon-amino group using unprotected insulin in carbonate buffer, since under those conditions the B29 amino group is the most reactive of the three amino groups present in wild-type insulin. In an exemplary synthesis, the framework containing N-terminal activated esters is dissolved at 60 mM in anhydrous DMSO followed by the addition of triethylamine (TEA). The solution is stirred rapidly for 10 minutes at room temperature. In parallel, a 448 mM solution of ligand is prepared in an appropriate volume of anhydrous DMSO. Once dissolved, enough ligand solution is added dropwise over the course of ten minutes to provide a number of reactive equivalents equal to 1.5 times the number of activated ester groups on the framework, N, minus one. For example, if there are N=3 initial activated ester groups per framework, then (3×(3−1)×60 mM/370 mM)=0.973 ml of ligand solution are added. If there are N=4 initial activated ester groups per framework, then (3×(4−1)×60 mM/370 mM)=1.46 ml of ligand solution are added, and so on. After the ligand solution is added, the solution is stirred for one hour at room temperature.

The amine-bearing drug is then dissolved separately at 17.2 mM in sodium carbonate buffer (0.1 M, pH 11) and the pH subsequently adjusted to 10.8 with 1.0 N sodium hydroxide. Once dissolved, the entire framework/DMSO/ligand/TEA solution is added dropwise over the course of 75 minutes to the drug/carbonate buffer solution. During the addition, the pH of the resulting mixture is adjusted every 5 minutes to 10.8 if necessary using dilute HCl or NaOH. The solution is allowed to stir for an additional 15 minutes after the dropwise addition to ensure complete reaction.

The resulting solution is then superdiluted by 10× into a 20 mM pH 5.0 HEPES buffered saline solution containing 0.150 M NaCl followed by pH adjustment with dilute HCl to a final pH of 8.0. The aqueous solution is first purified by size exclusion using an appropriate solid phase for the desired separation of conjugated and unconjugated materials. The solution passing through the column void volume is then concentrated using an appropriately sized ultrafiltration membrane to approximately 40 ml. This solution is further purified to obtain the desired product using preparative reverse phase HPLC. Once collected, the solution is rotovapped to remove acetonitrile and lyophilized to obtain pure conjugate.

Furthermore, under the carbonate buffer conditions, the A1 amino group is the second most reactive amino group of wild-type insulin. Thus, in certain embodiments, A1,B29-disubstituted insulin-conjugates are synthesized using the conditions described above with approximately ten times the amount of multivalent active ester framework and ligand per insulin molecule compared to the B29-monosubstituted insulin-conjugate synthesis.

In another aspect, B29-monosubstituted insulin-conjugates are synthesized using N-terminal protecting amino acid sequences using similar methods to those reported in U.S. Pat. No. 7,402,565. Specifically, N-terminal peptide sequences are engineered onto the insulin A-chain and B-chain such that the protecting amino acid sequences contain $Arg^{A0}$ and $Arg^{B0}$ to give an insulin intermediate. Conjugation takes places at $Lys^{B29}$ on the insulin intermediate, while the N-termini are protected from conjugation side-products. The conjugated insulin intermediate is treated with trypsin to cleave the N-terminal protecting amino acid sequences to give an insulin-conjugate wherein solely $Lys^{B29}$ is conjugated. In some embodiments, the insulin intermediate is derived from a single chain insulin precursor as described in U.S. Pat. No. 7,402,565. In some embodiments, the insulin intermediate is a mutant that contains a conjugation site other than $Lys^{B29}$ and an analogous synthesis to the one described for $Lys^{B29}$ is performed.

It will be appreciated that these exemplary procedures may be used to produce other conjugates with different ligands and drugs, different conjugation chemistries, different separations between framework components, and/or different valencies by substituting the TSAT-C6 framework with a different framework as described below.

For example, if yet more distance is required between framework components and/or a preserved charge is required at the site of conjugation, then an appropriately-sized amine-bearing diethyl acetal (e.g., aminopropionaldehyde diethyl acetal (APDA) or aminobutyraldehyde diethyl acetal (ABDA)) may be conjugated to one of the reactive groups on the frameworks listed here followed by complete reaction of the remaining reactive groups with the ligand of interest (e.g., AEM, AEBM, or AETM). A reactive aldehyde group can then be revealed from the diethyl acetal under acidic conditions followed by a reductive amination with insulin to complete the drug conjugation step then ABDA-TSAT, ABDA-LCT-SAT, etc. may be employed.

In yet another example, tetrakis-(N-succinimidyl carboxypropyl)pentaerythritol (TSPE), may be used to attach three ligands per conjugation site for increased multivalency. It will also be appreciated by those skilled in the art that any of the above teachings may be used to produce hyperbranched (e.g., dendrimer-like) conjugates with even higher order valencies. For example, Rickendorf and Lindhorst provide a comprehensive review of current approaches for producing hyperbranched structures in *Topics in Current Chemistry*. 217: 202-238, 2001.

Furthermore, ligands already containing a predetermined degree of multivalency may again be reacted according to the procedures described above to produce even higher orders of ligand multiplicity. For example, a divalent AEM-2, AEBM-2, or AETM-2 molecule containing a terminal reactive amine may be prepared by conjugating two of each ligand to a suitable framework to which a reactive amine is also conjugated. A trivalent AEM-3, AEBM-3, or AETM-3 molecule containing a terminal reactive amine may be prepared by conjugating three of each ligand to a suitable framework to which a reactive amine is also conjugated. The $NH_2$-divalent saccharides may be reacted with the same frameworks described above to produce drug conjugates with 4 and 6 ligands per drug molecule. The $NH_2$-trivalent saccharides may be reacted with the same frameworks described above to produce drug conjugates with 6 and 9 ligands per drug molecule.

In all cases, it should be recognized that a mixture of different ligands may be conjugated to the same drug via a multivalent framework by adjusting the framework chemistry, valency, and the ligand:framework stoichiometry. For example, Insulin-AEM-1-AEBM-1, Insulin-AEBM-1-AETM-1, Insulin-AEM-2-AETM-2, and Insulin-AEM-1-AETM-2 may all be synthesized according to this mixed ligand method.

In some cases, it may be desirable to conjugate the ligand to the framework through a different means than the drug. For example, a divalent maleimide/monovalent activate ester functionalized framework (e.g., succinimidyl-3,5-dimaleimidophenyl benzoate (SDMB)) may be used to conjugate two sulfhydryl functionalized ligands and one amine-functionalized drug in separate steps. For example, insulin or another amine-containing drug may be conjugated to the activated ester portion of the framework using methods described herein. In a separate step, the aminoethyl saccharide (AEM, AEBM, AETM) may be converted to a terminal sulfhydryl-bearing ligand by reaction with 4-iminothiolane. Finally, the framework-di-maleimide-insulin conjugate may be mixed with an excess of sulfhydryl-functionalized saccharide to produce the resulting divalent-ligand-insulin conjugate.

Sustained Release Formulations

As discussed in the Examples, in certain embodiments it may be advantageous to administer a conjugate in a sustained fashion (i.e., in a form that exhibits an absorption profile that is more sustained than soluble recombinant human insulin). This will provide a sustained level of conjugate that can respond to fluctuations in glucose on a timescale that it more closely related to the typical glucose fluctuation timescale (i.e., hours rather than minutes). In certain embodiments, the sustained release formulation may exhibit a zero-order release of the conjugate when administered to a mammal under non-hyperglycemic conditions (i.e., fasted conditions).

It will be appreciated that any formulation that provides a sustained absorption profile may be used. In certain embodiments this may be achieved by combining the conjugate with other ingredients that slow its release properties into systemic circulation.

For example, PZI (protamine zinc insulin) formulations may be used for this purpose. As described in the Examples, we have found that in certain embodiments the absorption profile and stability of PZI formulations prepared with conjugates of the present disclosure are sensitive to the absolute and relative amounts of protamine and zinc included in the formulation. For example, whereas commercial PZI and NPH (neutral protamine Hagedorn) insulin formulations require only about 0.05 to about 0.2 mg protamine/mg insulin, some PZI-conjugate preparations required about 1 to about 5 mg protamine/mg conjugate in order to effectively sustain the absorption profile. Furthermore, while commercial protamine insulin preparations contain about 0.006 mg zinc/mg insulin, we have found that increasing the zinc concentration along with the protamine concentration can, in certain embodiments, lead to more stable, easily dispersible formulations. In some cases, the zinc content is in the range of about 0.05 to about 0.5 mg zinc/mg conjugate. Furthermore, we have also unexpectedly found that in certain embodiments, insulin conjugates substituted at the B1-amine group require more protamine and zinc to effectively sustain the release profile versus an insulin conjugate substituted at the B29-amine group. The present disclosure encompasses amorphous and crystalline forms of these PZI formulations.

Thus, in certain embodiments, a formulation of the present disclosure includes from about 0.05 to about 10 mg protamine/mg conjugate. For example, from about 0.2 to about 10 mg protamine/mg conjugate, e.g., about 1 to about 5 mg protamine/mg conjugate.

In certain embodiments, a formulation of the present disclosure includes from about 0.006 to about 0.5 mg zinc/mg conjugate. For example, from about 0.05 to about 0.5 mg zinc/mg conjugate, e.g., about 0.1 to about 0.25 mg zinc/mg conjugate.

In certain embodiments, a formulation of the present disclosure includes protamine and zinc in a ratio (w/w) in the range of about 100:1 to about 5:1, for example, from about 50:1 to about 5:1, e.g., about 40:1 to about 10:1. In certain embodiments, a PZI formulation of the present disclosure includes protamine and zinc in a ratio (w/w) in the range of about 20:1 to about 5:1, for example, about 20:1 to about 10:1, about 20:1 to about 15:1, about 15:1 to about 5:1, about 10:1 to about 5:1, about 10:1 to about 15:1.

The Examples also describe the benefits of including one or more of the following components in a PZI formulation: an antimicrobial preservative, an isotonic agent, and/or an unconjugated insulin molecule.

In certain embodiments a formulation of the present disclosure includes an antimicrobial preservative (e.g., m-cresol, phenol, methylparaben, or propylparaben). In certain embodiments the antimicrobial preservative is m-cresol. For example, in certain embodiments, a formulation may include from about 0.1 to about 1.0% v/v m-cresol. For example, from about 0.1 to about 0.5% v/v m-cresol, e.g., about 0.15 to about 0.35% v/v m-cresol.

In certain embodiments a formulation of the present disclosure includes a polyol as isotonic agent (e.g., mannitol, propylene glycol or glycerol). In certain embodiments the isotonic agent is glycerol. In certain embodiments, the isotonic agent is a salt, e.g., NaCl. For example, a formulation may comprise from about 0.05 to about 0.5 M NaCl, e.g., from about 0.05 to about 0.25 M NaCl or from about 0.1 to about 0.2 M NaCl.

In certain embodiments a formulation of the present disclosure includes an amount of unconjugated insulin molecule. In certain embodiments, a formulation includes a molar ratio of conjugated insulin molecule to unconjugated insulin molecule in the range of about 100:1 to 1:1, e.g., about 50:1 to 2:1 or about 25:1 to 2:1.

The present disclosure also encompasses the use of standard sustained (also called extended) release formulations that are well known in the art of small molecule formulation (e.g., see *Remington's Pharmaceutical Sciences,* 19$^{th}$ ed., Mack Publishing Co., Easton, Pa., 1995). The present disclosure also encompasses the use of devices that rely on pumps or hindered diffusion to deliver a conjugate on a gradual basis. In certain embodiments, a long acting formulation may (additionally or alternatively) be provided by using a modified insulin molecule. For example, one could use insulin glargine (LANTUS®) or insulin detemir (LEVEMIR®) instead of wild-type human insulin in preparing the conjugate. Insulin glargine is an exemplary long acting insulin analog in which Asp-A21 has been replaced by glycine, and two arginines have been added to the C-terminus of the B-chain. The effect of these changes is to shift the isoelectric point, producing a solution that is completely soluble at pH 4. Insulin detemir is another long acting insulin analog in which Thr-B30 has been deleted, and a C14 fatty acid chain has been attached to Lys-B29.

Uses of Conjugates

In another aspect, the present disclosure provides methods of using conjugates. In general, the conjugates can be used to controllably provide a bioactive drug in response to a saccharide (e.g., glucose or an exogenous saccharide such as mannose, alpha-methyl mannose, L-fucose, etc. as described herein). The disclosure encompasses treating a disease or condition by administering a conjugate of the present disclosure. Although the conjugates can be used to treat any patient (e.g., dogs, cats, cows, horses, sheep, pigs, mice, etc.), they are most preferably used in the treatment of humans. A conjugate can be administered to a patient by any route. In general the most appropriate route of administration will depend upon a variety of factors including the nature of the disease or condition being treated, the nature of the drug, the condition of the patient, etc. In general, the present disclosure encompasses administration by oral, intravenous, intramuscular, intra-arterial, subcutaneous, intraventricular, transdermal, rectal, intravaginal, intraperitoneal, topical (as by powders, ointments, or drops), buccal, or as an oral or nasal spray or aerosol. General considerations in the formulation and manufacture of pharmaceutical compositions for these different routes may be found, for example, in *Remington's Pharmaceutical Sciences,* 19$^{th}$ ed., Mack Publishing Co., Easton, Pa., 1995. In various embodiments, the conjugate may be administered subcutaneously, e.g., by injection. The conjugate can be dissolved in a carrier for ease of delivery. For example, the carrier can be an aqueous solution including, but not limited to, sterile water, saline or buffered saline.

In general, a therapeutically effective amount of a drug in the form of a conjugate will be administered. By a "therapeutically effective amount" of a drug is meant a sufficient amount of the drug to treat the disease or condition at a reasonable benefit/risk ratio, which involves a balancing of the efficacy and toxicity of the drug. In general, therapeutic efficacy and toxicity may be determined by standard pharmacological procedures in cell cultures or with experimental animals, e.g., by calculating the $ED_{50}$ (the dose that is therapeutically effective in 50% of the treated subjects) and the $LD_{50}$ (the dose that is lethal to 50% of treated subjects). The $ED_{50}/LD_{50}$ represents the therapeutic index of the drug. Although in general drugs having a large therapeutic index are preferred, as is well known in the art, a smaller therapeutic index may be acceptable in the case of a serious disease or condition, particularly in the absence of alternative therapeutic options. Ultimate selection of an appropriate range of doses for administration to humans is determined in the course of clinical trials.

In various embodiments, the drug is insulin and the average daily dose of insulin is in the range of 10 to 200 U, e.g., 25 to 100 U (where 1 Unit of insulin is ~0.04 mg). In certain embodiments, an amount of conjugate with these insulin doses is administered on a daily basis. In certain embodiments, an amount of conjugate with 5 to 10 times these insulin doses is administered on a weekly basis. In certain embodiments, an amount of conjugate with 10 to 20 times these insulin doses is administered on a bi-weekly basis. In certain embodiments, an amount of conjugate with 20 to 40 times these insulin doses is administered on a monthly basis. Those skilled in the art will recognize that this same approach may be extrapolated to other approved drugs with known dose ranges, e.g., any of the approved insulin sensitizers and insulin secretagogues described herein. Typically, the dose of conjugated drug will be higher than the normal dose of unconjugated drug.

In certain embodiments, a conjugate of the present disclosure may be used to treat hyperglycemia in a patient (e.g., a mammalian patient). In certain embodiments, the patient is diabetic. However, the present methods are not limited to treating diabetic patients. For example, in certain embodiments, a conjugate may be used to treat hyperglycemia in a patient with an infection associated with impaired glycemic control. In certain embodiments, a conjugate may be used to treat diabetes.

In certain embodiments, when a conjugate or formulation of the present disclosure (with an insulin molecule as the drug) is administered to a patient (e.g., a mammalian patient) it induces less hypoglycemia than an unconjugated version of the insulin molecule. In certain embodiments, a formulation of the present disclosure (with a conjugate that includes an insulin molecule as the drug) induces a lower HbA1c value in a patient (e.g., a mammalian patient) than a formulation comprising an unconjugated version of the insulin molecule. In certain embodiments, the formulation leads to an HbA1c value that is at least 10% lower (e.g., at least 20% lower, at least 30% lower, at least 40% lower, at least 50% lower) than a formulation comprising an unconjugated version of the insulin molecule. In certain embodiments, the formulation leads to an HbAlc value of less than 7%, e.g., in the range of about 4 to about 6%. In certain embodiments, a formulation comprising an unconjugated version of the insulin molecule leads to an HbAlc value in excess of 7%, e.g., about 8 to about 12%.

It will be understood that the total daily usage of a drug for any given patient will be decided by the attending physician within the scope of sound medical judgment. The specific therapeutically effective amount for any particular patient will depend upon a variety of factors including the disease or condition being treated; the activity of the specific drug employed; the specific composition employed; the age, body weight, general health, sex and diet of the patient; the time of administration, route of administration and rate of excretion of the specific drug employed; the duration of the treatment; drugs used in combination or coincidental with the specific drug employed; and like factors well known in the medical arts. In various embodiments, a conjugate of the present disclosure may be administered on more than one occasion. For example, the present disclosure specifically encompasses methods in which a conjugate is administered by subcutaneous injection to a patient on a continuous schedule (e.g., once a day, once every two days, once a week, once every two weeks, once a month, etc.).

In various embodiments, a conjugate of the present disclosure may be administered to a patient who is receiving at least one additional therapy. In various embodiments, the at least one additional therapy is intended to treat the same disease or disorder as the administered conjugate. In various embodiments, the at least one additional therapy is intended to treat a side-effect of the primary drug. The two or more therapies may be administered within the same, overlapping or non-overlapping timeframes as long as there is a period when the patient is receiving a benefit from both therapies. The two or more therapies may be administered on the same or different schedules as long as there is a period when the patient is receiving a benefit from both therapies. The two or more therapies may be administered within the same or different formulations as long as there is a period when the patient is receiving a benefit from both therapies. In certain embodiments, a single conjugate of the present disclosure may include more than one drug for treating the same disease or disorder. In certain embodiments, two or more separate conjugates of the present disclosure may be administered (as a mixture or separately) that include different drugs for treating the same disease or disorder. In certain embodiments, an unconjugated secondary drug may be admixed with a conjugate of the present disclosure (i.e., a drug which is simply mixed with the conjugate formulation and not covalently bound to the conjugate). For example, in certain embodiments, any of these approaches may be used to administer more than one anti-diabetic drug to a subject. Certain exemplary embodiments of this approach are described in more detail below in the context of insulin-related therapies; however, it will be appreciated from the foregoing that other therapies will benefit from such combination approaches.

Insulin sensitizers (e.g., biguanides such as metformin, glitazones) act by increasing a patient's response to a given amount of insulin. A patient receiving an insulin sensitizer will therefore require a lower dose of an insulin conjugate of the present disclosure than an otherwise identical patient would. Thus, in certain embodiments, an insulin conjugate may be administered to a patient who is also being treated with an insulin sensitizer. In various embodiments, the conjugate of the present disclosure may be administered at up to 75% of the normal dose required in the absence of the insulin sensitizer. In various embodiments, up to 50, 40, 30 or 20% of the normal dose may be administered.

Insulin resistance is a disorder in which normal amounts of insulin are inadequate to produce a normal insulin response. For example, insulin-resistant patients may require high doses of insulin in order to overcome their resistance and provide a sufficient glucose-lowering effect. In these cases, insulin doses that would normally induce hypoglycemia in less resistant patients fail to even exert a glucose-lowering effect in highly resistant patients. Similarly, the conjugates of the present disclosure are only effective for this subclass of patients when they provide high levels of bioactive insulin in a suitable timeframe. In certain embodiments, the treatment of this subclass of patients may be facilitated by combining the two approaches. Thus in certain embodiments, a traditional insulin-based therapy is used to provide a baseline level of insulin and a conjugate of the present invention is administered to provide a controlled supplement of bioactive insulin when needed by the patient. Thus, in certain embodiments, insulin conjugates may be administered to a patient who is also being treated with insulin. In various embodiments, the insulin may be administered at up to 75% of the normal dose required in the absence of a conjugate of the present disclosure. In various embodiments, up to 50, 40, 30 or 20% of the normal dose may be administered. It will be appreciated that this combination approach may also be used with insulin resistant patients who are receiving an insulin secretagogue (e.g., a sulfonylurea, GLP-1, exendin-4, etc.) and/or an insulin sensitizer (e.g., a biguanide such as metformin, a glitazone).

Exogenous Trigger

As mentioned previously, the methods, conjugates and compositions that are described herein are not limited to glucose responsive-conjugates. As demonstrated in the Examples, several exemplary glucose-responsive conjugates were also responsive to exogenous saccharides such as alpha-methyl mannose and L-fucose. It will therefore be appreciated that in certain embodiments a conjugate may be triggered by exogenous administration of a saccharide other than glucose such as alpha-methyl mannose and L-fucose or any other saccharide that can alter the PK or PD properties of the conjugate.

Once a conjugate has been administered as described above (e.g., as a sustained release formulation) it can be triggered by administration of a suitable exogenous saccharide. In a certain embodiment, a triggering amount of the exogenous saccharide is administered. As used herein, a "triggering amount" of exogenous saccharide is an amount sufficient to cause a change in at least one PK and/or PD property of the conjugate (e.g., $C_{max}$, AUC, half-life, etc. as discussed previously). It is to be understood that any of the aforementioned methods of administration for the conjugate apply equally to the exogenous saccharide. It is also be to be understood that the methods of administration for the conjugate and exogenous saccharide may be the same or different. In various embodiments, the methods of administration are different (e.g., for purposes of illustration the conjugate may be administered by subcutaneous injection on a weekly basis while the exogenous saccharide is administered orally on a daily basis). The oral administration of an exogenous saccharide is of particular value since it facilitates patient compliance. In general, it will be appreciated that the PK and PD properties of the conjugate will be related to the PK profile of the exogenous saccharide. Thus, the conjugate PK and PD properties can be tailored by controlling the PK profile of the exogenous saccharide. As is well known in the art, the PK profile of the exogenous saccharide can be tailored based on the dose, route, frequency and formulation used. For example, if a short and intense activation of the conjugate is desired then an oral immediate release formulation might be used. In contrast, if a longer less intense activation of conjugate is desired then an oral extended release formulation might be used instead. General considerations in the formulation and manufacture of immediate and extended release formulation may be found, for example, in *Remington's Pharmaceutical Sciences*, 19$^{th}$ ed., Mack Publishing Co., Easton, Pa., 1995.

It will also be appreciated that the relative frequency of administration of a conjugate of the present disclosure and an exogenous saccharide may be the same or different. In certain embodiments, the exogenous saccharide is administered more frequently than the conjugate. For example, in certain embodiment, the conjugate may be administered daily while the exogenous saccharide is administered more than once a day. In certain embodiment, the conjugate may be administered twice weekly, weekly, biweekly or monthly while the exogenous saccharide is administered daily. In certain embodiments, the conjugate is administered monthly and the exogenous saccharide is administered twice weekly, weekly, or biweekly. Other variations on these schemes will be recognized by those skilled in the art and will vary depending on the nature of the conjugate and formulation used.

EXAMPLES

Figure 45:
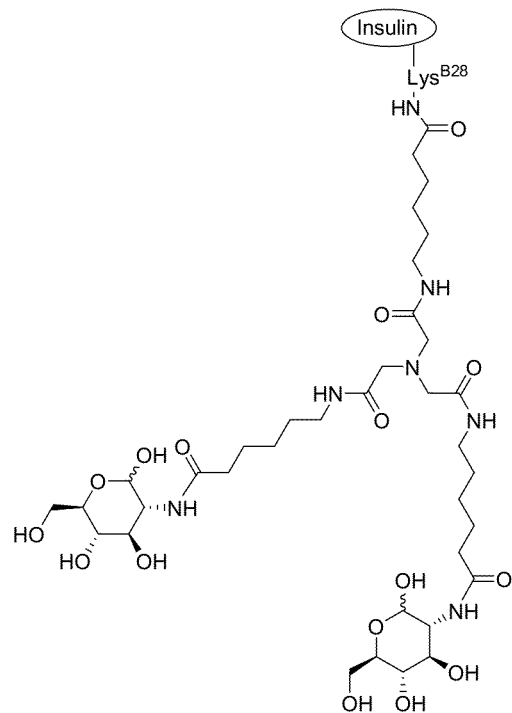
FIG. 45: Structures of exemplary insulin-conjugates. As described in the Examples, these conjugates were each prepared with recombinant wild-type human insulin (see FIG. 63 for the structure of wild-type human insulin). The symbol "insulin" inside an oval as shown in FIG. 45 is therefore primarily intended to represent a wild-type human insulin. As discussed herein, it is to be understood that the present disclosure also encompasses inter alia versions of these and other conjugates that include an insulin molecule other than wild-type human insulin.
Figure 45:
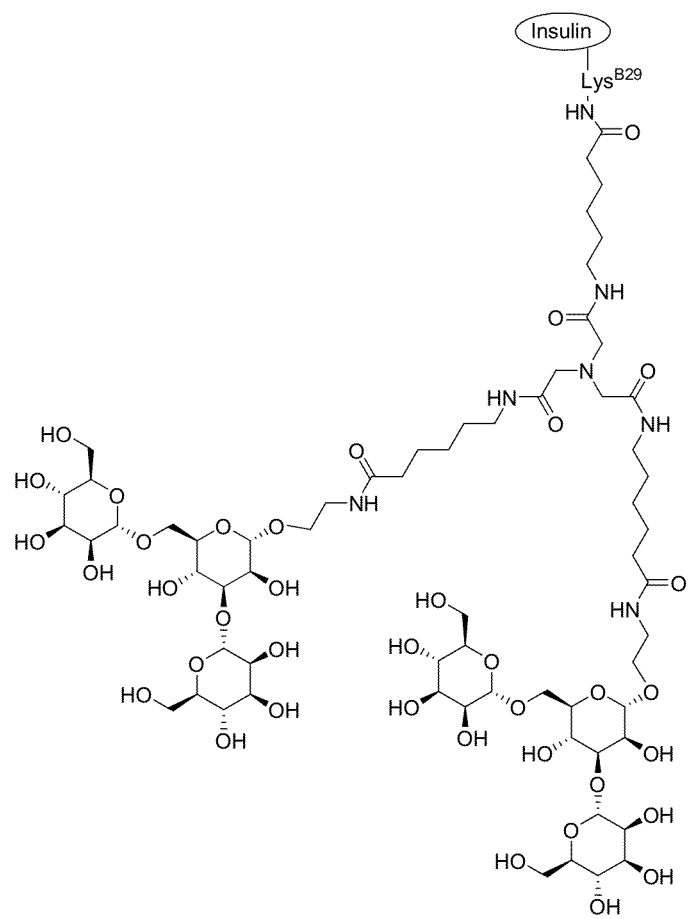
Figure 45:
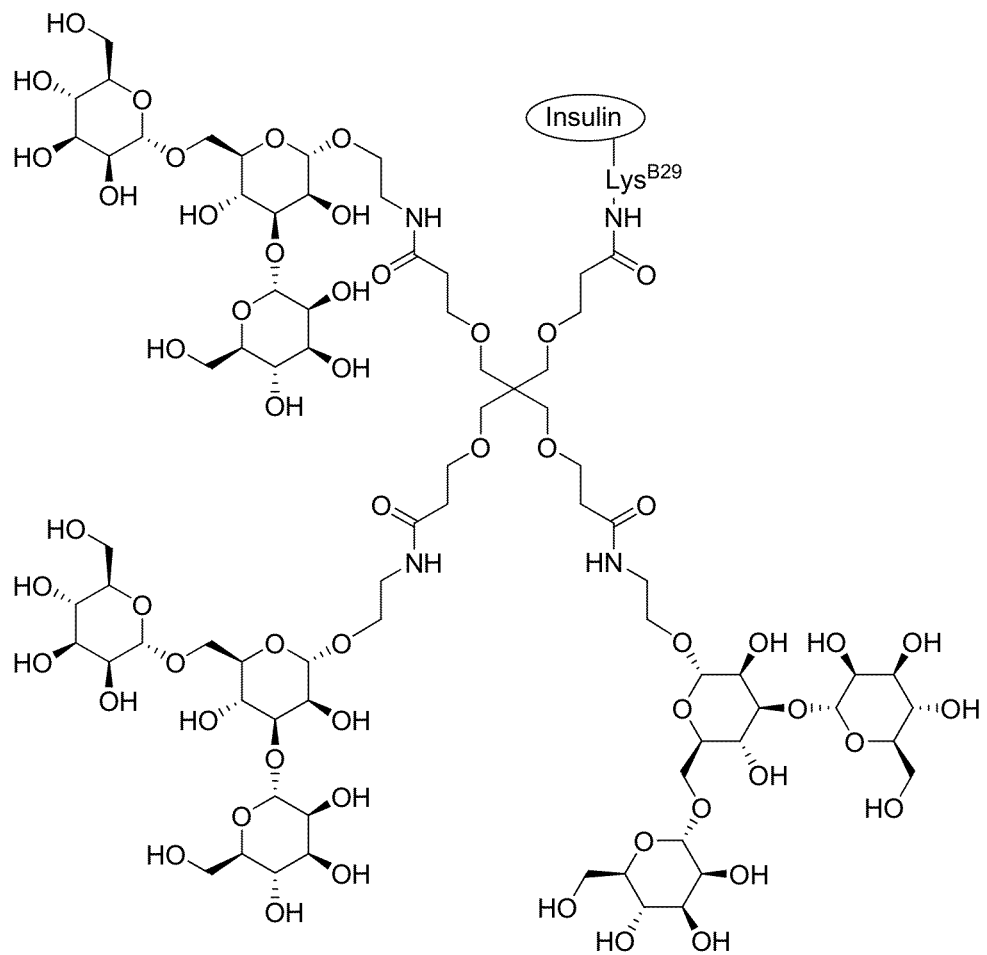
Figure 45:
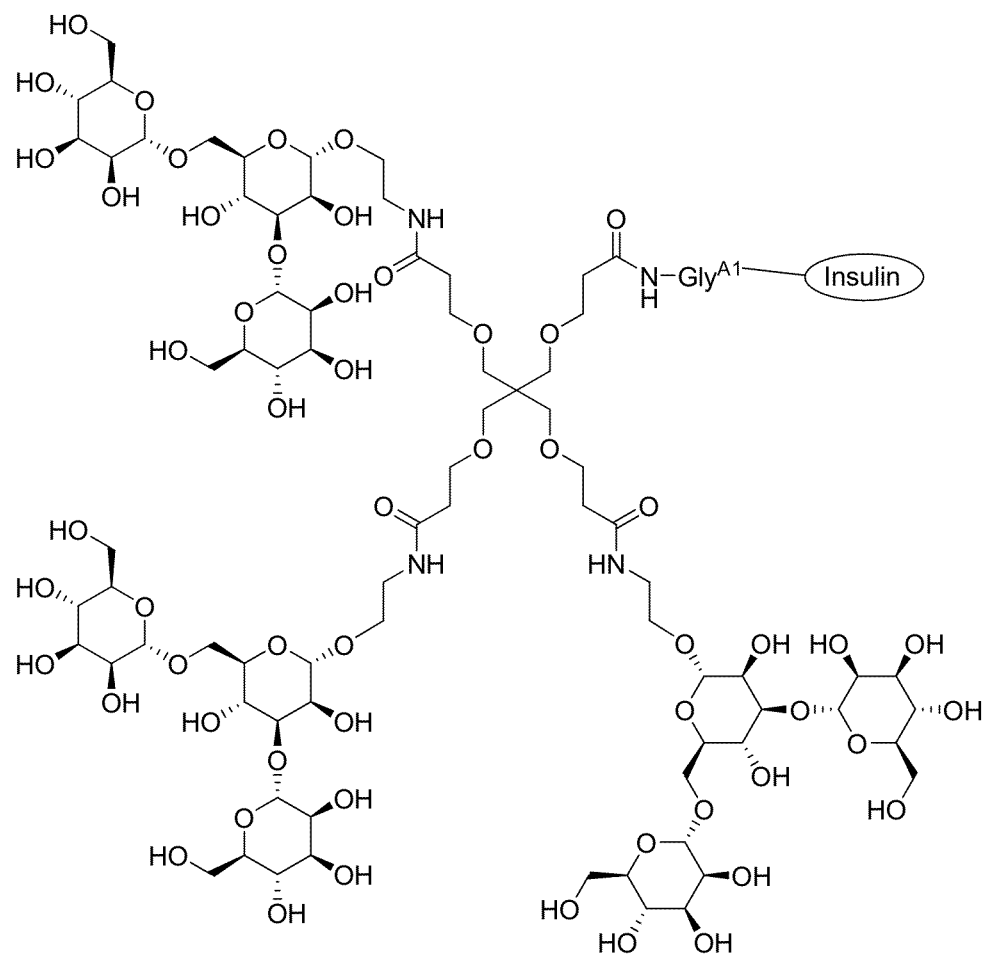
Figure 45:
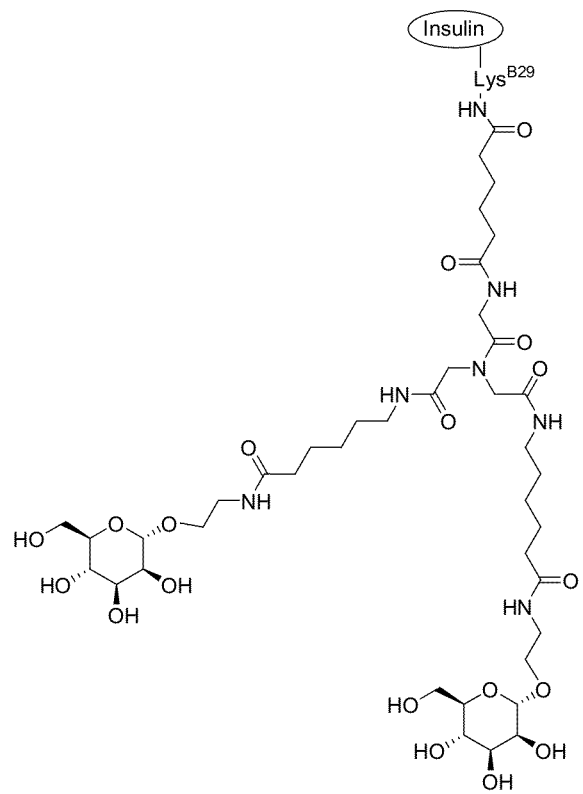
Figure 45:
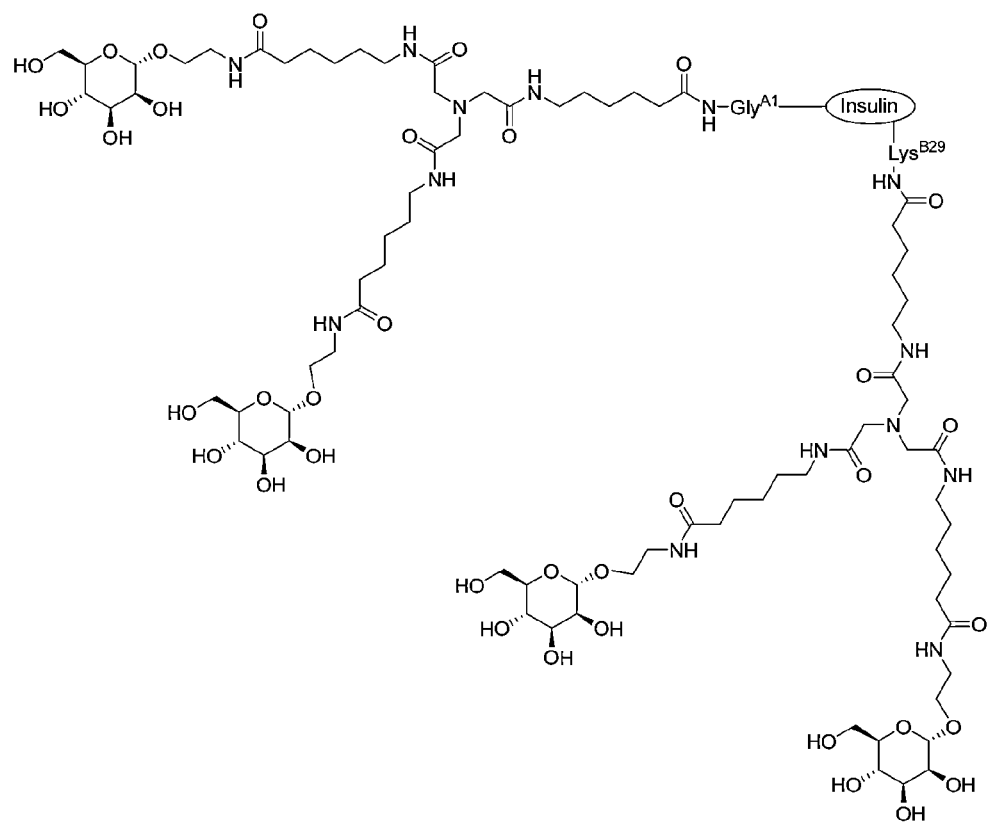
Figure 45:
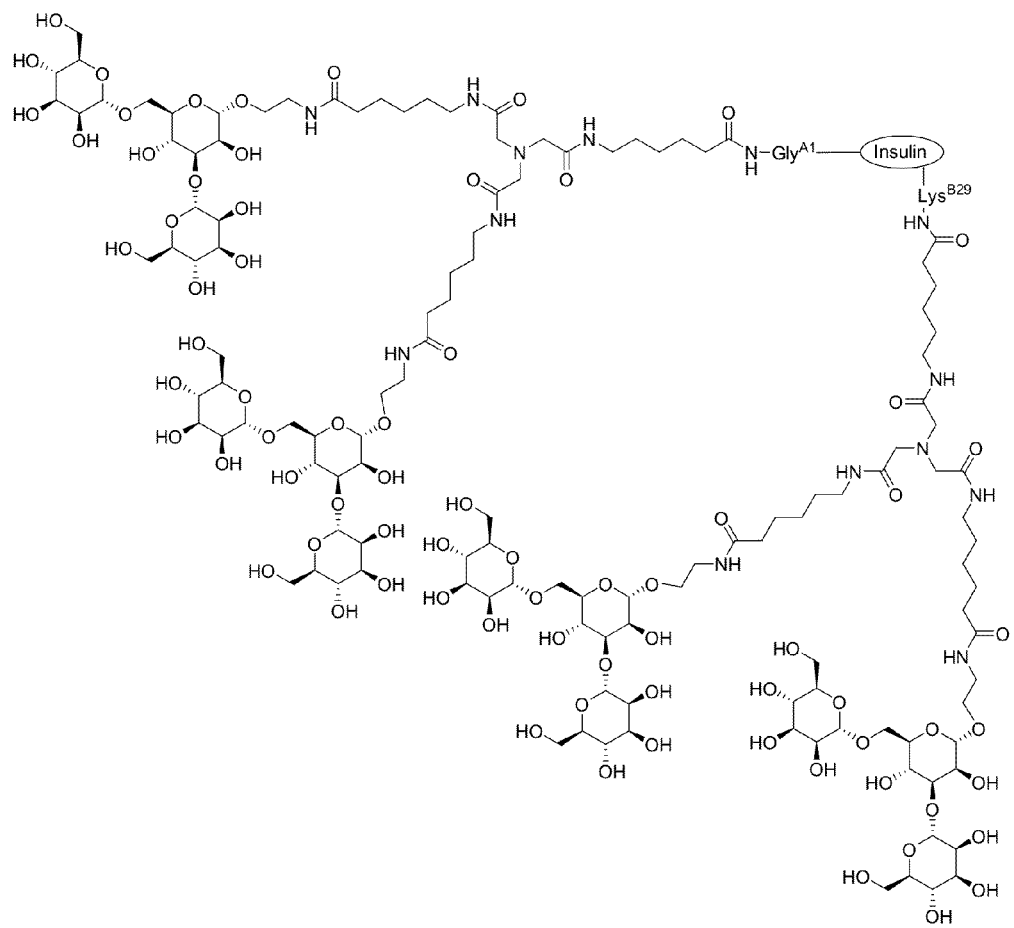
Figure 45:
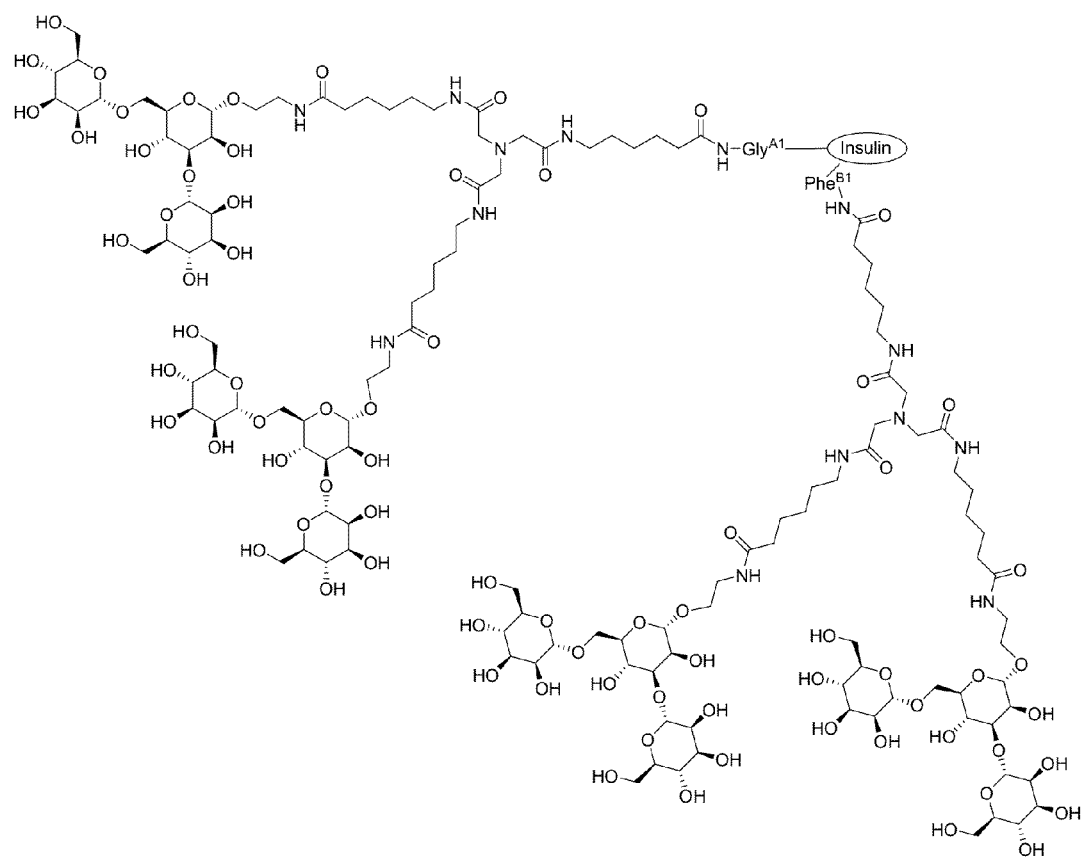
Figure 45:
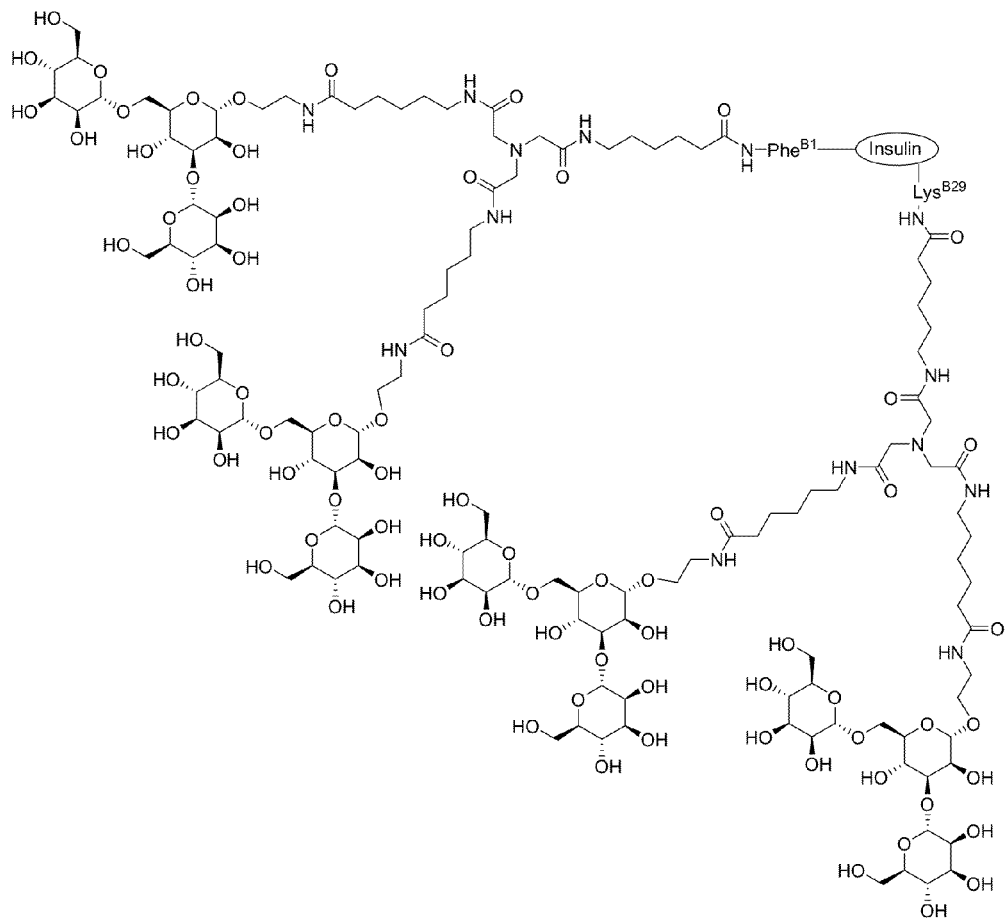
Figure 45:
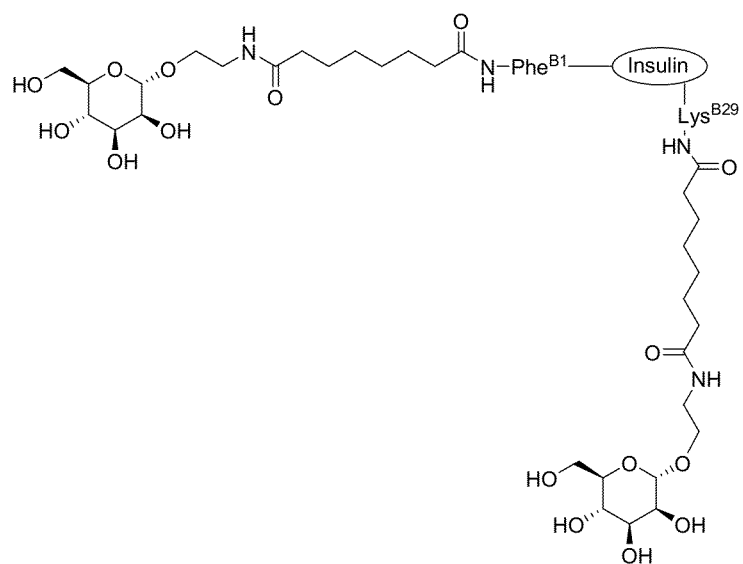

The structures of exemplary conjugates I-1 to I-17 and II-1 to II-7 that are described and used in the Examples are shown in FIG. 45.

I. Methods of Making Exemplary Conjugates

This first set of examples describes various methods for making exemplary conjugates. The examples also include assays for purifying and assaying the starting ingredients and final products. It is to be understood that these methods can be modified to produce other conjugates that fall within the scope of the invention.

Example 1

Synthesis of Azidoethylglucose (AzEG)

a. Synthesis of Bromoethyleglucose

DOWEX 50Wx4 resin (Alfa Aesar, Ward Hill, Mass.) was washed with deionized water to remove color. A mixture of 225 gm D-glucose (1.25 mol; 1 equiv., Alfa Aesar) and 140 gm DOWEX 50Wx4 was treated with 2.2 L 2-bromoethanol (30.5 mol, 25 equiv.; 124.97 gm/mol; 1.762 gm/mL; BP=150 C; Alfa Aesar) and the stirred mixture heated to 80 C for 4 hours. The reaction was monitored by TLC (20% methanol/dichloromethane (DCM)). Reaction was complete after about four hours, and it was allowed to cool to room temperature. The solution was filtered to remove the resin, and the resin washed with ethyl acetate and DCM. The resulting filtrate was stripped to an amber oil in a rotory evaporator. A total of 400 gm after stripping.

The amber oil was purified on silica gel (4 kg silica packed in DCM) in the following manner. The crude was dissolved in DCM and loaded onto the column, and then eluted with 2×4 L 10% methanol/DCM; 2×4 L 15% methanol/DCM; and 3×4 L 20% methanol/DCM. Product containing fractions (on the basis of TLC) were pooled and stripped to dryness to afford 152 gm of 1-α-bromoethyl-glucose (42%).

b. Conversion of Bromoethylglucose to Azidoethylglucose (AzEM)

A 5 L round bottom three-necked flask, equipped with a heating mantle, an overhead stirrer, and a thermometer, was charged with 150 gm bromoethylglucose (525 mmol). The oil was dissolved in 2 L water and treated with 68.3 gm sodium azide (1.05 mol, 2 equiv.; 65 gm/mol; Alfa-Aesar) followed by 7.9 gm sodium iodide (52.5 mmol, 0.08 equiv.; 149.89 gm/mol; Alfa-Aesar) and the solution warmed to 50 C and stirred overnight. The solution was cooled to room temperature and concentrated to dryness on the rotovap. The solid residue was digested with 3×500 mL of 5:1 vol. CHCl$_3$:MeOH at 40 C. The combined organic portions were filtered and evaporated to dryness to afford azidoethylglucose (86 gm) as an off-white solid. TLC (20% MeOH/DCM; char with H$_2$SO$_4$): single spot, indistinguishable from the starting material.

c. Repurification of Azidoethylglucose 32 gm of azidoethylglucose was taken into 100 mL water. The turbid solution was filtered through a glass microfibre filter (Whatman GF/B). The golden filtrate was evaporated to a solid on a rotovapor. The solid was taken into methanol (100 mL) and the turbid solution was again filtered through a glass microfibre filter. The resulting pale yellow filtrate was stripped to a solid under vacuum.

The solid was taken into a minimum of methanol (50 mL) and ethyl acetate (150 mL) was added slowly with stirring. The heavy slurry was cooled and filtered. The solid was air dried (hygroscopic) and put in a 60 C oven overnight. TLC has very little origin material. Yield 15.4 gm. The Mother Liquor was evaporated under vacuum to a yellow gum. No attempt was made to further purify this material at this time.

Example 2

Synthesis of Azidoethylmannose (AzEM)

a. Synthesis of Bromoethylmannose

DOWEX 50Wx4 resin (Alfa Aesar, Ward Hill, Mass.) is washed with deionized water to remove color. A mixture of 225 gm D-mannose (1.25 mol; 1 equiv., Alfa Aesar) and 140 gm DOWEX 50Wx4 is treated with 2.2 L 2-bromoethanol (30.5 mol, 25 equiv.; 124.97 gm/mol; 1.762 gm/mL; BP=150 C; Alfa Aesar) and the stirred mixture heated to 80 C for 4 hours. The reaction is monitored by TLC (20% methanol/dichloromethane (DCM)). Reaction is complete after about four hours, and then allowed to cool to room temperature. The solution is filtered to remove the resin, and the resin washed with ethyl acetate and DCM. The resulting filtrate is stripped to an amber oil in a rotory evaporator.

The amber oil is purified on silica gel (4 kg silica packed in DCM) in the following manner. The crude is dissolved in DCM and loaded onto the column, and then eluted with 2×4 L 10% methanol/DCM; 2×4 L 15% methanol/DCM; and 3×4 L 20% methanol/DCM. Product containing fractions (on the basis of TLC) are pooled and stripped to dryness to afford 152 gm of 1-α-bromoethyl-mannose (42%).

b. Conversion of Bromoethylmannose to Azidoethylmannose (AzEM)

A 5 L round bottom three-necked flask, equipped with a heating mantle, an overhead stirrer, and a thermometer, is charged with 150 gm bromoethylmannose (525 mmol). The oil is dissolved in 2 L water and treated with 68.3 gm sodium azide (1.05 mol, 2 equiv.; 65 gm/mol; Alfa-Aesar) followed by 7.9 gm sodium iodide (52.5 mmol, 0.08 equiv.; 149.89 gm/mol; Alfa-Aesar) and the solution warmed to 50 C and stirred overnight. The solution is cooled to room temperature and concentrated to dryness on the rotovap. The solid residue is digested with 3×500 mL of 5:1 vol. CHCl$_3$:MeOH at 40 C. The combined organic portions are filtered and evaporated to dryness to afford azidoethylmannose as an off-white solid.

c. Repurification of Azidoethylmannose 32 gm of azidoethylmannose is taken into 100 mL water. The turbid solution is filtered through a glass microfibre filter (Whatman GF/B). The filtrate is evaporated to a solid on a rotovapor. The solid is taken into Methanol (100 mL) and the turbid solution is again filtered through a glass microfibre filter. The resulting pale yellow filtrate is stripped to a solid under vacuum.

The solid is taken into a minimum of methanol (50 mL) and ethyl acetate (150 mL) is added slowly with stirring. The heavy slurry is cooled and filtered. The solid is air dried (hygroscopic) and put in a 60 C oven overnight. The Mother Liquor is evaporated under vacuum to a yellow gum.

Example 3

Synthesis of Azidoethylmannobiose (AzEBM)

The AzEM compound from Example 2 is selectively protected using benzene dimethyl ether, purified by column chromatography and subsequently reacted with benzyl bromide to give 1-α-(2-azidoethyl)-4,6-benzaldehyde diacetal-3-benzyl-mannopyranoside. The product is subsequently glycosylated with 1-α-bromo-2,3,4,6-tetrabenzoylmannopyranoside using silver triflate chemistry under rigorously anhydrous conditions to give the protected-azidoethylmannobiose product. The intermediate product is then deprotected to remove the benzoyl groups to give AzEBM.

Example 4

Synthesis of Azidoethylmannotriose (AzETM)

a. 1-α-bromo-2,3,4,6-tetrabenzoyl-mannose

To a 500 mL 3-neck flask containing a stir bar and nitrogen inlet was added 40 gm (60.9 mmole) of pentabenzoylmannose and 80 mL methylene chloride. The resulting solution was cooled in an ice bath to <5 C, and 80 mL 33% HBr-acetic acid solution was added via an addition funnel at such a rate to maintain the reaction temperature <10 C. Upon complete addition (~30 min.) the ice bath was removed and stirring was continued for 3 hours.

The reaction solution was diluted with an equal volume (160 mL) of DCM and extracted successively with water (2×500 mL), saturated bicarbonate (2×50 mL) and Brine (1×50 mL), dried over magnesium sulfate and the solvent evaporated to give 41 gm of solid foam. (Theoretical yield 40.1 gm) and was stored under N$_2$ in a freezer. This material was used without further purification. The reaction was monitored by TLC: silica gel (Hexane/Ethyl Acetate, 7/3) starting material R$_f$ 0.65, product R$_f$ 0.8 UV visualization. $^1$H NMR (CDCl$_3$) δ 8.11 (d, 2H), 8.01 (m, 4H), 7.84 (d, 2H), 7.58 (m, 4H), 7.41 (m, 6H), 7.28 (t, 2H), 6.58 (s, 1H), 6.28 (m, 2H), 5.8 (m, 1H), 4.75 (dd, 1H) 4.68 (dd, 1H) 4.5 (dd, 1H).

b. 1-Azidoethyl-2,4-dibenzoylmannose

To a 1.0 L, 3-neck flask containing a stir bar, nitrogen inlet and 300 mL of anhydrous acetonitrile was added 25 gm 1-azidoethylmannose (100.4 mmole), and 50 mL triethyl orthobenzoate (220 mmole, 2.2 equiv.). The resulting slurry was stirred at room temperature and 0.8 mL (10 mmole) trifluoroacetic acid (TFA) was added neat. The solution cleared within 10 minutes and stirring was continued for an additional two hours, then 25 mL of 10% aqueous TFA was added and stirring was continued for an additional 2 hours to hydrolyze the intermediate to the ester isomers. The solvent was evaporated under vacuum to a viscous oil, which was triturated with 50 mL DCM and again evaporated to a viscous oil.

Toluene (70 mL) was added to the residue and the viscous solution was seeded with 2,4-dibenzoylazidoethylmannose. A fine precipitate formed within 15 minutes and stirring was continued overnight at room temperature. The resulting heavy suspension was set in the freezer for 2-4 hours, then filtered and the solid washed with ice cold toluene (2×10 mL). The solid was air dried to a constant weight to give 21 gm (TY 22.85 gm 50% isomeric purity) of ~95% isomeric purity. The product was taken into 40 mL toluene, stirred for 1 hour and then set in the freezer for an additional 2 hours. The solid was filtered and washed (2×10 mL) with ice cold toluene and air dried to a constant weight to give 18.5 gm of the single isomer product 2,4-dibenzoylazidoethylmannose in 83% yield. The mother liquors contained the undesired isomer and a small amount of the desired isomer. The reaction was monitored by TLC: SG (Hexane/Ethyl Acetate 7/3) Starting Material R$_f$ 0.0, orthoester intermediate R$_f$ 0.9. (Hexane/Ethyl Acetate: 8/2) SM R$_f$ 0.8, desired isomer R$_f$ 0.4, un-desired isomer R$_f$ 0.2 $^1$H NMR 300 MHz (CDCl$_3$) δ 8.12 (t, 4H), 7.66 (t, 2H), 7.5 (m, 4H), 5.56 (t, 1H), 5.48 (m, 1H), 5.14 (m, 1H), 4.5 (dd, 1H), 4.0 (m, 2H), 3.8 (m, 3H), 3.56 (m, 1H), 3.44 (m, 1H).

c. Perbenzoylated-man(α-1,3)-man(α-1.6)-α-1-azidoethylmannopyranoside

To a 1.0 L 3-neck flask with a stir bar, nitrogen inlet was added 41 gm crude 1-bromo-tetrabenzoymannose (60.9 mmole, ~2.5 equiv.) in 185 mL DCM. To this was added 11.2 gm 2,4-dibenzoylazidoethylmannose (24.5 mmole) followed by 11.2 gm 4A sieves. The slurry was stirred a room temperature for 10 minutes and cooled to −15° C. in a methanol/ice bath.

In a separate dark vessel was added 190 mL toluene followed by 15.1 gm silver-trifluoromethanesulfonate (AgOTf) (58.8 mmole, 2.4 equiv.) and was stirred into solution in the dark. This solution was transferred to a large addition funnel, and added drop-wise to the stirring suspension while protecting the reaction from light. The reaction temperature was maintained <−10 C by adjusting the AgOTf addition rate. Upon complete addition (~30 minutes) the cold bath was removed and the reaction stirred for an additional 2 hours until a single product remained by TLC (SG, Hexane/Ethyl Acetate: 7/3, Bromo R$_f$ 0.9, azido R$_f$ 0.4, trios product R$_f$ 0.5, uv visualization).

Triethylamine (7 mL, 5.0 equiv.) was added followed by 200 mL DCM. The resulting slurry was filtered through a pad of silica gel and celite and washed with 2×75 mL DCM. The solvent was evaporated under vacuum and the residue taken into ethyl acetate and washed sequentially with water (2×100 mL), bicarb (2×50 mL), brine (1×75 mL) and dried over magnesium sulfate. The solvent was evaporated under vacuum to give 39 gm of solid foam (TY 39.5 gm). $^1$H NMR 300 MHz (CDCl$_3$) δ 8.3 (d, 2H), 8.2 (m, 8H), 7.85 (d, 4H), 7.75 (dd, 4H), 7.3-7.65 (m, 30H), 7.2 (t, 2H), 6.05 (m, 4H), 5.9 (t, 2H), 5.63 (m, 2H), 5.38 (s, 2H), 5.18 (d, 1H), 4.65 (m, 4H), 4.5 (m, 2H), 4.35 (m, 4H), 3.8 (m, 2H), 3.54 (m, 2H).

d. Man(α-1,3)-man(α-1.6)-α-1-azidoethylmannopyranoside

To a stirring suspension of 3.0 gm perbenzoylated-man (α-1,3)-man(α-1.6)-α-1-azidoethylmannopyranoside (1.86 mmole) in 40 mL methanol was added 0.2 mL 4.28M sodium methoxide in methanol. The resulting suspension was stirred 20 hours at room temperature giving a clear solution. The completion of the reaction was monitored by TLC, (SG, hexane/ethyl acetate: 8/2 SM $R_f$ 0.4, product $R_f$ 0.0).

The methanol was evaporated under vacuum giving an oily semi-solid. The residue was taken into ethyl acetate (50 mL) and stirred for 3 hours. The solid was filtered, washed with fresh ethyl acetate (2×20 mL) and air dried to a constant weight to give 1.09 gm (TY 1.07 gm) of product. The mother liquors contained residual methyl benzoate, the de-protection by-product.

Example 5

Synthesis of Aminoethyl-Saccharides (AEG, AEM, AEBM, AETM) from Azidoethyl-Saccharides (AzEG, AzEM, AzEBM, AzETM)

Figure 10:
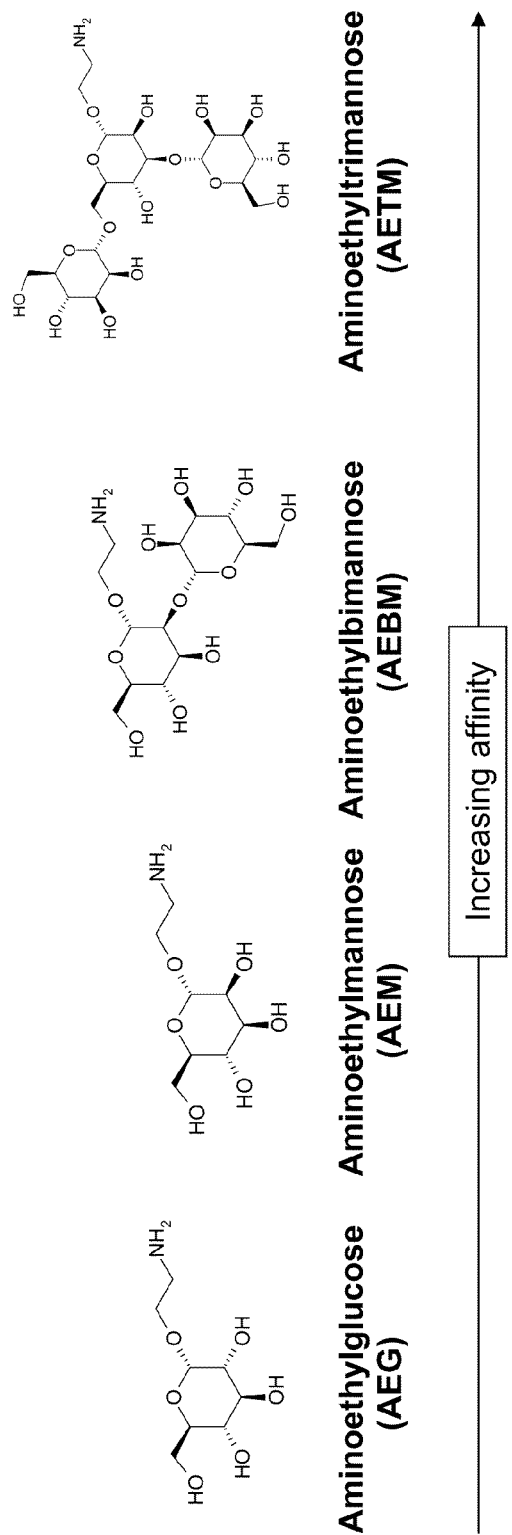
FIG. 10: Chemical structures of AEG, AEM, AEBM and AETM. The affinity of these saccharide based ligands for Con A increases as shown.
Figure 11:
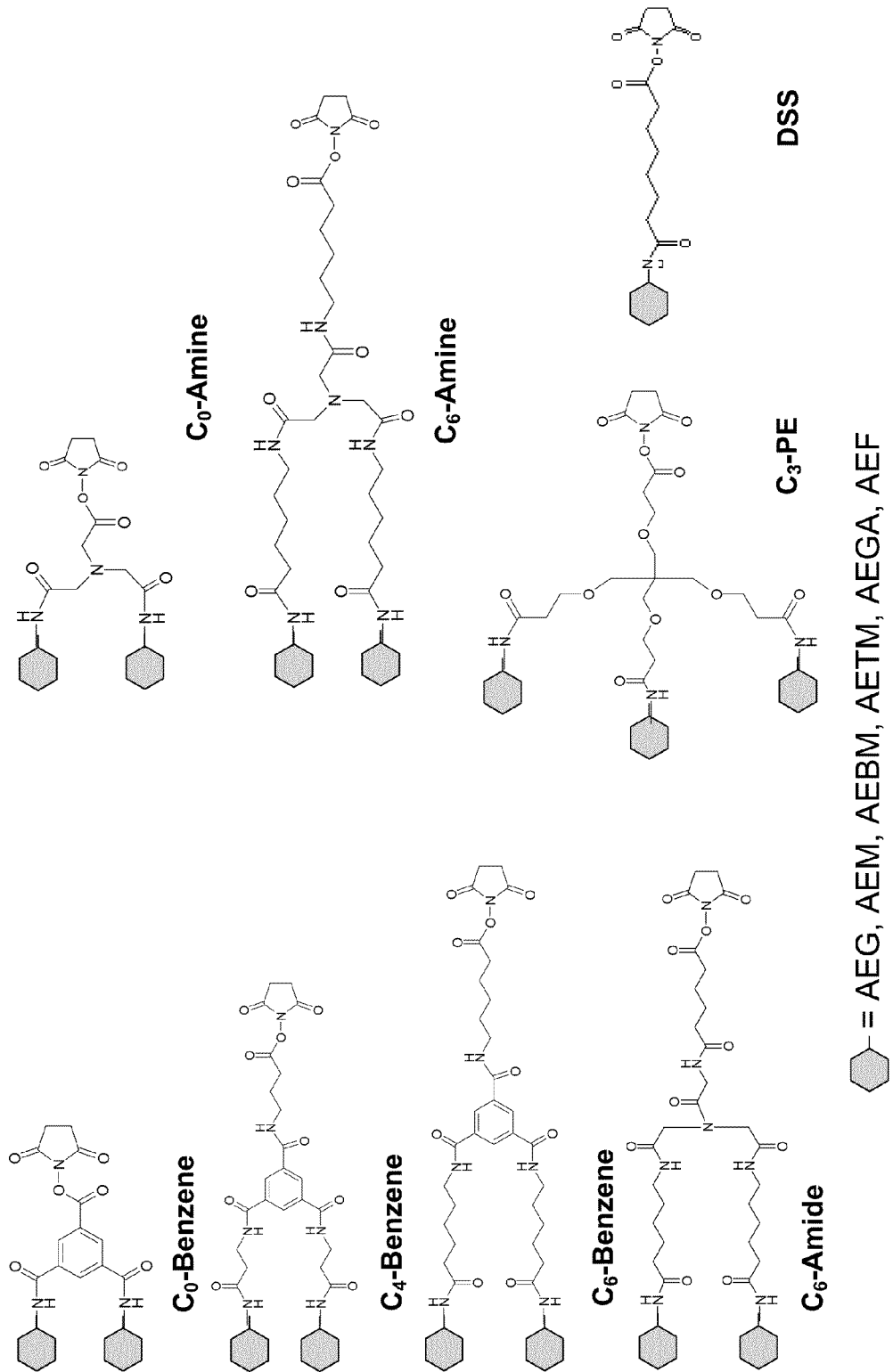
FIG. 11: Chemical structures of some exemplary non-dendrimeric conjugate intermediates. Exemplary conjugate ligands that include a saccharide are also shown for illustrative purposes (AEG, AEM, AEBM, AETM, AEGA and AEF).

The azido-terminated compounds from Examples 1-4 are readily hydrogenated at room temperature by using palladium/carbon catalyst, a small amount of acetic acid, and ethanol as a solvent to give the corresponding amine-terminated compounds. FIG. 10 shows the chemical structures of AEG, AEM, AEBM, AETM. The process is identical to the one described for AETM below, except that those skilled in the art will understand that the amounts of reagents, solvents, etc. should be scaled to the number of moles of saccharide-ligand to be hydrogenated.

a. Man (α-1,3)-Man(α-1.6)-α-1-aminoethylmannopyranoside ("aminoethyltrimannose", AETM)

To a solution of 5.3 gm (9.25 mmole) man(α-1,3)-man(α-1.6)-α-1-azidoethylmannopyranoside in 100 mL water and 50 mL ethanol was added 0.8 gm 5% Pd/C. The vigorously stirring suspension was hydrogenated at 30-40 psi for 48 hours or until no starting material was apparent by TLC (SG, Methanol, SM $R_f$ 0.75, Pdt $R_f$ 0.0, PMA vis.). The suspension was filtered over celite, which was rinsed with ethanol (2×50 mL) and the filtrate concentrated under vacuum.

HPLC of this material (C18, 3% Acetonitrile/97% 0.1% $H_3PO_4$, 220 nm, 2 ml/min) gave uv adsorption of the injection column void material, Rt 2.5 minutes, indicative of benzoate ester.

The filtrate was diluted with 70 mL water and 12 mL of 1N NaOH and the solution stirred overnight at room temperature (HPLC: no uv material at column void Rt 2.5 min., uv material at Rt 10.5 minutes co-eluting with benzoic acid). 2 gm of decolorizing charcoal were added and the stirring suspension heated to 80 C, cooled to room temperature and filtered over celite. The filtrate pH was adjusted to 8.0 with 2N HCl and the colorless solution concentrated under vacuum to about 50% volume.

The solution was loaded onto a resin column (Dowex 50W, 50 gm) and washed with water until eluting fractions were neutral to pH (6×75 mL) removing any residual acid byproducts. The amine product was washed off the column with 0.25N ammonium hydroxide (6×75 mL) and the fractions containing the amine product-ninhydrin detection were combined and concentrated to 25-30 mL under vacuum. This concentrated solution was added drop-wise to 300 mL stirring ethanol and stirring continued for an additional 2 hours. The product was filtered, washed with fresh ethanol (2×50 mL) and air dried to a constant weight. The resulting white amorphous solid was dried further in a vacuum oven at 80 C for 5 hours to give 4.1 gm of a white granular solid (TY 5.1 gm). The NMR was clean of any aromatic protons. $^1$H NMR 300 MHz ($D_2O$) δ 5.08 (s, 1H), 4.87 (s, 1H), 4.81 (s, 1H), 4.8-3.6 (m, 18H), 2.9 (m, 2H).

Example 6

Dipropargyl Saccharide Synthesis and Production of AE-Ligand a. Synthesis of diethyl dipropargylmalonate

Diethylmalonate (122.5 g, 0.7648 mol) was added to absolute ethanol (800 ml) containing sodium ethoxide (prepared from sodium metal, 38.5 g, 1.67 mol). After 30 min, propargyl bromide (200 g, 1.68 mol) was slowly added to the stirred suspension, keeping the temperature under 60 C. The mixture was refluxed overnight (15 hours). The precipitated salts were removed by filtration and washed with ethanol. Solvent was removed in vacuo, and the residue diluted with water and extracted with ethanol (2×200 ml). The combined extracts were dried over MgSO4, filtered, washed with Et2O and the solvent removed in vacuo to afford a golden colored oil. The oil was placed on high vacuum (40 C) for 3 hours and allowed to stand. Solids began to crystallize forming an oily solid. Let stand overnight (16 hours). Cyclohexane was charged to flask, solids broken-up, filtered, and washed with cyclohexane to afford white crystalline product (81 gm, 44.8% yield). Reaction was followed by GC.

b. Synthesis of dipropargylmalonic acid

Diethyl dipropargyl malonate (80 gm, 0.339 mol) was refluxed in 600 ml of 10% alcoholic potassium hydroxide overnight (15 hours). Solvent was removed in vacuo and the residue was acidified with 3N HCl. The residue was extracted with Et2O (2×300 ml). The combined extracts were dried over MgSO4, filtered, washed with Et2O and concentrated in vacuo to an oil. Placed on high vac (40 C) for 2 hours and let stand to afford dipropargylmalonic acid as an oil (46 gm, 75.4% yield). Reaction was followed by GC.

c. Synthesis of dipropargylacetic acid

The dipropargylmalonic acid (26 gm, 0.443 mol) was heated neat at 135 C until $CO_2$ stopped evolving. It was then allowed to cool to an oil. The oil was distilled at 0.5 psi. The remaining oily residue in the distillation flask and solid were combined (15.7 gm, 79.9% yield) and was used as is in the next step.

d. Synthesis of [2-(3-prop-2-ynyl-hex-5-ynoylamino)-ethyl]-carbamic acid t-butyl ester N-boc-ethylenediamine (18.3 gm, 0.1143 mol) in 50 ml of $CH_3CN$ was added slowly via an addition funnel to a stirred solution containing dipropargylacetic acid (15.56 gm, 0.1143 mol), TBTU (36.74 gm, 0.114 mol) and DIPEA (29.6 gm, 0.229 mol) in 300 ml of $CH_3CN$ at 0 C. Precipitation occurred. The ice bath was removed and the product was stirred at ambient temperature overnight (16 hours). The reaction was now totally homogeneous. The solution was concentrated in vacuo and the residue was diluted with 800 ml of water. The resulting solids were filtered, washed copiously with water, and vacuum dried to give 14.3 gm of crude product. Re-crystallization (2×) from DCM, filtration and washing with hexanes affords the product (9.85 gm, 31% yield, 98% purity by HPLC (214 nm)).

e. Click reaction of azidosaccharide to [2-(3-prop-2-ynyl-hex-5-ynoylamino)-ethyl]-carbamic acid t-butyl ester To 1,1 dipropargyl-acetyl-(-1N, 2N—BOC-1,2-diaminoethyl)amide (DP, 418 mg, 1.5 mmole) in DCM (20 mL) was added drop-wise TFA (4 mL) over 5 minutes at 0 C. The darkening solution was stirred at room temperature overnight. The volatiles were evaporated under reduced pressure. Toluene (20 mL) was added to the residue and stripped under reduced pressure two times. The resulting dark oil was used without further purification.

To this residue was added THF (20 mL) and water (20 mL) with stirring for 15 minutes. Copper Sulfate (225 mg, 0.9 mmole) was added followed by sodium ascorbate (180 mg, 0.9 mmole). The resulting mixture was heated to 55-60 C for 6 hours and then stirred at room temperature for 18 hours. The solution was evaporated under reduced pressure to approx. half volume and filtered through a microfibre glass filter. The resulting clear solution was placed on a resin column (Dowex 50X-2) which was washed with water (6×75 mL) until neutral pH, and then washed with 10% $NH_4OH$ (8×75 mL). The fractions staining positive with Ninhydrin were combined and evaporated under reduced pressure to a glassy solid. The glass residue was taken into water (250 mL) and treated with 0.5 gm charcoal and heated to reflux. The cooled slurry was filtered over celite and a microfibre filter. The resulting pale yellow solution was evaporated to a glassy solid under reduced pressure and methanol was added and evaporated (2×) to give a off white foam (0.9 gm, TY 1.0 gm).

Example 7

Tripropargyl Saccharide Synthesis and Production of AE-Ligand a. 2-(2-BOC-aminoethyl)thioacetamide-tris[(propargyloxy)methyl]aminomethane To a solution of t-butyl N-(2-mercaptoethyl)carbamate (Frontrun Organix, Ipswich, Mass.; 177.26 mg, 1 mmole) in ethanol (5 mL) was added NaOH (1.1 mmole) with stirring at room temperature. To this solution was added 2-bromoacetamide-tris[(propargyloxy)methyl]aminomethane (356 mg, 1.0 mmole, see J. Org. Chem. 73, 5602, 2008) and stirring was continued for 20 hours (TLC SG 8/2 hexane/ethyl acetate, pdt $R_f$ 0.4). The solvent was evaporated under vacuum and the residue was taken into ethyl acetate (40 mL) and washed successively with water (25 mL), 0.5 N NaOH (25 mL) and Brine (25 mL), dried over $Na_2SO_4$ filtered and concentrated to an oil (360 mg, TY 452.3 mg). NMR $CDCl_3$, (ppm): 7.05 (s, 1H, N—H); 5.25 ((s, 1H, N—H); 4.85 (s, 6H); 3.85 (s, 6H); 3.3 (m, 2H); 3.15 (s, 2H); 2.7 (m, 2H); 2.42 (s, 3H); 1.22 (s, 9H).

b. 2-(2-aminoethyl)thioacetamide-tris[(triazolo-1-(2-ethylmannose) 4-methoxy)methyl]aminomethane To a stirring solution of 2-(2-BOC-aminoethyl)thioacetamide-tris[(propargyloxy)methyl]aminomethane (1 gm, 2.21 mmole) in DCM (40 mL) at room temperature was added TFA (4 mL) dropwise. The resulting solution was stirred overnight. The solvents were removed under vacuum and the residue taken into toluene (15 mL) and evaporated to dryness.

The residue was taken into THF (40 mL), water (40 mL) and stirred into solution. Azidoethylmannose (3.75 eq., 2.0 gm, 8.3 mmole) was added followed by copper sulfate (500 mg, 2.0 mmole) and sodium ascorbate (400 mg, 2.0 mmole) and the resultant mixture stirred at 55-60 C (oil bath) for 6 hours, cooled to room temperature and stirred overnight. The resulting mixture was concentrated under vacuum to one half volume and filtered thru a micro-glass filter. The filtrate was loaded on a resin column (Dowex 50w 50×4-100) and eluted with water (6×75 mL) until neutral. The column was then eluted with 15% Ammonium Hydroxide (10×75 mL) and the fractions positive to ninhydrin were pooled and concentrated to a glassy foam (1.29 gm, TY (MW 1099 g/mol), 53% over two steps).

Example 8

Synthesis of $NH_2$—B1-BOC2(A1,B29)-insulin

In a typical synthesis, 4 g of powdered insulin (Sigma Aldrich, St. Louis, Mo.) is dissolved in 100 ml of anhydrous DMSO at room temperature followed by the addition of 4 ml of triethylamine (TEA). The solution is stirred for 30 minutes at room temperature. Next, 1.79 ml (2.6 equivalents) of di-tert-butyl-dicarbonate/THF solution (Sigma Aldrich, St. Louis, Mo.) is slowly added to the insulin-TEA solution and mixed for approximately one hour. The reaction is quenched via the addition of 4 ml of a stock solution containing 250 ul of ethanolamine in 5 ml of DMSO followed by mixing for five minutes. After quenching, the entire solution is poured into 1600 ml of acetone and mixed briefly with a spatula. Next, 8×400 µl aliquots of a 18.9% HCl:water solution are added dropwise over the surface of the mixture to precipitate the reacted insulin. The precipitated material is then centrifuged and the supernatant decanted into a second beaker while the precipitate cake is set aside. To the supernatant solution, another 8×400 µl aliquots of a 18.9% HCl:water solution are added dropwise over the surface of the mixture to obtain a second precipitate of reacted insulin. This second precipitate is centrifuged and the supernatant is discarded. The combined centrifuge cakes from the two precipitation steps are washed once with acetone followed by drying under vacuum at room temperature to yield the crude powder which typically contains 60% of the desired BOC2 product and 40% of the BOC3 material.

A preparative reverse phase HPLC method is used to isolate the pure BOC2-insulin from the crude powder. Buffer A is deionized water containing 0.1% TFA and Buffer B is acetonitrile containing 0.1% TFA. The crude powder is dissolved at 25 mg/ml in a 70% A/30% B mixture and syringe filtered prior to injection on the column. Before purification, the column (Waters SymmetryPrep C18, 7 um, 19×150 mm) is equilibrated at 15 ml/minutes with a 70% A/30% B mobile phase using a Waters DeltaPrep 600 system. Approximately 5 ml of the crude powder solution is injected onto the column at a flow rate of 15 ml/minutes over the course of 5 minutes after which a linear gradient is employed from 70% A/30% B to 62% A/38% B over the course of the next 3.5 minutes and held there for an additional 2.5 minutes. Using this method, the desired BOC2 peak elutes at approximately 10.6 minutes followed closely by the BOC3 peak. Once collected, the solution is rotovapped to remove acetonitrile and lyophilized to obtain pure BOC2-insulin powder. Identity is verified by LC-MS (HT Laboratories, San Diego, Calif.) and site of conjugation determined by N-terminal sequencing (Western Analytical, St. Louis, Mo.).

Example 9

Synthesis of benzene-1,3,5-tricarboxy-(N-ω-aminoacid-NHS ester) amide frameworks A solution of 1,3,5-benzenetricarbonyl chloride (1 gm, 3.8 mmole) in dichloromethane (DCM) (5 mL) is added dropwise to a vigorously stirring solution of an ω-aminoacid (3.1 equivalents) in 1N NaOH (25 mL) in an ice bath. The ice bath is removed and stirring is continued for 4 hours at room temperature. 2N HCl (~15 mL) is added dropwise to approximately pH 2 and the resulting slurry is stirred for an additional 2 hours. The precipitate is filtered, washed with cold water (2×20 mL) and dried in air under vacuum and then in a 60 C oven overnight. The resulting white solid is used without further purification. Yield for each ω-aminoacid (4-aminobutyric acid: yield 1.6 gm, 91%; 6-aminocaproic acid: yield 1.9 gm, 92%)

The above material is taken into DMSO (5 mL) containing N-hydroxysuccinimide (3.1 mmole, 3.1 equiv.) and N-(3-dimethylaminopropyl)-N'-ethylcarbodiimide (EDCI, 3.6 mmole, 3.6 equiv.) is added at room temperature. The resulting solution is stirred for 24 hours, diluted with water (125 mL) and extracted with ethyl acetate (3×50 mL). The combined organic phase is washed with water (2×50 mL), brine (1×50 mL) and dried over MgSO$_4$. The solvent is evaporated and the semi-solid residue triturated with acetonitrile (10 mL). The solid is filtered and washed with cold solvent, dried in air under vacuum and then in a 60 C oven overnight. The product is free of urea bi-product. Benzene-1,3,5-tricarboxy-(N-6-aminocaproic-NHS ester)amide (TSB-C6): 304 mg, 36%, mp 140-142 C. Benzene-1,3,5-tricarboxy-(N-4-butyric-NHS-ester)amide (TSB-C4): 245 mg, 45%, mp 182-184 C.

Example 10

Dendritic Framework Synthesis a. Hydrogenation of Nitro-Group Containing, Alkyne-Terminally Functionalized Dendrons Dendrons containing either n=2, 4, or 8 terminal alkynes and a nitropropionic acid core are obtained (e.g., from Polymer Factory, Sweden) and used without further purification. The dendron is dissolved in 100 mL a 50:50 vol. mixture of DCM and ethanol, and 0.8 gm of 5% Pd/C is added. The vigorously stirring suspension is hydrogenated at 30-40 psi for 48 hours or until no starting material is apparent by TLC. The suspension is filtered over celite, which is rinsed with ethanol (2×50 mL) and the filtrate concentrated under vacuum.

The filtrate is diluted with 70 mL water and 12 mL of 1N NaOH and the solution stirred overnight at room temperature. 2 gm of decolorizing charcoal are added and the stirring suspension heated to 80 C, cooled to room temperature and filtered over celite. The filtrate pH is adjusted to 8.0 with 2N HCl and the colorless solution concentrated under vacuum to about 50% volume.

The solution is loaded onto a resin column (Dowex 50W, 50 gm) and washed with water until eluting fractions are neutral to pH (6×75 mL) removing any residual acid by-products. The amine product is washed off the column with 0.25N ammonium hydroxide (6×75 mL) and the fractions containing the amine product (ninhydrin detection) are combined and evaporated to vacuum using a rotary evaporator.

b. Reaction of Dendron (Amine, Alkyne-4) with Azidoethyl Mannose

The dendron product containing the amino core and four terminal alkyne groups obtained after hydrogenation (8.3 mmol) is taken into THF (40 mL), water (40 mL) and stirred into solution. Azidoethylmannose (4.75 eq., 2.53 gm, 10.51 mmole) is added followed by copper sulfate (500 mg, 2.0 mmole) and sodium ascorbate (400 mg, 2.0 mmole) and the resultant mixture stirred at 55-60 C (oil bath) for 6 hours, cooled to room temperature and stirred overnight. The resulting mixture is concentrated under vacuum to one half volume and filtered thru a micro-glass filter. The filtrate is loaded on a resin column (Dowex 50w 50×4-100) and eluted with water (6×75 mL) until neutral. The column is then eluted with 15% ammonium hydroxide (10×75 mL) and the fractions positive to ninhydrin are pooled and concentrated to a glassy foam.

Example 11

Amine-Functionalized Drug Conjugation with Multivalent Activated Esters in Organic Solvent (Drug Added First)

A framework containing N-terminal activated esters is dissolved at 60 mM in 1.0 ml of anhydrous DMSO followed by the addition of 400 ul (excess) of triethylamine (TEA). The solution is stirred rapidly for 10 minutes at room temperature. The amine-bearing drug is then dissolved separately in 7.9 ml of DMSO at a concentration of 7.4 mM. Once dissolved, the entire drug solution is added dropwise over the course of 10 minutes to the framework/DMSO/TEA solution followed by room temperature mixing for two hours. The remaining activated esters are then reacted with amine-functionalized ligands in the following manner. A 370 mM solution of ligand is prepared in an appropriate volume of dry DMSO. Once dissolved, enough solution is added to provide a number of reactive equivalents equal to three times the number of initial activated ester groups, N, minus one. For example, if there are N=3 initial activated ester groups per framework, then (3×(3−1)×60 mM/370 mM)=0.973 ml of ligand solution are added. If there are N=4 initial activated ester groups per framework, then (3×(4−1)×60 mM/370 mM)=1.46 ml of ligand solution are added, and so on. After the ligand solution is added, the solution is stirred for one more hour at room temperature to ensure complete reaction.

The resulting solution is then superdiluted by 10× into a 20 mM pH 5.0 HEPES buffered saline solution containing 0.150 M NaCl followed by pH adjustment with dilute HCl to a final pH of 8.0. The aqueous solution is first purified by size exclusion using an appropriate solid phase for the desired separation of conjugated and unconjugated materials. The solution passing through the column void volume is then concentrated using an appropriately sized ultrafiltration membrane to approximately 10 ml. This solution is further purified to obtain the desired product using preparative reverse phase HPLC on a Waters C8, 7 um, 19×150 mm column. Buffer A is deionized water containing 0.1% TFA and Buffer B is acetonitrile containing 0.1% TFA. Before purification, the column is equilibrated at 15 ml/minutes with a 80% A/20% B mobile phase using a Waters DeltraPrep 600 system. Approximately 5 ml of the crude solution is injected onto the column over the course of 2 minutes at a flow rate of 15 ml/minutes after which a linear gradient is employed from 80% A/20% B to 75% A/25% B over the next 5 minutes followed by a slower linear gradient from 75% A/25% B to 62% A/38% B over the next 22 minutes. The retention time of the desired peak will vary depending on the drug, framework, and ligand used. Once collected, the solution is rotovapped to remove acetonitrile and lyophilized to obtain pure conjugate whose identity may be verified by LC-MS (HT Laboratories, San Diego, Calif.).

Example 12

B1-Insulin Conjugates with Multivalent Saccharides—Homogeneous Ligand

Using the method described in Example 11 and the amine-bearing drug, $NH_2$—B1-BOC2(A1,B29)-insulin (MW=6,008 g/mol) of Example 8, insulin conjugates were prepared with the following frameworks and ligands. Tris-Succinimidyl-1,3,5-benzenetricarboxylate (TSB), tris-Succinimidyl aminotriacetate (TSAT), tris-Succinimidyl (6-aminocaproyl) aminotriacetate (TSAT-C6), and tetrakis-(N-succinimidyl carboxypropyl)pentaerythritol TSPE activated ester frameworks were purchased from Molecular Biosciences (Boulder, Colo.) and used without further purification. The TSB-C4 and TSB-C6 frameworks were synthesized according to Example 9. The AEM, AEBM, and AETM ligands were synthesized according to Examples 1-5. The appropriately sized size exclusion medium is Biogel P2 (Bio-Rad Laboratories, Hercules, Calif.), and the appropriately sized ultrafiltration membrane molecular weight cutoff is 3 kD.

In all cases, the BOC protecting groups were removed by dissolving the lyophilized powder obtained according to Example 11 in 90% TFA/10% anisole for one hour at 4 C followed by 10× superdilution in 25 mM HEPES pH 8.2 buffer containing 0.150M NaCl. The pH was adjusted to between 7.0 and 8.0 using NaOH solution after which the material is passed through a Biogel P2 column to remove anisole, BOC and other low MW byproducts of deprotection, as well as any other contaminating salts. The deprotected, purified aqueous conjugate solution was then concentrated using Amicon 3K membranes (Millipore, Billerica, Mass.) to approximately 58 U of insulin/ml (based on A280 measurements) and stored at 4 C until needed. Because the starting $NH_2$—B1-BOC2(A1,B29)-insulin material only possesses one free amine group at the Phe-B1 terminus, the Phe-B1 is the only site of insulin conjugation to the framework as verified in each deprotected final product by N-terminal sequencing.

In the following table (and others like it in the Examples) the framework MW values are for the activated esters of the frameworks. This is so one can immediately calculate the mass of activated ester framework to add to the reaction mixture. Once reacted, the framework loses the activated esters and so the MW contribution in the final product is much lower.

| Conjugate | Framework | Framework MW | Ligand | AE-sugar MW | Purity (HPLC) | MW (LC-MS) | Sugar/Insulin |
|---|---|---|---|---|---|---|---|
| TSB-AEM-2 (B1) | TSB | 501 | AEM | 223 | 97% | 6410 | 2.0 |
| TSB-AEBM-2 (B1) | TSB | 501 | AEBM | 385 | 94% | 6734 | 2.0 |
| TSB-AETM-2 (B1) | TSB | 501 | AETM | 547 | 96% | 7057 | 2.0 |
| TSB-C4-AEM-2 (B1) | TSB-C4 | 755 | AEM | 223 | 95% | 6665 | 2.0 |
| TSB-C4-AEBM-2 (B1) | TSB-C4 | 755 | AEBM | 385 | 97% | 6989 | 2.0 |
| TSB-C4-AETM-2 (B1) | TSB-C4 | 755 | AETM | 547 | 95% | 7313 | 2.0 |
| TSB-C6-AEM-2 (B1) | TSB-C6 | 882 | AEM | 223 | 99% | 6791 | 2.0 |
| TSB-C6-AEBM-2 (B1) | TSB-C6 | 882 | AEBM | 385 | 99% | 7114 | 2.0 |
| TSB-C6-AETM-2 (B1) | TSB-C6 | 882 | AETM | 547 | 95% | 7438 | 2.0 |
| TSAT-AEM-2 (B1) | TSAT | 482 | AEM | 223 | 98% | 6390 | 2.0 |
| TSAT-AEBM-2 (B1) | TSAT | 482 | AEBM | 385 | 95% | 6714 | 2.0 |
| TSAT-AETM-2 (B1) | TSAT | 482 | AETM | 547 | 94% | 7038 | 2.0 |
| I-1: TSAT-C6-AEM-2 (B1) | TSAT-C6 | 822 | AEM | 223 | 97% | 6730 | 2.0 |
| I-3: TSAT-C6-AEBM-2 (B1) | TSAT-C6 | 822 | AEBM | 385 | 99% | 7054 | 2.0 |
| I-2: TSAT-C6-AETM-2 (B1) | TSAT-C6 | 822 | AETM | 547 | 97% | 7378 | 2.0 |
| I-16: TSPE-AEM-3 (B1) | TSPE | 813 | AEM | 223 | 98% | 6829 | 3.0 |
| TSPE-AEBM-3 (B1) | TSPE | 813 | AEBM | 385 | 97% | 7314 | 3.0 |
| TSPE-AETM-3 (B1) | TSPE | 813 | AETM | 547 | 94% | 7802 | 3.0 |

Example 13

B1-Insulin Conjugates with Multivalent Saccharides—Mixed Ligands

Using the method described in Example 11 and the amine-bearing drug, $NH_2$—B1-BOC2(A1,B29)-Insulin (MW=6,008 g/mol) of Example 8, insulin conjugates were prepared which possessed a mixture of saccharide ligands connected to the framework.

The TSAT-C6 and TSPE activated ester frameworks were purchased from Molecular Biosciences (Boulder, Colo.) and used without further purification. The AEM, AEBM, and AETM were synthesized according to Examples 1-5. The appropriately sized size exclusion medium is Biogel P2 (Bio-Rad Laboratories, Hercules, Calif.), and the appropriately sized ultrafiltration membrane molecular weight cutoff is 3 kD.

In all cases, the BOC protecting groups were removed by dissolving the lyophilized powder obtained according to Example 11 in 90% TFA/10% anisole for one hour at 4 C followed by 10× superdilution in 25 mM HEPES pH 8.2 buffer containing 0.150M NaCl. The pH was adjusted to between 7.0 and 8.0 using NaOH solution after which the material was passed through a Biogel P2 column to remove anisole, BOC and other low MW byproducts of deprotection, as well as any other contaminating salts. The deprotected, purified aqueous conjugate solution was then concentrated using Amicon 3K membranes (Millipore, Billerica, Mass.) to the desired level and stored at 4 C until needed. Because the starting $NH_2$—B1-BOC2(A1,B29)-insulin material only possesses one free amine group at the Phe-B1 terminus, the Phe-B1 is the only site of insulin conjugation to the framework as verified in each deprotected final product by N-terminal sequencing.

between 7.0 and 8.0 using NaOH solution after which the material is passed through a Biogel P2 column to remove anisole, BOC and other low MW byproducts of deprotection, as well as any other contaminating salts. The deprotected, purified aqueous conjugate solution is then concentrated using Amicon 3K membranes (Millipore, Billerica, Mass.) to the desired level and stored at 4 C until needed. Because the starting $NH_2$—B1-BOC2(A1,B29)-Insulin material only possesses one free amine group at the Phe-B1 terminus, the Phe-B1 is the only site of insulin conjugation to the framework as verified in each deprotected final product by N-terminal sequencing.

| Conjugate Identity | Framework | Framework MW | Mixed Ligand | AE-sugar MW | Purity (HPLC) | MW (LC-MS) | Sugar/Insulin |
|---|---|---|---|---|---|---|---|
| TSPE-AEM-1-AETM-2 (B1) | TSPE | 813 | AEM/AETM (33/67 mol/mol) | 223/547 | 94% | 7478 | 1.0 AEM, 2.0 AETM |
| TSPE-AEM-2-AETM-1 (B1) | TSPE | 813 | AEM/AETM (67/33 mol/mol) | 223/547 | 94% | 7152 | 2.0 AEM, 1.0 AETM |
| TSAT-C6-AEM-1-AEBM-1(B1) | TSAT-C6 | 822 | AEM/AEBM (50/50 mol/mol) | 223/385 | 96% | 6892 | 1.0 AEM, 1.0 AEBM |
| I-4: TSAT-C6-AEBM-1-AETM-1 (B1) | TSAT-C6 | 822 | AEBM/AETM (50/50 mol/mol) | 385/547 | 95% | 7216 | 1.0 AEBM, 1.0 AETM |

Example 14

B1-Insulin Conjugates with Multivalent Saccharides Using Premade Multivalent Saccharides Using the method described in Example 11 and the amine-bearing drug, $NH_2$—B1-BOC2(A1,B29)-insulin (MW=6,008 g/mol) of Example 8, the following insulin conjugates are prepared from pre-synthesized multivalent amine-containing ligands. The disuccinimidyl suberate (DSS) and TSAT-C6 activated ester frameworks are purchased from Molecular Biosciences (Boulder, Colo.) and used without further purification. Divalent AEM-2, AEBM-2, and AETM-2 molecules containing a terminal reactive amine are prepared by conjugating two of each ligand to a suitable framework to which a reactive amine is also conjugated. Trivalent AEM-3, AEBM-3, and AETM-3 molecules containing a terminal reactive amine are prepared by conjugating three of each ligand to a suitable framework to which a reactive amine is also conjugated. The appropriately sized size exclusion medium is Biogel P2 (Bio-Rad Laboratories, Hercules, Calif.), and the appropriately sized ultrafiltration membrane molecular weight cutoff is 3 kD.

In all cases, the BOC protecting groups are removed by dissolving the lyophilized powder obtained according to Example 11 in 90% TFA/10% anisole for one hour at 4 C followed by 10× superdilution in 25 mM HEPES pH 8.2 buffer containing 0.150 M NaCl. The pH is adjusted to

| | Synthesis Conditions | | | | Expected Conjugate Characterization | | |
|---|---|---|---|---|---|---|---|
| Conjugate Identity | Framework | Framework MW | Ligand | AE-sugar MW | MW (LC-MS) | Sugar/Insulin | |
| DSS-(AEM-2)-1 (B1) | DSS | 368 | AEM-2 | 676 | 6621 | 2.0 AEM | |
| DSS-(AEM-2)-1 (B1) | DSS | 368 | AEBM-2 | 1000 | 6945 | 2.0 AEBM | |
| DSS-(AEM-2)-1 (B1) | DSS | 368 | AETM-2 | 1324 | 7269 | 2.0 AETM | |
| DSS-(AEM-3)-1 (B1) | DSS | 368 | AEM-3 | 1085 | 7031 | 3.0 AEM | |
| DSS-(AEM-3)-1 (B1) | DSS | 368 | AEBM-3 | 1571 | 7517 | 3.0 AEBM | |
| DSS-(AEM-3)-1 (B1) | DSS | 368 | AETM-3 | 2057 | 8003 | 3.0 AETM | |
| TSAT-C6-(AEM-2)-2 (B1) | TSAT-C6 | 822 | AEM-2 | 676 | 7637 | 4.0 AEM | |
| TSAT-C6-(AEBM-2)-2 (B1) | TSAT-C6 | 822 | AEBM-2 | 1000 | 8285 | 4.0 AEBM | |
| TSAT-C6-(AEM-2)-2 (B1) | TSAT-C6 | 822 | AETM-2 | 1324 | 8933 | 4.0 AETM | |
| TSAT-C6-(AEM-3)-2 (B1) | TSAT-C6 | 822 | AEM-3 | 1085 | 8046 | 6.0 AEM | |

-continued

| Conjugate Identity | Synthesis Conditions | | | Expected Conjugate Characterization | | |
|---|---|---|---|---|---|---|
| | Framework | Framework MW | Ligand | AE-sugar MW | MW (LC-MS) | Sugar/Insulin |
| TSAT-C6-(AEBM-3)-2 (B1) | TSAT-C6 | 822 | AEBM-3 | 1571 | 9018 | 6.0 AEBM |
| TSAT-C6-(AEM-3)-2 (B1) | TSAT-C6 | 822 | AETM-3 | 2057 | 9990 | 6.0 AETM |

Example 15

B1-Insulin Conjugates with Multivalent Saccharides Using Dendritic Framework—Homogeneous Ligand 0.1 gm (0.098 mmol) dendron containing an amino core and four terminal alkyne groups prepared in Example 10b is dissolved at 100 mg/ml in anhydrous DMSO. The solution is added dropwise to a solution containing disuccinimidyl suberate (DSS, Molecular Biosciences, 0.098 mmol) and triethylamine (400 uL) and allowed to react for 1 hour at room temperature. This mixture is then added dropwise to a 50 mg/ml solution containing the $NH_2$—B1-BOC2(A1,B29)-insulin (MW=6,008 g/mol) of Example 8 (0.588 g, 0.098 mmol) and allowed to react for 2 hours.

The resulting conjugate is superdiluted in water, and the pH adjusted to 8.0. The solution is desalted using BioGel P2, followed by concentration using Amicon 3 k ultrafiltration devices. The resulting solution is purified by reverse phase chromatography, rotovapped to remove acetonitrile, and lyophilized. The BOC protecting groups are removed by dissolving the lyophilized powder in 90% TFA/10% anisole for one hour at 4 C followed by 10× superdilution in 25 mM HEPES pH 8.2 buffer containing 0.150 M NaCl. The pH is adjusted to between 7.0 and 8.0 using NaOH solution after which the material is passed through a Biogel P2 column to remove anisole, BOC and other low MW byproducts of deprotection, as well as any other contaminating salts. The deprotected, purified aqueous conjugate solution is then concentrated using Amicon 3K membranes (Millipore, Billerica, Mass.) to the desired level and stored at 4 C until needed. Because the starting $NH_2$—B1-BOC2(A1,B29)-insulin material only possesses one free amine group at the Phe-B1 terminus, the Phe-B1 is the only site of insulin conjugation to the framework and is verified in each deprotected final product by N-terminal sequencing.

Example 16

Synthesis of $NH_2$—B29-BOC2(A1,B1)-insulin a. Fmoc-1-(B29)-Insulin

In a typical synthesis, 4 gm of powdered insulin (Sigma Aldrich, St. Louis, Mo.) is dissolved in 100 ml of anhydrous DMSO at room temperature followed by the addition of 4 ml of triethylamine (TEA). The solution is stirred for 30 minutes at room temperature. Next, 1.2 equivalents of 9-fluorenylmethyl N-succinimidyl carbonate (Fmoc-NHS) (Sigma Aldrich, St. Louis, Mo.) is slowly added to the insulin-TEA solution as a 1.0 M solution of the Fmoc-NHS in THF. The reaction is mixed for approximately one hour. The reaction is quenched via the addition of 4 ml of a stock solution containing 250 ul of ethanolamine in 5 ml of DMSO followed by mixing for five minutes. After quenching, the entire solution is poured into 1600 ml of acetone and mixed briefly with a spatula. Next, 8×400 µl aliquots of a 18.9% HCl:water solution are added dropwise over the surface of the mixture to precipitate the reacted insulin. The precipitated material is then centrifuged and the supernatant decanted into a second beaker while the precipitate cake is set aside. To the supernatant solution, another 8×400 µl aliquots of a 18.9% HCl:water solution are added dropwise over the surface of the mixture to obtain a second precipitate of reacted insulin. This second precipitate is centrifuged and the supernatant is discarded. The combined centrifuge cakes from the two precipitation steps are washed once with acetone followed by drying under vacuum at room temperature to yield the crude powder which typically contains 20% of the Fmoc1 product, 65% of the Fmoc2 product, and 15% of unreacted insulin.

A preparative reverse phase HPLC method is used to isolate the pure desired Fmoc1-insulin from the crude powder. Buffer A is deionized water containing 0.1% TFA and Buffer B is acetonitrile containing 0.1% TFA. The crude powder is dissolved at 25 mg/ml in a 70% A/30% B mixture and syringe filtered prior to injection on the column. Before purification, the column (Waters SymmetryPrep C18, 7 um, 19×150 mm) is equilibrated at 15 ml/minutes with a 70% A/30% B mobile phase using a Waters DeltaPrep 600 system. Approximately 5 ml of the crude powder solution is injected onto the column at a flow rate of 15 ml/minutes over the course of 5 minutes after which a linear gradient is employed from 70% A/30% B to 62% A/38% B over the course of the next 3.5 minutes and held there for an additional 2.5 minutes. Using this method, the desired Fmoc1 peak elutes at approximately 3 minutes after the unreacted RHI peak, followed closely by the Fmoc2-insulin peak. Once collected, the solution is rotovapped to remove acetonitrile and lyophilized to obtain pure Fmoc1-insulin powder. Identity is verified by LC-MS (HT Laboratories, San Diego, Calif.) and site of conjugation determined by N-terminal sequencing (Western Analytical, St. Louis, Mo.).

b. BOC2(A1,B1)-Fmoc-(B29)-Insulin

In a typical synthesis, 1 g of Fmoc1-(B29)-insulin is dissolved in 25 ml of anhydrous DMSO at room temperature followed by the addition of 1 ml of triethylamine (TEA). The solution is stirred for 30 minutes at room temperature. Next, 0.379 ml (2.2 equivalents) of di-tert-butyl-dicarbonate/THF solution (Sigma Aldrich, St. Louis, Mo.) is slowly added to the insulin-TEA solution and mixed for approximately one hour. The reaction is quenched via the addition of 1 ml of a stock solution containing 250 ul of ethanolamine in 5 ml of DMSO followed by mixing for five minutes. After quenching, the entire solution is poured into 400 ml of acetone and mixed briefly with a spatula. Next, 8×100 µl aliquots of a 18.9% HCl:water solution are added dropwise over the surface of the mixture to precipitate the reacted insulin. The precipitated material is then centrifuged and the supernatant decanted into a second beaker while the precipitate cake is set aside. To the supernatant solution, another 8×100 µl aliquots of a 18.9% HCl:water solution are added dropwise over the surface of the mixture to obtain a second precipitate of reacted insulin. This second precipitate is centrifuged and the supernatant is discarded. The combined centrifuge cakes from the two precipitation steps are washed once with acetone followed by drying under vacuum at room temperature to yield the crude powder which typically contains greater than 90% of the desired BOC2-Fmoc-1 product.

A preparative reverse phase HPLC method is used to isolate the pure BOC2-Fmoc-1-insulin from the crude powder. Buffer A is deionized water containing 0.1% TFA and Buffer B is acetonitrile containing 0.1% TFA. The crude powder is dissolved at 25 mg/ml in a 70% A/30% B mixture and syringe filtered prior to injection on the column. Before purification, the column (Waters SymmetryPrep C18, 7 um, 19×150 mm) is equilibrated at 15 ml/minutes with a 70% A/30% B mobile phase using a Waters DeltraPrep 600 system. Approximately 5 ml of the crude powder solution is injected onto the column at a flow rate of 15 ml/minutes over the course of 5 minutes after which a linear gradient is employed from 70% A/30% B to 62% A/38% B over the course of the next 3.5 minutes and held there for an additional 2.5 minutes. Using this method, the desired BOC2-Fmoc-1 peak elutes at approximately 5 minutes after the Fmoc1-insulin starting material. Once collected, the solution is rotovapped to remove acetonitrile and lyophilized to obtain pure BOC2(A1,B1)-Fmoc(B29)-insulin powder. Identity is verified by LC-MS (HT Laboratories, San Diego, Calif.) and site of conjugation determined by N-terminal sequencing (Western Analytical, St. Louis, Mo.).

c. $NH_2$—(B29)-BOC2(A1,B)-Insulin

The Fmoc protecting group of the BOC2(A1,B1)-Fmoc (B29) is removed by dissolving the lyophilized powder obtained according to the previous step in 20% piperidine in dimethylformamide (DMF) for 30 minutes at 4 C followed by 10× superdilution in 25 mM HEPES pH 8.2 buffer containing 0.150 M NaCl. The pH is adjusted to between 7.0 and 8.0 using NaOH solution after which the material is passed through a Biogel P2 column to remove Fmoc, DMF, and any other contaminating salts. The $NH_2$—(B29)-BOC2(A1,B1)-insulin is lyophilized into a powder if needed or used directly in aqueous solution if desired.

Example 17

Synthesis of $NH_2$—B29-BOC2(A1,B1)-Insulin Conjugates

All of the multivalent-ligand-drug conjugates described in previous examples using the $NH_2$—B1-BOC2(A1,B29)-insulin of Example 8 may be prepared instead using the $NH_2$—B29-BOC2(A1,B1)-insulin of Example 16. All of the resulting conjugates will possess the same MW and degree of substitution characteristics, but the site of conjugation to the insulin molecule will be at the epsilon B29 amino group and not the N-terminal Phe-B1. This can be confirmed by N-terminal sequencing.

Example 18

Amine-Functionalized Drug Conjugation with Multivalent Activated Esters in Organic Solvent (Drug Added Last)

This example describes an alternative to the method described in Example 11 in which the drug is added to the framework before the ligand(s). In this example the ligand(s) are added to the framework before the drug.

A framework containing N terminal activated esters is dissolved at 60 mM in 1 ml of anhydrous DMSO followed by the addition of 400 ul (excess) of triethylamine (TEA). The solution is stirred rapidly for 10 minutes at room temperature. In parallel, a 122 mM solution of ligand is prepared in an appropriate volume of anhydrous DMSO. Once dissolved, enough ligand solution is added dropwise over the course of ten minutes to provide a number of reactive equivalents equal to exactly the number of activated ester groups on the framework, N, minus one. For example, if there are N=3 activated ester groups on the framework, then (1×(3-1)×60 mM/122 mM)=0.98 ml of ligand solution are added. If there are N=4 activated ester groups on the framework, then (1×(4-1)×60 mM/122 mM)=1.5 ml of ligand solution are added, and so on. After the ligand solution is added, the solution is stirred for two hours at room temperature.

The amine-bearing drug is then dissolved separately in 7.5 ml of anhydrous DMSO at a concentration of 8.1 mM. Once dissolved, the entire drug solution is added over the course of one minute to the framework/DMSO/ligand/TEA solution followed by room temperature mixing for an additional two hours to ensure complete reaction.

The resulting solution is then superdiluted by 10× into a 20 mM pH 5.0 HEPES buffered saline solution containing 0.150 M NaCl followed by pH adjustment with dilute HCl to a final pH of 8.0. The aqueous solution is first purified by size exclusion using an appropriate solid phase for the desired separation of conjugated and unconjugated materials. The solution passing through the column void volume is then concentrated using an appropriately sized ultrafiltration membrane to approximately 10 ml. This solution is further purified to obtain the desired product using preparative reverse phase HPLC on a Waters SymmetryPrep C18, 7 um column, 19×150 mm. Buffer A is deionized water containing 0.1% TFA and Buffer B is acetonitrile containing 0.1% TFA. Before purification, the column is equilibrated at 15 ml/minutes with a 80% A/20% B mobile phase using a Waters DeltraPrep 600 system. Approximately 5 ml of the crude solution is injected onto the column over the course of 2 minutes at a flow rate of 15 ml/minutes after which a linear gradient is employed from 80% A/20% B to 75% A/25% B over the next 5 minutes followed by a slower linear gradient from 75% A/25% B to 62% A/38% B over the next 22 minutes. The retention time of the desired peak will vary depending on the drug, framework, and ligand used. Once collected, the solution is rotovapped to remove acetonitrile and lyophilized to obtain pure conjugate whose identity may be verified by LC-MS (HT Laboratories, San Diego, Calif.).

Example 19

B29-Insulin Conjugates with Multivalent Saccharides Produced in Organic Solvent from Unprotected Insulin This example makes use of the fact that in unprotected insulin, the Lys-B29 epsilon-amino moiety is the most reactive amine, followed by the A1 and then the B1. Therefore, when unprotected insulin is used as the amine-containing drug the resulting conjugate should be predominantly substituted at the Lys-B29 position. Using the method described in Example 18 and recombinant human insulin (MW=5808 Da, Sigma Aldrich, St. Louis, Mo.) as the amine-containing drug, the following insulin conjugates were prepared using the TSAT-C6 activated ester framework purchased from Molecular Biosciences (Boulder, Colo.). The AEM and AETM were synthesized as described previously. The appropriately sized size exclusion medium was Biogel P2 (Bio-Rad Laboratories, Hercules, Calif.), and the appropriately sized ultrafiltration membrane molecular weight cutoff was 3 kDa.

| Conjugate | Framework | Framework MW | Ligand | AE-sugar MW | Purity (HPLC) | MW (LC-MS) | Sugar/Insulin |
|---|---|---|---|---|---|---|---|
| I-7: TSAT-C6-AEM-2 (B29) | TSAT-C6 | 822 | AEM | 223 | 93% | 6729 | 2.0 |

-continued

| Conjugate | Framework | Framework MW | Ligand | AE-sugar MW | Purity (HPLC) | MW (LC-MS) | Sugar/Insulin |
|---|---|---|---|---|---|---|---|
| I-6: TSAT-C6-AETM-2 (B29) | TSAT-C6 | 822 | AETM | 547 | 95% | 7378 | 2.0 |

According to N-terminal sequencing, approximately 85% of the AEM-containing framework was conjugated to insulin via the Lys-B29 and approximately 87% of the AETM-containing framework was conjugated to insulin via the Lys-B29.

Example 20

Amine-Functionalized Drug Conjugation with Multivalent Activated Esters in Aqueous Solvent (Drug Added Last)

This example describes an alternative to the method described in Example 18 in which the reaction is performed in aqueous solvent instead of organic solvent.

The framework containing N terminal activated esters is dissolved at 60 mM in 6.25 ml of anhydrous DMSO followed by the addition of 2 ml (excess) of triethylamine (TEA). The solution is stirred rapidly for 10 minutes at room temperature. In parallel, a 448 mM solution of ligand is prepared in an appropriate volume of anhydrous DMSO. Once dissolved, enough ligand solution is added dropwise over the course of ten minutes to provide a number of reactive equivalents equal to 1.5 times the number of activated ester groups on the framework, N, minus one. For example, if there are N=3 activated ester groups on the framework, then (1.5×(3−1)×60 mM/448 mM)×6.25 ml=2.5 ml of ligand solution are added. If there are N=4 activated ester groups on the framework, then (1.5×(4−1)×60 mM/448 mM)×6.25 ml=3.8 ml of ligand solution are added, and so on. After the ligand solution is added, the solution is stirred for one hour at room temperature.

The amine-bearing drug is then dissolved separately at 17.2 mM in 2.67 ml of a 0.1M, pH 11 sodium carbonate buffer and the pH subsequently adjusted to 10.8 with 1.0N sodium hydroxide. Once dissolved, the entire framework/DMSO/ligand/TEA solution is added dropwise over the course of 75 minutes to the drug/carbonate buffer solution. During the addition, the pH of the resulting mixture is adjusted every 5 minutes to 10.8 if necessary using dilute HCl or NaOH. The solution is allowed to stir for an additional 15 minutes after the dropwise addition to ensure complete reaction.

The resulting solution is then superdiluted by 10× into a 20 mM pH 5.0 HEPES buffered saline solution containing 0.150 M NaCl followed by pH adjustment with dilute HCl to a final pH of 8.0. The aqueous solution is first purified by size exclusion using an appropriate solid phase for the desired separation of conjugated and unconjugated materials. The solution passing through the column void volume is then concentrated using an appropriately sized ultrafiltration membrane to approximately 40 ml. This solution is further purified to obtain the desired product using preparative reverse phase HPLC on a Waters SymmetryPrep C18, 7 um, 19×150 mm column. Buffer A is deionized water containing 0.1% TFA and Buffer B is acetonitrile containing 0.1% TFA. Before purification, the column is equilibrated at 15 ml/minutes with a 80% A/20% B mobile phase using a Waters DeltaPrep 600 system. Approximately 5 ml of the crude solution is injected onto the column over the course of 2 minutes at a flow rate of 15 ml/minutes after which a linear gradient is employed from 80% A/20% B to 75% A/25% B over the next 5 minutes followed by a slower linear gradient from 75% A/25% B to 62% A/38% B over the next 22 minutes. The retention time of the desired peak will vary depending on the drug, framework, and ligand used. Once collected, the solution is rotovapped to remove acetonitrile and lyophilized to obtain pure conjugate whose identity may be verified by LC-MS (HT Laboratories, San Diego, Calif.).

Example 21

B29-AEM-2-Insulin Conjugate Synthesized in Aqueous Solvent from Unprotected Insulin This example makes use of the fact that in unprotected insulin, the Lys-B29 epsilon-amino moiety is the most reactive amine, followed by the A1 and then the B1. Therefore, when unprotected insulin is used as the amine-containing drug the resulting conjugate should be predominantly substituted at the Lys-B29 position. Using the method described in Example 20 and recombinant human insulin (MW=5808, Sigma Aldrich, St. Louis, Mo.) as the amine-containing drug, an AEM-2 insulin conjugate was prepared using the TSAT-C6 activated ester framework purchased from Molecular Biosciences (Boulder, Colo.). The AEM used as the insulin analog was synthesized as described previously. The appropriately sized size exclusion medium was Biogel P2 (Bio-Rad Laboratories, Hercules, Calif.), and the appropriately sized ultrafiltration membrane molecular weight cutoff was 3 kD. The final product (95% pure by HPLC) was found to have the desired MW of 6729 g/mol (LC-MS), representing a total of 2.0 AEM molecules conjugated per insulin, with greater than 85% of the conjugate molecules conjugated at the Lys-B29 site (N-terminal sequencing).

Example 22

Generalized Amine-Functionalized Drug Conjugation with Aldehyde-Containing Framework a. Framework Functionalized with More than One Ligand and One Terminal Aldehyde First, a framework containing N terminal activated esters is dissolved at 60 mM in 27.0 ml of anhydrous DMSO followed by the addition of 800 ul (excess) of triethylamine (TEA). The solution is stirred rapidly for 10 minutes at room temperature. A stock solution of amine-bearing diethyl acetal is prepared at 580 mM in 5 ml of anhydrous DMSO. Once dissolved, 2.9 ml of the diethyl acetal solution are added dropwise over the course of 5 minutes to the framework/DMSO/TEA solution followed by room temperature mixing for an additional 15 minutes. The remaining activated esters are then reacted with amine-functionalized ligands in the following manner. A 370 mM solution of ligand is prepared in an appropriate volume of dry DMSO. Once dissolved, enough solution is added to provide a number of reactive equivalents equal to 1.5 times the number of initial activated ester groups, N, minus one. For example, if there are N=3 initial activated ester groups per framework, then (1.5×(3−1)×60 mM×27/370 mM)=13 ml of ligand solution are added. If there are N=4 initial activated ester groups per framework, then (1.5×(4−1)×60 mM×27/370 mM)=20 ml of ligand solution are added, and so on. After the ligand solution is added, the solution is stirred for an additional hour and 45 minutes at room temperature to ensure complete reaction. After reaction, the entire solution is diluted by a factor of ten with diethyl ether, mixed vigorously, and centrifuged to separate the dense bottom phase containing the desired material from the supernatant. After discarding the supernatant, the same volume of ethanol is added to generate a solid precipitated mass. After centrifuging and discarding the supernatant, the material is washed extensively with ethanol and ether and then dried under vacuum to yield the crude framework containing multiple ligands and a diethyl acetal group.

b. Conjugation of Amine-Functionalized Drug with Terminal Aldehyde

Once dried, the aldehyde group is generated from the diethyl acetal by dissolving the collected material in 60 ml of DI water with the solution pH adjusted to 1.0. The solution is mixed for 30 minutes after which 6 ml of a 200 mM HEPES pH 8.2 buffer containing 1.5 M NaCl is added and the solution pH adjusted to 6.5 using dilute NaOH solution. 48 mmol of the amine containing drug are added to the solution and the pH readjusted to 6.5 if necessary. Separately, a stock solution of reducing agent is prepared by dissolving 1.5 g of sodium cyanoborohydride (Sigma Aldrich, St. Louis, Mo.) in 15 ml of a 20 mM HEPES pH 7.0 buffer containing 0.150 M NaCl and the pH carefully adjusted to 6.5 with dilute HCl solution. 13 ml of the cyanoborohydride stock solution are added to the drug/framework/aldehyde solution and allowed to react overnight at room temperature.

The resulting aqueous solution is first purified by size exclusion using an appropriate solid phase for the desired separation of conjugated and unconjugated materials. The solution passing through the column void volume is then concentrated using an appropriately sized ultrafiltration membrane to approximately 10 ml. This solution is further purified to obtain the desired product using preparative reverse phase HPLC on a Waters SymmetryPrep C18, 7 um column, 19×150 mm. Buffer A is deionized water containing 0.1% TFA and Buffer B is acetonitrile containing 0.1% TFA. Before purification, the column is equilibrated at 15 ml/minutes with a 80% A/20% B mobile phase using a Waters DeltraPrep 600 system. Approximately 5 ml of the crude solution is injected onto the column over the course of 2 minutes at a flow rate of 15 ml/minutes after which a linear gradient is employed from 80% A/20% B to 75% A/25% B over the next 5 minutes followed by a slower linear gradient from 75% A/25% B to 62% A/38% B over the next 22 minutes. The retention time of the desired peak will vary depending on the drug, framework, and ligand used. Once collected, the solution is rotovapped to remove acetonitrile and lyophilized to obtain pure conjugate whose identity may be verified by LC-MS (HT Laboratories, San Diego, Calif.).

Example 23

AEM-2-Framework Containing a Terminal Reactive Aldehyde Group and Subsequent Insulin Conjugation at B1 a. TSAT Functionalized with 2 AEM and 1 Aminobutyraldehyde Diethyl Acetal (ABDA)

This material was synthesized according to the method described in Example 22a using TSAT (Molecular Biosciences, Boulder, Colo.) as the multivalent activated ester framework and 4-aminobutyraldehyde diethyl acetal (Sigma Aldrich, St. Louis, Mo.) as the amine-bearing diethyl acetal. AEM (MW=223 g/mol), synthesized as described previously was used as the ligand.

b. Conjugation of TSAT-AEM-2-ABDA with $NH_2$—B1-BOC2(A1,B29)-Insulin

This material was synthesized using the method described in Example 22b and the TSAT-AEM-2-ABDA produced in (a) above along with the amine-bearing drug, $NH_2$—B1-BOC2(A1,B29)-insulin (MW=6,008 g/mol), synthesized according to Example 8. The appropriately sized size exclusion medium was Biogel P2 (Bio-Rad Laboratories, Hercules, Calif.), and the appropriately sized ultrafiltration membrane molecular weight cutoff was 3 kD. Because the starting $NH_2$—B1-BOC2(A1,B29)-insulin material only possesses one free amine group at the Phe-B1 terminus, the Phe-B1 is the only site of insulin conjugation to the framework. The BOC protecting groups were removed by dissolving the lyophilized powder in 90% TFA/10% anisole for one hour at 4 C followed by 10× superdilution in 25 mM HEPES pH 8.2 buffer containing 0.150 M NaCl. The pH was adjusted to between 7.0 and 8.0 using NaOH solution after which the material was passed through a Biogel P2 column to remove anisole, BOC and other low MW byproducts of deprotection, as well as any other contaminating salts. The deprotected, purified aqueous conjugate solution was then concentrated using Amicon 3K membranes (Millipore, Billerica, Mass.) to the desired level and stored at 4 C until needed.

The final product (95% pure by HPLC) was found to have the desired MW of 6462 g/mol (LC-MS), representing a total of 2.0 AEM molecules conjugated per insulin, 99% of which were conjugated at the Phe-B1 site (N-terminal sequencing).

Example 24

AEM-3-Framework Containing a Terminal Reactive Aldehyde Group and Subsequent Insulin Conjugation at B1 a. TSPE Functionalized with 3 AEM and 1 Aminobutyraldehyde Diethyl Acetal (ABDA)

This material was synthesized according to the method described in Example 22a using TSPE (Molecular Biosciences, Boulder, Colo.) as the multivalent activated ester framework and 4-aminobutyraldehyde diethyl acetal (Sigma Aldrich, St. Louis, Mo.) as the amine-bearing diethyl acetal. AEM (MW=223 g/mol), synthesized as described previously, was used as the ligand.

b. Conjugation of TSPE-AEM-3-ABDA with $NH_2$—B—BOC2(A1,B29)-Insulin

This material was synthesized using the method described in Example 22b and the TSPE-AEM-3-ABDA produced in (a) above along with the amine-bearing drug, $NH_2$—B1-BOC2(A1,B29)-insulin (MW=6,008 g/mol), synthesized according to Example 8. The appropriately sized size exclusion medium was Biogel P2 (Bio-Rad Laboratories, Hercules, Calif.), and the appropriately sized ultrafiltration membrane molecular weight cutoff was 3 kD. Because the starting $NH_2$—B1-BOC2(A1,B29)-insulin material only possesses one free amine group at the Phe-B1 terminus, the Phe-B1 is the only site of insulin conjugation to the framework. The BOC protecting groups are removed by dissolving the lyophilized powder in 90% TFA/10% anisole for one hour at 4 C followed by 10× superdilution in 25 mM HEPES pH 8.2 buffer containing 0.150 M NaCl. The pH was adjusted to between 7.0 and 8.0 using NaOH solution after which the material was passed through a Biogel P2 column to remove anisole, BOC and other low MW byproducts of deprotection, as well as any other contaminating salts. The deprotected, purified aqueous conjugate solution was then concentrated using Amicon 3K membranes (Millipore, Billerica, Mass.) to the desired level and stored at 4 C until needed.

The final product (95% pure by HPLC) was found to have the desired MW of 6897 g/mol (LC-MS), representing a total of 3.0 AEM molecules conjugated per insulin, 99% of which were conjugated at the Phe-B1 site (N-terminal sequencing).

Example 25

AEM-3-Scaffold Containing a Terminal Reactive Aldehyde Group and Subsequent Insulin Conjugation at B1 Using Unprotected Insulin a. TSPE Functionalized with 3 AEM and 1 Aminobutyraldehyde Diethyl Acetal (ABDA)

This material is synthesized according to the method described in Example 22a using TSPE (Molecular Biosciences, Boulder, Colo.) as the multivalent activated ester scaffold and 4-aminobutyraldehyde diethyl acetal (Sigma Aldrich, St. Louis, Mo.) as the amine-bearing diethyl acetal. AEM (MW=223 g/mol), synthesized as described previously, was used as the ligand.

b. Conjugation of TSPE-AEM-3-ABDA with $NH_2$—B1-BOC2(A1,B29)-Insulin

This material was synthesized using the method described in Example 22b and the TSPE-AEM-3-ABDA produced in (a) above along with the amine-bearing drug, unmodified insulin (MW=5,808 g/mol, Sigma-Aldrich, St. Louis, Mo.). The appropriately sized size exclusion medium was Biogel P2 (Bio-Rad Laboratories, Hercules, Calif.), and the appropriately sized ultrafiltration membrane molecular weight cutoff was 3 kD. Although the starting unprotected insulin material possesses three free amine groups, the Phe-B1 is the predominant site of insulin conjugation to the scaffold due to the fact that the Phe-B1 (pKa~6.8) is the most reactive amine at pH 6.5. The lyophilized powder was dissolved in 25 mM HEPES pH 8.2 buffer containing 0.150 M NaCl. The pH was adjusted to between 7.0 and 8.0 using NaOH solution after which the material was then concentrated using Amicon 3K membranes (Millipore, Billerica, Mass.) to the desired level and stored at 4 C until needed.

The final product (95% pure by HPLC) was found to have the desired MW of 6897 g/mol (LC-MS), representing a total of 3.0 AEM molecules conjugated per insulin, >85% of which were conjugated at the Phe-B1 site (N-terminal sequencing).

Example 26

Mixed Framework Chemistry and Corresponding Separate Conjugation of Drug and Ligands Succinimidyl-3,5-dimaleimidophenyl benzoate (SDMB) can be purchased from Molecular Biosciences (Boulder, Colo.) and used in the following example without further purification. SDMB is dissolved at 60 mM in 1.0 ml of anhydrous DMSO followed by the addition of 400 ul (excess) of triethylamine (TEA). The solution is stirred rapidly for 10 minutes at room temperature. The amine-bearing drug is then dissolved separately in 7.5 ml of anhydrous DMSO at a concentration of 8.1 mM. Once dissolved, the entire SDMB solution is added dropwise over the course of ten minutes to the DMSO-drug solution followed by room temperature mixing for an additional two hours to ensure complete reaction.

The resulting solution is then superdiluted by 10× into a 20 mM pH 5.0 HEPES buffered saline solution containing 0.150 M NaCl followed by pH adjustment with dilute HCl to a final pH of 8.0. The aqueous solution is first purified by size exclusion using an appropriate solid phase for the desired separation of conjugated and unconjugated materials. The solution passing through the column void volume is then concentrated using an appropriately sized ultrafiltration membrane to approximately 10 ml.

Separately, 6.0 mmol of an amine-containing ligand is dissolved in a 20 mM pH 8.2 HEPES buffered saline solution containing 0.150 M NaCl at a concentration of 450 mM. To this solution, 6.6 mmol of iminothiolane (Sigma-Aldrich, St. Louis, Mo.) is added and allowed to react at pH 8.2 for 30 minutes at room temperature to convert the amine-terminal groups to terminal sulfhydryl groups. The resulting material is mixed with the 10 ml solution of drug-framework-di-maleimide conjugate produced in the previous step. The maleimide groups are allowed to react with the indicator-anolog sulfydryl groups at pH 8.2 for 2 hours to ensure complete reaction. The resulting solution is then purified by size exclusion using an appropriate solid phase for the desired separation of conjugated and unconjugated materials. The solution passing through the column void volume is then concentrated using an appropriately sized ultrafiltration membrane to approximately 10 ml.

Finally, this solution is further purified to obtain the desired product using preparative reverse phase HPLC on a Waters SymmetryPrep C18, 7 um column, 19×150 mm. Buffer A is deionized water containing 0.1% TFA and Buffer B is acetonitrile containing 0.1% TFA. Before purification, the column is equilibrated at 15 ml/minutes with a 80% A/20% B mobile phase using a Waters DeltaPrep 600 system. Approximately 5 ml of the crude solution is injected onto the column over the course of 2 minutes at a flow rate of 15 ml/minutes after which a linear gradient is employed from 80% A/20% B to 75% A/25% B over the next 5 minutes followed by a slower linear gradient from 75% A/25% B to 62% A/38% B over the next 22 minutes. The retention time of the desired peak will vary depending on the drug, framework, and ligand used. Once collected, the solution is rotovapped to remove acetonitrile and lyophilized to obtain pure conjugate whose identity may be verified by LC-MS (HT Laboratories, San Diego, Calif.).

Example 27

Insulin-Conjugated to Aminoethyl Saccharides Using Mixed Framework Chemistry Using the method described in Example 26 and the amine-bearing drug, $NH_2$—B1-BOC2(A1,B29)-insulin (MW=6,008 g/mol), synthesized according to Example 8, the following specific drug conjugates are obtained. AEM (MW=223 g/mol), AEBM (MW=385 g/mol), and AETM (MW=547 g/mol) are synthesized as previously described and used as the ligands in the synthesis. The appropriately sized size exclusion medium is Biogel P2 (Bio-Rad Laboratories, Hercules, Calif.), and the appropriately sized ultrafiltration membrane molecular weight cutoff is 3 kD.

In all cases, the BOC protecting groups are removed by dissolving the lyophilized powder obtained according to Example 26 in 90% TFA/10% anisole for one hour at 4 C followed by 10× superdilution in 25 mM HEPES pH 8.2 buffer containing 0.150 M NaCl. The pH is adjusted to between 7.0 and 8.0 using NaOH solution after which the material is passed through a Biogel P2 column to remove anisole, BOC and other low MW byproducts of deprotection, as well as any other contaminating salts. The deprotected, purified aqueous conjugate solution is then concentrated using Amicon 3K membranes (Millipore, Billerica, Mass.) to approximately 58 U of insulin/ml (based on A280 measurements) and stored at 4 C until needed. Because the starting $NH_2$—B1-BOC2(A1,B29)-insulin material only possesses one free amine group at the Phe-B1 terminus, the Phe-B1 will be the only site of insulin conjugation to the framework. This can be verified in each deprotected final product by N-terminal sequencing.

Synthesis Conditions

| Ligand | AE-sugar MW | AE-iminothiolane intermediate MW | Expected Conjugate Characterization | |
|---|---|---|---|---|
| | | | MW (LC-MS) | Sugar/Insulin |
| AEM | 223 | 360 | 6822 | 2.0 AEM |
| AEBM | 385 | 522 | 7146 | 2.0 AEBM |
| AETM | 547 | 684 | 7470 | 2.0 AETM |

Example 28

Generalized Click Chemistry for Drug Conjugation with Complementary Frameworks

A framework (8.3 mmol) containing at least one amino functionality and one or more terminal alkyne groups is taken into THF (40 mL), water (40 mL) and stirred into solution. An azidoethyl group-bearing drug (10.51 mmole) is added followed by copper sulfate (500 mg, 2.0 mmole) and sodium ascorbate (400 mg, 2.0 mmole). The resulting mixture is stirred at 55-60 C (oil bath) for 6 hours, cooled to room temperature, stirred overnight and concentrated under vacuum to one half volume and filtered thru a micro-glass filter. The filtrate is loaded on a resin column (Dowex 50w 50×4-100) and eluted with water (6×75 mL) until neutral. The column is then eluted with 15% ammonium hydroxide (10× 75 mL) and the fractions positive to ninhydrin are pooled and concentrated to a glassy foam.

Example 29

Conjugates Prepared Using Natural Insulins from Other Species Such as Bovine and Porcine Insulins from other species which contain at least one reactive amine functionality (e.g., bovine and porcine insulin) may be coupled using any of the methods used to conjugate human insulin. Those skilled in the art will appreciate that the molecular weights of the resulting conjugates made from bovine or porcine insulins will differ from those made from human insulin by the amounts listed in the following table.

| Type of Insulin | Molecular Weight (g/mol) | Difference in MW human insulin (g/mol) |
|---|---|---|
| Human insulin | 5808 | — |
| Porcine insulin | 5778 | −30 |
| Bovine insulin | 5733 | −75 |

Those skilled in the art will also appreciate that the resulting conjugates made from bovine or porcine insulin may have chromatographic peak retention times that differ slightly from those conjugates made from human insulin, due to the small differences in structures between the insulins.

Example 30

Conjugates Prepared with Insulin Analogs Such as Lispro, as Part, Glulysine, Glargine, and Detemir All known insulin analogs which contain at least one reactive amine functionality (e.g., lispro, as part, glulysine, glargine, and detemir) may be coupled using any of the methods used to conjugate human insulin. Those skilled in the art will appreciate that the molecular weights of the resulting conjugates made from insulin analogs will differ from those made from human insulin by the amounts listed in the following table.

| Type of Insulin | Molecular Weight (g/mol) | Difference in MW human insulin (g/mol) |
|---|---|---|
| Human insulin | 5808 | — |
| Insulin lispro | 5808 | — |
| Insulin aspart | 5832 | +24 |
| Insulin glulisine | 5823 | +15 |
| Insulin glargine | 6063 | +255 |
| Insulin detemir | 5913 | +105 |

Those skilled in the art will also appreciate that the resulting conjugates made from insulin analogs may have chromatographic peak retention times that differ slightly from those conjugates made from human insulin, due to the small differences in structures between the insulins.

The use of insulin glulisine (which does not contain a B29 lysine, but rather a B3 lysine) will give predominantly B3 conjugates when using unprotected insulin glulisine. However, if B1-insulin glulisine conjugates are desired, then BOC-(A1,B3)-insulin glulisine is first synthesized using the same protocol as BOC-(A1,B29)-human insulin as described in Example 8.

Example 31

Conjugates Prepared with Peptidic Insulin Secretagogue Conjugates

Peptidic insulin secretagogues (e.g., without limitation GLP-1 or the GLP-1 analog exanitide) which contain an N-terminal amine functionality may be coupled using any of the methods used to conjugate insulin.

II. In Vitro Assays of Exemplary Conjugates

This second set of examples describes various experiments investigating the in vitro properties of some exemplary conjugates.

Example 32

Synthesis of Insulin-Glycogen Conjugates

This comparative example describes the synthesis of an insulin-glycogen conjugate according to U.S. Patent Application Publication No. 20070099820. Briefly, 1 gm of commercially available, unpurified oyster glycogen (Type II, Sigma-Aldrich, St. Louis, Mo.) is dissolved in deionized water at a concentration of 10 mg/ml. Solid CNBr is added to the resulting solution at a CNBr to glycogen mass ratio of 0.68 and the pH maintained constant at 10.7+/−0.2 using 3N sodium hydroxide (NaOH) solution. After stirring for 15 minutes, another equal mass of solid CNBr equal is added and the pH maintained constant at 10.7+/−0.2 while stirring for 45 minutes. Insulin is then added to the solution at an insulin to glycogen mass ratio of 0.60 and the pH adjusted to 9.15 using solid sodium bicarbonate. The solution is stirred overnight, ultrafiltered exhaustively against deionized water using a 50 kDa MWCO polyethersulfone disc membrane filter (Millipore, Bedford, Mass.), and lyophilized. The resulting powder is then purified from unconjugated insulin by gel filtration HPLC (Waters, Milford, Mass.) using a 1 M acetic acid mobile phase over a Superdex™ 30 HiLoad 16/60 (Amersham Biosciences, Piscataway, N.J.) packed column. The insulin glycogen fraction is then lyophilized to obtain the conjugate as a pure white powder. The resulting purified material contained 1.0 wt % of insulin per insulin-glycogen conjugate as measured using amino acid analysis (UCLA Biopolymers Laboratory, Los Angeles, Calif.).

Example 33

Liquid Chromatography Analysis

This example describes the differences between the RP-HPLC profiles of insulin-glycogen synthesized according to Example 32 and an exemplary conjugate synthesized according to the present invention. 100 ul of a 5 mg/ml solution of insulin-glycogen synthesized according to Example 32 and 100 ul of a 1 mg/ml solution of exemplary conjugate were injected separately onto a Waters Symmetry C8 5 um column (4.6 mm×250 mm), equilibrated with a 80% Water/20% Acetonitrile (CH3CN) mobile phase (each containing 0.1% TFA). The exemplary conjugate used in this study was synthesized using TSAT-C6 as the framework, AEM as the ligand, and $NH_2$—B1-BOC2(A1,B29)-insulin as the drug.

Figure 1:
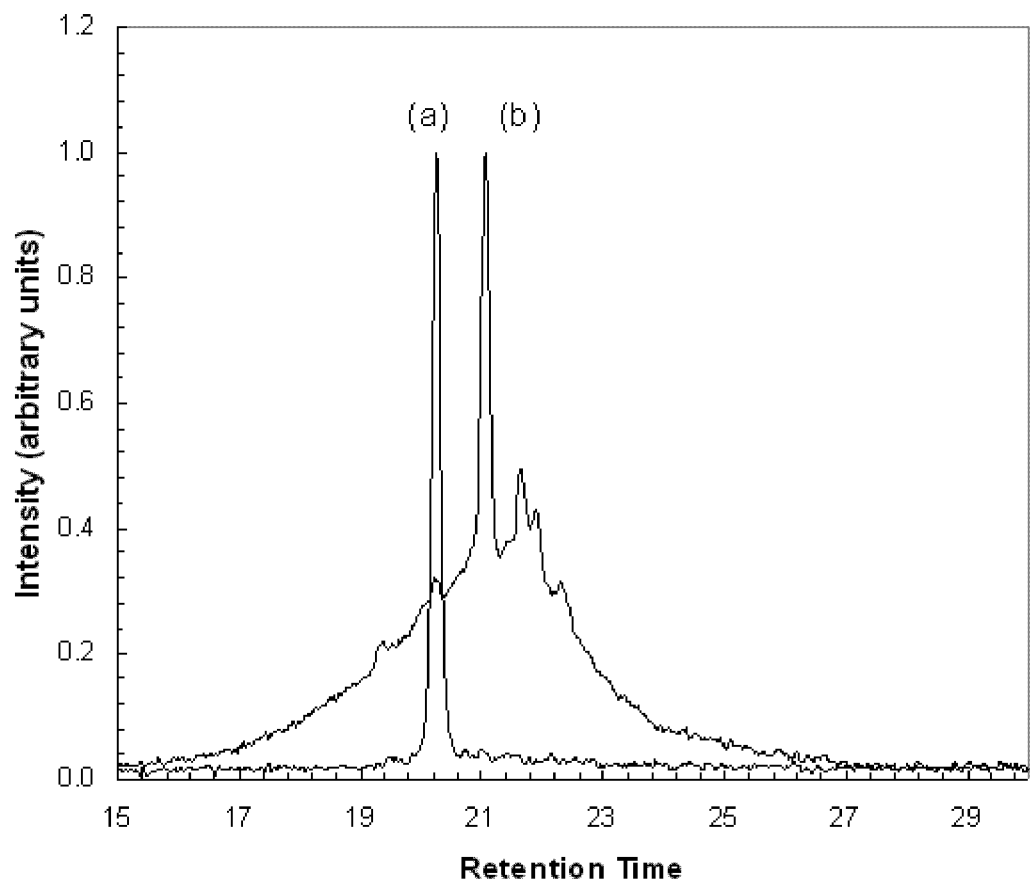
FIG. 1: Comparison between RP-HPLC chromatograms obtained for (a) exemplary conjugate synthesized using TSAT-C6 as the scaffold, AEM as the ligand, and $NH_2$—B1-BOC2(A1,B29)-insulin as the drug (conjugate I-1) and (b) an insulin-glycogen conjugate synthesized according to Example 32.

The samples were eluted at 1.0 ml/minutes using the following gradient method: 0-5 minutes—constant 80% Water/20% CH3CN, 5-35 minutes—linear gradient to 50% Water/50% CH3CN. The elution profiles in FIG. 1 show a single spike for the exemplary conjugate indicating a single chemically distinct species as compared to a broad and heterogenous elution profile for the insulin-glycogen conjugate, indicating a broad distribution of different chemical and/or molecular weight entities.

Example 34

Molecular Weight Distribution Analysis

This example describes the difference in MW and MW distribution between the insulin-glycogen synthesized according to Example 32 and the same exemplary conjugate. The MW and MW distribution of the insulin-glycogen conjugate was determined by injecting 1 ml of a 25 mg/ml solution in pH 7 HEPES buffered saline onto an Ultrahydrogel Size Exclusion Column (Waters Corporation, Millford, Mass.) equilibrated with HEPES buffered saline. The column was eluted over the course of 30 minutes at 0.5 ml per min, and the elution profile was measured as an absorbance at 280 nm. In separate experiments using the same protocol, dextran MW standards of 1000, 5000, 12000, 25000, 50000, 80000, 150000, 270000, and 410000 g/mol (Sigma-Aldrich, St. Louis, Mo.) were injected to establish a calibration curve of MW versus retention time. Based on the calibration curve and the elution profile of the insulin-glycogen conjugate, the average MW was determined to be 500,000 g/mol with 67% of the distribution eluting over the broad range of 250,000 to 1,000,000 g/mol (data not shown). In contrast, the exemplary conjugate was determined to have just a single MW of exactly 6,730 g/mol as determined by LC/MS (HT Laboratories, San Diego, Calif.) (data not shown).

Example 35

Chemical and Physical Stability of Conjugates

Figure 2:
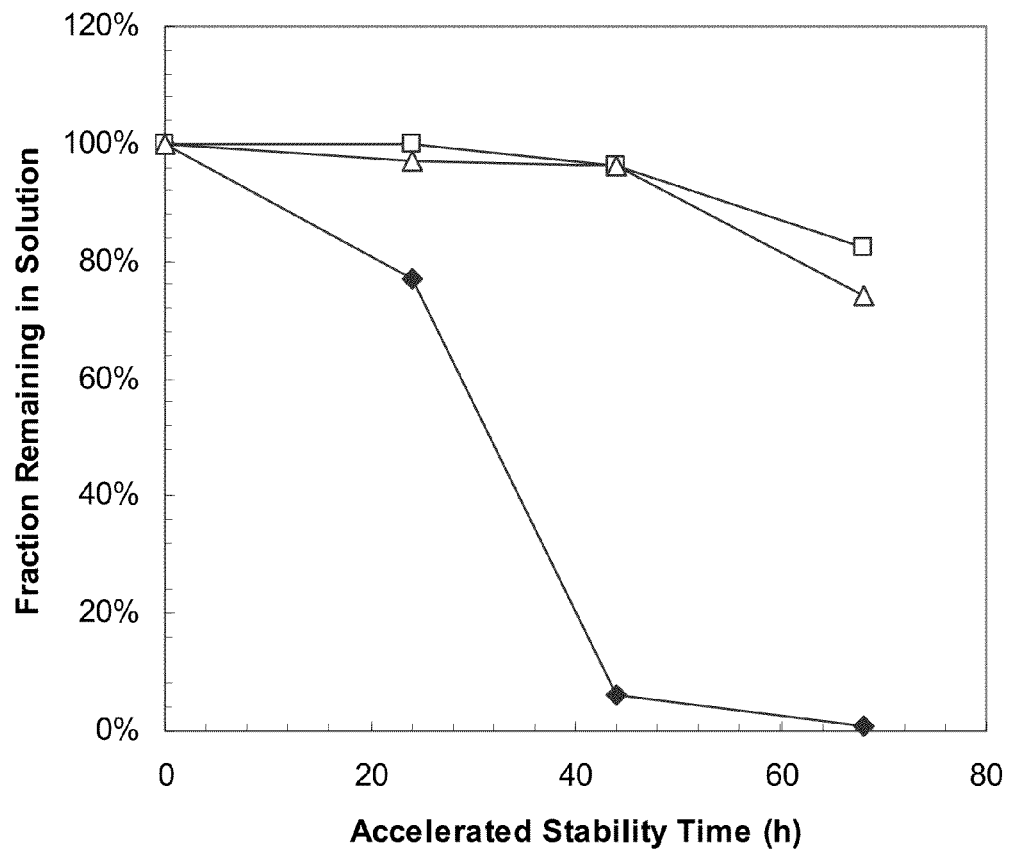
FIG. 2: Accelerated stability testing (AST) aggregation assay for conjugate I-1 (□), conjugate I-16 (△), and RHI (♦) in PBS buffer. The conjugates demonstrate greatly enhanced stability over pharmaceutical grade RHI.

This example compares the stability of an exemplary conjugate with that of unconjugated insulin under accelerated conditions according to the method described in Hinds et al. (*Bioconj. Chem.* 11:195-201, 2000) at 37 C and a mechanical agitation rate of 150 strokes/min. Pharmaceutical grade recombinant human insulin (RHI) was selected as the control for the accelerated stability study. Holcombe et al. (*Diabetes Care* 27:1241-1242, 2004) describes that under non-accelerated conditions RHI stability is maintained for at least 30 days at room temperature (RT) and considerably longer when refrigerated. FIG. 2 shows the results from the aggregation stability assay for RHI and two exemplary conjugates in pH 7.4 phosphate buffered saline (PBS) at 50 U/ml. In all cases, the % remaining in solution was determined by centrifuging (4500×g, 5 min) the solution at a given time point, measuring the A280 of the supernatant, and dividing the supernatant A280 by that of the original starting solution. Conjugate I-1 (see FIG. 45) was synthesized using TSAT-C6 as the framework, AEM as the ligand, and $NH_2$—B1-BOC2(A1,B29)-insulin as the drug. Conjugate I-16 (see FIG. 45) was synthesized using TSPE as the framework, AEM as the ligand, and $NH_2$—B1-BOC2(A1,B29)-insulin as the drug.

After 48 hours of continuous agitation at 37 C, less than 6% of the RHI remained stable in solution, while the majority of the RHI precipitated out as insoluble aggregates. After the same amount of time, both conjugates remained substantially more stable, as 96%-99% of the conjugates remained intact and soluble in the PBS solution. The data conclusively show that the conjugates are significantly more stable than RHI under these conditions.

RP-HPLC was used to assess the chemical stability of the conjugates (see FIG. 3a). After 48 hours of accelerated stability the conjugate solutions were analyzed using a C8-reverse phase column using a water-acetonitrile elution gradient. The retention times of the pre- and post-stability conjugate samples are shown along with the percentage of unconjugated (free) insulin and desamido insulin found in the resulting LC traces. No detectable amounts of free insulin or desamido were observed, indicating that (i) the covalent linkage between the saccharides and the insulin molecule is stable, and (ii) no significant chemical degradation of the conjugate occurs during the accelerated stability test (AST). Prior to and in parallel with the AST, the conjugate was also subjected to a 90-day non-accelerated stability test that included daily thermal cycling between 4° C. and RT. At the conclusion of the parallel study, RP-HPLC demonstrated that the conjugate was still chemically and physically stable (data not shown).

Further confirmation of the conjugate chemical stability in HEPES buffer is provided from the LC-MS data obtained before and after subjecting the conjugate to the AST. Interestingly, the 48 hour AST conjugate samples in PBS showed that substantial degradation had occurred, while the 48 hour AST conjugate samples in HEPES buffer were completely intact and stable (see FIG. 3b). Conjugate I-7 stored in HEPES has a MW of 6730 Da before and after the AST, demonstrating that both mannose residues, the conjugate framework, and insulin are all chemically unchanged and quite stable. To ensure conjugate stability, all buffers used for storage, in vitro testing, and in vivo testing contain HEPES as the buffering agent. In certain embodiments, the present disclosure provides a composition comprising an inventive conjugate in a HEPES buffer.

The LC-MS data greatly enhances FDA manufacturing regulatory compliance, as the LC-MS test can readily act as the chemical identity assay of the conjugate. Since the drug (e.g., insulin), conjugate framework, and conjugate all have discrete molecular weights, the resulting ligand ratio can be readily calculated by subtracting the conjugate framework MW from the conjugate MW to give the remaining mass due to the saccharide groups. In the case of conjugate I-7, the mannose:insulin molar ratio is calculated as exactly 2.0.

Example 36

Functional Stability of Conjugates

Figure 4:
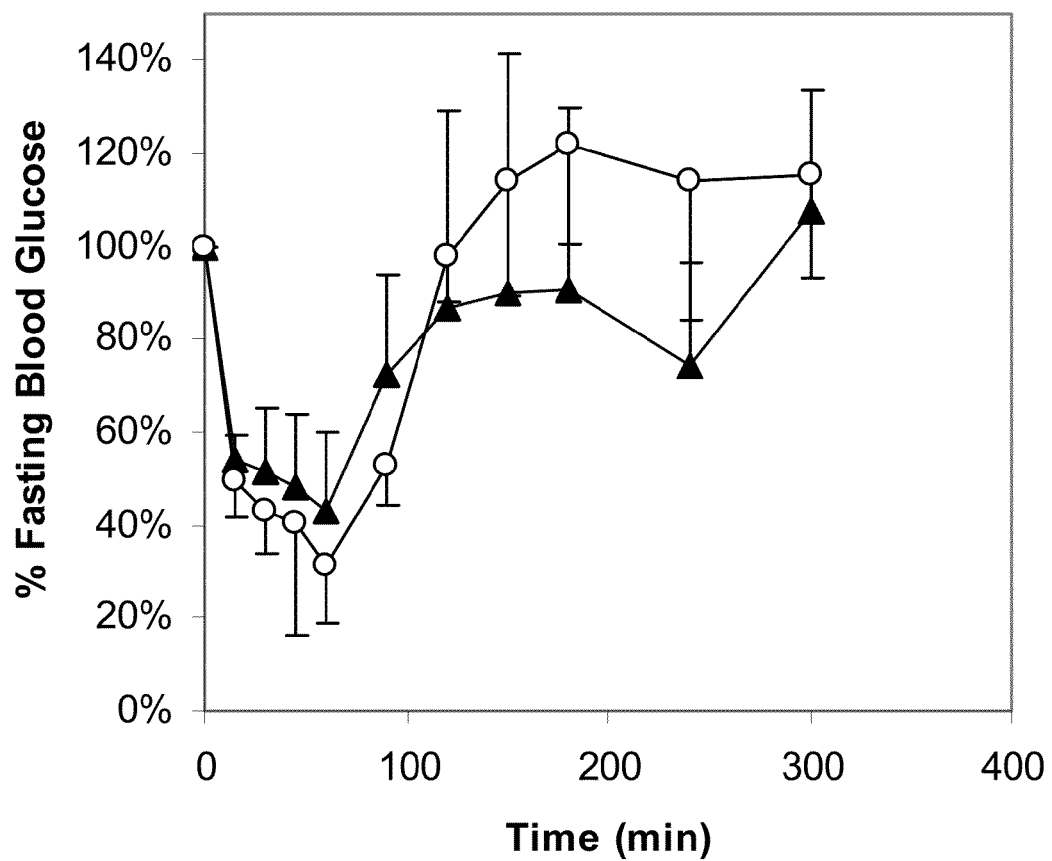
FIG. 4: In vivo bioactivity in (n=4) non-diabetic, male Sprague-Dawley (SD) rats for fresh conjugate (▲) and 72 hr AST conjugate (○). The 72 hr AST conjugate bioactivity was indistinguishable from that of the fresh conjugate (p>0.21 for all timepoints).

After demonstrating that the conjugate was chemically and physically stable, a 72 hour AST conjugate was assessed for its subcutaneous bioactivity in vivo vs. fresh conjugate using Sprague-Dawley rats at 5 U/kg (see FIG. 4).

Analysis of the 72 hour HEPES AST conjugate data showed that the time to reach the glucose nadir ($T_{nadir}$) was 60 minutes, and the time to return to 70% of the fasting blood glucose values ($T_{70\% BG}$) was less than 128±15 min. A comparison of fresh conjugate vs. 72 hour AST conjugate bioactivity curves at each timepoint using the student t-test (n=4 for each group) showed no significant differences (all p-values>0.21). These results were within specified targets for the formulation, indicating that preserved conjugate chemical stability translates into preserved in vivo functional performance.

III. In Vivo Assays of Exemplary Conjugates

This third set of examples describes various experiments investigating the in vivo properties of some exemplary conjugates.

Example 37

Conjugate Bioactivity Versus RHI and Dextran or Glycogen Conjugates (a) Insulin-Dextran Bioactivity This comparative example evaluates the in vivo pharmacodynamic profile of subcutaneously administered insulin-dextran (Sigma-Aldrich, MW~70K). As shown below, the insulin-dextran conjugates synthesized according to U.S. Patent Publication No. 20040202719 act relatively slowly after subcutaneous injection, because the high MW of the conjugate polymer significantly hinders the absorption rate into systemic circulation. Insulin-dextran was synthesized using a modified cyanogen bromide (CNBr) coupling reaction. Briefly, 500 mg of dextran (MW=70K, Sigma-Aldrich) was dissolved in 50 ml of deionized water. 56 mg of solid CNBr was added to the resulting solution and the pH was maintained at 10.7±0.2 using 5 N NaOH solution. After stirring for 15 min, another 56 mg of solid CNBr was added and the pH was maintained at 10.7±0.2 while stirring for 45 minutes. 300 mg of recombinant human insulin (RHI) was then added to the solution, and the pH was adjusted to 9.15 using solid sodium bicarbonate. The solution was stirred overnight, ultrafiltered exhaustively against DI water using a 10K MWCO polyethersulfone disc membrane filter (Millipore, Bedford, Mass.), and lyophilized. The resulting powder was then purified from unconjugated insulin by high performance liquid chromatography (Waters, Milford, Mass.) using a 1 M acetic acid mobile phase over a Superdex™75 packed column (Amersham Biosciences, Piscataway, N.J.). The insulin-dextran fraction was then lyophilized to obtain the conjugate as a pure powder. The degree of insulin conjugation was % (w/w) as determined by amino acid analysis (UCLA Biopolymers Laboratory, Los Angeles, Calif.).

Figure 5:
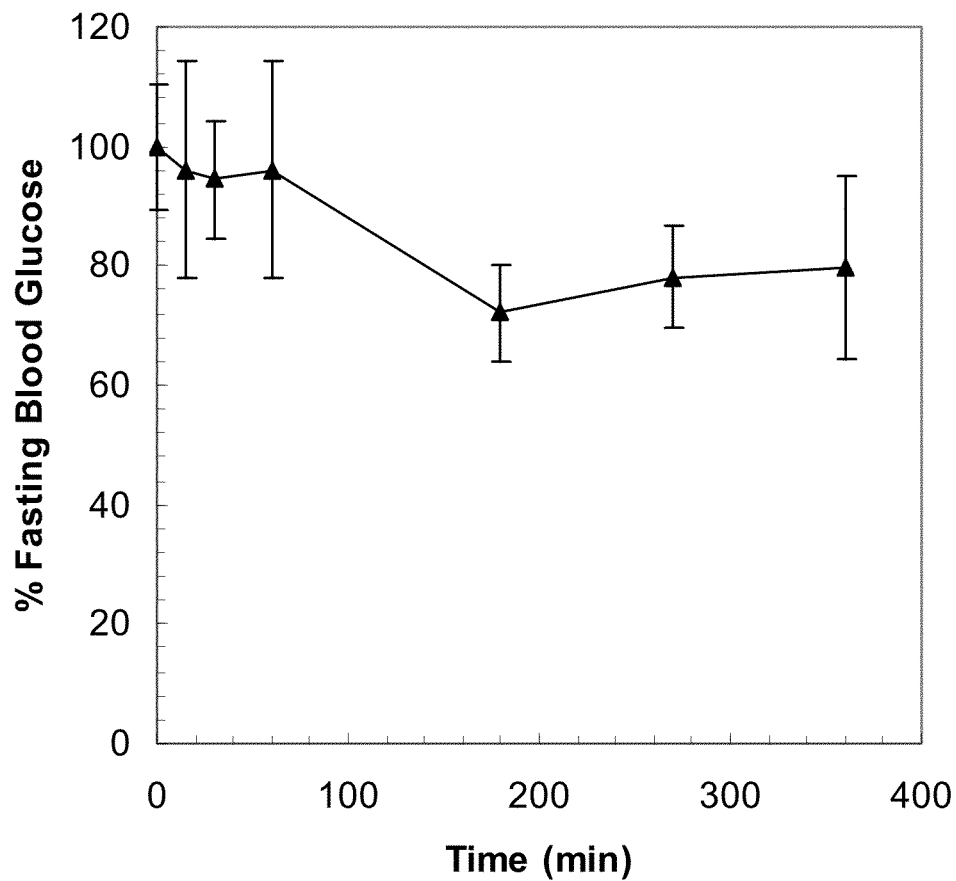
FIG. 5: Blood glucose depression profile in non-diabetic, male SD rats (n=3) for subcutaneously injected (▲) insulin-dextran (70 K) at a dose of ~20 U of insulin equivalents/kg.

Subcutaneous injections of the insulin-dextran were administered using 0.25 ml of a sterilized 1×PBS solution (20 U of equivalent insulin/ml) behind the neck of fasted normal non-diabetic rats (Male Sprague-Dawley, 200-250 g, n=4). Blood samples were collected via tail vein bleeding at −15 and 0 minutes, and at 15, 30, 45, 60, 90, 120, 180, 240, 300 and 360 minutes after injection. Blood glucose values were measured using commercially available test strips (Precision Xtra, Abbott Laboratories, Abbott Park, Ill.). As shown in FIG. 5, the times to reach the glucose nadir ($T_{nadir}$) concentration was found to be about 3 hours after injection, and the serum glucose levels remain depressed for at least five hours post injection.

(b) Insulin-Glycogen Bioactivity

Figure 6:
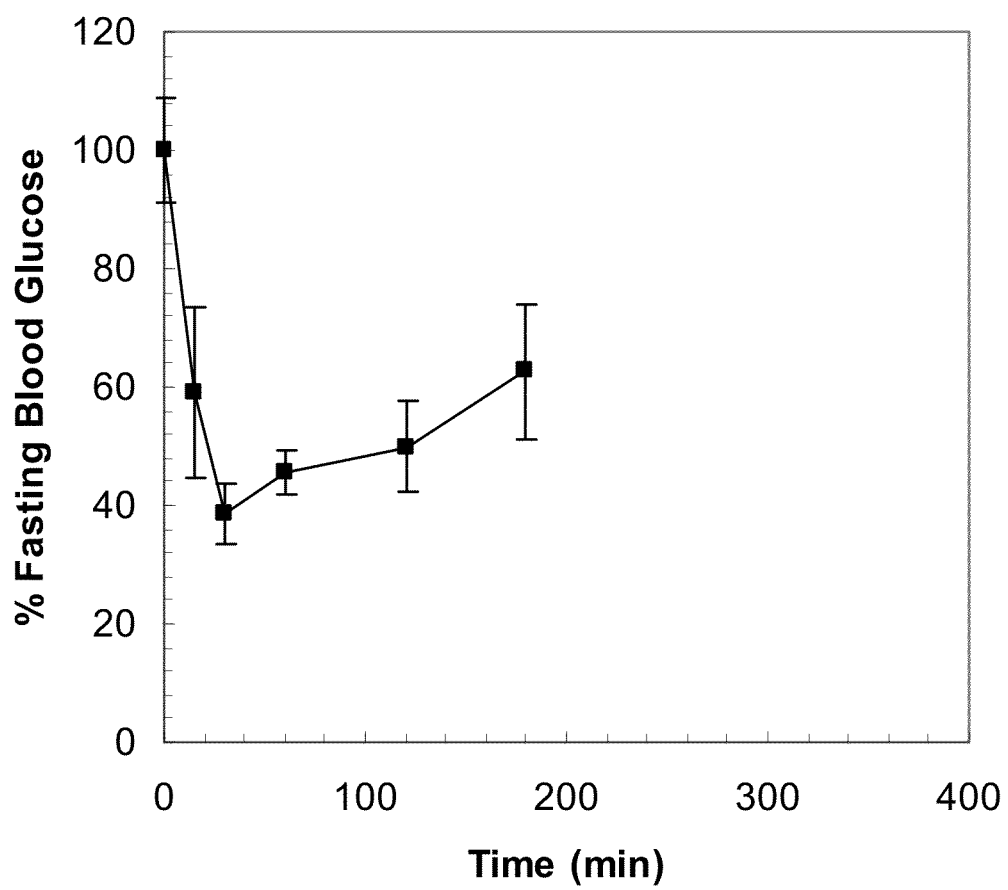
FIG. 6: Blood glucose depression profile in non-diabetic, male SD rats (n=3) for subcutaneously injected (■) insulin-glycogen (Type II oyster) at a dose of ~2.5 U of insulin equivalents/kg.

This example evaluates the in vivo pharmacodynamic profile of subcutaneously administered insulin-glycogen. The insulin-glycogen conjugate was synthesized according to Example 32. The bioactivity of the insulin-glycogen conjugate was evaluated by injecting a 2.5 equivalent U of insulin/kg dose behind the neck of fasted normal non-diabetic rats (Male Sprague-Dawley, 200-250 g, n=4). Blood samples were collected via tail vein bleeding at −15 and 0 minutes, and at 15, 30, 45, 60, 90, 120, 180, 240, 300 and 360 minutes after injection. Blood glucose values were measured using commercially available test strips (Precision Xtra, Abbott Laboratories, Abbott Park, Ill.). As compared to the insulin-dextran conjugates above, the high MW insulin-glycogen conjugates lower glucose levels much more rapidly and to a greater extent (see FIG. 6). This rapid action and elimination profile is due to the rapid enzymatic digestion of the high MW glycogen polymer chain following subcutaneous injection.

(c) an Exemplary Conjugate and RHI Bioactivity

Figure 7:
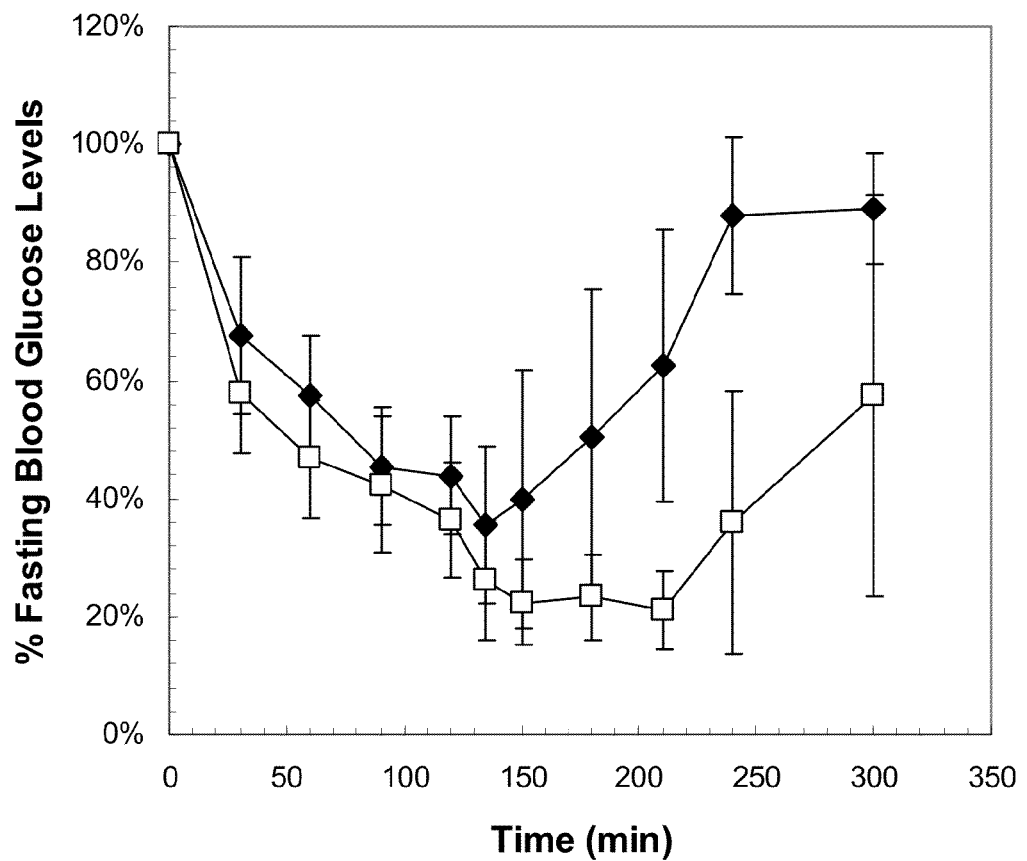
FIG. 7: Blood glucose levels resulting from a 3.5 U equivalent insulin/kg subcutaneous dose of (♦) TSAT-C6-AEM-2 insulin conjugate I-1 and (□) soluble recombinant human insulin (RHI) in male non-diabetic SD rats. Each set of data represents the average and standard deviation for n=6 rats.

This example evaluates and compares the in vivo pharmacodynamic profile of a subcutaneously administered exemplary conjugate and recombinant human insulin (RHI). The exemplary conjugate, I-1 in FIG. 45, was synthesized using TSAT-C6 as the scaffold, AEM as the indicator analog, and $NH_2$—B1-BOC2(A1,B29)-insulin as the drug. In each case, the conjugate or RHI was injected at 3.5 U/kg behind the neck of fasted normal non-diabetic rats (Male Sprague-Dawley, 400-500 g, n=6). Blood samples were collected via tail vein bleeding at 0 minutes and at 30, 60, 90, 120, 150, 180, 210, 240, and 300 minutes after injection. Blood glucose values were measured using commercially available test strips (Precision Xtra, Abbott Laboratories, Abbott Park, Ill.). As shown in FIG. 7, the glucose depression profiles for RHI and the exemplary conjugate are nearly identical despite the inability for the exemplary conjugate to be enzymatically digested in vivo. The rapid action and elimination profiles of the conjugate are most likely due to the fact that the conjugate is only 14% larger than RHI making any effect of increased MW almost negligible in terms of pharmacodynamic properties.

Example 38

PK Comparison with RHI

Figure 8:
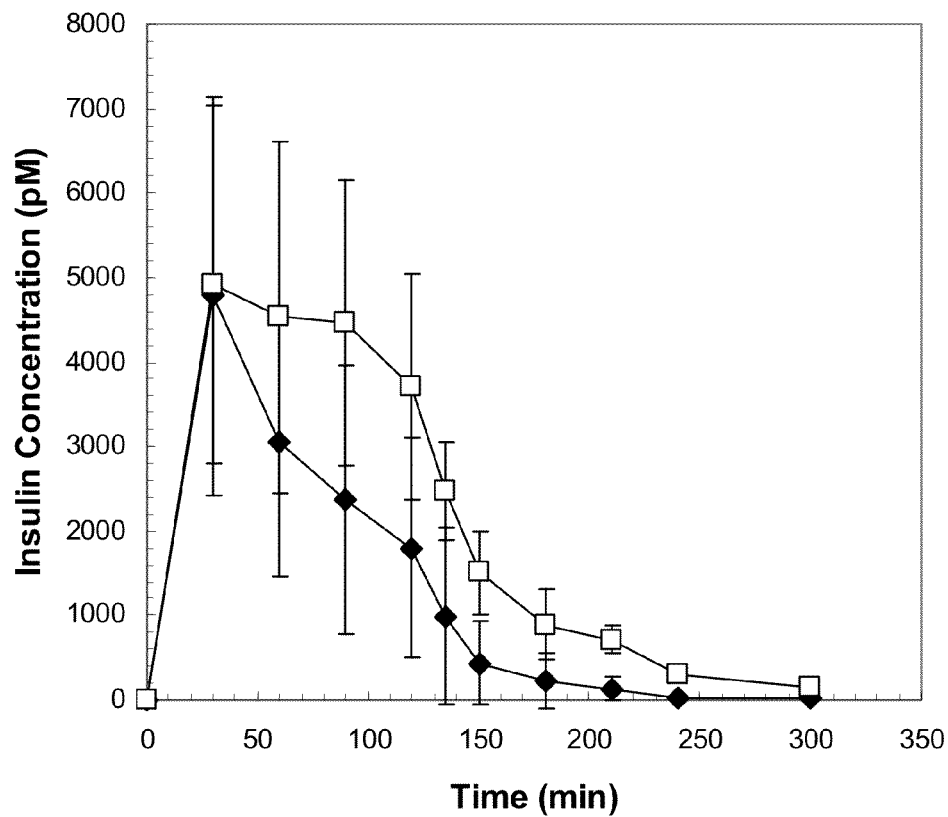
FIG. 8: Serum insulin concentrations resulting from a 3.5 U equivalent insulin/kg subcutaneous dose of (♦) TSAT-C6-AEM-2 insulin conjugate I-1 and (□) soluble recombinant human insulin (RHI) in male non-diabetic SD rats. Each set of data represents the average and standard deviation for n=6 rats.

This example describes and compares the serum insulin profiles obtained for a subcutaneously administered exemplary conjugate and recombinant human insulin (RHI). The exemplary conjugate, I-1 in FIG. 45, was synthesized using TSAT-C6 as the framework, AEM as the ligand, and $NH_2$—B1-BOC2(A1,B29)-insulin as the drug. In each case, the conjugate or RHI was injected at 3.5 U/kg behind the neck of fasted normal non-diabetic rats (Male Sprague-Dawley, 400-500 g, n=6). Blood samples were collected via tail vein bleeding at 0 minutes and at 30, 60, 90, 120, 150, 180, 210, 240, and 300 minutes after injection. Blood from each timepoint was centrifuged at 4 C to collect the serum. Serum insulin concentrations were subsequently measured with a commercially available ELISA kit (Human Insulin ELISA, Mercodia, Uppsala, Sweden). As can be seen in FIG. 8, the pharmacokinetic profile for the conjugate is statistically indistinguishable from that of RHI, demonstrating that this conjugate is rapidly absorbed into and eliminated from serum following a subcutaneous injection.

Example 39

Figure 9:
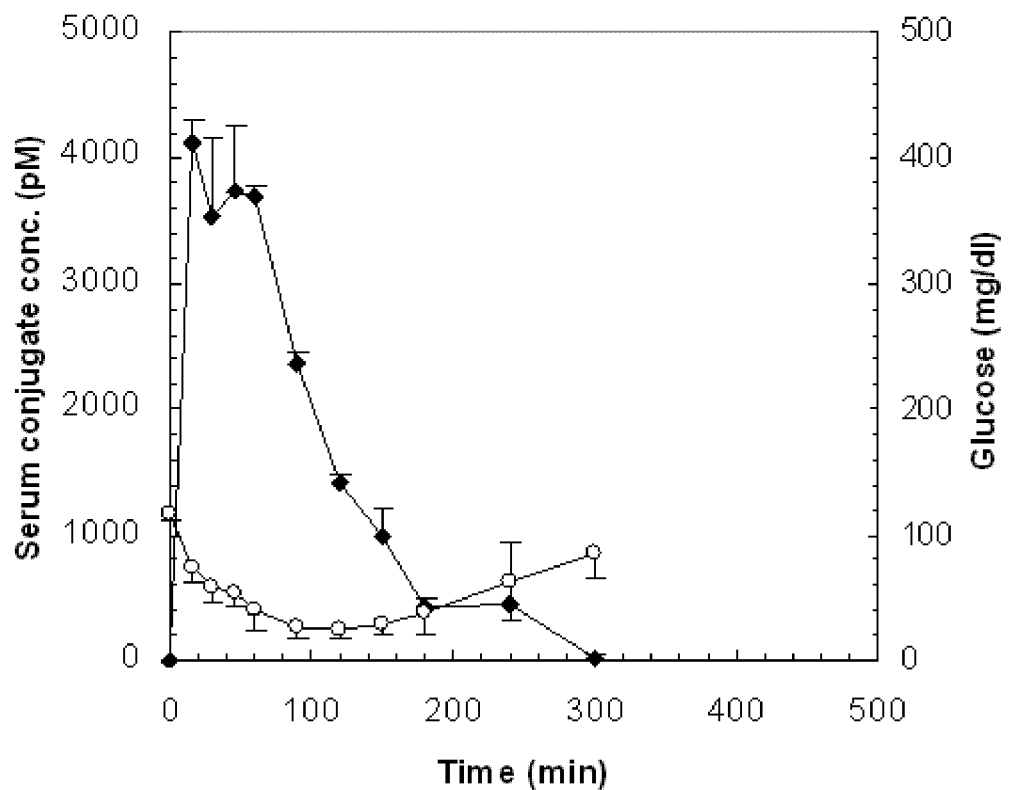
FIG. 9: Plot of (♦) serum insulin and (○) blood glucose levels following subcutaneous injection in non-diabetic, male SD rats at time 0 with TSAT-C6-AEM-2 (B29-substituted) insulin conjugate I-7 (5 U/kg). Data represents the average and standard deviation for n=3 rats.

PK and Bioactivity of a B29-Substituted Version of the AEM-2-TSAT-C6-Insulin Conjugate This example describes the serum insulin and blood glucose depression profiles obtained for a subcutaneously administered exemplary conjugate. The exemplary conjugate, I-7 in FIG. 45, was synthesized using TSAT-C6 as the framework, AEM as the ligand, and recombinant human insulin as the drug (to produce a B29-substituted conjugate instead of a B1-substituted conjugate as in Examples 37 and 38). In this case, the conjugate was injected at 5 U/kg behind the neck of fasted normal non-diabetic rats (Male Sprague-Dawley, 400-500 g, n=3). Blood samples were collected via tail vein bleeding at 0 minutes and at 30, 60, 90, 120, 150, 180, 210, 240, and 300 minutes after injection. Blood glucose values were measured using commercially available test strips (Precision Xtra, Abbott Laboratories, Abbott Park, Ill.). In addition, blood from each timepoint was centrifuged at 4 C to collect the serum. Serum insulin concentrations were subsequently measured with a commercially available ELISA kit (Human Insulin ELISA, Mercodia, Uppsala, Sweden). As can be seen in FIG. 9, the pharmacokinetic profile for the B29-substituted conjugate is statistically indistinguishable from that of RHI as well as the B1-substituted conjugate from Example 38, demonstrating that this conjugate is also rapidly absorbed into and eliminated from serum following a subcutaneous injection.

Example 40

PK and Bioactivity Comparison with Lispro

This example compares the serum insulin and blood glucose profiles obtained for a subcutaneously administered exemplary conjugate and insulin lispro. Insulin lispro (HUMALOG®) is a rapid acting insulin analog in which the penultimate lysine and proline residues on the C-terminal end of the B-chain have been reversed. This modification blocks the formation of insulin multimers. Data from soluble recombinant human insulin (RHI) is also provided for comparison (see Example 38 and FIG. 8).

Figure 12:
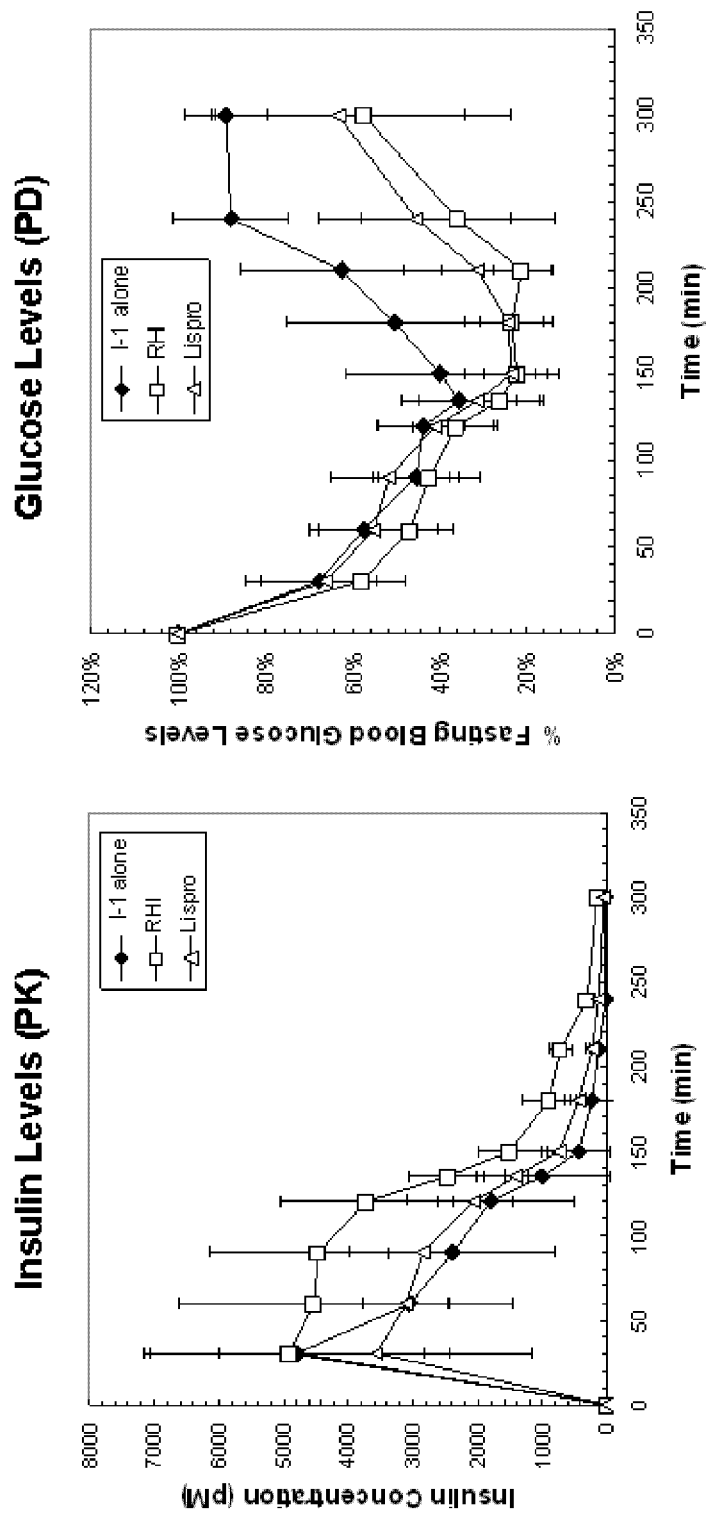
FIG. 12: Plot of serum insulin (left) and blood glucose (right) levels following subcutaneous injection in non-diabetic, male SD rats at time 0 with TSAT-C6-AEM-2 insulin conjugate I-1 (♦), soluble recombinant human insulin, (○) and insulin lispro (△) (all 3.5 U/kg). Data represents the average and standard deviation for n=6 rats.

The exemplary conjugate, I-1 in FIG. 45, was synthesized using TSAT-C6 as the framework, AEM as the ligand, and NH$_2$—B1-BOC2(A1,B29)-insulin as the drug. In each case, the conjugate or insulin lispro was injected at 3.5 U/kg behind the neck of fasted normal non-diabetic rats (Male Sprague-Dawley, 400-500 gm, n=6). Blood samples were collected via tail vein bleeding at 0 minutes and at 30, 60, 90, 120, 150, 180, 210, 240, and 300 minutes after injection. Blood glucose values were measured using commercially available test strips (Precision Xtra, Abbott Laboratories, Abbott Park, Ill.). In addition, blood from each timepoint was centrifuged at 4 C to collect the serum. Serum insulin concentrations were subsequently measured with a commercially available ELISA kit (Human Insulin ELISA, Mercodia, Uppsala, Sweden). As can be seen in FIG. 12, the pharmacokinetic profile for the conjugate is statistically indistinguishable from that of insulin lispro.

Example 41

Effect of Ligand on Bioactivity

This example compares the blood glucose profiles obtained for a series of subcutaneously administered exemplary conjugates. The exemplary conjugates were synthesized using TSAT-C6 as the framework, and NH$_2$—B1-BOC2(A1,B29)-insulin as the drug. The ligand composition was varied across the conjugates to cover a range of affinities: AEM-2, AEBM-2, AETM-1-AEBM-1 and AETM-2 (from lowest to highest affinity). The insulin conjugates are shown as I-1, I-2, I-3, and I-4 in FIG. 45. In each case, the conjugates were injected at 5 U/kg (3.5 U/kg for AEM-2) behind the neck of fasted normal non-diabetic rats (Male Sprague-Dawley, 400-500 gm, n=6). Blood samples were collected via tail vein bleeding at 0 minutes and at 30, 60, 90, 120, 150, 180, 210, 240, and 300 minutes after injection. Blood glucose values were measured using commercially available test strips (Precision Xtra, Abbott Laboratories, Abbott Park, Ill.). In addition, blood from each timepoint was centrifuged at 4 C to collect the serum. Serum insulin concentrations were subsequently measured with a commercially available ELISA kit (Human Insulin ELISA, Mercodia, Uppsala, Sweden).

Figure 13:
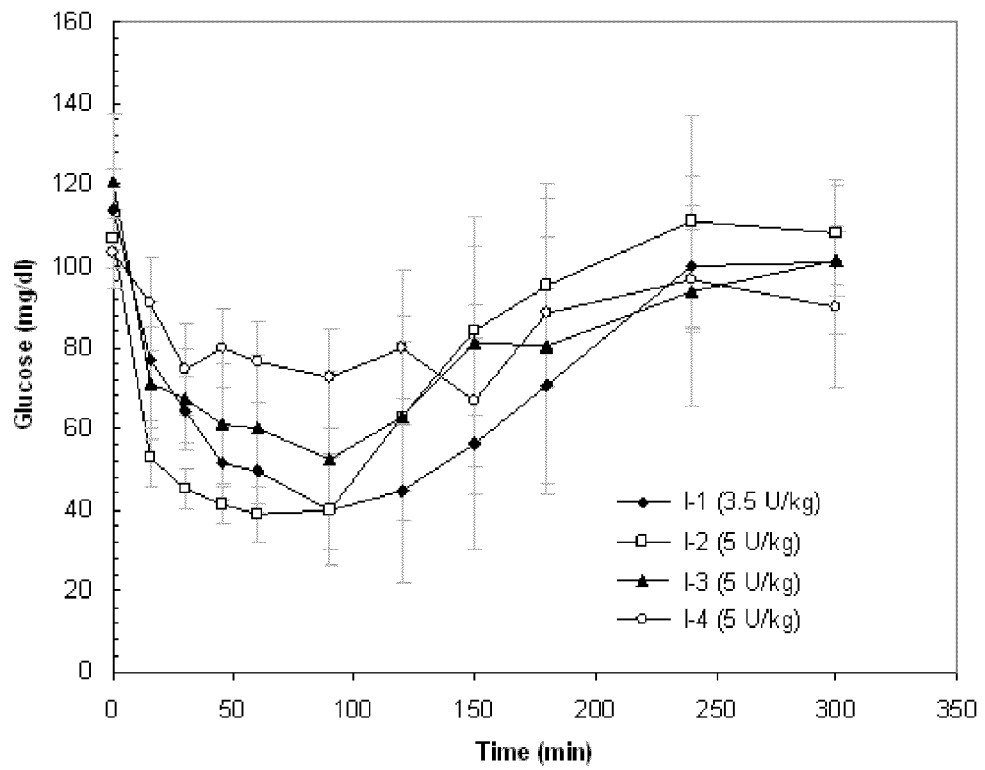
FIG. 13: Plot of blood glucose levels following subcutaneous injection in non-diabetic, male SD rats (n=3 for each formulation) at time 0 with TSAT-C6 based insulin conjugates with the different ligands as shown. The glucose lowering response decreases as the affinity of the ligand increases.
Figure 14:
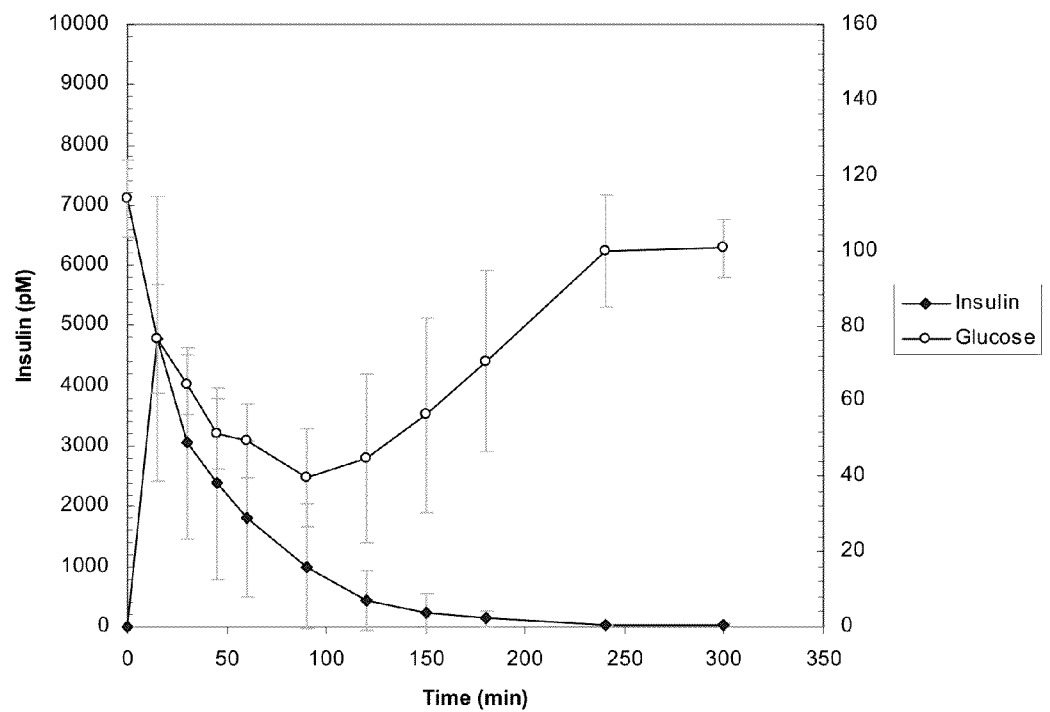
FIG. 14: Plot of serum insulin (left) and blood glucose (right) levels following subcutaneous injection in non-diabetic, male SD rats (n=3) at time 0 with TSAT-C6-AEM-2 conjugate I-1 (3.5 U/kg).
Figure 15:
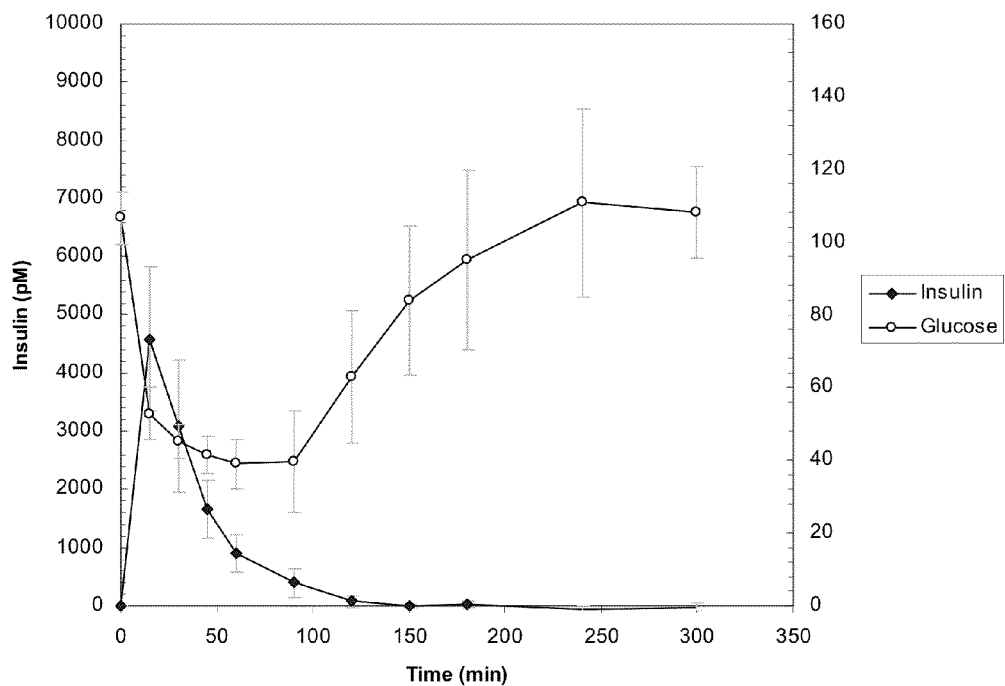
FIG. 15: Plot of serum insulin (left) and blood glucose (right) levels following subcutaneous injection in non-diabetic, male SD rats (n=3) at time 0 with TSAT-C6-AEBM-2 I-3 conjugate (5 U/kg).
Figure 16:
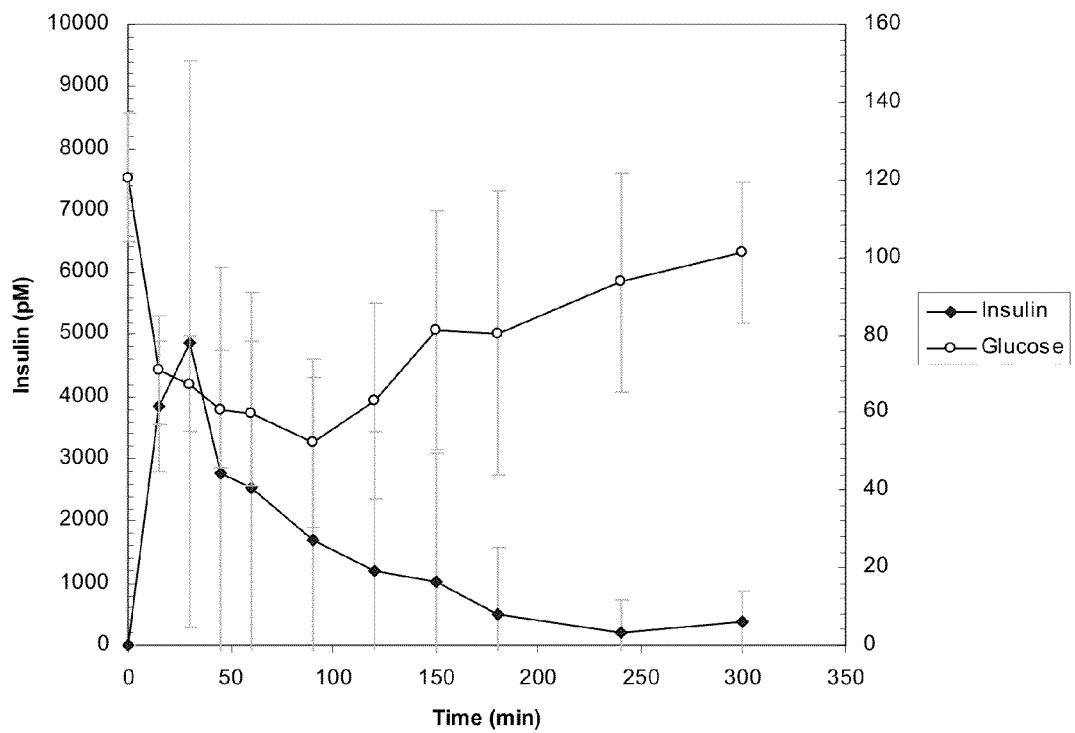
FIG. 16: Plot of serum insulin (left) and blood glucose (right) levels following subcutaneous injection in non-diabetic, male SD rats (n=3) at time 0 with TSAT-C6-AEBM-1 AETM-1 conjugate I-4 (5 U/kg).
Figure 17:
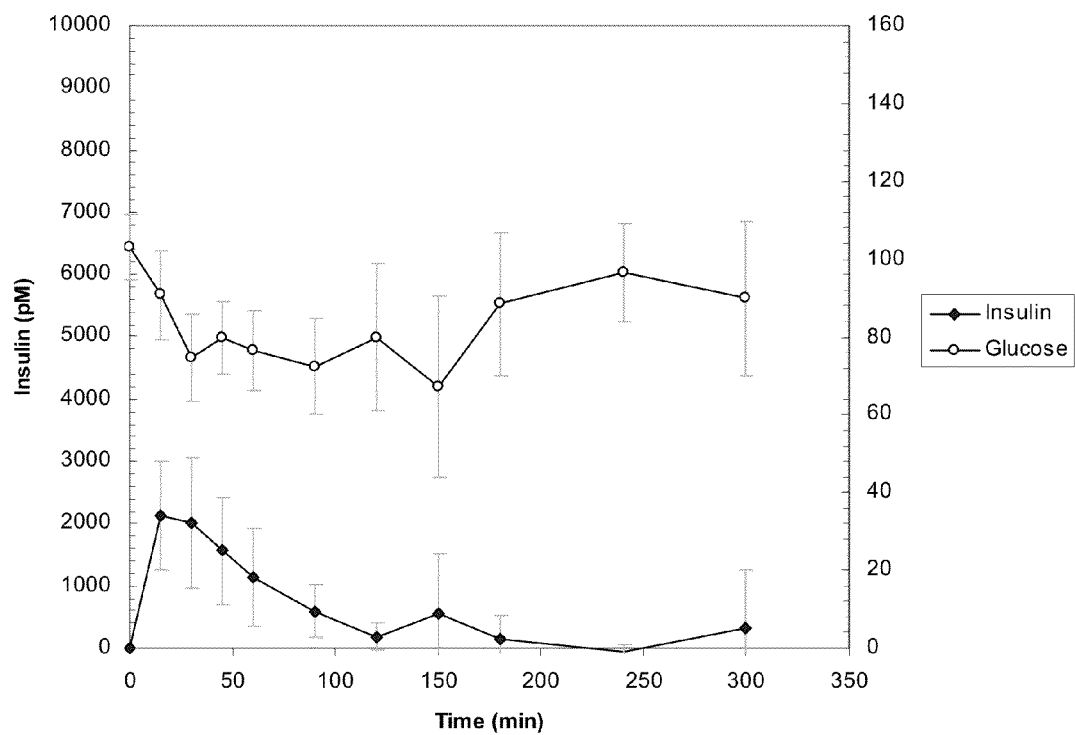
FIG. 17: Plot of serum insulin (left) and blood glucose (right) levels following subcutaneous injection in non-diabetic, male SD rats (n=3) at time 0 with TSAT-C6-AETM-2 conjugate I-2 (5 U/kg).

As can be seen in FIG. 13, the glucose lowering response decreased as the affinity of the ligand increased. This data provided the first indication that the nature of the ligand may affect the bioactivity of the conjugate. FIGS. 14-16 show the blood glucose levels alongside the serum insulin levels for each of the four conjugates tested. These results show quite clearly that the reduced glucose response for conjugates with higher affinity ligands results from the reduced PK profile of the conjugate (compare FIG. 14 for AEM-2 with FIG. 17 for AETM-2).

Example 42

Effect of Exogenous Inhibitors on PK and Bioactivity

In view of the data described in Example 41 we hypothesized that the reduced PK profile and bioactivity observed with conjugates having higher ligands might result from stronger binding to endogenous saccharide binding molecules. For example, without wishing to be limited to any particular theory, we hypothesized that binding to endogenous "lectin-like" proteins such as surfactant proteins A and D or members of the selectin family might be causing these conjugates to be cleared more rapidly than conjugates with lower affinity ligands.

In order to test this hypothesis we ran a set of experiments to determine whether exogenous ligands could compete for binding to these proposed endogenous saccharide binding molecules and thereby increase the PK profile of the conjugates post-administration. The high affinity AETM-2 conjugate I-2 was used for all experiments. In each case, the same dose of conjugate was injected behind the neck of fasted normal non-diabetic rats (Male Sprague-Dawley, 400-500 gm, n=6). After a 15 minute delay a dose of the exogenous ligand was injected IP. Blood samples were collected via tail vein bleeding at 0 minutes and at 30, 60, 90, 120, 150, 180, 210, 240, and 300 minutes after the initial conjugate injection. Blood glucose values were measured using commercially available test strips (Precision Xtra, Abbott Laboratories, Abbott Park, Ill.). In addition, blood from each timepoint was centrifuged at 4 C to collect the serum. Serum insulin concentrations were subsequently measured with a commercially available ELISA kit (Human Insulin ELISA, Mercodia, Uppsala, Sweden). A control was performed by injecting saline instead of the exogenous ligand after 15 minutes.

Figure 18:
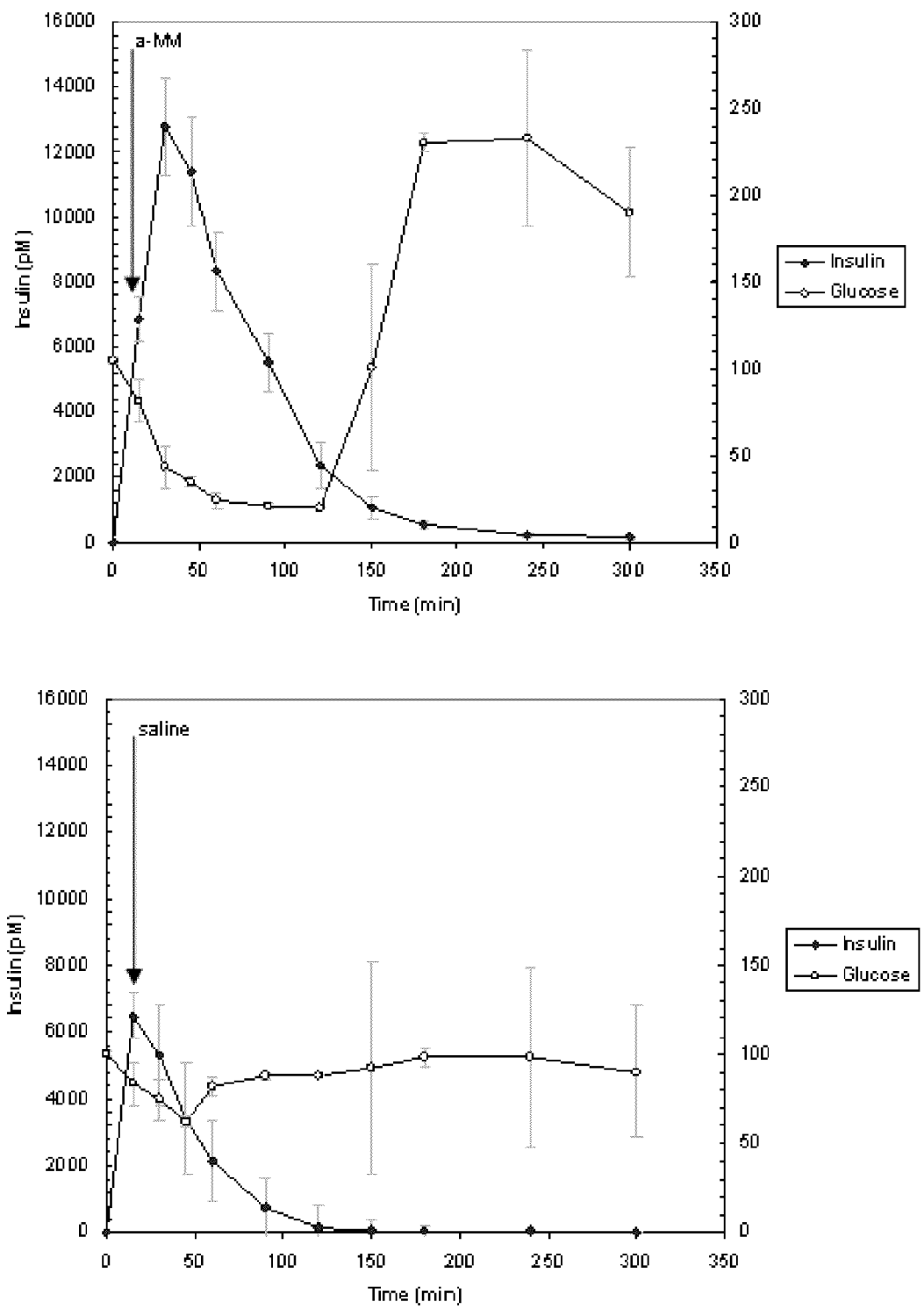
FIG. 18: Plot of serum insulin and blood glucose levels following subcutaneous injection in non-diabetic, male SD rats (n=3) at time 0 with TSAT-C6-AETM-2 conjugate I-2 followed by IP injection of alpha-methyl mannose (left) or saline (right) after 15 minutes. Alpha-methyl mannose is a very high affinity saccharide which is capable of competing with AETM for binding to lectins such as Con A. As shown, the change in PK/PD profile that results from injection of alpha-methyl mannose is very significant ($p<0.05$).

FIG. 18 shows the results obtained when alpha-methyl mannose was administered. Alpha-methyl mannose is a very high affinity saccharide which is capable of competing with AETM for binding to lectins such as Con A. As shown, the change in PK/PD profile that resulted from injection of alpha-methyl mannose was very significant ($p<0.05$).

Figure 19:
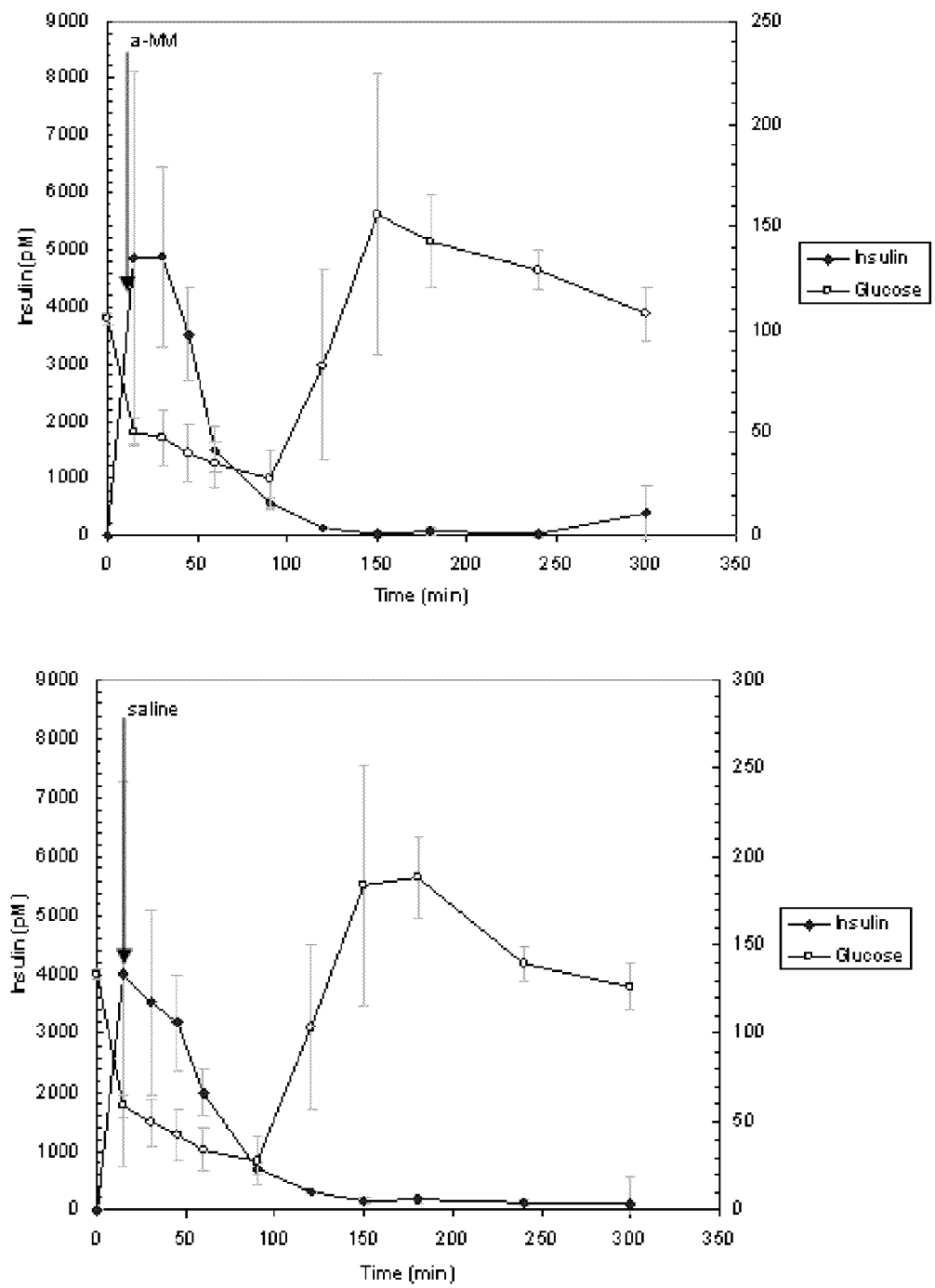
FIG. 19: Plot of serum insulin and blood glucose levels following subcutaneous injection in non-diabetic, male SD rats (n=3) at time 0 with soluble recombinant human insulin (RHI) followed by IP injection of alpha-methyl mannose (left) or saline (right) after 15 minutes. As shown, no change in PK/PD profile results from injection of alpha-methyl mannose ($p>>0.05$).

FIG. 19 is a control experiment in which soluble recombinant human insulin (RHI) was used for the initial injection instead of the AETM-2 conjugate. As shown, there was no change in PK/PD profile when alpha-methyl mannose was injected ($p>>0.05$).

Figure 20:
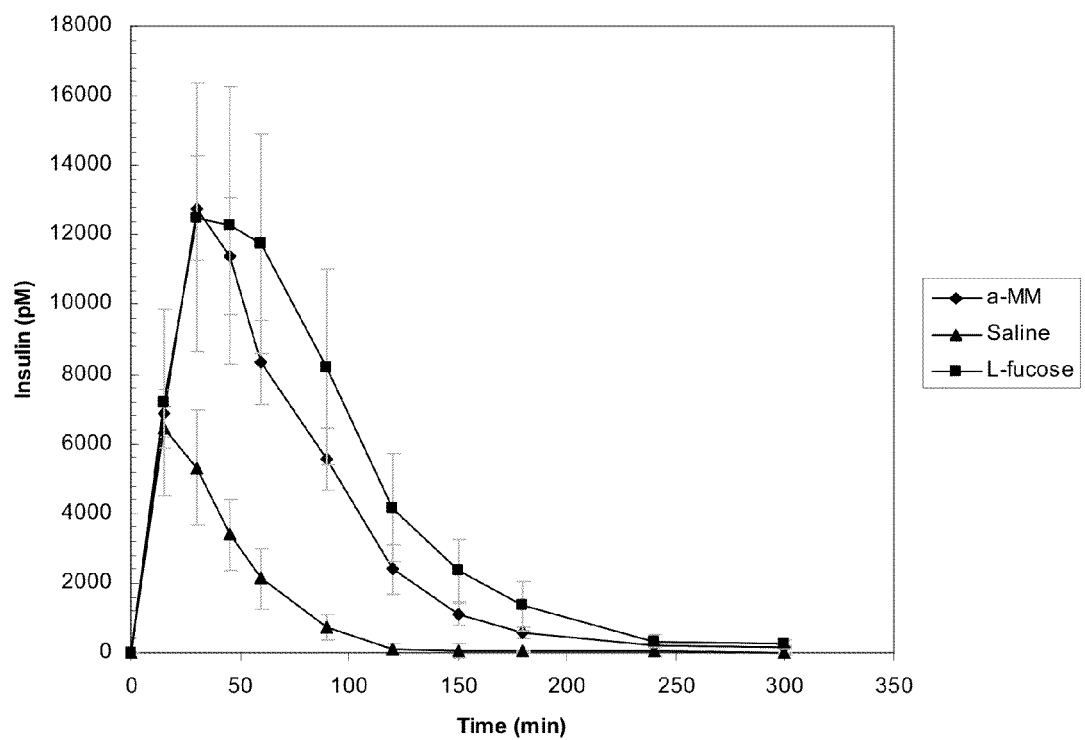
FIG. 20: Plot of serum insulin levels following subcutaneous injection in non-diabetic, male SD rats (n=3 for each expt.) at time 0 with TSAT-C6-AETM-2 conjugate I-2 followed by IP injection of alpha-methyl mannose (♦), L-fucose (■) or saline (▲) after 15 minutes. As shown, alpha-methyl mannose and L-fucose appear to exhibit the same kind of effect.
Figure 21:
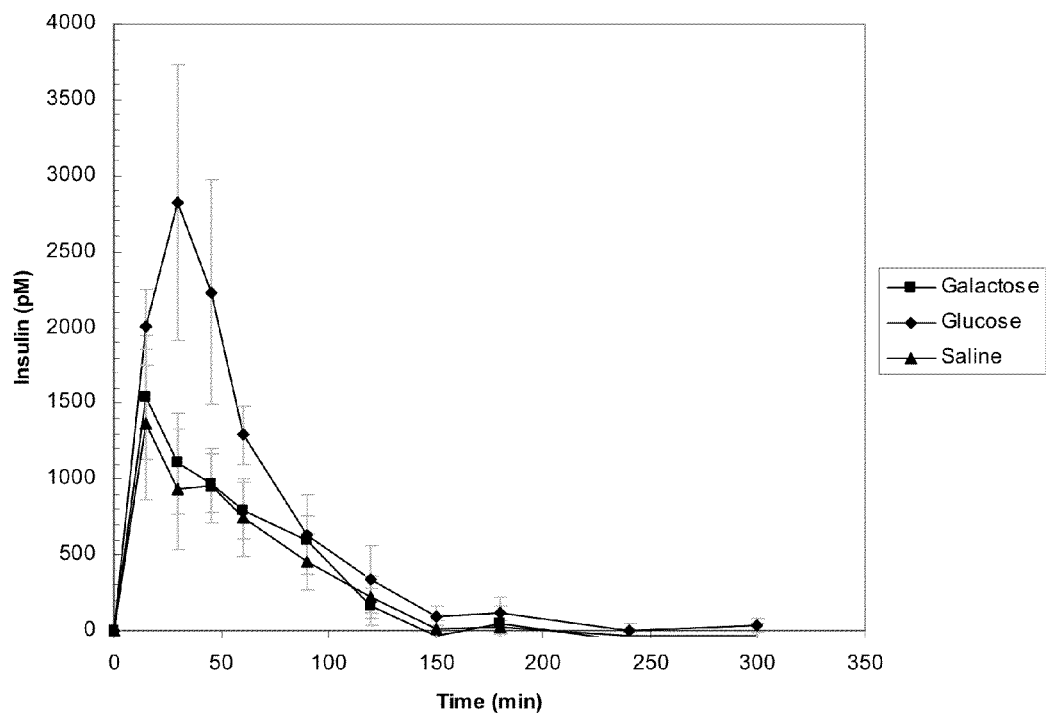
FIG. 21: Plot of serum insulin levels following subcutaneous injection in non-diabetic, male SD rats at time 0 with TSAT-C6-AETM-2 conjugate I-2 followed by IP injection of glucose (♦), galactose (■) or saline (▲) after 15 minutes. As shown, galactose exhibits no effect as compared to saline. Glucose appears to exhibit a small effect; however, this is complicated by the fact that the exogenous insulin from the conjugate quickly lowers the glucose, so the sustained effect observed with alpha-methyl mannose and L-fucose does not occur.

The endogenous mannan-binding lectin (MBL) is known to bind saccharides with the following relative affinities: D-mannose, L-fucose>D-glucose, N-acetyl-D-glucosamine>>D-galactose. We therefore decided to run two experiments comparing the effects of L-fucose (high affinity ligand), D-glucose (intermediate affinity ligand) and D-galactose (low affinity ligand) on the PK/PD profile for the AETM-2 conjugate. The results with L-fucose are compared with the results obtained with alpha-methyl mannose in FIG. 20. As shown, alpha-methyl mannose and L-fucose appear to exhibit the same kind of effect. The results with D-glucose and D-galactose are compared in FIG. 21. Galactose exhibits no effect as compared to saline. Glucose appears to exhibit a small effect; however, this is complicated by the fact that the exogenous insulin from the conjugate quickly lowers the glucose, so the sustained effect observed with alpha-methyl mannose and L-fucose does not occur.

Example 43

Effect of Exogenous Inhibitor at the Local Injection Site

In view of the data described in Example 42, we set out to determine whether the alpha-methyl mannose (a-MM) induced increase in serum conjugate concentration and bioactivity was a result of an increased rate of absorption from the subcutaneous injection site. The high affinity TSAT-C6-AETM-2 conjugate I-2 was used for this experiment. First, the conjugate was diluted to a concentration of 5 U/ml (0.2 mg/ml insulin equivalent) using either a buffered saline solution or a buffered saline solution containing 1 M a-MM. Each solution was injected sub-Q at a dose of 5 U/kg into the back of the neck of each of three non-diabetic, male SD rats at time 0 and blood samples were collected via tail vein bleeding at 0 minutes and at 15, 30, 45, 60, 90, 120, 150, 180, 240, and 300 minutes after injection. Blood glucose values were measured using commercially available test strips (Precision Xtra, Abbott Laboratories, Abbott Park, Ill.). In addition, blood from each timepoint was centrifuged at 4 C to collect the serum. Serum insulin concentrations were subsequently measured with a commercially available ELISA kit (Iso Insulin ELISA, Mercodia, Uppsala, Sweden). In this experiment, rats that received the a-MM conjugate solution also received an injection of buffered saline solution sub-Q at a separate hind quarter injection site at 15 minutes. Rats that received the saline conjugate solution also received an injection of a-MM solution sub-Q at a separate hind quarter injection site at 15 minutes. These 15-minute delayed injections were used to make sure that the amount of a-MM injected sub-Q with the conjugate solution would not raise the systemic concentration of a-MM high enough to invoke the kind of a-MM induced effects exhibited in FIG. 18.

Figure 22:
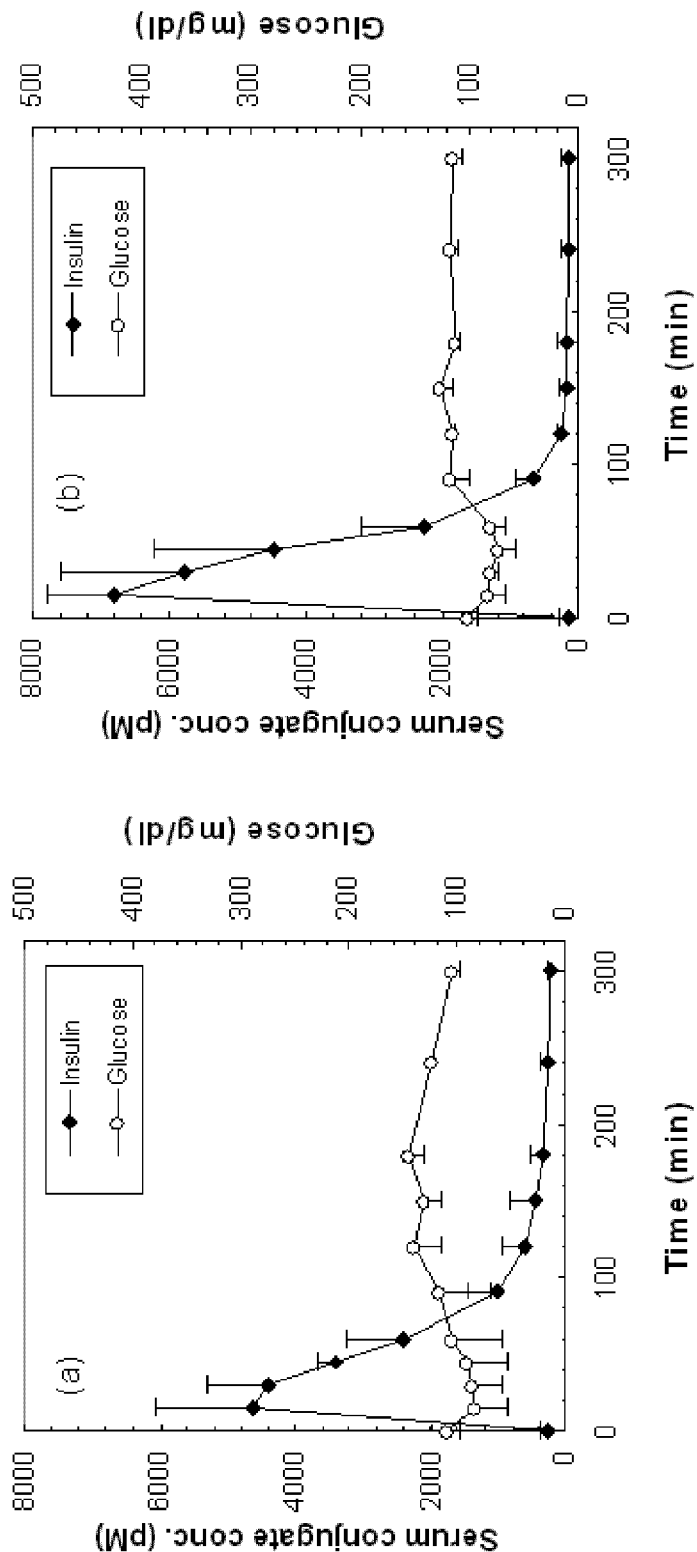
FIG. 22: Plot of serum insulin and blood glucose levels following subcutaneous injection in non-diabetic, male SD rats (n=3) at time 0 with TSAT-C6-AETM-2 conjugate I-2 solution at 5 U/kg dissolved in either (a) buffered saline containing 1M alpha-methyl mannose or (b) buffered saline. In (a) the rats were subsequently injected at 15 min. with the same volume of saline solution used in (b) at a different subcutaneous site than the one used for the conjugate solution. In (b) the rats were subsequently injected at 15 min. with the same volume of 1M alpha-methyl mannose solution used in (a) at a different subcutaneous site than the one used for the conjugate solution. As shown, the serum insulin levels do not increase and the blood glucose levels do not decrease in experiment (a) relative to experiment (b).

The results shown in FIG. 22 indicate that within experimental error, the conjugate PK and bioactivity profiles were not enhanced at all by purposefully co-injecting a high concentration of a-MM inhibitor with the conjugate. These results are consistent with the hypothesis that the exogenous saccharides do not act on the conjugates by changing the absorption profile into systemic circulation from the site of injection.

Example 44

Effect of Delaying the Exogenous Inhibitor Injection after the Initial Conjugate Injection Based on the results in FIG. 22, the a-MM-enhanced PK and bioactivity results cannot be explained by increased injection site absorption but rather must be the result of a systemic effect that occurs after the conjugate has been absorbed. The following two hypotheses could explain such behavior: (a) the conjugate is being eliminated from the body via a lectin dependent mechanism that can be disrupted by the competitive saccharide or (b) the conjugate is binding to lectins within the body and is only released into circulation in the presence of the competitive saccharide. In the case of (b) one would expect that introduction of a-MM into the animal after the conjugate has been fully absorbed from the sub-Q depot would cause the absorbed conjugate to release from the lectin sites in the body thereby increasing its serum concentration and bioactivity. However, if an elimination mechanism is at work as described in (a) then injecting a-MM after the conjugate has been fully absorbed from the sub-Q depot will not produce any increase in serum concentration or bioactivity because the conjugate will have already been completely eliminated from the body.

To determine the likely mechanism, the high affinity TSAT-C6-AETM-2 conjugate I-2 was injected at 5 U/kg behind the neck of fasted normal non-diabetic rats (Male Sprague-Dawley, 400-500 gm, n=3 per group). After four different delay times (15 minutes, 60 minutes, 120 minutes, and 240 minutes) a 4 g/kg dose of a-MM solution was injected IP. Blood samples were collected via tail vein bleeding at 0 minutes and at the following intervals for each experiment:

| IP a-MM injection delay time (min) | Sample time points (min post injection) |
|---|---|
| 15 | 15, 30, 45, 60, 90, 120, 150, 180, 240, 300, 360 |
| 60 | 15, 30, 45, 60, 75, 90, 120, 150, 180, 240, 300, 360 |
| 120 | 15, 30, 45, 60, 90, 120, 135, 150, 180, 240, 300, 360 |
| 240 | 15, 30, 45, 60, 120, 180, 240, 255, 270, 300, 360 |

Blood glucose values were measured using commercially available test strips (Precision Xtra, Abbott Laboratories, Abbott Park, Ill.). In addition, blood from each timepoint was centrifuged at 4 C to collect the serum. Serum insulin concentrations were subsequently measured with a commercially available ELISA kit (Iso Insulin ELISA, Mercodia, Uppsala, Sweden).

Figure 23:
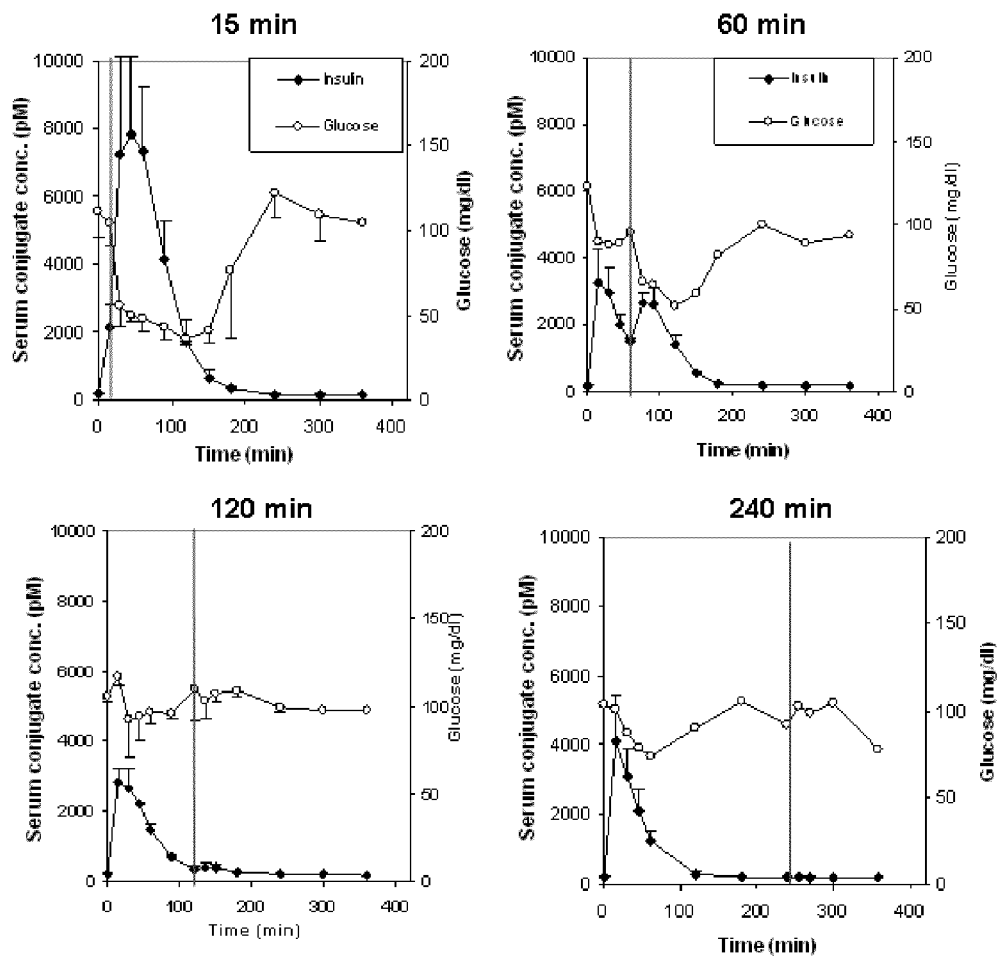
FIG. 23: Plot of serum insulin and blood glucose levels following subcutaneous injection in non-diabetic, male SD rats (n=3) at time 0 with TSAT-C6-AETM-2 conjugate I-2 solution at 5 U/kg. At 15 min, 60 min, 120 min, or 240 min after the conjugate injection, the rats were given a 4 g/kg IP a-MM injection.

As shown in FIG. 23, the increase in serum conjugate concentration and bioactivity due to IP a-MM injection is less and less prevalent the longer the delay time between the conjugate injection and the IP a-MM injection. For example, after 240 minutes no increase in serum conjugate concentration is observed indicating that there is no lectin-bound depot of conjugate present in the body after complete conjugate absorption. These results are consistent with proposed mechanism (a) and inconsistent with proposed mechanism (b). It is to be understood that while we hypothesize that mechanism (a) may be responsible for the PK properties observed with the conjugates of the present disclosure, the claims presented herein are in no way limited to a specific mechanism of action.

Example 45

Effect of a-MM on PK and Bioactivity as a Function of Ligand Affinity

In view of the data described in Example 42, we set out to determine the pharmacokinetic and pharmacodynamic behavior of conjugates synthesized using different saccharide ligands than the AETM ligand used in Example 42. In this example, the TSAT-C6 framework was used and the following conjugates were synthesized according to the methods described in Example 20 (note glucosamine-HCl or GA-HCl was purchased from Sigma-Aldrich (St. Louis, Mo.) and used without further purification):

| Conjugate | Framework | Framework MW | Ligand | AE-sugar MW | Purity (HPLC) | MW (LC-MS) | Sugar/Insulin |
|---|---|---|---|---|---|---|---|
| I-7: TSAT-C6-AEM-2 (B29) | TSAT-C6 | 822 | AEM | 223 | 95% | 6729 | 2.0 |
| I-5: TSAT-C6-GA-2 (B29) | TSAT-C6 | 822 | GA-HCl | 216 | 95% | 6641 | 2.0 |

According to N-terminal sequencing, approximately 90% of each saccharide-containing framework was conjugated to insulin via the Lys-B29. TSAT-C6-AEM-2 (B29) and TSAT-C6-GA-2 (B29) are shown in FIG. 45 as conjugates I-7 and I-5, respectively.

The same type of experiments described in Example 42 were repeated for the conjugates described in the table above. In each case, the same dose of conjugate (5 U/kg) was injected behind the neck of fasted normal non-diabetic rats (Male Sprague-Dawley, 400-500 gm, n=3). After a 15 minute delay a 4 g/kg dose of a-MM was injected IP. Blood samples were collected via tail vein bleeding at 0 minutes and at 30, 60, 90, 120, 150, 180, 210, 240, and 300 minutes after the initial conjugate injection. Blood glucose values were measured using commercially available test strips (Precision Xtra, Abbott Laboratories, Abbott Park, Ill.). In addition, blood from each timepoint was centrifuged at 4 C to collect the serum. Serum insulin concentrations were subsequently measured with a commercially available ELISA kit (ISO Insulin ELISA, Mercodia, Uppsala, Sweden). A control was performed by injecting saline instead of a-MM after 15 minutes.

Figure 24:
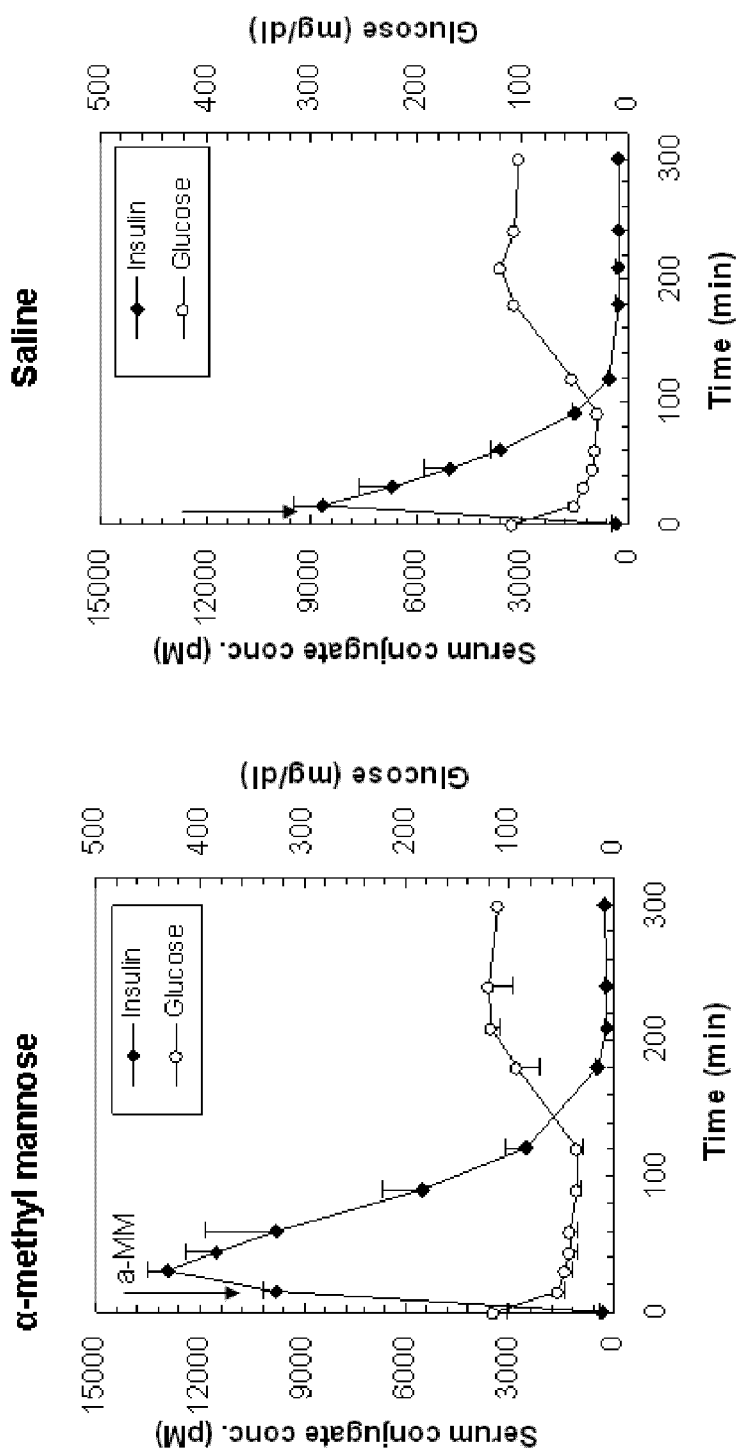
FIG. 24: Plot of serum insulin and blood glucose levels following subcutaneous injection in non-diabetic, male SD rats (n=3) at time 0 with TSAT-C6-AEM-2 conjugate I-7 followed by IP injection of alpha-methyl mannose (left) or saline (right) after 15 minutes. Alpha-methyl mannose is a very high affinity saccharide which is capable of competing with AEM for binding to lectins such as Con A. As shown, the change in PK/PD profile that results from injection of alpha-methyl mannose is very significant ($p<0.05$).
Figure 25:
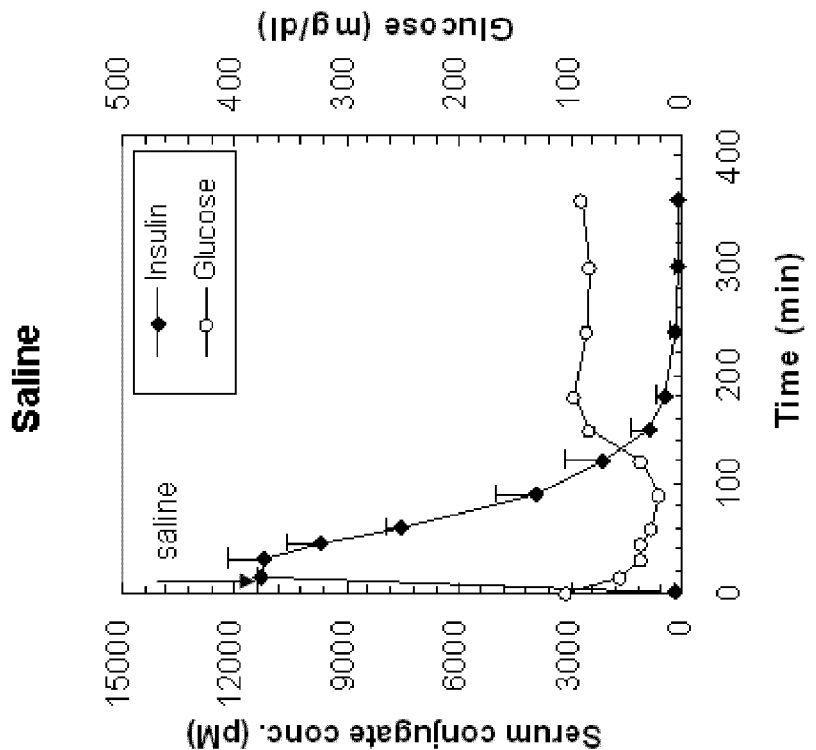
FIG. 25: Plot of serum insulin and blood glucose levels following subcutaneous injection in non-diabetic, male SD rats (n=3) at time 0 with TSAT-C6-GA-2 conjugate I-5 followed by IP injection of alpha-methyl mannose (left) or saline (right) after 15 minutes. Alpha-methyl mannose is a very high affinity saccharide which is capable of competing with AEM for binding to lectins such as Con A. As shown, the change in PK/PD profile that results from injection of alpha-methyl mannose is not significant.

FIGS. 24 and 25 show the results obtained when a-MM was administered by IP injection 15 minutes after the sub-Q injection of I-7 and I-5, respectively. As shown, the increase in PK/PD profile that resulted from injection of a-MM was very significant (p<0.05) for conjugate I-7 when compared to the saline injection control group. However, the extent of the a-MM-induced increase in serum conjugate concentration was less than that obtained for the AETM-2 conjugates from Example 42. The I-5 conjugate profile was unaffected by the a-MM injection, just like the results obtained for RHI in FIG. 19. Taken together, these data illustrate that both mannose-derived conjugates (AEM-2 and AETM-2) exhibit the a-MM-enhanced PK/PD profile while the lower affinity-glucosamine derived conjugates do not. Furthermore, the relative change in PK profile for the lower affinity AEM-2 conjugates is less than the change observed for the higher affinity AETM-2 conjugates.

Example 46

Effect of a-MM on PK and Bioactivity as a Function of Ligand Valency

In this example, we set out to determine the pharmacokinetic and pharmacodynamic behavior of conjugates to which an increasing number of exemplary saccharide ligands have been covalently attached. All conjugates were synthesized according to the methods described in Example 20 using the frameworks and saccharide ligands specified below:

| Conjugate | Framework | Framework MW | Ligand | AE-sugar MW | Purity (HPLC) | MW (LC-MS) | Sugar/Insulin |
|---|---|---|---|---|---|---|---|
| I-8: DSS-AEM-1 (B29) | DSS | 368 | AEM | 223 | >95% | 6168 | 1.0 |
| I-9: TSPE-AEM-3 (B29) | TSPE | 813 | AEM | 223 | >95% | 6829 | 3.0 |
| I-10: DSS-AETM-1 (B29) | DSS | 368 | AETM | 547 | >95% | 6491 | 1.0 |
| I-11: TSPE-AETM-3 (B29) | TSPE | 813 | AETM | 547 | >95% | 7800 | 3.0 |

According to N-terminal sequencing, approximately 90% of each saccharide-containing framework was conjugated to insulin via the Lys-B29. The conjugates are shown in FIG. 45 as I-8, I-9, I-10, and I-11.

The same type of experiment described in Example 45 was repeated for the conjugates described in the table above. In each case, the same dose of conjugate (5 U/kg) was injected behind the neck of fasted normal non-diabetic rats (Male Sprague-Dawley, 400-500 gm, n=3). After a 15 minute delay a 4 g/kg dose of a-MM was injected IP. Blood samples were collected via tail vein bleeding at 0 minutes and at 30, 60, 90, 120, 150, 180, 210, 240, and 300 minutes after the initial conjugate injection. Blood glucose values were measured using commercially available test strips (Precision Xtra, Abbott Laboratories, Abbott Park, Ill.). In addition, blood from each timepoint was centrifuged at 4 C to collect the serum. Serum insulin concentrations were subsequently measured with a commercially available ELISA kit (ISO Insulin ELISA, Mercodia, Uppsala, Sweden). A control was performed by injecting saline instead of a-MM after 15 minutes.

Figure 26:
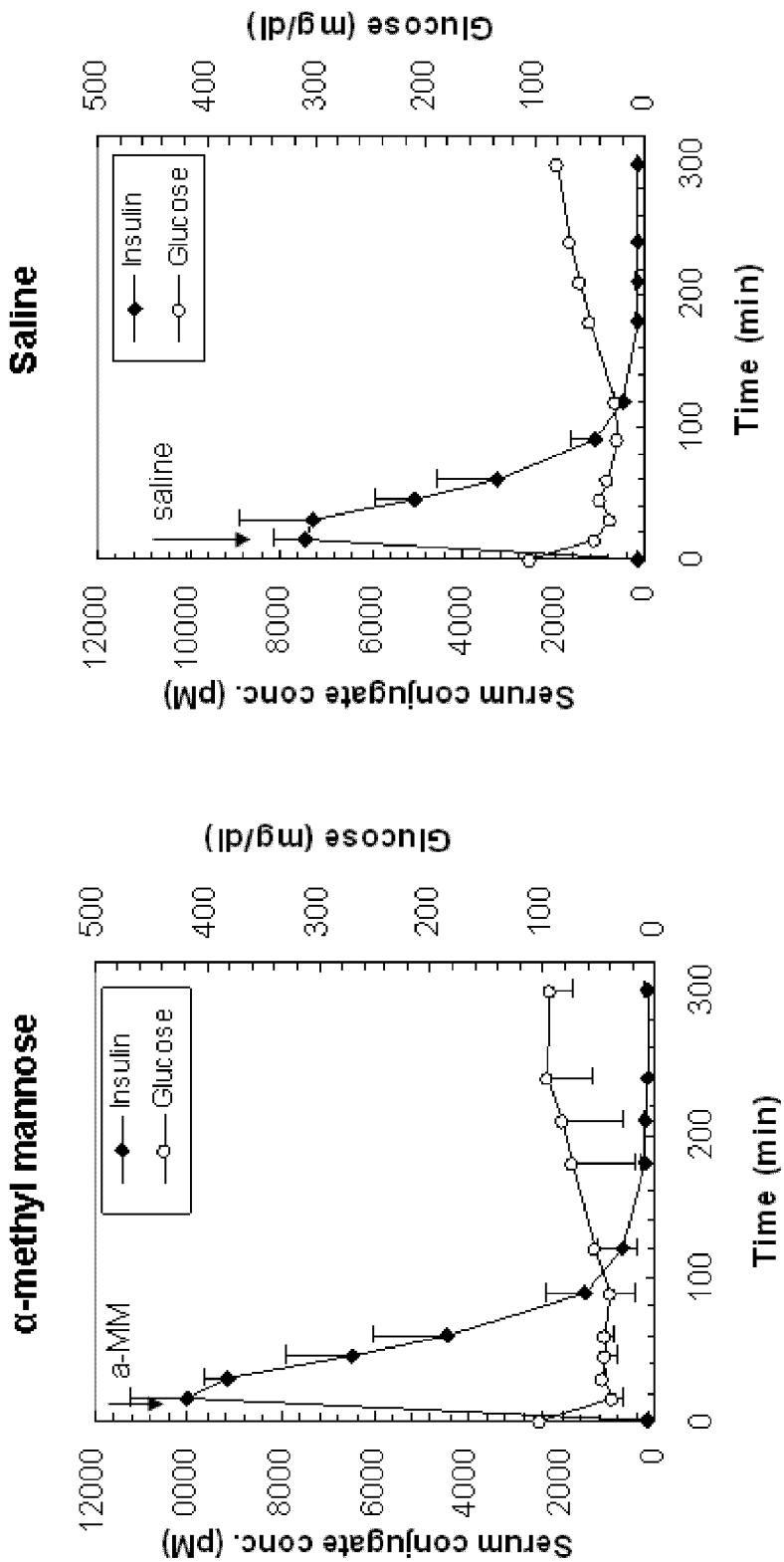
FIG. 26: Plot of serum insulin and blood glucose levels following subcutaneous injection in non-diabetic, male SD rats (n=3) at time 0 with DSS-C6-AEM-1 conjugate I-8 followed by IP injection of alpha-methyl mannose (left) or saline (right) after 15 minutes. Alpha-methyl mannose is a very high affinity saccharide which is capable of competing with AEM for binding to lectins such as Con A. As shown, the change in PK/PD profile that results from injection of alpha-methyl mannose is as not significant.

FIGS. 26 and 27 show the results obtained when a-MM was administered by IP injection 15 minutes after the sub-Q injection of I-8 and I-9, respectively. As shown, the increase in PK/PD profile that resulted from injection of a-MM was very significant (p<0.05) for I-9 and less so for I-8 when compared to the saline injection control group. Furthermore, the I-9 conjugate exhibited approximately the same a-MM-induced PK profile as the I-2 conjugate from Example 42, both of which were much more pronounced than that obtained from I-8.

Figure 28:
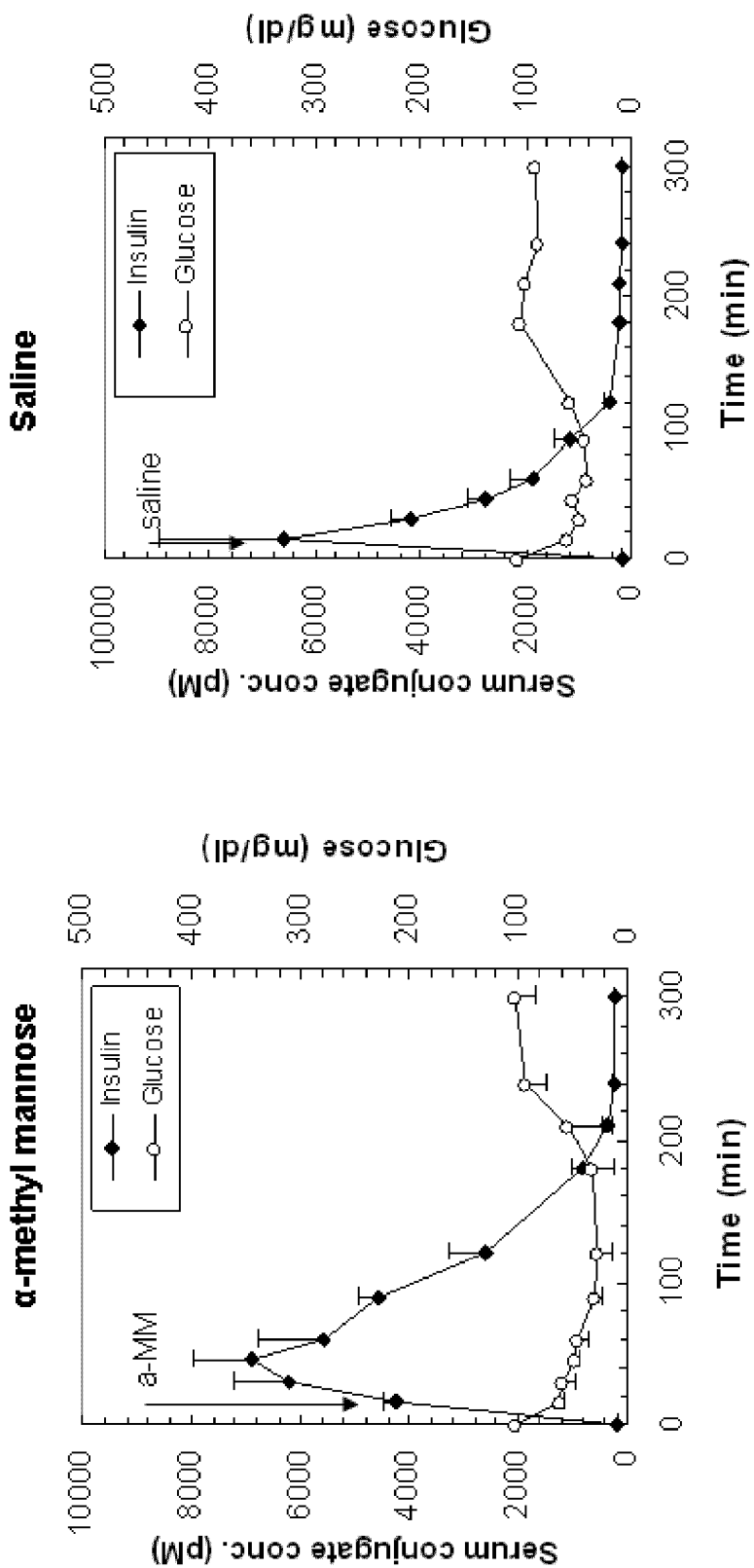
FIG. 28: Plot of serum insulin and blood glucose levels following subcutaneous injection in non-diabetic, male SD rats (n=3) at time 0 with DSS-AETM-1 conjugate I-10 followed by IP injection of alpha-methyl mannose (left) or saline (right) after 15 minutes. Alpha-methyl mannose is a very high affinity saccharide which is capable of competing with AEM for binding to lectins such as Con A. As shown, the change in PK/PD profile that results from injection of alpha-methyl mannose is significant ($p<0.05$).
Figure 29:
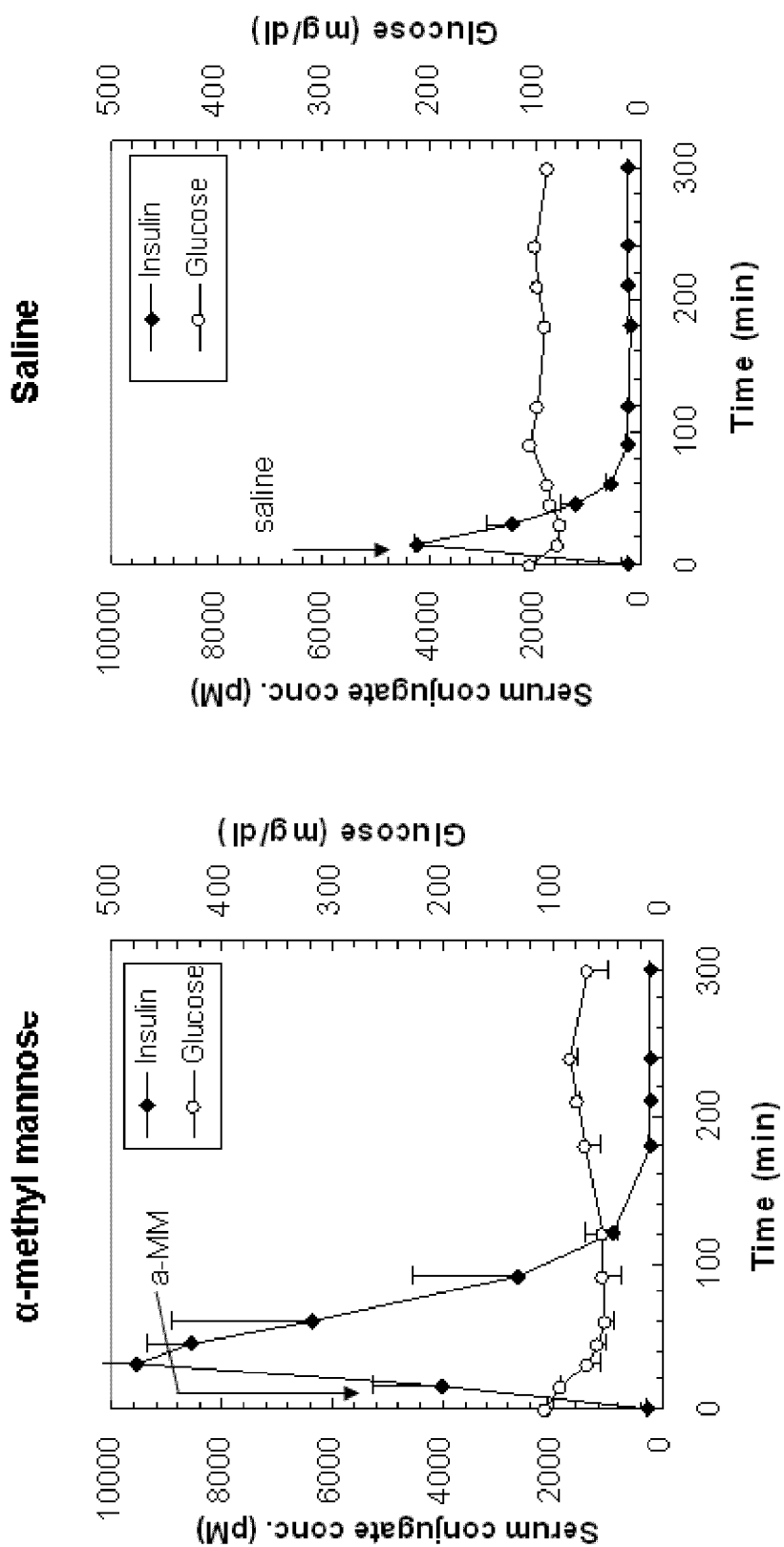
FIG. 29: Plot of serum insulin and blood glucose levels following subcutaneous injection in non-diabetic, male SD rats (n=3) at time 0 with TSPE-AETM-3 conjugate I-11 followed by IP injection of alpha-methyl mannose (left) or saline (right) after 15 minutes. Alpha-methyl mannose is a very high affinity saccharide which is capable of competing with AEM for binding to lectins such as Con A. As shown, the change in PK/PD profile that results from injection of alpha-methyl mannose is significant ($p<0.05$).

FIGS. 28 and 29 show the results obtained when a-MM was administered by IP injection 15 minutes after the sub-Q injection of I-10 and I-11, respectively. As shown, the increase in PK/PD profile that resulted from injection of a-MM was very significant (p<0.05) for I-11 and slightly less so for I-10 when compared to the saline injection control group. Furthermore, the I-11 conjugate exhibited approximately the same a-MM-induced PK profile as the I-2 conjugate from Example 42, both of which were slightly more pronounced than that obtained from I-10.

Example 47

In Vivo Half Life/Elimination Rate Comparison

The results obtained in Example 44 are consistent with the exemplary conjugates being eliminated from the body via a lectin dependent mechanism that can be disrupted by the presence of a competitive saccharide. In order to explore this mechanism in more detail, we conducted the following experiments on exemplary conjugates to determine the rate at which they were cleared from serum in vivo versus unconjugated insulin. All conjugates used in this study were synthesized according to the general methods described in Example 20.

In each case the soluble conjugate was dosed at 0.4 mg conjugate/kg body weight into dual jugular vein cannulated male Sprague-Dawley rats (Taconic, JV/JV, 350-400 g, n=3). A sterile conjugate solution or control insulin was injected intravenously via one JV cannula, followed immediately by a chase solution of heparin-saline to ensure that all of the conjugate dose was administered into the animal. The second cannula was used to collect blood samples at t=0 (pre-dose), and at 1, 2, 4, 8, 15, 30, 60, 90, 120, and 180 minutes post-dose.

Blood glucose values were measured using commercially available test strips (Precision Xtra, Abbott Laboratories, Abbott Park, Ill.). In addition, blood from each timepoint was centrifuged at 4 C to collect the serum. Serum insulin or serum conjugate concentrations were subsequently measured with a commercially available ELISA kit (Iso-Insulin ELISA, Mercodia, Uppsala, Sweden).

Figure 30:
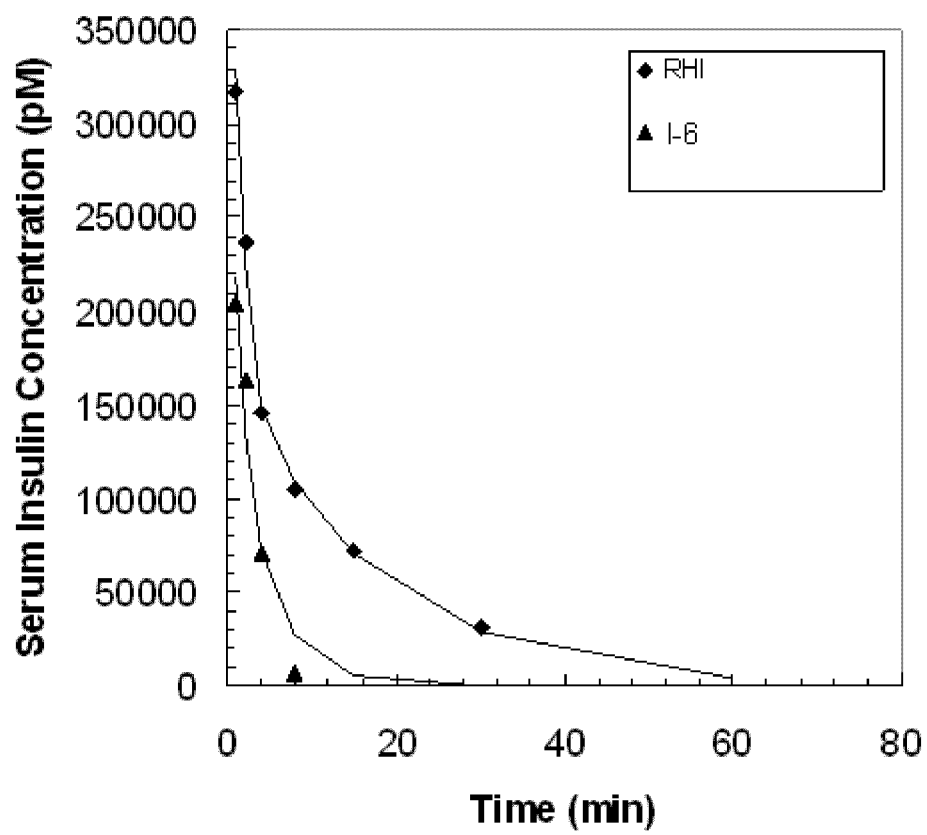
FIG. 30: Plot of serum insulin concentration as a function of time for 0.4 mg/kg i.v. injections of (♦) RHI and (▲) TSAT-C6-AETM-2 conjugate I-6 into non-diabetic, male SD rats (n=3 per group). Data (average of n=3) is fit using a two-compartment bi-exponential model. The TSAT-C6-AETM-2 conjugate is eliminated from serum much faster than RHI.

FIG. 30 shows the serum concentration of either RHI or TSAT-C6-AETM-2 conjugate, shown as I-6 in FIG. 45, as a function of time following the intravenous injection. Clearly, I-6 is eliminated much more rapidly from serum than is RHI. The data is best fit using a two-compartment bi-exponential model with the following general formula: $C(t)=A_o \exp(-at)+B_o \exp(-bt)$ where t is time, C(t) is the concentration in serum as a function of time, $A_o$ is the first compartment concentration constant, a is the first compartment exponential time constant, $B_o$ is the second compartment concentration constant, and b is the second compartment exponential time constant. The elimination half-lives (in minutes) associated with each compartment are $t\frac{1}{2}(a)=0.693/a$ and $t\frac{1}{2}(b)=0.693/b$. In FIG. 30, for RHI the $t\frac{1}{2}(a)=0.76$ and $t\frac{1}{2}(b)=11.46$ and for I-6 the $t\frac{1}{2}(a)=0.47$ and $t\frac{1}{2}(b)=2.87$. In other words, the $t\frac{1}{2}(b)$ for I-6 is about four times shorter than the $t\frac{1}{2}(b)$ for RHI.

The following table summarizes the $t\frac{1}{2}$ parameters for a number of conjugates tested using exactly the same procedure described above (structures are shown in FIG. 45):

| Formulation | $t\frac{1}{2}$ (a) | $t\frac{1}{2}$ (b) | Ratio to RHI $t\frac{1}{2}$ (a) | Ratio to RHI $t\frac{1}{2}$ (b) |
|---|---|---|---|---|
| RHI | 0.76 | 11.46 | 1.00 | 1.00 |
| I-5: TSAT-C6-GA-2 | 0.81 | 12.02 | 1.07 | 1.05 |
| I-8: DSS-AEM-1 | 0.90 | 9.61 | 1.18 | 0.84 |
| I-7: TSAT-C6-AEM-2 | 0.45 | 2.77 | 0.60 | 0.24 |
| I-9: TSPE-AEM-3 | 0.66 | 2.62 | 0.87 | 0.23 |
| I-10: DSS-AETM-1 | 0.82 | 4.48 | 1.08 | 0.39 |
| I-6: TSAT-C6-AETM-2 | 0.47 | 2.87 | 0.62 | 0.25 |
| I-11: TSPE-AETM-3 | 0.22 | 1.33 | 0.29 | 0.12 |

This data is consistent with the hypothesis that the exemplary conjugates are eliminated from serum more rapidly than unconjugated insulin, the extent of which is governed by the affinity of the particular conjugate for the endogenous lectin and the number of ligands substituted per conjugate. Furthermore, the a-MM induced increase in PK/PD profiles demonstrated in Examples 42, and 44-46 correlates well with the reduction in Phase b half-life for each of the conjugates tested.

Example 48

In Vivo Half Life/Elimination Rate Under Glucose Infusion

In this example, it was further hypothesized that the clearance rate of exemplary conjugates could be inhibited by the presence of physiological concentrations of glucose. In order to determine the rate at which the conjugates were cleared from serum in vivo under hyperglycemic conditions, the following experiment was conducted. In each case, I-7 was dosed at 0.4 mg conjugate/kg body weight into dual jugular vein cannulated male Sprague-Dawley rats (Taconic, JV/JV, 350-400 g, n=3).

One hour before the start of the experiment one rat cannula was connected to a syringe infusion pump containing a sterile 50% w/v glucose solution. The pump infusion rate was adjusted by the experimenter to ensure that the blood glucose levels in the animal remained above 300 mg/dL at all times during the experiment. Blood glucose was measured using commercially available test strips (Precision Xtra, Abbott Laboratories, Abbott Park, Ill.). In a typical experiment, it was found that the infusion pump rate required to keep the animals above 300 mg/dL was typically greater than 85 uL/min. A blood sample was taken at t=0 min, after which a sterile conjugate solution or control insulin was injected intravenously via the second rat cannula, followed immediately by a chase solution of heparin-saline to ensure that all of the conjugate dose was administered into the animal. After an additional flush of the cannula line with heparin-saline, the second cannula was used to collect blood samples at t=1, 2, 4, 8, 15, 30, 60, 90, 120, and 180 minutes post-dose.

Blood from each timepoint was centrifuged at 4 C to collect the serum, and serum insulin or serum conjugate concentrations were subsequently measured with a commercially available ELISA kit (Iso-Insulin ELISA, Mercodia, Uppsala, Sweden). Insulin or conjugate serum concentration vs. time data was best fit with the sum of two independent decaying exponentials ($C(t)=a \exp(-k_a t)+b \exp(-k_b t)$) according to the two-compartment model, where $t\frac{1}{2}(a)=(\ln 2)/k_a$ and $t\frac{1}{2}(b)=(\ln 2)/k_b$. The following table summarizes the $t\frac{1}{2}$ parameters for I-7 with and without the glucose infusion along with those obtained for RHI from Example 47:

| Infusion | Formulation | t½ (a) | t½ (b) | Ratio to RHI t½ (a) | Ratio to RHI t½ (b) |
|---|---|---|---|---|---|
| None | RHI | 0.76 | 11.46 | 1.00 | 1.00 |
| Saline | TSAT-C6-AEM-2 (I-7) | 0.45 | 2.77 | 0.60 | 0.24 |
| Glucose (400 mg/dl) | TSAT-C6-AEM-2 (I-7) | 0.64 | 5.11 | 0.84 | 0.45 |

We can conclude from these data that glucose is able to inhibit the accelerated serum elimination for this conjugate thereby doubling the Phase b elimination half life from 2.77 to 5.11 minutes.

Example 49

In Vivo Half Life/Elimination Rate Under a-MM Infusion

In this example, it was further hypothesized that the clearance rate of insulin-saccharide conjugates could be inhibited by the presence of arbitrarily high concentrations of inhibitory saccharides other than glucose, such as α-methyl-mannose (a-MM). In order to determine the rate at which exemplary conjugates were cleared from serum in vivo in the presence of a-MM, the following experiment was conducted. In each case the soluble conjugate was dosed at 0.4 mg conjugate/kg body weight into dual jugular vein cannulated male Sprague-Dawley rats (Taconic, JV/JV, 350-400 g, n=3).

One hour before the start of the experiment one rat cannula was connected to a syringe infusion pump containing a sterile 25% w/v a-MM solution. The pump infusion rate was adjusted by the experimenter, but was typically set at 85 uL/min. A blood sample was taken at t=0 min, after which a sterile conjugate solution or control insulin was injected intravenously via the second rat cannula, followed immediately by a chase solution of heparin-saline to ensure that all of the conjugate dose was administered into the animal. After an additional flush of the cannula line with heparin-saline, the second cannula was used to collect blood samples at t=1, 2, 4, 8, 15, 30, 60, 90, 120, and 180 minutes post-dose.

In addition, blood glucose was measured using commercially available test strips (Precision Xtra, Abbott Laboratories, Abbott Park, Ill.). Blood from each timepoint was centrifuged at 4 C to collect the serum, and serum insulin or serum conjugate concentrations were subsequently measured with a commercially available ELISA kit (Iso-Insulin ELISA, Mercodia, Uppsala, Sweden). Insulin or conjugate serum concentration vs. time data was best fit with the sum of two independent decaying exponentials ($C(t) = a \exp(-k_a t) + b \exp(-k_b t)$) according to the two-compartment model, where $t\frac{1}{2}(a) = (\ln 2)/k_a$ and $t\frac{1}{2}(b) = (\ln 2)/k_b$. The following table summarizes the t½ parameters for the TSAT-C6-AEM-2 conjugate with and without the a-MM infusion along with those obtained with glucose infusion from Example 48 and those obtained for RHI with no saccharide infusion from Example 47:

| Infusion | Formulation | t½ (a) | t½ (b) | Ratio to RHI t½ (a) | Ratio to RHI t½ (b) |
|---|---|---|---|---|---|
| None | RHI | 0.76 | 11.46 | 1.00 | 1.00 |
| Saline | TSAT-C6-AEM-2 (I-7) | 0.45 | 2.77 | 0.60 | 0.24 |
| a-MM | TSAT-C6-AEM-2 (I-7) | 0.92 | 10.09 | 1.21 | 0.88 |
| Glucose (400 mg/dl) | TSAT-C6-AEM-2 (I-7) | 0.64 | 5.11 | 0.84 | 0.45 |

We can conclude from these data that not only does a-MM inhibit the accelerated serum elimination for this conjugate, it does so to an even greater extent than does glucose. In this case, the Phase b elimination half life nearly quadruples from 2.77 to 10.09 minutes.

IV. Other Examples

This fourth set of examples describes various experiments investigating the synthesis, formulation, and properties of some exemplary conjugates.

Example 50

Long Acting Insulin Conjugates Using Protamine, Zinc, and Other Excipients

Given that the data from previous examples is consistent with a saccharide-dependent serum elimination mechanism, we set out to develop formulations of conjugates that would provide a steady, sustained rate of absorption from a subcutaneous injection site. At a steady absorption rate, the serum conjugate concentration at any point in time will be governed primarily by the saccharide-dependent elimination rate. In such a way, we can formulate a long acting, sustained-release insulin exhibiting a saccharide-responsive PK profile.

In order to generate long acting conjugates, we prepared PZI (protamine zinc insulin) formulations from the conjugate solutions. Conjugates substituted with insulin at the B1-terminus do not form amorphous or crystalline PZI formulations as readily, so we used B29-substituted conjugates prepared based on the methods of Example 20. The excipients used in these formulations comprise protamine, zinc, m-cresol, and salt all of which were obtained commercially from Sigma-Aldrich (St. Louis, Mo.). The concentrations of these components may be varied in order to obtain an optimally flat, sustained absorption rate. In addition, in some cases it was found that the addition of a small amount of unmodified insulin helped stabilize the formulation. In these cases, the concentration of unmodified insulin contained in the sample was varied to obtain an optimally flat, sustained absorption rate. In all formulations tested, the following recipe was used:

| Component | Variable | Volume (ml) |
|---|---|---|
| Conjugate solution at 2.7 mg/ml | % unmodified insulin content (M/M) | 1.000 |
| 250 mM HEPES buffered saline | NaCl concentration (M) | 0.111 |
| Zinc acetate solution | Zinc concentration (mg/ml) | 0.124 |
| Cresol solution in water | v/v % | 0.159 |
| pH 7.2 Protamine solution in 25 mM HEPES buffered saline | Protamine concentration (mg/ml) | 4 × 0.194 aliquots |

Unless otherwise specified, once the formulations were prepared after addition of the components in the order described in the table above, they were gently mixed for 30 minutes prior to in vivo testing.

To test the sustained release profile for a given formulation as well as the glucose-responsive PK profile, the following experiment was conducted. The formulation was injected at a predetermined dose (~15 U/kg in most cases unless otherwise specified) behind the neck of fasted normal non-diabetic rats (Male Sprague-Dawley, 400-500 gm, n=3). After a 240 minute delay, a glucose dose (4 g/kg) was injected IP. Blood samples were collected via tail vein bleeding at 0 minutes and at 30, 60, 90, 120, 150, 180, 210, 240, and 300 minutes after the initial conjugate injection. Blood glucose values were measured using commercially available test strips (Precision Xtra, Abbott Laboratories, Abbott Park, Ill.). In addition, blood from each timepoint was centrifuged at 4 C to collect the serum. Serum insulin concentrations were subsequently measured with a commercially available ELISA kit (Iso-Insulin ELISA, Mercodia, Uppsala, Sweden). According to the manufacturer's assay specifications, the Iso-Insulin ELISA is 71% cross-reactive with rat insulin. The serum samples were diluted by 10× in order to minimize the amount of endogenous rat insulin detected in each sample but the possibility of rat insulin detection could not be completely ruled out. Therefore, the results are generally reported as "measured insulin," which can consist of some amount of endogenous rat insulin in addition to the conjugate or RHI, depending on the experiment. Nevertheless, all samples collected in each of the following examples were treated identically and can be directly compared for differences in performance.

Example 51

Effect of Protamine Concentration on Long Acting Insulin Conjugate Performance

The purpose of this example was to demonstrate the effect of protamine concentration on the time action and glucose-responsive PK profile of an exemplary conjugate. In this example I-6, synthesized according to the methods described in Example 20, was tested using the generalized formulation and in vivo protocol described in Example 50:

| Component | Variable | Volume (ml) |
| --- | --- | --- |
| TSAT-C6-AETM-2 (I-6) solution at 2.7 mg/ml | unmodified insulin = 16.7% | 1.000 |
| 250 mM HEPES buffered saline | NaCl concentration = 1.5M | 0.111 |
| Zinc acetate solution | Zinc concentration (mg/ml) = see below | 0.124 |
| Cresol solution in water | 3% v/v | 0.159 |
| pH 7.2 Protamine solution in 25 mM HEPES buffered saline | Protamine concentration (mg/ml) = see below | 4 × 0.194 aliquots |

| Formulation | Zinc concentration (mg/ml) | Protamine concentration (mg/ml) |
| --- | --- | --- |
| 1xP-1xZ | 1.15 | 1.25 |
| 4xP-4xZ | 4.60 | 5.00 |
| 10xP-4xZ | 4.60 | 12.50 |

Figure 31:
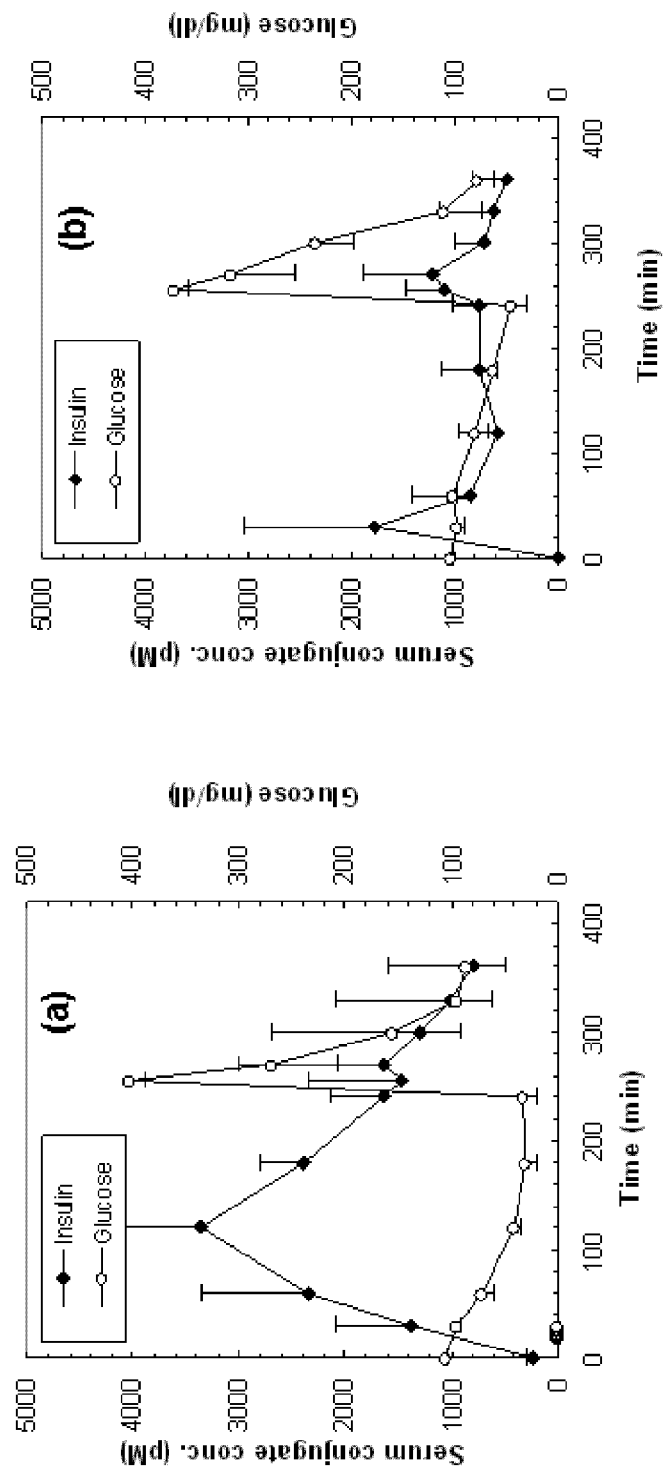
FIG. 31: Plots of serum insulin (♦) and blood glucose (○) levels following subcutaneous injection in non-diabetic, male SD rats (n=3 per dose) at time 0 with long-acting TSAT-C6-AETM-2 (I-6) conjugates followed by IP injection of glucose (4 g/kg) at 240 minutes. Formulations were prepared as described in Example 51: (a) 1×P–1×Z, (b) 4×P–4×Z, and (c) 10×P–4×Z.
Figure 31:
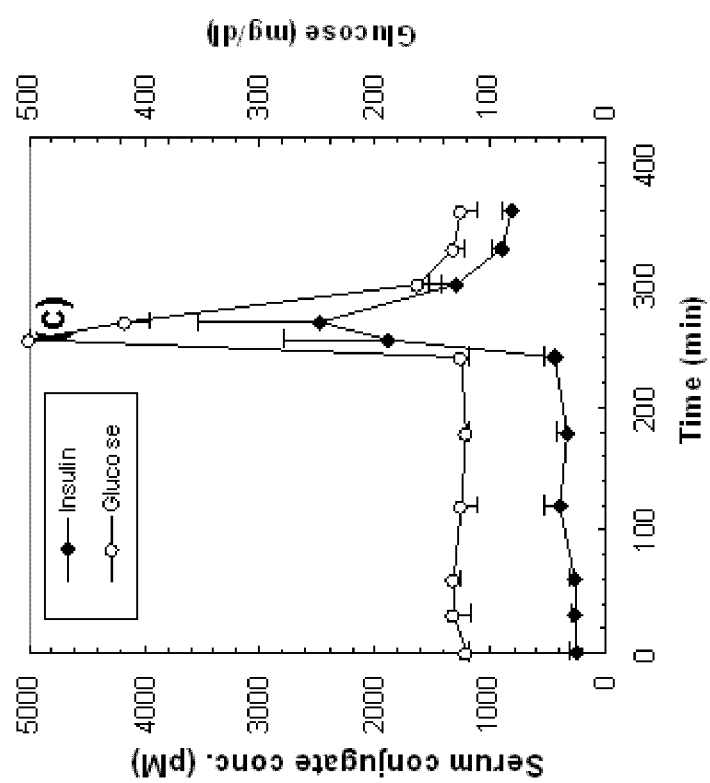
Figure 32:
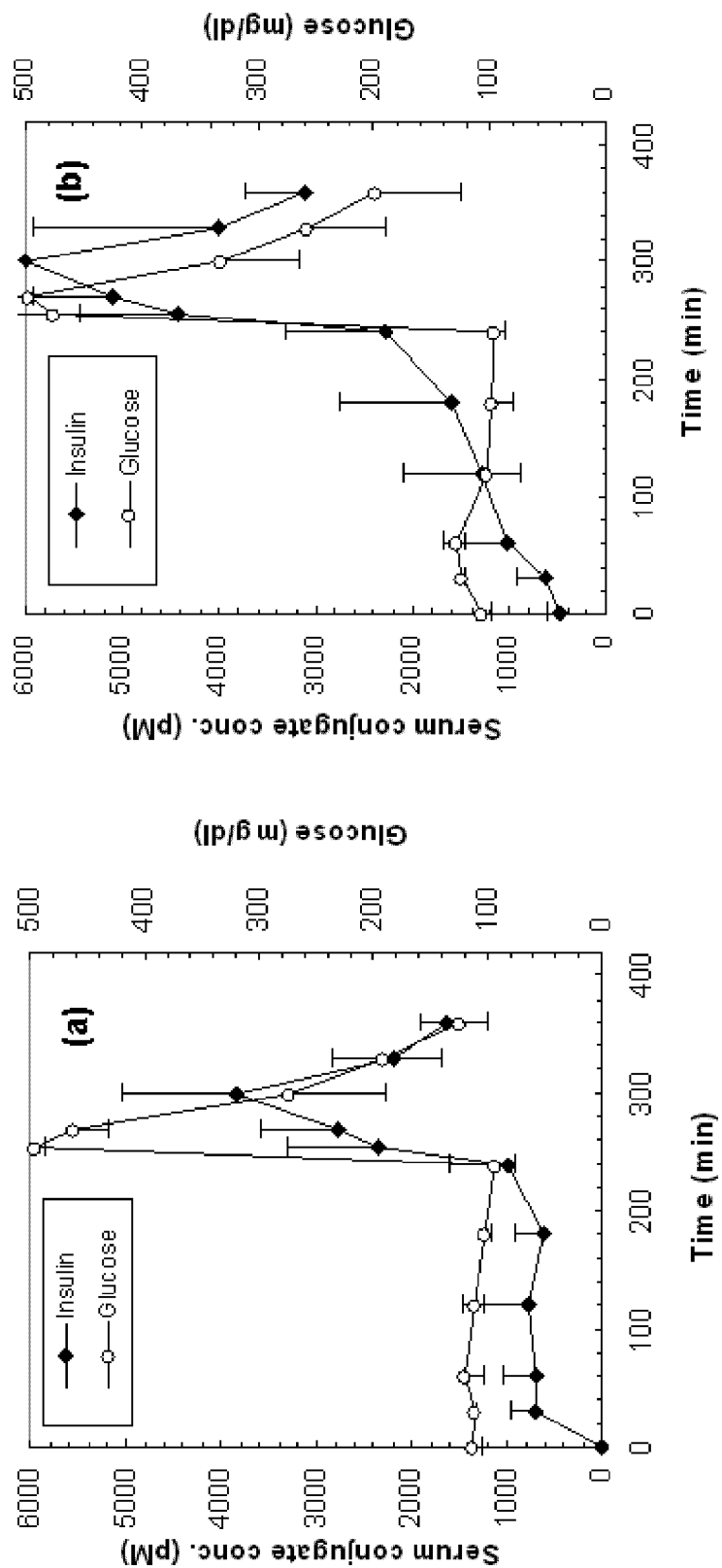
FIG. 32: Plots of serum insulin (♦) and blood glucose (○) levels following subcutaneous injection in non-diabetic, male SD rats (n=3 per dose) at time 0 with long-acting TSAT-C6-AETM-2 (I-6) conjugates followed by IP injection of glucose (4 g/kg) at 240 minutes. Formulations were prepared as described in Example 52: (a) 4×P–1×Z and (b) 4×P–2×Z.
Figure 33:
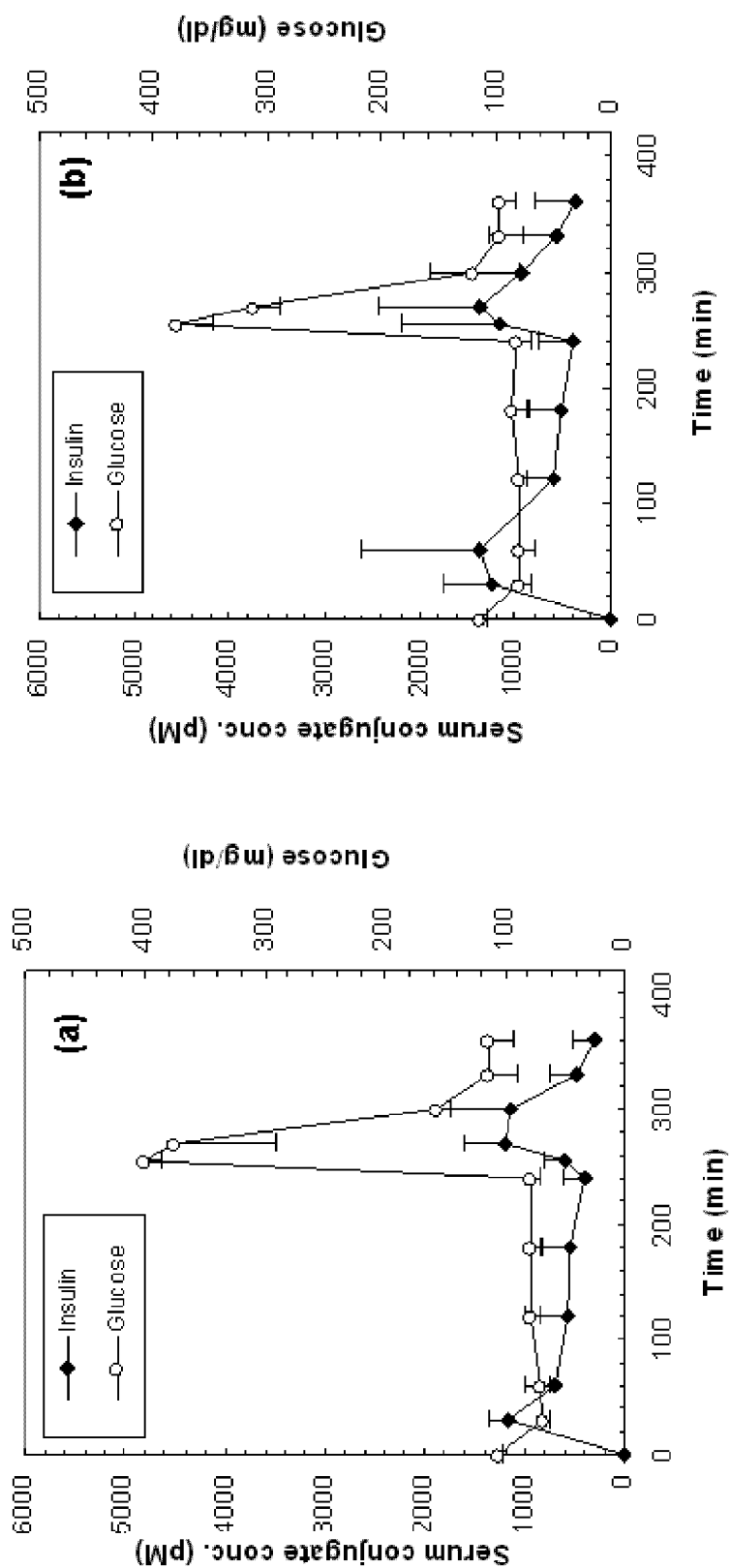
FIG. 33: Plots of serum insulin (♦) and blood glucose (○) levels following subcutaneous injection in non-diabetic, male SD rats (n=3 per dose) at time 0 with long-acting TSAT-C6-AETM-2 (I-6) conjugates followed by IP injection of glucose (4 g/kg) at 240 minutes. Formulations were prepared as described in Example 52: (a) 10×P–1×Z and (b) 10×P–2×Z.

The four hour IP glucose injection (4 g/kg) experiments were performed by dosing 15 U/kg (body weight in grams/1.87=microliters of injection volume) of each of the three formulations described above. The results shown in FIG. 31a-c demonstrate that as the protamine concentration in the formulation increases, the more protracted the resulting formulation and the more pronounced the measured increase in serum insulin profile after the four hour glucose injection.

The 1xP-1xZ formulation released a significant portion of the insulin conjugate payload over a short period of time immediately following the injection such that very little signal was detected after the IP glucose challenge. On the other hand, the 10xP-4xZ formulation released a low basal amount of insulin over the first four hours with no hypoglycemia and subsequently attained >4× increase in measured insulin concentration immediately following the IP glucose injection.

Example 52

Effect of Zinc Concentration on Long Acting Insulin Conjugate Performance

The purpose of this example was to demonstrate the effect of zinc concentration on the formulation stability, time action and glucose-responsive PK profile of an exemplary conjugate. In this example I-6, synthesized according to the methods described in Example 20, was tested using the generalized formulation and in vivo protocol described in Example 50:

| Component | Variable | Volume (ml) |
| --- | --- | --- |
| TSAT-C6-AETM-2 (I-6) solution at 2.7 mg/ml | unmodified insulin = 0% | 1.000 |
| 250 mM HEPES buffered saline | NaCl concentration = 1.5M | 0.111 |
| Zinc acetate solution | Zinc concentration (mg/ml) = see below | 0.124 |
| Cresol solution in water | 3% v/v | 0.159 |
| pH 7.2 Protamine solution in 25 mM HEPES buffered saline | Protamine concentration (mg/ml) = see below | 4 × 0.194 aliquots |

| Formulation | Zinc concentration (mg/ml) | Protamine concentration (mg/ml) |
| --- | --- | --- |
| 4xP-1xZ | 1.15 | 5.00 |
| 4xP-2xZ | 2.30 | 5.00 |
| 10xP-1xZ | 1.15 | 12.5 |
| 10xP-2xZ | 2.30 | 12.5 |

The four hour IP glucose injection (4 g/kg) experiments were performed by dosing 15 U/kg (body weight in grams/1.87=microliters of injection volume) of each of the four formulations described above. The results shown in FIGS. 32a-b and 33a-b demonstrate that within experimental error, the concentration of zinc did not have a significant effect on the overall sustained release nature of the formulation or the glucose-responsive profile. In all cases, a statistically significant increase in measured insulin concentration was observed following the IP glucose injection. As demonstrated in Example 51, the higher protamine (10×P) formulations released less conjugate over time than the lower protamine (4×P) formulations regardless of the zinc concentration. However, when the formulations were left at room temperature for greater than 24 hours, both 10×P formulations transformed from an easily dispersible particulate solution into a sticky, agglomerated, two-phase solution. This did not happen with the corresponding 10×P-4×Z formulation. Similarly, the 4×P-1×Z formulation was found to transform the same way as the 10×P-1×Z formulation whereas the 4×P-2×Z was relatively stable at room temperature for weeks. Therefore, the zinc concentration for a given protamine concentration can be adjusted to prepare easily dispersible formulations that are stable over long periods of time.

Example 53

Effect of m-Cresol Concentration on Long Acting Insulin Conjugate Performance The purpose of this example was to demonstrate the effect of m-cresol concentration on the time action and glucose-responsive PK profile of an exemplary conjugate. In this example I-6, synthesized according to the methods described in Example 20, was tested using the generalized formulation and in vivo protocol described in Example 50:

| Component | Variable | Volume (ml) |
| --- | --- | --- |
| TSAT-C6-AETM-2 (I-6) solution at 2.7 mg/ml | unmodified insulin = 0% | 1.000 |
| 250 mM HEPES buffered saline | NaCl concentration = 1.5M | 0.111 |
| Zinc acetate solution | Zinc concentration = 4.6 mg/ml | 0.124 |
| Cresol solution in water | v/v % = see below | 0.159 |
| pH 7.2 Protamine solution in 25 mM HEPES buffered saline | Protamine concentration = 12.5 mg/ml | 4 × 0.194 aliquots |

| Formulation | Cresol concentration |
| --- | --- |
| No cresol | 0 |
| 4x cresol | 12% v/v |

Figure 34:
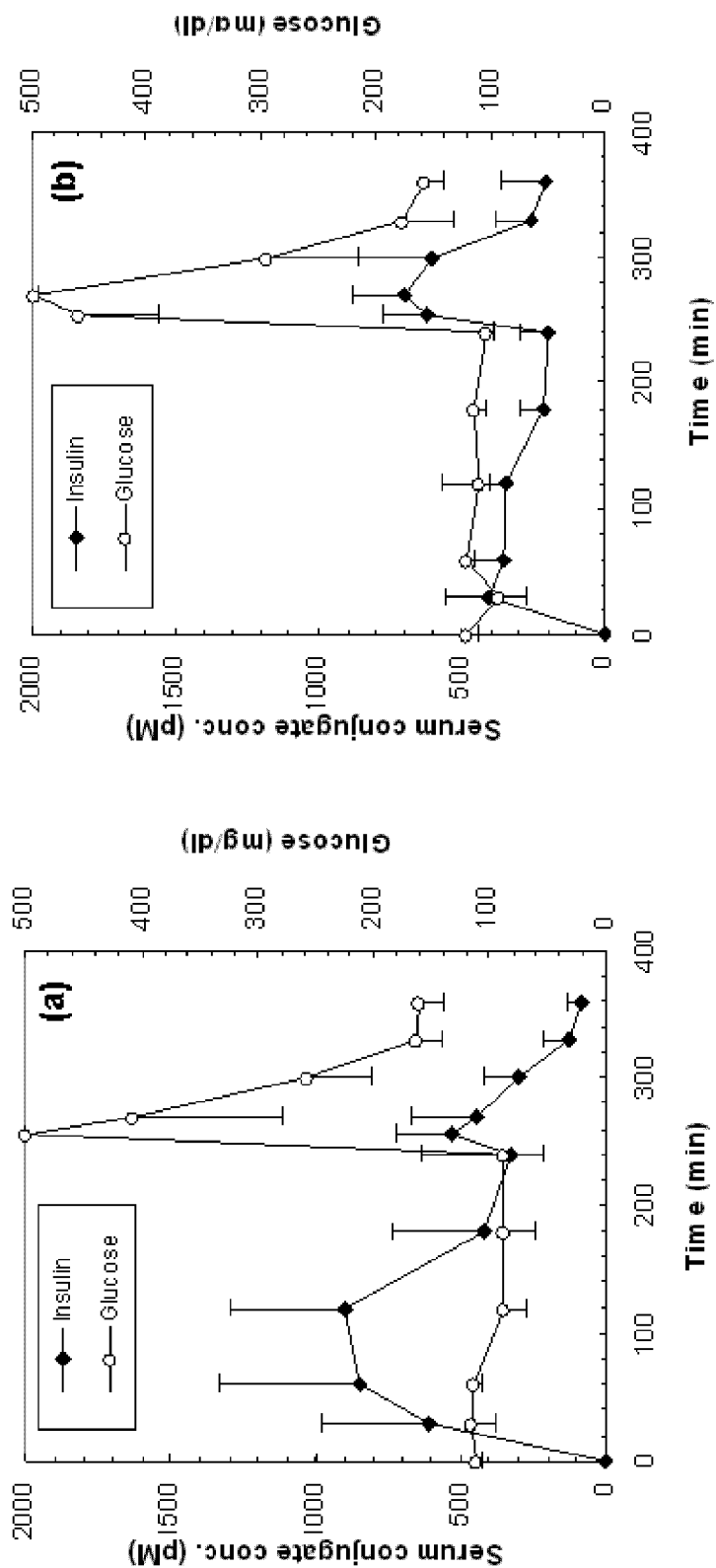
FIG. 34: Plots of serum insulin (♦) and blood glucose (○) levels following subcutaneous injection in non-diabetic, male SD rats (n=3 per dose) at time 0 with long-acting TSAT-C6-AETM-2 (I-6) conjugates followed by IP injection of glucose (4 g/kg) at 240 minutes. Formulations were prepared as described in Example 53: (a) no cresol and (b) 4× cresol.

The four hour IP glucose injection (4 g/kg) experiments were performed by dosing 15 U/kg (body weight in grams/1.87=microliters of injection volume) of the two formulations described above. The results shown in FIG. 34a-b demonstrate that the presence of m-cresol maintains a more protracted formulation. The no cresol formulation releases a significant portion of the insulin conjugate payload over a short period of time immediately following the injection such that very little increase in measured insulin concentration was observed when challenged with IP glucose. On the other hand, the 4x cresol formulation releases a low basal amount of insulin over the first four hours with no hypoglycemia and subsequently attains a 3-4x increase in measured insulin concentration immediately following the IP glucose injection.

Example 54

Effect of Salt/Isotonic Agent Concentration on Long Acting Insulin Conjugate Performance The purpose of this example was to demonstrate the effect of salt concentration and choice of isotonic agent on the time action and glucose-responsive PK profile of an exemplary conjugate. In this example I-6, synthesized according to the methods described in Example 20, was tested using the generalized formulation and in vivo protocol described in Example 50:

| Component | Variable | Volume (ml) |
| --- | --- | --- |
| TSAT-C6-AETM-2 (I-6) solution at 2.7 mg/ml | unmodified insulin = 16.7% | 1.000 |
| 250 mM HEPES buffered saline | NaCl or glycerol concentration (M) = see below | 0.111 |
| Zinc acetate solution | Zinc concentration = 4.6 mg/ml | 0.124 |
| Cresol solution in water | 3% v/v | 0.159 |
| pH 7.2 Protamine solution in 25 mM HEPES buffered saline | Protamine concentration = 12.5 mg/ml | 4 × 0.194 aliquots |

| Formulation | NaCl concentration |
| --- | --- |
| No salt | 0.0M |
| 3.3x salt | 5.0M |
| Glycerol | Neat glycerol solution instead of buffered saline |

Figure 35:
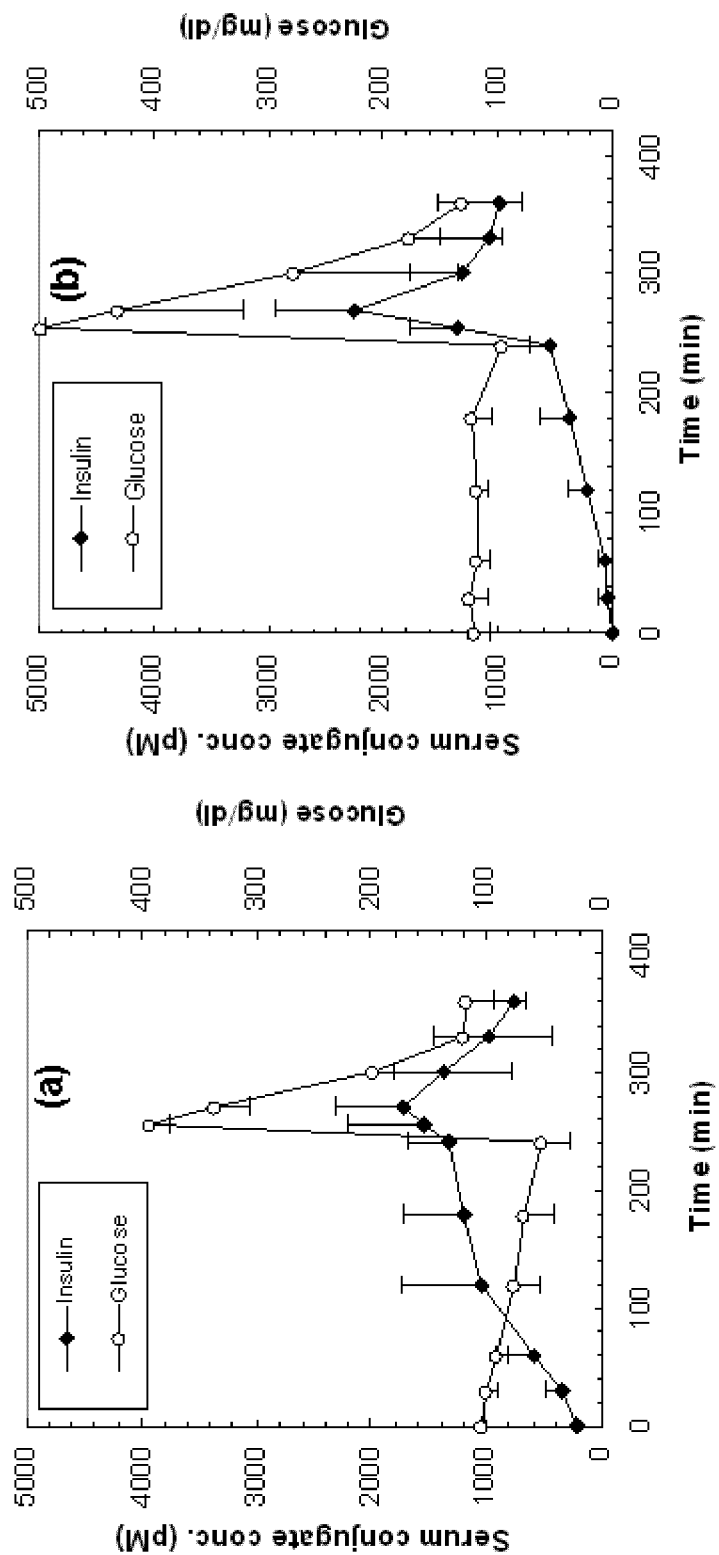
FIG. 35: Plots of serum insulin (♦) and blood glucose (○) levels following subcutaneous injection in non-diabetic, male SD rats (n=3 per dose) at time 0 with long-acting TSAT-C6-AETM-2 (I-6) conjugates followed by IP injection of glucose (4 g/kg) at 240 minutes. Formulations were prepared as described in Example 54: (a) no salt, (b) 3.3× salt, and (c) glycerol.
Figure 35:
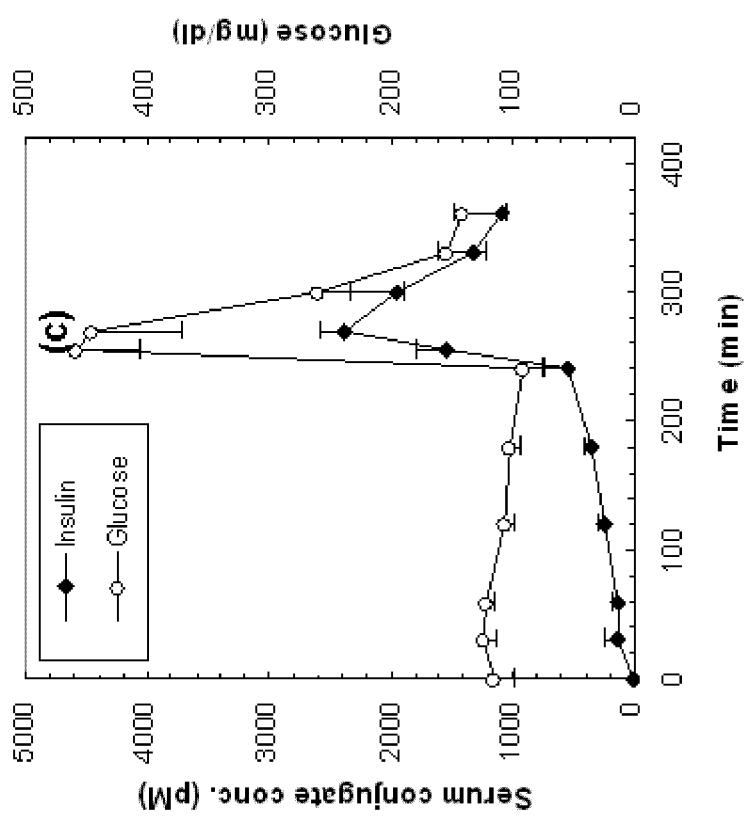

The four hour IP glucose injection (4 g/kg) experiments were performed by dosing 15 U/kg (body weight in grams/1.87=microliters of injection volume) of each of the three formulations described above. The results shown in FIG. 35a-c demonstrate that the presence of salt in the formulation maintains a more protracted formulation. The no salt formulation released a significant portion of the insulin conjugate payload over the first four hours of the experiment such that very little increase in measured insulin concentration was observed when challenged with IP glucose. On the other hand, the 3.3x salt formulation released a low basal amount of conjugate over the first four hours with no hypoglycemia and subsequently attained a ~4x increase in measured insulin concentration immediately following the IP glucose injection. This performance was similar to that obtained with the 10xP-4xZ formulation from Example 51, which was exactly the same as the 3.3x salt formulation but contained approximately 1/3 the salt concentration (1.5 M as compared to 5.0 M). Finally, substituting glycerol for NaCl as the isotonic agent does not appear to adversely affect the protracted nature of the formulation.

Example 55

Effect of Unmodified Insulin Concentration on Long Acting Insulin Conjugate Performance The purpose of this example was to demonstrate the effect of including different concentrations of unmodified insulin on the time action and glucose-responsive PK profile of an exemplary conjugate. In this example I-6, synthesized according to the methods described in Example 20, was tested using the generalized formulation and in vivo protocol described in Example 50:

| Component | Variable | Volume (ml) |
| --- | --- | --- |
| TSAT-C6-AETM-2 (I-6) solution at 2.7 mg/ml | % unmodified insulin = see below | 1.000 |
| 250 mM HEPES buffered saline | NaCl concentration = 1.5M | 0.111 |
| Zinc acetate solution | Zinc concentration = 4.6 mg/ml | 0.124 |
| Cresol solution in water | 3% v/v | 0.159 |
| pH 7.2 Protamine solution in 25 mM HEPES buffered saline | Protamine concentration = 12.5 mg/ml | 4 × 0.194 aliquots |

| Formulation | % unmodified insulin |
| --- | --- |
| 1/24 | 4.17 |
| 1/12 | 8.33 |
| 1/6 | 16.7 |

Figure 36:
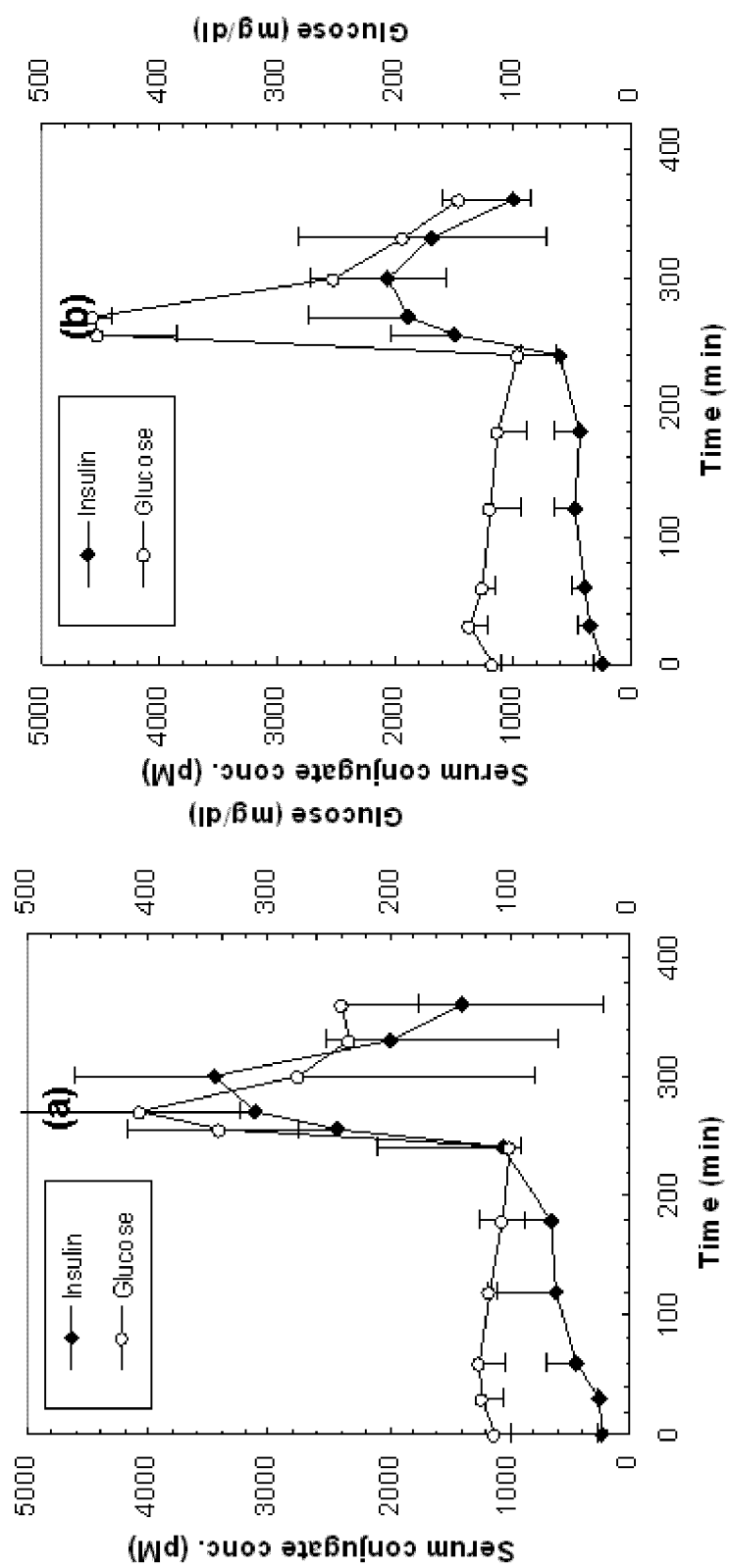
FIG. 36: Plots of serum insulin (♦) and blood glucose (○) levels following subcutaneous injection in non-diabetic, male SD rats (n=3 per dose) at time 0 with long-acting TSAT-C6-AETM-2 (I-6) conjugates followed by IP injection of glucose (4 g/kg) at 240 minutes. Formulations were prepared containing increasing amounts of unmodified insulin as described in Example 55: (a) 1/24, (b) 1/12, and (c) 1/6.
Figure 36:
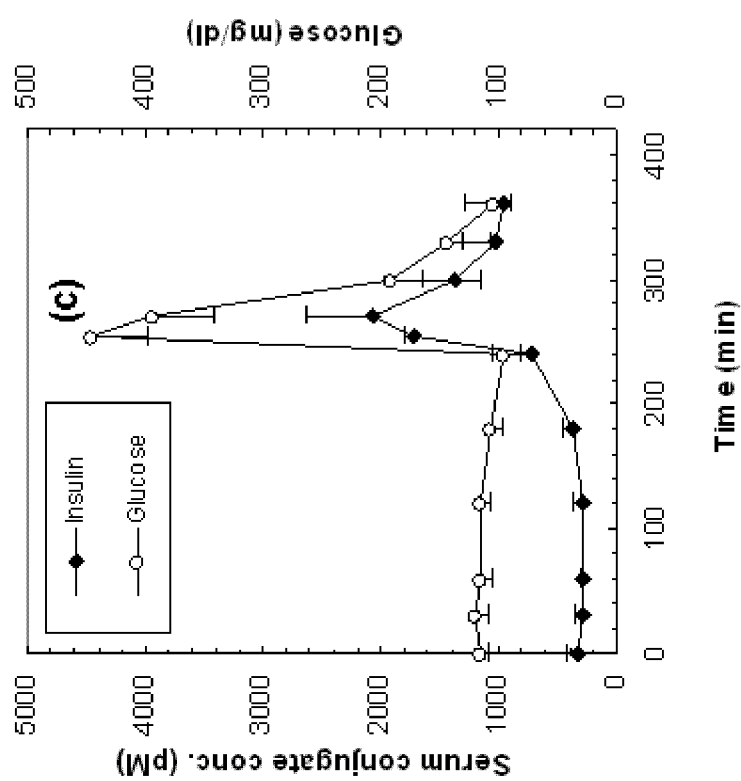

The four hour IP glucose injection (4 g/kg) experiments were performed by dosing 15 U/kg (body weight in grams/1.87=microliters of injection volume) of each of the three formulations described above. The results shown in FIG. 36a-c demonstrate that the presence of unmodified insulin in the formulation beneficially produces a more protracted formulation with substantial increase in measured insulin concentration following an IP glucose injection. Furthermore, the presence of unmodified insulin helps preserve the formulation performance even after several weeks of room temperature incubation (see Example 57 below).

Example 56

Long Acting Insulin Conjugates—Dose Response Effect

In this example, we evaluated the dose-response effect of a particular formulation of a long-acting exemplary conjugate. Conjugate I-6, synthesized according to the methods described in Example 20, was tested using the generalized formulation and in vivo protocol described in Example 50:

| Component | Variable | Volume (ml) |
|---|---|---|
| TSAT-C6-AETM-2 (I-6) solution at 2.7 mg/ml | unmodified insulin = 16.7% | 1.000 |
| 250 mM HEPES buffered saline | NaCl concentration = 1.5M | 0.111 |
| Zinc acetate solution | Zinc concentration = 4.6 mg/ml | 0.124 |
| Cresol solution in water | 3% v/v | 0.159 |
| pH 7.2 Protamine solution in 25 mM HEPES buffered saline | Protamine concentration = 12.5 mg/ml | 4 × 0.194 aliquots |

The four hour IP glucose injection (4 g/kg) experiment was performed by dosing 5 or 15 U/kg (body weight in grams/1.87=microliters of injection volume) of the formulation described above.

Figure 37:
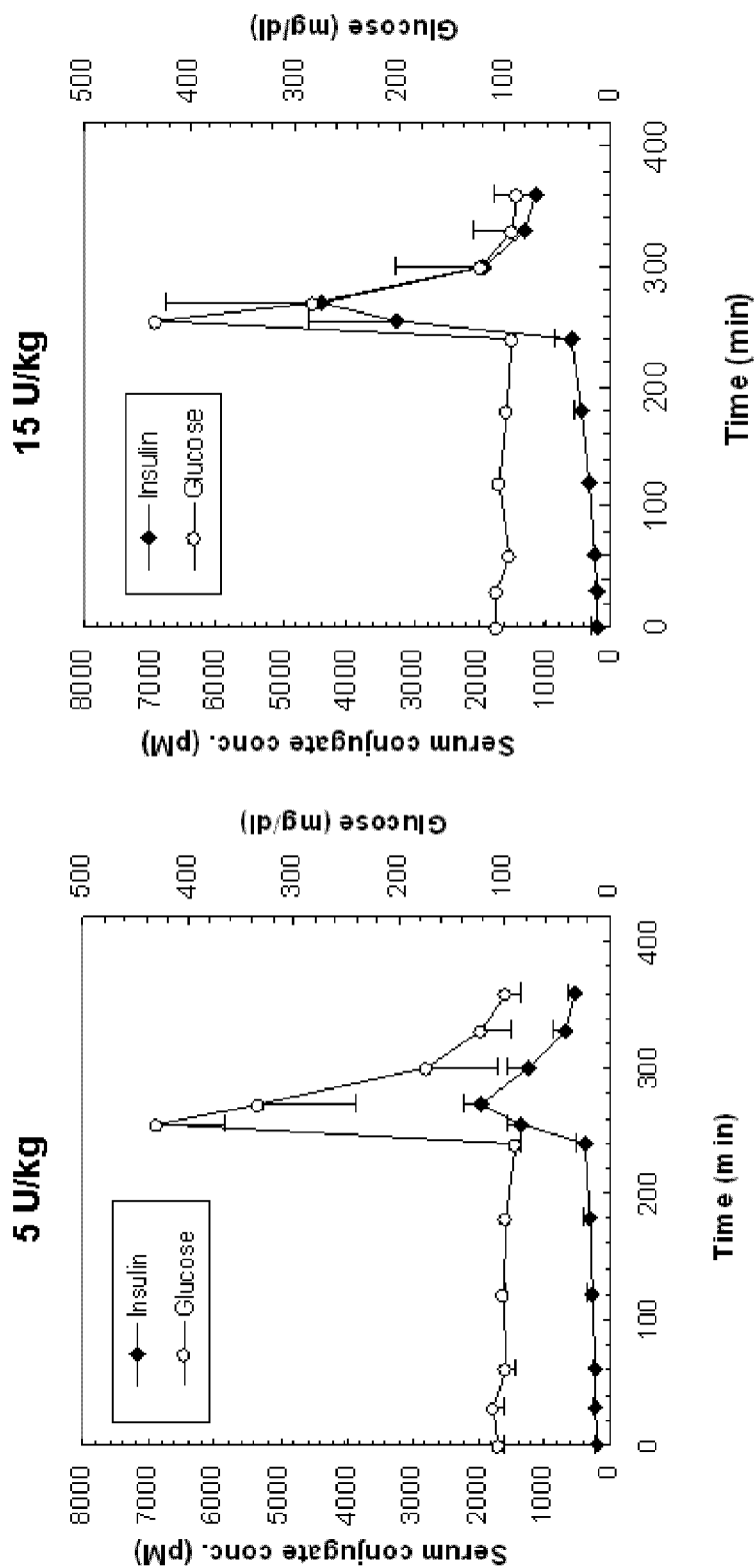
FIG. 37: Plot of serum insulin (♦) and blood glucose (○) levels following subcutaneous injection in non-diabetic, male SD rats (n=3 per dose) at time 0 with a long-acting TSAT-C6-AETM-2 conjugate I-6 prepared according to Example 56 followed by IP injection of glucose (4 g/kg) at 240 minutes.

As shown in FIG. 37, the conjugate exhibited a flat PK profile until the glucose was injected. The increase in measured insulin concentration following the IP glucose challenge was dramatic and dose-dependent (compare data obtained with a 5 U/kg (left) and 15 U/kg (right) dose of conjugate). No hypoglycemia was observed at early or late time points.

Example 57

Stability of Exemplary Long-Acting, Glucose-Responsive Conjugates

Figure 38:
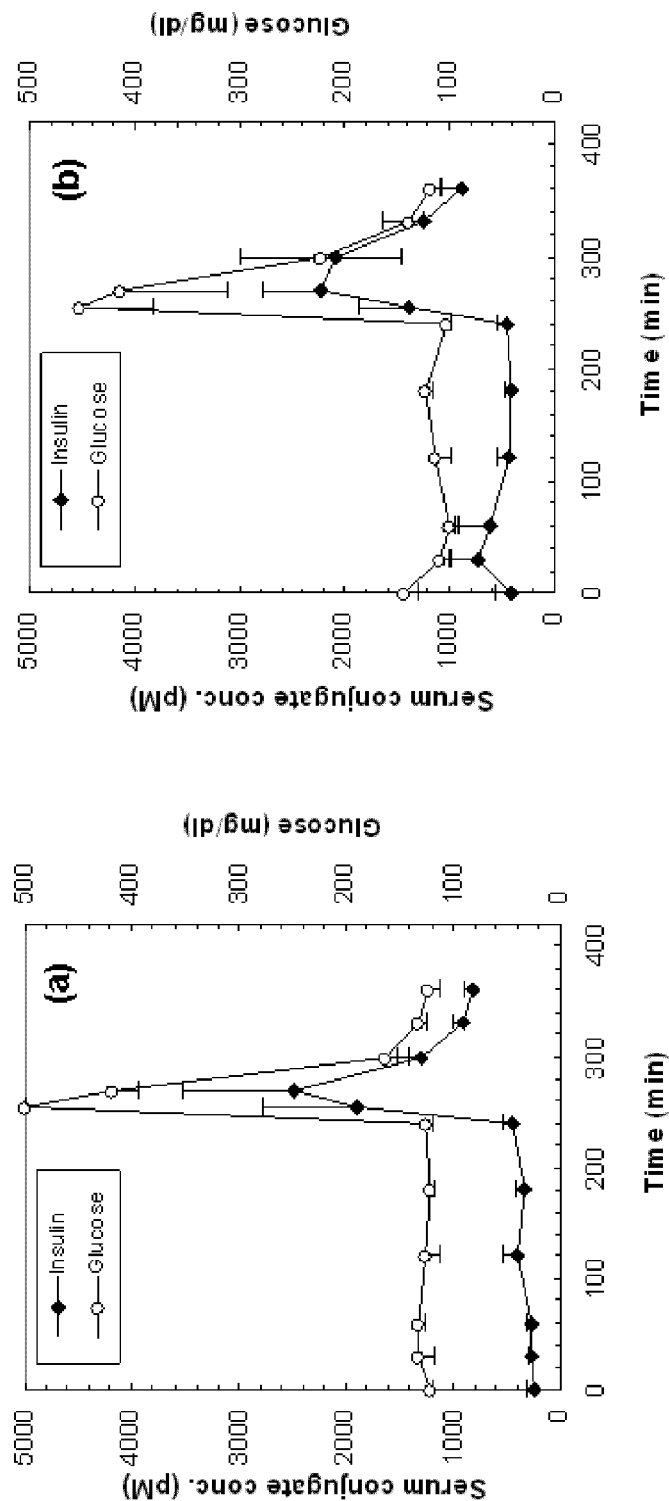
FIG. 38: Plot of serum insulin (♦) and blood glucose (○) levels following subcutaneous injection in non-diabetic, male SD rats (n=3 per dose) at time 0 with a long-acting TSAT-C6-AETM-2 conjugate I-6 prepared according to Example 57 followed by IP injection of glucose (4 g/kg) at 240 minutes. The material was injected after storage at 2-8 C for (a) one week or (b) two weeks.
Figure 39:
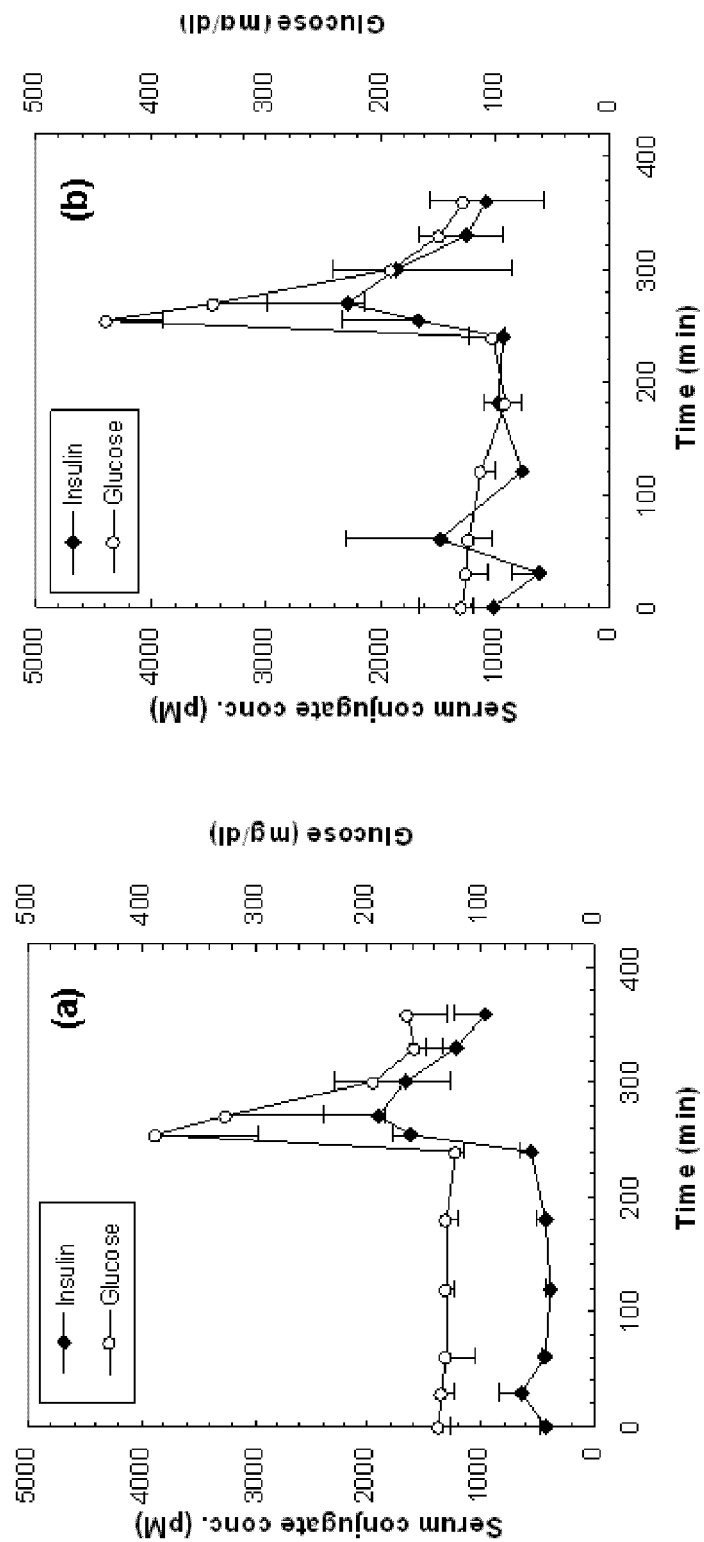
FIG. 39: Plot of serum insulin (♦) and blood glucose (○) levels following subcutaneous injection in non-diabetic, male SD rats (n=3 per dose) at time 0 with a long-acting TSAT-C6-AETM-2 conjugate I-6 prepared according to Example 57 followed by IP injection of glucose (4 g/kg) at 240 minutes. The material was injected after storage at room temperature for (a) one week or (b) two weeks.
Figure 40:
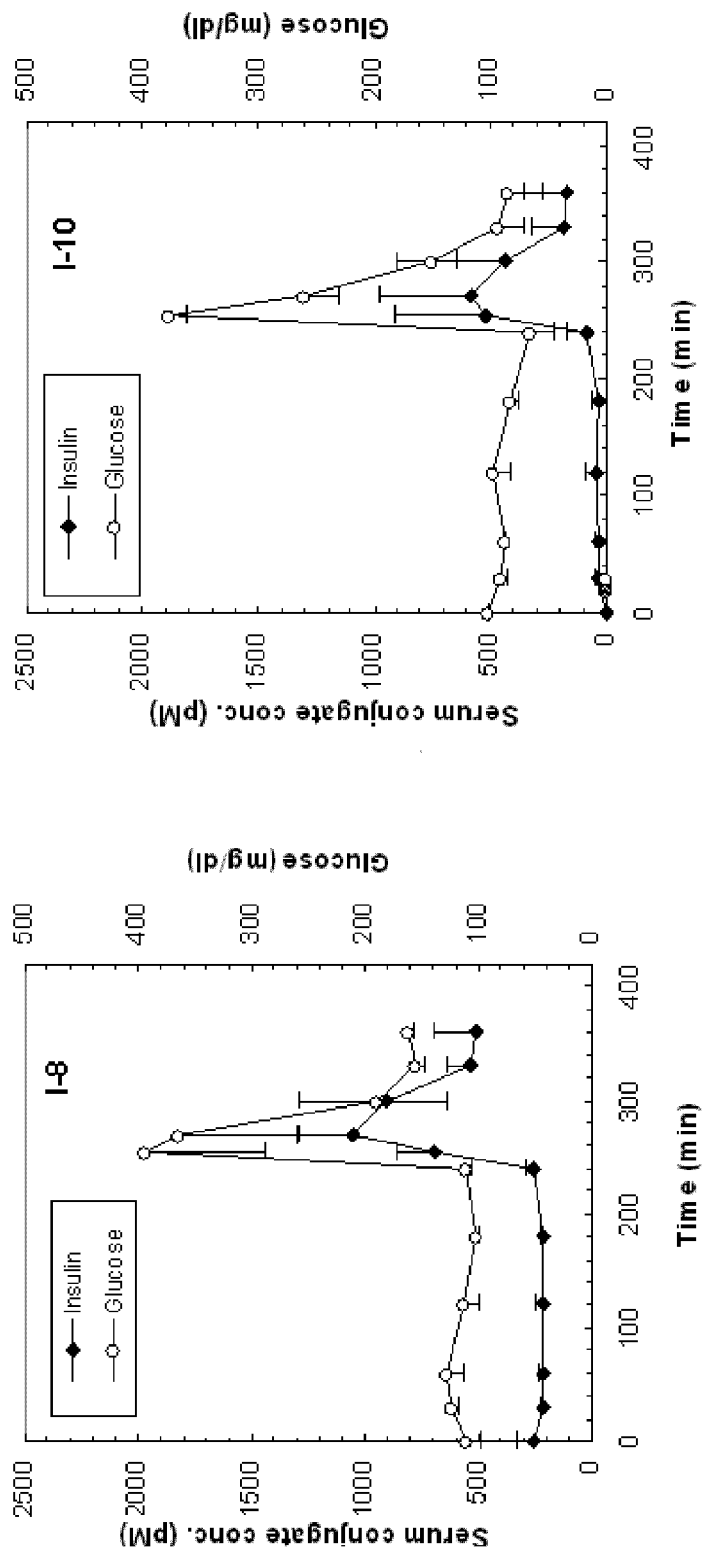
FIG. 40: Plot of serum insulin (♦) and blood glucose (○) levels following subcutaneous injection in non-diabetic, male SD rats (n=3 per dose) at time 0 with long-acting conjugate formulations prepared according to Example 58 followed by IP injection of glucose (4 g/kg) at 240 minutes. The conjugates are DSS-AEM-1 (I-8), DSS-AETM-1 (I-10), TSAT-C6-AEM-2 (I-7), C6-amide-AEM-2 (I-17), TSPE-AEM-3 (I-9), and TSPE-AETM-3 (I-11).
Figure 40:
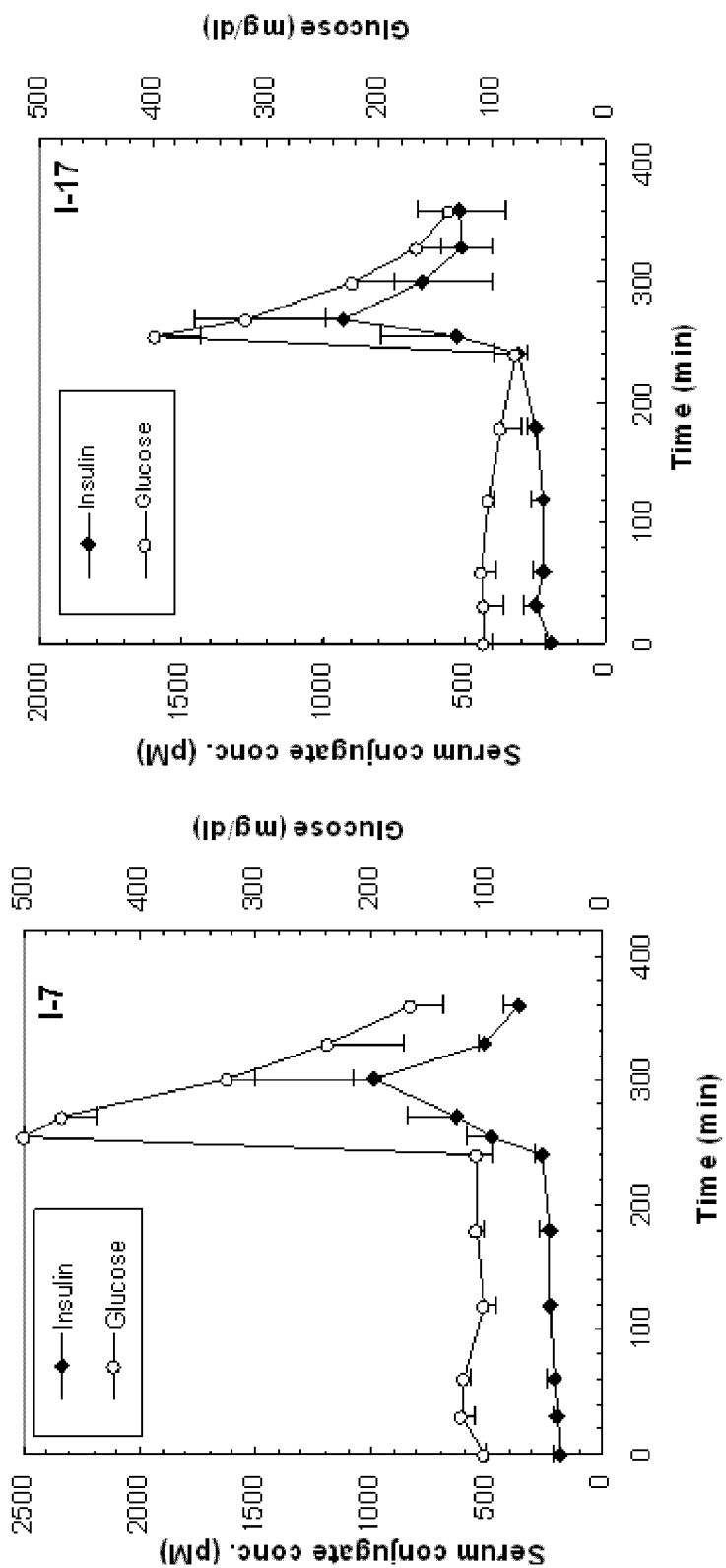
Figure 40:
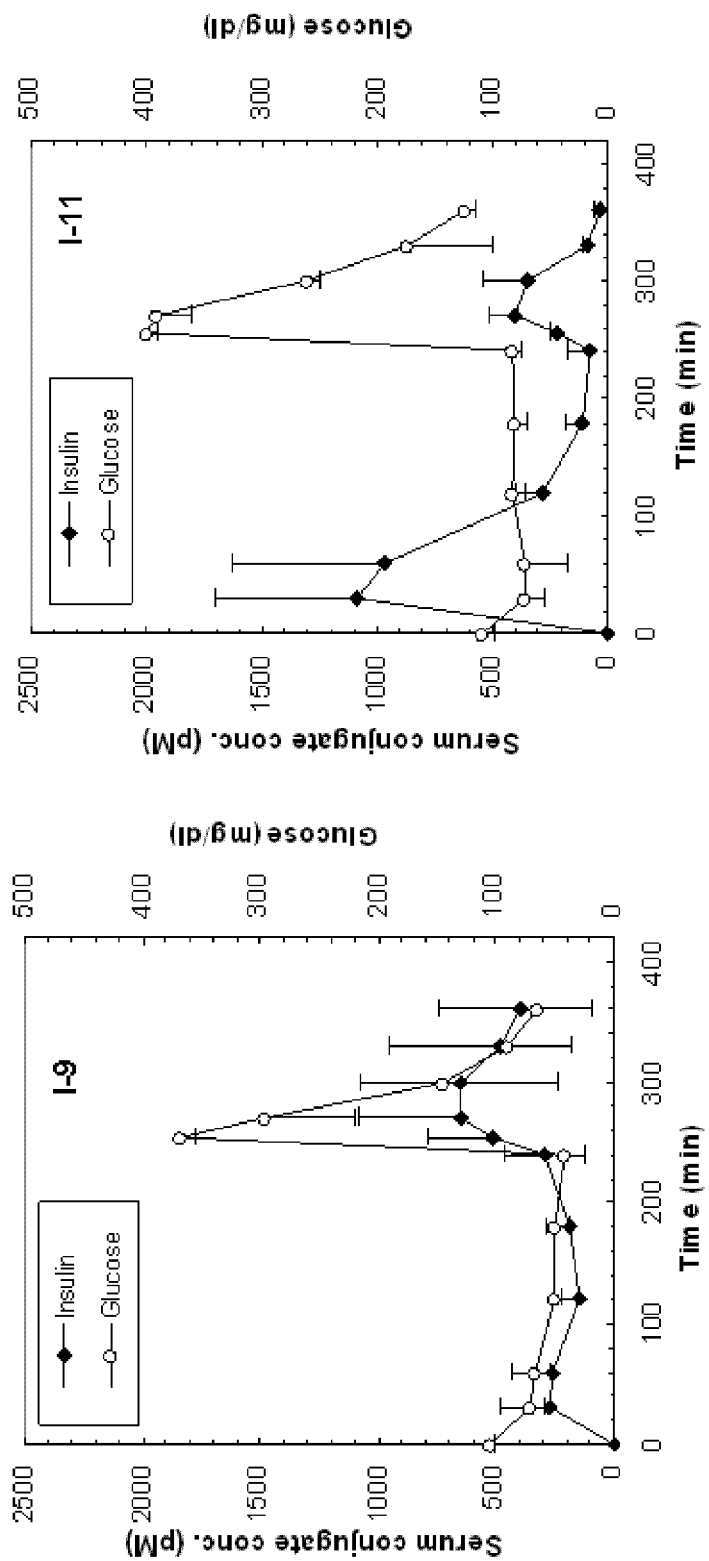

In this example, we synthesized the same exact long acting formulation from Example 56 at a 2× scale. Half of the material was stored at 2-8 C and the other half stored at room temperature for one week or two weeks. After the specified storage time, the material was redispersed and tested using the same four hour IP glucose injection protocol described in Example 56 at a 15 U/kg dose (body weight in grams/1.87=microliters of injection volume). As shown in FIGS. 38-39, this formulation demonstrates similar performance even after being stored refrigerated (FIG. 38) or at room temperature (FIG. 39) for at least two weeks.

Example 58

Performance of Long Acting Conjugates Prepared from Conjugates with Varying Ligand Affinity and Multivalency In this example, we set out to determine the time action and glucose-responsive PK profile of long-acting formulations of conjugates constructed from different types and numbers of ligands. All conjugates for this example were synthesized according to the methods described in Example 20 using the frameworks and saccharide ligands specified below:

| Conjugate | Framework | Framework MW | Ligand | AE-sugar MW | Purity (HPLC) | MW (LC-MS) | Sugar/Insulin |
|---|---|---|---|---|---|---|---|
| I-8: DSS-AEM-1 (B29) | DSS | 368 | AEM | 223 | >95% | 6168 | 1.0 |
| I-7: TSAT-C6-AEM-2 (B29) | TSAT-C6 | 822 | AEM | 223 | 95% | 6729 | 2.0 |
| I-9: TSPE-AEM-3 (B29) | TSPE | 813 | AEM | 223 | >95% | 6829 | 3.0 |
| I-10: DSS-AETM-1 (B29) | DSS | 368 | AETM | 547 | >95% | 6491 | 1.0 |
| I-11: TSPE-AETM-3 (B29) | TSPE | 813 | AETM | 547 | >95% | 7800 | 3.0 |
| I-17: C6-amide-AEM-2 (B29) | C6-amide | 838 | AEM | 223 | 95% | 6745 | 2.0 |

The following long-acting formulation was used for each conjugate:

| Component | Variable | Volume (ml) |
|---|---|---|
| Conjugate solution at 2.7 mg/ml | unmodified insulin = 16.7% | 1.000 |
| 250 mM HEPES buffered saline | NaCl concentration = 1.5M | 0.111 |
| Zinc acetate solution | Zinc concentration = 4.6 mg/ml | 0.124 |
| Cresol solution in water | 3% v/v | 0.159 |
| pH 7.2 Protamine solution in 25 mM HEPES buffered saline | Protamine concentration = 12.5 mg/ml | 4 × 0.194 aliquots |

The four hour IP glucose injection (4 g/kg) experiments were performed by dosing 15 U/kg (body weight in grams/1.87=microliters of injection volume) of each of the conjugates described above. As shown in FIG. 40a-e, all conjugates exhibited a protracted absorption profile with some element of increase in measured serum insulin concentration following the 4 hour glucose injection. It appears that there was some significant conjugate absorption in the first four hours after injection of the long acting TSPE-AETM-3 conjugate I-11. However, all other conjugates exhibited flat absorption profiles like the ones observed for TSAT-C6-AETM-2 conjugates. These results correlate well with the fact that the half-lives of these conjugates are all less than unmodified insulin as described in Examples 47-48 and that each of them demonstrates an a-MM-induced increase in PK/PD profile as described in Examples 45-46.

Example 59

Performance of Long Acting Conjugates Under IP a-MM Testing Conditions

In this example, we tested the a-MM-responsive profile of long-acting formulations of conjugates constructed from TSAT-C6-AETM-2 (I-6) and TSAT-C6-GA-2 (I-5) conjugates. Both conjugates were prepared according to the general methods described in Example 20. In addition, the following long-acting formulation was used for each conjugate:

| Component | Variable | Volume (ml) |
| --- | --- | --- |
| Conjugate solution at 2.7 mg/ml | unmodified insulin = 16.7% | 1.000 |
| 250 mM HEPES buffered saline | NaCl concentration = 1.5M | 0.111 |
| Zinc acetate solution | Zinc concentration = 4.6 mg/ml | 0.124 |
| Cresol solution in water | 3% v/v | 0.159 |
| pH 7.2 Protamine solution in 25 mM HEPES buffered saline | Protamine concentration = 12.5 mg/ml | 4 × 0.194 aliquots |

To test the sustained release nature of the formulations as well as the a-MM-responsive PK profile, the following experiment was conducted. The formulations were injected at 15 U/kg (body weight in grams/1.87=microliters of injection volume) behind the neck of fasted normal non-diabetic rats (Male Sprague-Dawley, 400-500 gm, n=3). After a 240 minute delay, an a-MM dose (4 g/kg) was injected IP. Blood samples were collected via tail vein bleeding at 0 minutes and at 30, 60, 90, 120, 150, 180, 210, 240, and 300 minutes after the initial conjugate injection. Blood glucose values were measured using commercially available test strips (Precision Xtra, Abbott Laboratories, Abbott Park, Ill.). In addition, blood from each timepoint was centrifuged at 4 C to collect the serum. Serum insulin concentrations were subsequently measured with a commercially available ELISA kit (Iso-Insulin ELISA, Mercodia, Uppsala, Sweden).

Figure 41:
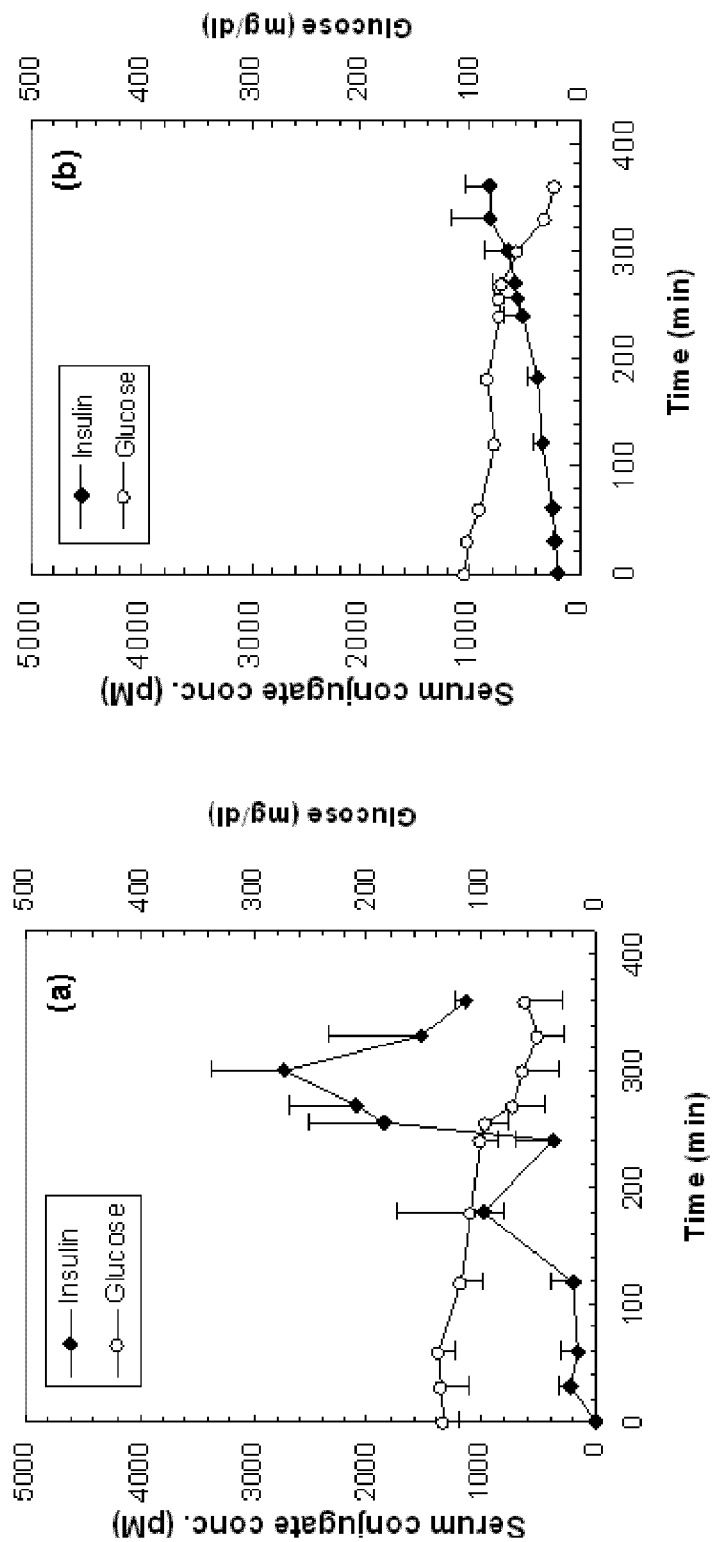
FIG. 41: Plot of serum insulin (♦) and blood glucose (○) levels following subcutaneous injection in non-diabetic, male SD rats (n=3 per dose) at time 0 with long-acting conjugate formulations prepared according to Example 59 followed by IP injection of alpha-methyl mannose (4 g/kg) at 240 minutes. The conjugates are (a) TSAT-C6-AETM-2 (I-6) and (b) TSAT-C6-GA-2.

As shown in FIG. 41a, the peak:baseline serum concentration ratio following the IP a-MM injection for the long-acting TSAT-C6-AETM-2 (I-6) formulation was even higher than that observed for the same formulation when glucose is substituted for a-MM. Furthermore, the TSAT-C6-GA-2 (I-5) formulation (FIG. 41b) did not demonstrate any increase in serum conjugate concentration following the a-MM challenge. These results correlate well with the fact that that the elimination half life of the TSAT-C6-GA-2 (I-5) conjugate was nearly identical to unmodified insulin (Example 47), and that it exhibited no a-MM-induced change in PK (Example 45).

Example 60

Long Acting Conjugates in Diabetics and Non-Diabetics

In order to confirm the in vivo utility of the long acting TSAT-C6-AETM-2 (I-6) formulation, we administered it (5, 10 and 20 U/kg) to normal and STZ-induced diabetic rats (Male Sprague-Dawley, 400-500 gm, n=6). The formulation was prepared using the following procedure:

| Component | Variable | Volume (ml) |
| --- | --- | --- |
| TSAT-C6-AETM-2 (I-6) solution at 2.7 mg/ml | unmodified insulin = 0% | 1.000 |
| 250 mM HEPES buffered saline | NaCl concentration = 1.5M | 0.111 |
| Zinc acetate solution | Zinc concentration = 4.6 mg/ml | 0.124 |
| Cresol solution in water | 3% v/v | 0.159 |
| pH 7.2 Protamine solution in 25 mM HEPES buffered saline | Protamine concentration = 12.5 mg/ml | 4 × 0.194 aliquots |

Figure 42:
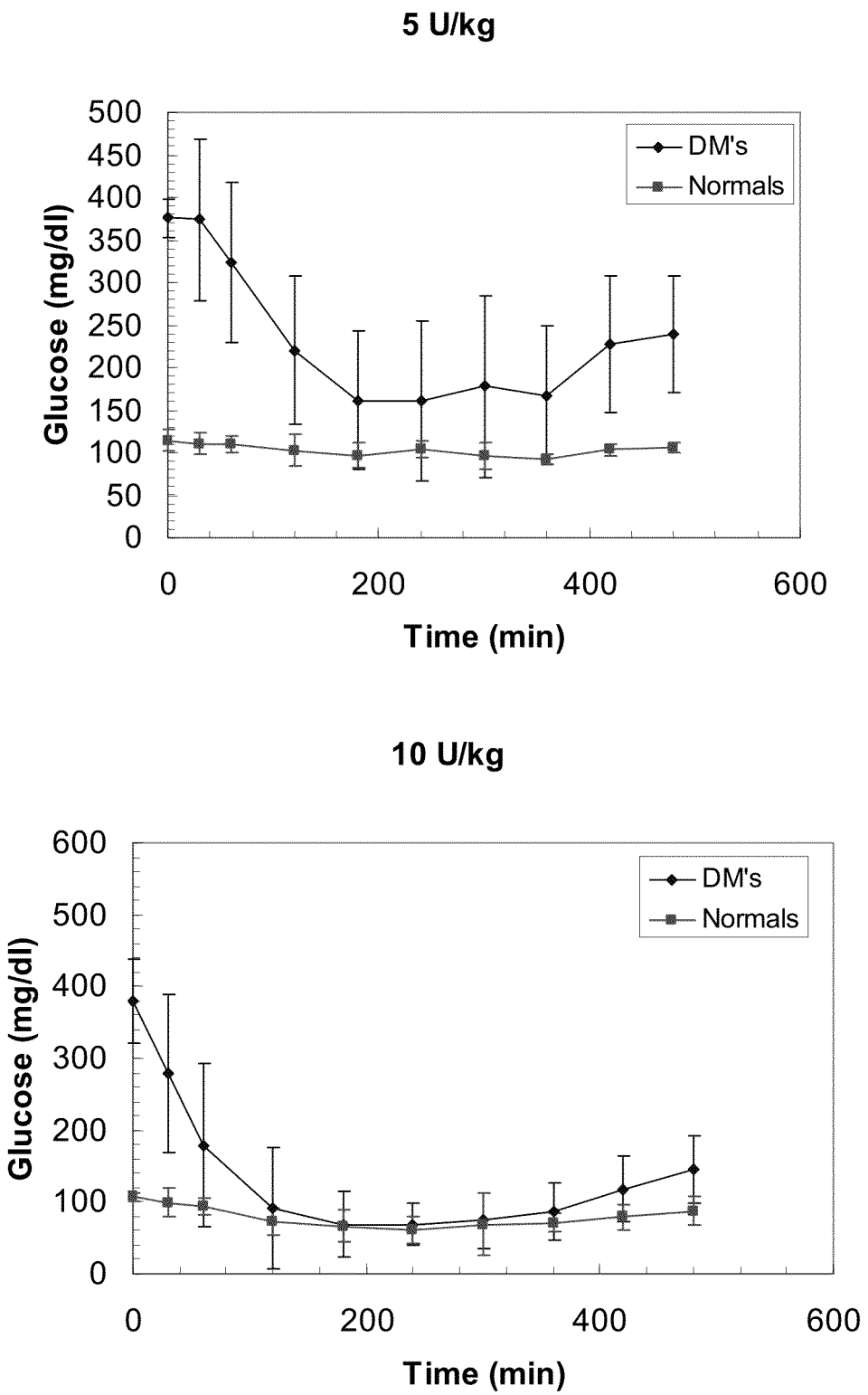
FIG. 42: Plot of blood glucose levels following subcutaneous injection in non-diabetic (normals) and diabetic (DM's) male SD rats at time 0 with TSAT-C6-AETM-2 (B29-substituted, PZI) conjugate I-6. The conjugate was administered at 5, 10 and 20 U/kg. As shown, the non-diabetic male SD rats did not show any hypoglycemia while the glucose levels in diabetic male SD rats showed a clear dose proportional response that lasted for over 8 hours at the highest dose.
Figure 42:
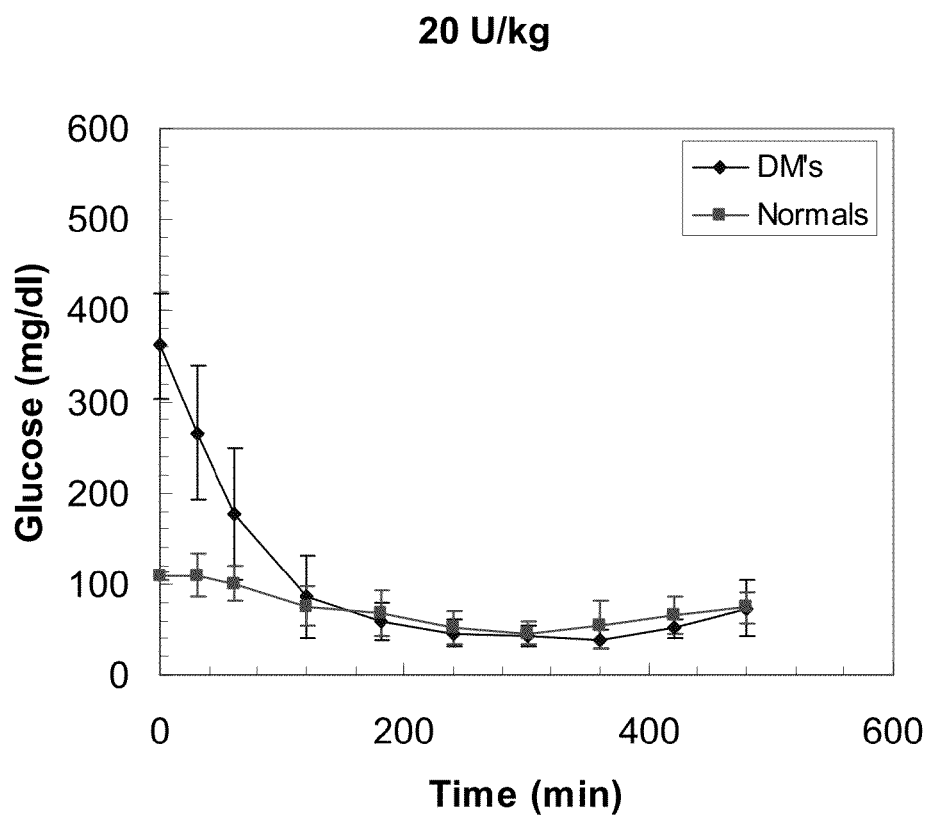

No external IP injections of glucose were used to trigger the bioactivity of the conjugates. Instead we relied on the endogenous levels of glucose in the rats to control the PK and PD profile of the conjugate formulation. Blood samples were collected via tail vein bleeding at various time points after the initial conjugate injection. Blood glucose values were measured using commercially available test strips (Precision Xtra, Abbott Laboratories, Abbott Park, Ill.). As shown in FIG. 42, no hypoglycemia was observed at early or late time points for the normal or diabetic rats. The glucose profiles observed with the diabetic rats are dramatic and demonstrate that the conjugates were activated by the higher glucose concentrations and exerted their glucose-lowering effect in a dose proportional manner over a long time period (over 8 hours at the highest dose).

Figure 43:
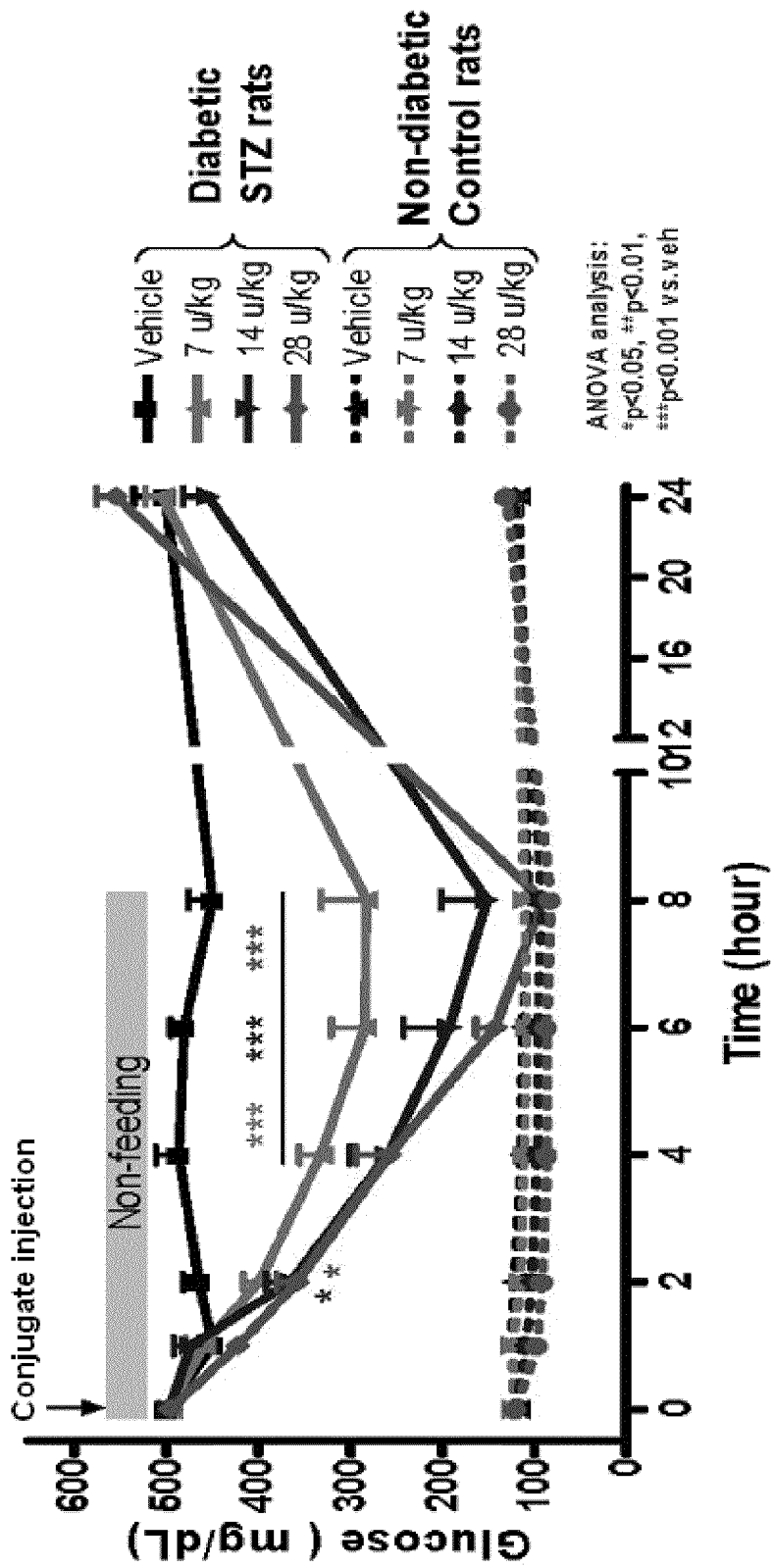
FIG. 43: Plot of blood glucose levels over 24 hours following subcutaneous injection in non-diabetic (normals) and diabetic (DM's) male SD rats at time 0 with TSAT-C6-AETM-2 (B29-substituted, PZI) conjugate I-6. The conjugate was administered at 7, 14 and 28 U/kg.

The experiment was repeated using different doses (7, 14 and 28 U/kg) and a longer time period (24 hours). Results from that experiment are shown in FIG. 43.

Example 61

Conjugation with Fatty Acid Esters to Generate Long Acting Formulations

It will be appreciated that we could have used an alternative approach to protamine zinc insulin for making a long acting form of an exemplary conjugate. In this example, we demonstrate how to convert a B1-substituted insulin conjugate into a long-acting formulation by covalently modifying the B29-epsilon-amine group with a long chain fatty acid. As described in U.S. Pat. No. 6,869,930, insulin acylation with C14-myristic acid, for example, leads to a soluble material with a flat, protracted time action profile. B1-substituted TSAT-C6-AETM-2 (I-2) is synthesized according to the methods in Example 12. The material may then be lyophilized into a dry powder and used as the starting material in the following procedure.

Myristic acid-NHS ester is dissolved at 60 mM in 1 ml of anhydrous DMSO followed by the addition of 400 ul (excess) of triethylamine (TEA). The solution is stirred rapidly for 10 minutes at room temperature. Conjugate I-2 is then dissolved separately in 7.5 ml of anhydrous DMSO at a concentration of 8.1 mM. Once dissolved, the entire solution is added over the course of one minute to the myristic acid-NHS ester solution followed by room temperature mixing for an additional two hours to ensure complete reaction.

The resulting solution is then superdiluted by 10× into a 20 mM pH 5.0 HEPES buffered saline solution containing 0.150 M NaCl followed by pH adjustment with dilute HCl to a final pH of 8.0. The aqueous solution is first purified by size exclusion using an appropriate solid phase for the desired separation of conjugated and unconjugated materials. The solution passing through the column void volume is then concentrated using an appropriately sized ultrafiltration membrane to approximately 10 ml. This solution is further purified to obtain the desired product using preparative reverse phase HPLC on a Waters SymmetryPrep C18, 7 um column, 19×150 mm. Buffer A is deionized water containing 0.1% TFA and Buffer B is acetonitrile containing 0.1% TFA. Before purification, the column is equilibrated at 15 ml/minutes with a 80% A/20% B mobile phase using a Waters DeltraPrep 600 system. Approximately 5 ml of the crude solution is injected onto the column over the course of 2 minutes at a flow rate of 15 ml/minutes after which a linear gradient is employed from 80% A/20% B to 75% A/25% B over the next 5 minutes followed by a slower linear gradient from 75% A/25% B to 62% A/38% B over the next 22 minutes. The retention time of the desired peak will vary depending on the drug, framework, and ligand used. Once collected, the solution is rotovapped to remove acetonitrile and lyophilized to obtain pure conjugate whose identity may be verified by LC-MS (HT Laboratories, San Diego, Calif.). The protracted and saccharide-responsive PK/PD profile of the resulting conjugate may then be evaluated using the 4 hour IP glucose or a-MM conditions described in Examples 50 and 59.

Example 62

Long-Acting Conjugates with Insulin Possessing a Neutral Isoelectric Point

It will be appreciated that we could have used yet other alternative approaches to protamine zinc insulin for making a long acting form of the conjugate. In this example, we demonstrate how to synthesize long-acting conjugates by substituting insulin glargine (LANTUS®), for example, instead of wild-type human insulin in preparing the conjugate. Any and

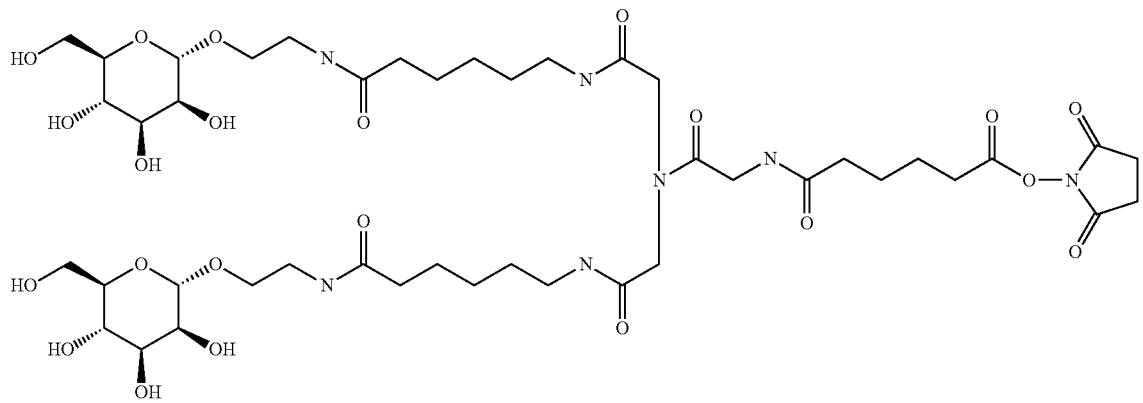 [SMILES: O=C(CCCCCNC(=O)CN(CC(=O)NCCCCCC(=O)NCCO[C@H]1O[C@H](CO)[C@@H](O)[C@H](O)[C@@H]1O)C(=O)CNC(=O)CCCCC(=O)ON1C(=O)CCC1=O)NCCO[C@H]1O[C@H](CO)[C@@H](O)[C@H](O)[C@@H]1O]

all synthesis methods described in the preceding examples may be used to form insulin glargine-conjugates. Insulin glargine is an exemplary long acting insulin analog in which Asp-A21 has been replaced by glycine, and two arginines have been added to the C-terminus of the B-chain. The effect of these changes is to shift the isoelectric point, producing a solution that is completely soluble at pH 4 but insoluble at physiological pH. Once synthesized and purified, the protracted and saccharide-responsive PK/PD profile of the resulting conjugate may then be evaluated using the 4 hour IP glucose or a-MM conditions described in Examples 50 and 59.

Example 63

Use of Soluble Conjugates in a Pump Delivery System

Instead of formulating the saccharide-responsive conjugates into long acting formulations, each may be continuously infused intravenously, subcutaneously, or intraperitoneally using a pump delivery system. The sterile solution of conjugate at a known concentration (typically 25-100 U/ml) is loaded into the pump reservoir and continuously delivered into the compartment of choice at a steady rate. This rate is adjusted to the maximal level at which no hypoglycemia is observed in the subject. Then, using the 4 hour IP glucose or a-MM conditions described in Examples 50 and 59, the glucose-responsive PK/PD profile may be evaluated. The pump method is advantageous in that no excipients are required to provide a steady input and absorption rate for the conjugates. A variety of insulin pumps have been described in the art and may be used for this purpose. For example, see any one of the pumps described in U.S. Pat. Nos. 4,435,173, 4,498,843, 4,923,375, 5,062,841, 6,650,951, 6,744,350, 6,852,104, 7,377,907, and 7,515,060, and U.S. Patent Publication Nos. 20080172028, 20090005726, 20090112165, 20090137957, 20090177142, 20090177154, and 20100004598, each of which is incorporated herein by reference.

Example 64

Synthesis of C6-Amide-AEM-2 Intermediate

This example describes a synthetic process for making a ZC-AEM-2 intermediate having the following chemical structure:

a. Intermediate Z2A

The first phase of the process involved combining reagents Z1A and Z1B to produce intermediate Z2A as shown in the following reaction scheme:

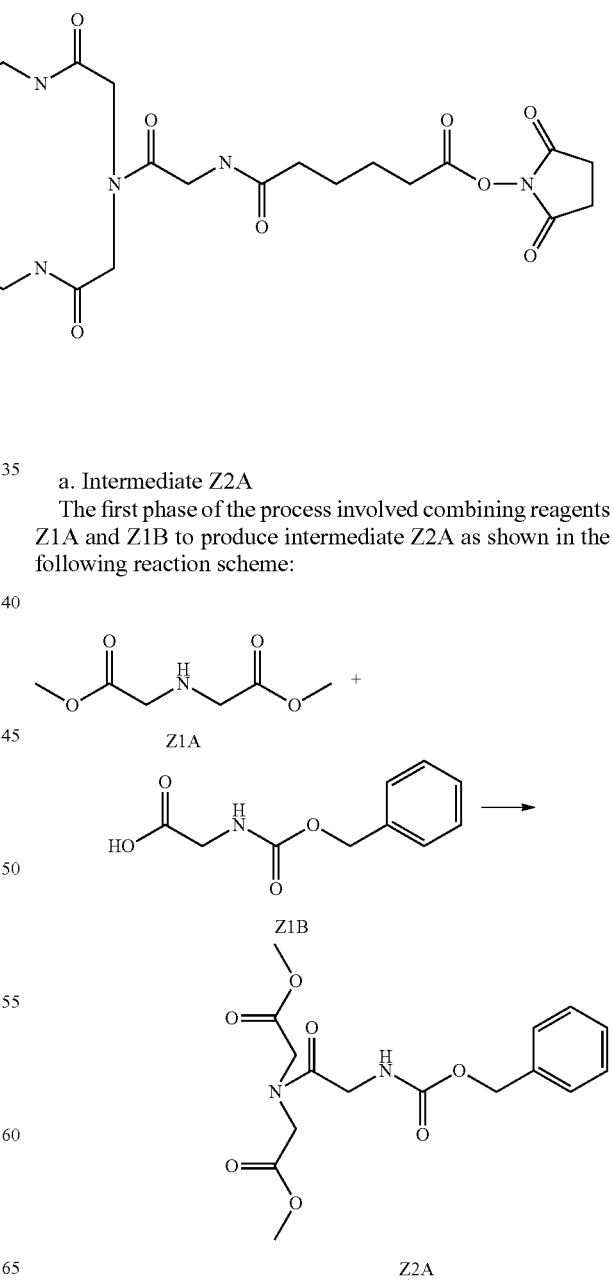

This was achieved as follows. To a 250 mL two neck flask was added compound Z1B (Sigma-Aldrich, St. Louis, Mo., 13.9 g), 1-hydroxybenzotriazole hydrate (HOBT, Sigma-Aldrich, St. Louis, Mo., 11.0 g) and dimethylformamide (DMF, Sigma-Aldrich, St. Louis, Mo.) at room temperature under nitrogen. The mixture was cooled to 0 C, after which time Compound Z1A (Sigma-Aldrich, St. Louis, Mo., 9.5 mL) and di-isopropylcarbodiimide (DIC, Sigma-Aldrich, St. Louis, Mo., 9.8 ml) were added to the mixture under nitrogen. The reaction solution was stirred at room temperature overnight. After 36 hours of reaction, (dimethylamino)pyridine (DMAP, Sigma-Aldrich, St. Louis, Mo., 7.71 g) was added, and after 48 hours the reaction mixture was filtered with a Buchner funnel. The filtrate was kept at 4 C overnight and worked up the following day.

The filtrate was evaporated, and the resulting residue was taken up in 120 mL of ethyl acetate and washed successively with 10% aqueous HCl solution (3×30 mL), saturated aqueous NaHCO$_3$ solution (3×30 mL), brine (3×20 mL), and dried over anhydrous sodium sulfate. The solution was concentrated to dryness in vacuo to yield the product which could be used without further purification.

b. Intermediate Z3A

The second phase of the process involved converting intermediate Z2A to intermediate Z3A as shown in the following reaction scheme:

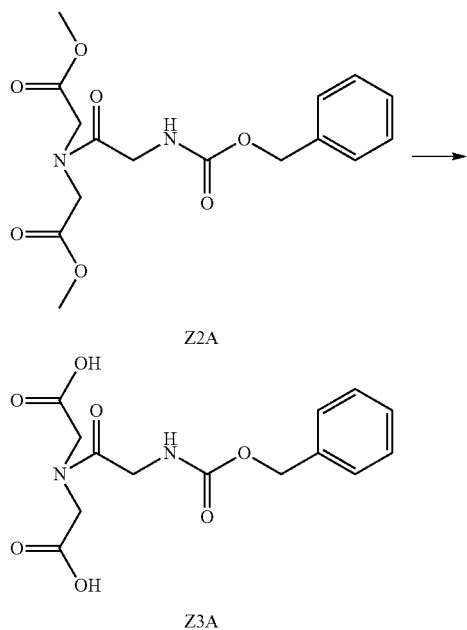

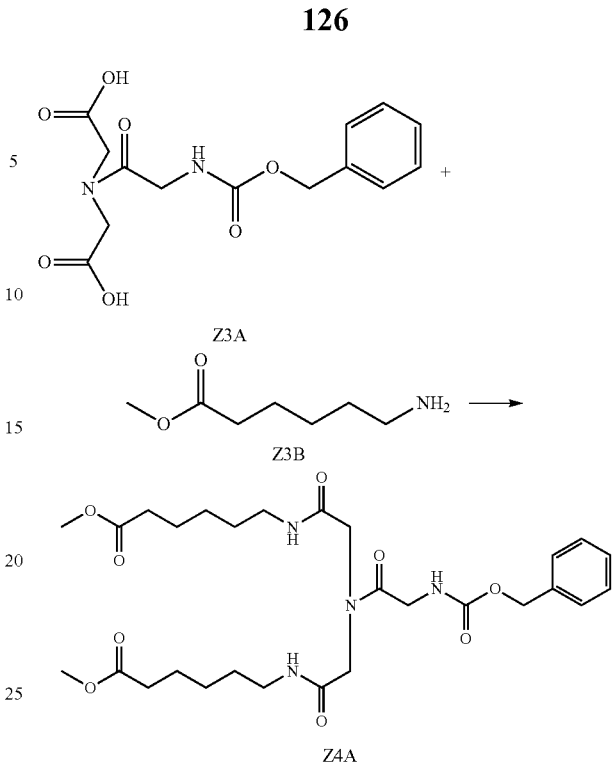

Compound Z2A (16.0 g) was dissolved in methanol (Sigma-Aldrich, St. Louis, Mo., 85 and the solution was cooled to 0 C. A 10% aqueous solution of sodium hydroxide (19 mL) was added dropwise and the reaction was stirred at 0 C for 3 hours. Afterwards, the suspension was dissolved with a minimum amount of water (15 mL). To this solution was added Amberlite IR-120 (Sigma-Aldrich, St. Louis, Mo., H+ form), in 15×2 g aliquots at 0 C. The bead suspension was stirred for 0.5 hr, resulting in a solution pH of ~5. The resulting mixture was filtered to remove the Amberlite beads, and the filtrate concentrated and dried in vacuo to yield a white-red solid, 13.0 g yield.

c. Intermediate Z4A

The third phase of the process involved combining intermediate Z3A with reagent Z3B to produce intermediate Z4A as shown in the following reaction scheme:

Compound Z3B (Sigma-Aldrich, St. Louis, Mo., 19.0 g) was dissolved in DMF (50 mL). The suspension was cooled to 0 C, after which time triethylamine (15.0 mL) was added to the solution. The temperature of the solution was maintained at 0° C. for 0.75 hours. Next, the solution was charged with a solution of Compound Z3A (13.0 g) dissolved in DMF (24 mL) at 0 C, followed by HOBT (Sigma-Aldrich, St. Louis, Mo., 15.9 g), DMF (50 mL), and DIC (Sigma-Aldrich, St. Louis, Mo., 15.0 mL). The resulting solution was stirred for an additional hour at 0 C and then allowed to warm to room temperature and react overnight for an additional 18 hours.

Next the reaction was recooled to 0 C, and N,N-diisopropylethylamine (DIPEA, Sigma-Aldrich, St. Louis, Mo., 15 mL) was added and the resulting solution stirred for 0.5 hr until the pH of the solution was approximately 9.0. Anhydrous methylene chloride (25 mL) and DIC (3.5 mL) were added and stirring was continued for another 10 hours. More compound Z3B was added (free base, 2.5 g) and the reaction was allowed to proceed for an additional 50 hours at room temperature under a nitrogen atmosphere.

Finally, the reaction mixture was filtered, and the filtrate concentrated via rotary evaporation. The residue was dissolved in methylene chloride (CH$_2$Cl$_2$, 400 mL), and the organic phase washed with a 5% HCl solution (3×200 mL). The organic layer was cooled to 0° C. and neutralized with a saturated sodium bicarbonate solution (3×100 mL) and brine (2×200 mL). The organic solution was dried over magnesium sulfate, which was then separated by filtration and concentrated using rotary evaporation. The residue was purified by column chromatography on silica gel (eluent phase: methylene chloride/methanol 50:1 to 5:1). Column fractions were concentrated and dried in vacuo overnight. A white solid was obtained as Z4A (18.9 g, yield 81%).

d. Intermediate Z5A

The fourth phase of the process involved converting intermediate Z4A to intermediate Z5A as shown in the following reaction scheme:

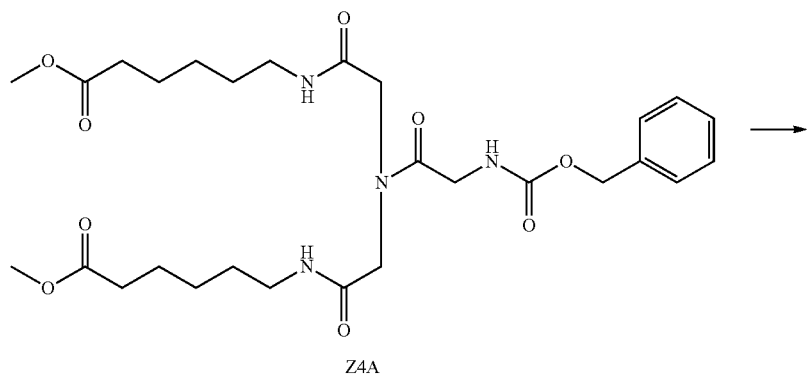

Z4A

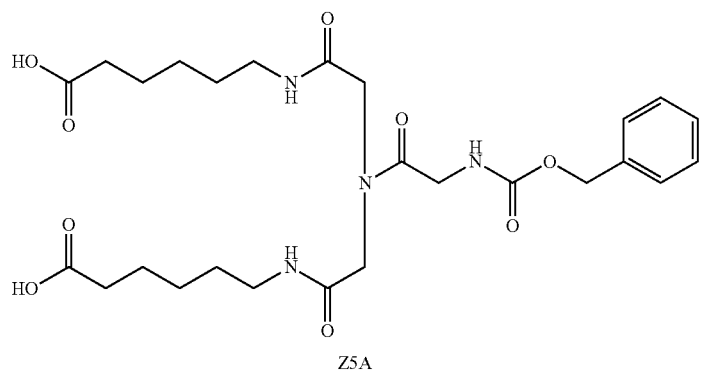

Z5A

Ester Z4A (2.27 g) was dissolved in methanol (10 mL), and to this solution 5.0 mL of 1.0M sodium hydroxide solution was added at room temperature. The mixture was stirred at room temperature for 38 hours. At the end of this time, an additional 1.5 mL of 2.0M aqueous sodium hydroxide solution was added, and the mixture was stirred at room temperature for another 14 hours.

Next, the reaction mixture was acidified with a 10% aqueous solution of HCl at 0° C. The product was extracted with ethyl acetate (3×25 mL). The combined organic layers were dried over magnesium sulfate, and then concentrated to dryness in vacuo overnight to yield Z5A as a white solid (2.2 g).

e. Intermediate Z6A

The fifth phase of the process involved combining intermediate Z5A with aminoethylmannose (AEM) to produce intermediate Z6A as shown in the following reaction scheme:

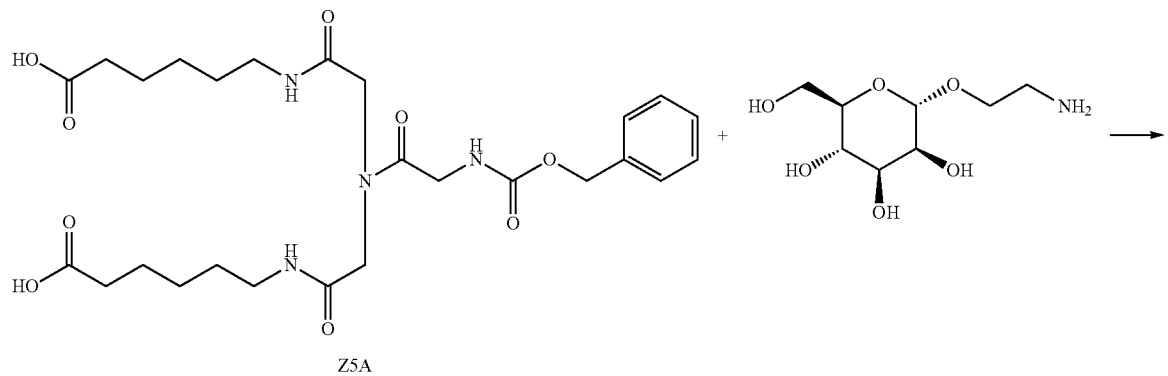

Z5A

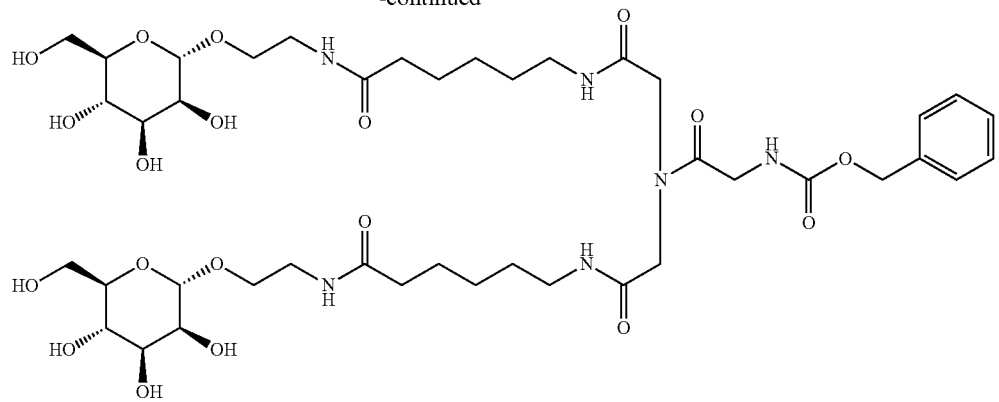

Z6A

Diacid compound Z5A (2.0 g), aminoethylmannose (1.46 g), O-(7-azabenzotriazol-1-yl)-N,N,N',N'-tetramethyl-uronium hexafluorophosphate (HATU, Sigma-Aldrich, St. Louis, Mo., 2.7 g) were dissolved in dry DMF (80 mL) under nitrogen at 0° C. DIPEA (Sigma-Aldrich, St. Louis, Mo., 3.0 mL) was added dropwise to the mixture at 0° C. under a nitrogen atmosphere. The mixture was stirred for 1 hr at 0° C. and then an additional 4 hr at room temperature. At this point, another aliquot of aminoethylmannose (0.5 g) and HATU (0.52 g) was added to the reaction solution at room temperature, and the solution was stirred for another 3 hours. The mixture was concentrated via rotary evaporation and the residue was purified by column chromatography on silica gel (methylene chloride/methanol 20:1, then 6:1 eluting to 1:1). Fractions were collected and evaporated in vacuo to yield purified product (TLC: upper spot, Rf 0.6, methylene chloride:methanol 1:3).

It will be appreciated that this entire process can be repeated to obtain conjugates with different ligands by replacing AEM with another amine containing reagent (e.g., without limitation AEG, AEBM, AETM, etc.) when converting intermediate Z5A to intermediate Z6A.

f. Intermediate Z7A

The sixth phase of the process involved converting intermediate Z6A to intermediate Z7A as shown in the following reaction scheme:

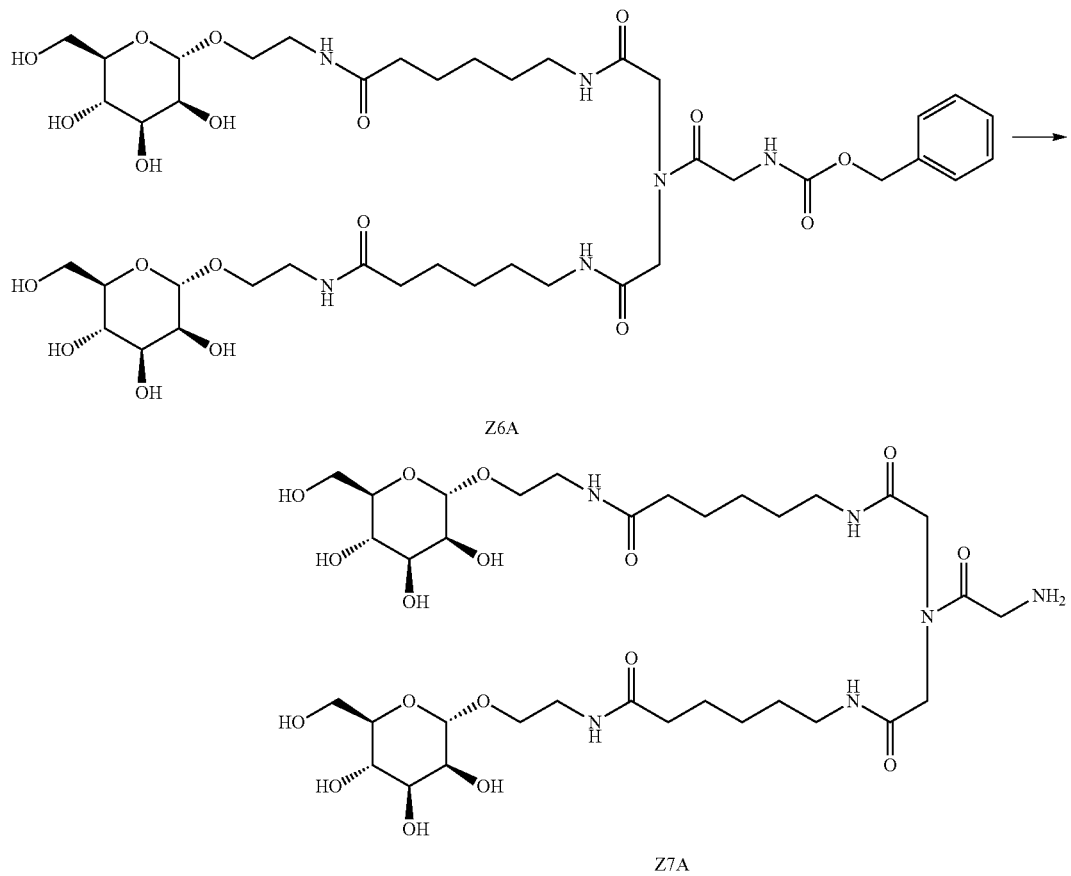

Compound Z6A (1.43 g) was dissolved in anhydrous methanol (100 mL). To this solution was added (1.00 g palladium on carbon (Pd/C)), and hydrogen gas was bubbled into the solution to reduce the protecting group to give the corresponding amine. It was found that the reaction had reached complete conversion after approximately 9 hours of reaction.

The reaction mixture was filtered through a pad of Celite, and the filtrate was concentrated and dried in vacuo. Compound Z7A was obtained as a brown solid (1.16 g, yield 94%).

g. Intermediate Z8A

The following scheme shows how the coupling agent Z8A was prepared:

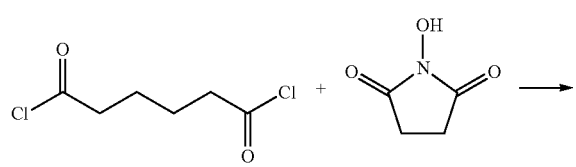

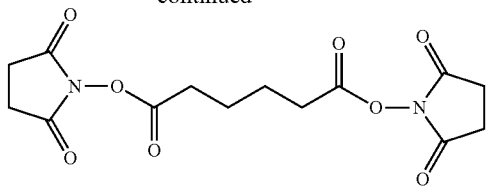

Z8A

To a cooled solution of N-hydroxysuccinimide (Sigma-Aldrich, St. Louis, Mo., NHS, 7.0 g) in dry $CH_2Cl_2$ (65 mL) at 0 C was added triethylamine (9.5 mL) and adipoyl chloride (3.97 mL, 5.0 g). The resulting mixture was stirred for 2 hr at 0 C. The mixture was washed with a saturated aqueous solution of NaCl (3×30 mL) and dried over magnesium sulfate. The solution was filtered and concentrated in vacuo, and then the residue purified via silica gel chromatography to obtain a white solid (6.6 g) as product Z8A.

h. Intermediate Z9A

The following scheme shows how the coupling agent Z8A was combined with intermediate Z7A to produce intermediate Z9A:

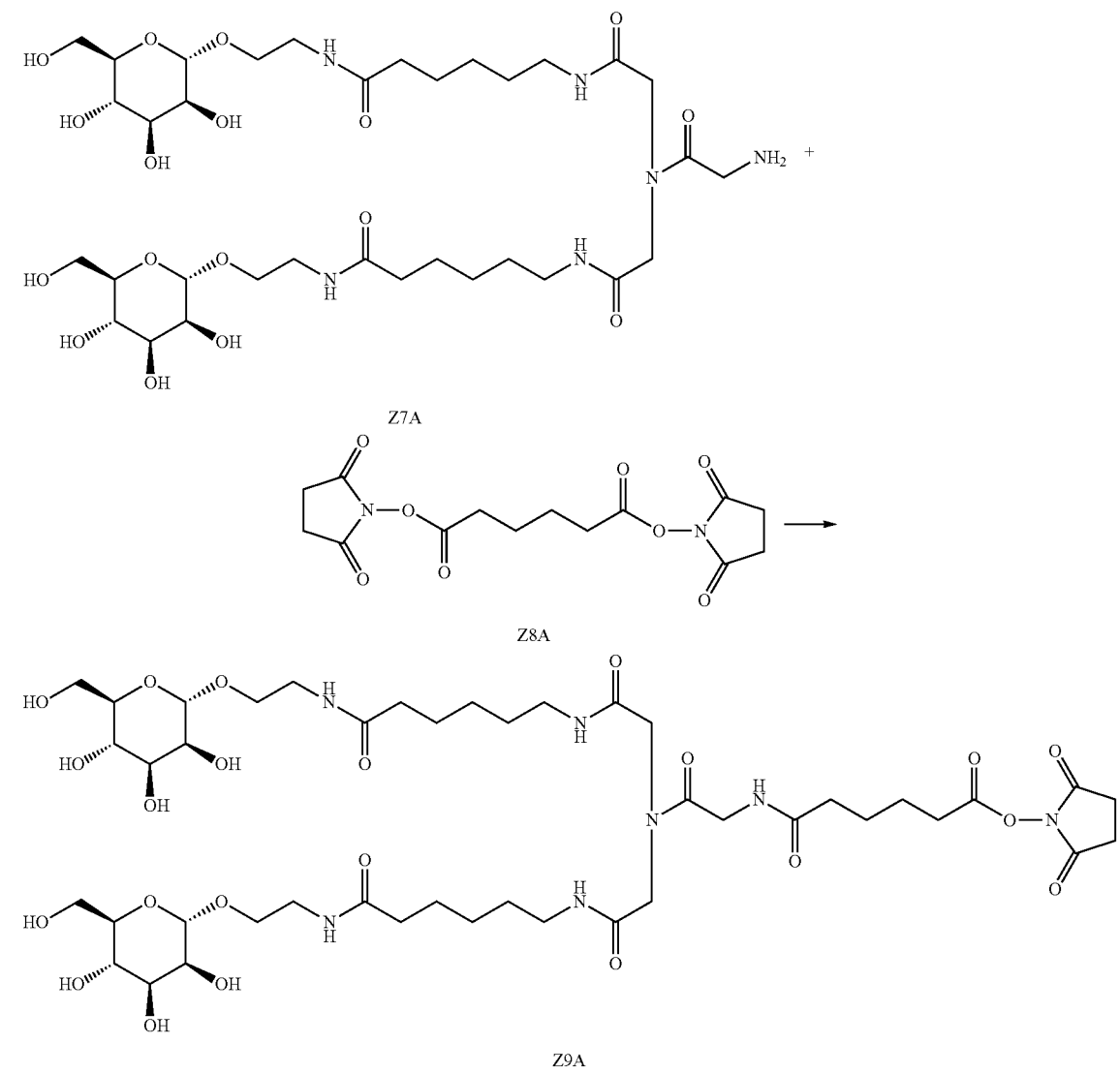

Compound Z7A (0.256 g) was dissolved in dry DMF, and the solution was cooled to 0 C. To this solution was added a solution of Z8A (0.710 g) in anhydrous DMF (15 mL) under a nitrogen atmosphere. The mixture was stirred at 0 C for 2 hours.

The solution volume was concentrated to one third and filtered off excess unreacted DSS. The filtrate was further concentrated to approximately 3 mL of column and purified by silica gel chromatography (eluent: methylene chloride/methanol 20:1 to 4:1, then 3:1 to 1:1). Collected fractions were concentrated and dried in vacuo to give 151 mg of purified product. $^1$H NMR (300 MHz, DMSO) $\delta$ 1.28-1.63 (band, 20H), 2.07-2.22 (band, 6H), 2.85 (s, 4H), 3.08-3.64 (band, 22H), 3.91 (s, 4H), 4.08 (s, 2H), 4.49 (s, 2H), 4.57 (d, 2H, J=5.70 Hz), 4.64 (s, 2H), 4.73 (t, 4H, J=5.10 Hz), 7.85 (s, 2H, amide NH), 8.68, 8.19, 7.98 (s, 3H, amide NH). LC-MS (Found 1074.67 [M+Na+], M=1051.57 Da; Calculated 1052.08 Da).

Example 65

Synthesis of C6-Amide-AEM-2 (B1) Conjugate

This example describes a method for preparing a B1-conjugated insulin from intermediate Z9A of Example 64. Compound Z9A was conjugated to insulin as follows. NH$_2$—B1-BOC2(A1,B29)-insulin synthesized according to Example 8 (0.167 g) was dissolved in dry DMSO (3 mL) at room temperature under nitrogen and stirred for 0.5 hours at room temperature. To this solution was added anhydrous triethylamine (0.013 mL) at room temperature under nitrogen. Compound Z9A (0.177 g) in dry DMSO (1.5 mL) was added via syringe pump at a rate of (4.2 uL/min) to the insulin-triethylamine mixture at room temperature at a stir rate of 80 rpm. The reaction conversion was monitored by analytical HPLC. After 4 hours, another 3 equivalents of TEA (0.010 mL) were added to the reaction mixture. After a total of 10.5 hours at room temperature, the reaction was stopped and placed in a −20 C freezer overnight.

The next day, the reaction mixture was thawed and placed onto a small packed column of ion exchange beads (SP Sephadex beads, Sigma-Aldrich, St. Louis, Mo., isocratic conditions). The column was centrifuged briefly for 4 min at 1000×g to purify the insulin conjugate (assessed by analytical HPLC). The collected fractions from the ion exchange column (6 mL) were added dropwise to dry acetone (30 mL) with stirring at 140 rpm for 10 min. The resulting suspension was poured into a 50 mL centrifuge tube which was spun for 10 min at 3500×g. The clear supernatant was removed from the tubes, and the cake kept and set aside. The supernatant was added to another 30 mL of acetone to obtain a second crop of precipitate (after adding a few drops of 5N HCl), which was then centrifuged for 10 min at 3500×g to obtain a second centrifuge cake.

The combined cakes were dried in vacuo for 1 hour, to obtain a white solid (197 mg, 92% yield) at >98% purity by analytical HPLC. The insulin conjugate BOC groups were removed by the procedure set forth in Example 12 to obtain the biologically active insulin conjugate.

The process described in this example has the advantage of producing a high yield, high purity insulin conjugate without requiring reverse phase HPLC.

Example 66

Synthesis of I-17: C6-Amide-AEM-2 (B29) Conjugate

This example describes one method for preparing a B29-conjugated insulin from intermediate Z9A of Example 64. Compound Z9A is conjugated to insulin as follows. NH$_2$—B29-BOC2(A1,B1)-insulin synthesized according to Example 16 (0.167 g) is dissolved in dry DMSO (3 mL) at room temperature under nitrogen and stirred for 0.5 hours at room temperature. To this solution is added anhydrous triethylamine (0.013 mL) at room temperature under nitrogen. Compound Z9A (0.177 g) in dry DMSO (1.5 mL) is added via syringe pump at a rate of (4.2 uL/min) to the insulin-triethylamine mixture at room temperature at a stir rate of 80 rpm. The reaction conversion is monitored by analytical HPLC. After 4 hours, another 3 equivalents of TEA (0.010 mL) are added to the reaction mixture. After a total of 10.5 hours at room temperature, the reaction is stopped and placed in a −20 C freezer overnight.

The next day, the reaction mixture is thawed and placed onto a small packed column of ion exchange beads (SP Sephadex beads, Sigma-Aldrich, St. Louis, Mo., isocratic conditions). The column is centrifuged briefly for 4 min at 1000×g to purify the insulin conjugate (assessed by analytical HPLC). The collected fractions from the ion exchange column (6 mL) are added dropwise to dry acetone (30 mL) with stirring at 140 rpm for 10 min. The resulting suspension is poured into a 50 mL centrifuge tube which is spun for 10 min at 3500×g. The clear supernatant is removed from the tubes, and the cake kept and set aside. The supernatant is added to another 30 mL of acetone to obtain a second crop of precipitate (after adding a few drops of 5N HCl), which is then centrifuged for 10 min at 3500×g to obtain a second centrifuge cake.

The combined cakes are dried in vacuo for 1 hour, to obtain a white solid. The insulin conjugate BOC groups are removed by the procedure set forth in Example 12 to obtain the biologically active insulin conjugate.

Example 67

Alternative Synthesis of I-17: C6-Amide-AEM-2 (B29) Conjugate

This example describes another method for preparing a B29-conjugated insulin from intermediate Z9A of Example 64. Specifically, this alternative method involves directly coupling compound Z9A to unprotected insulin at the B29 epsilon amino group. Compound Z9A was dissolved at 53 mM in 1.0 ml of anhydrous DMSO followed by the addition of 0.4 ml (excess) of triethylamine (TEA). The solution was stirred rapidly for 5 minutes at room temperature. Recombinant human insulin (RHI) powder was then dissolved separately at 17.2 mM in 1 ml of a 0.1 M, pH 11 sodium carbonate buffer and the pH was subsequently adjusted to 10.8 with 1.0N sodium hydroxide. Once dissolved, the entire solution of Compound Z9A was added dropwise over the course of 10 minutes to the insulin/carbonate buffer solution. The solution was allowed to stir for an additional 15 minutes after the dropwise addition to ensure complete reaction.

The resulting solution was then superdiluted by 10× into a 20 mM pH 5.0 HEPES buffered saline solution containing 0.150 M NaCl followed by pH adjustment with dilute HCl to a final pH of 8.0. The aqueous solution was first purified by size exclusion using Biogel P2 (Bio-Rad Laboratories, Hercules, Calif.) for the desired separation of conjugated and unconjugated materials. The solution passing through the column void volume was then concentrated using a 3 kDa ultrafiltration membrane to approximately 15 ml. This solution was further purified to obtain the desired product using preparative reverse phase HPLC on a Waters SymmetryPrep C18, 7 um, 19×150 mm column. Buffer A was deionized water containing 0.1% TFA and Buffer B was acetonitrile containing 0.1% TFA. Before purification, the column was equilibrated at 15 ml/minutes with a 80% A/20% B mobile phase using a Waters DeltraPrep 600 system. Approximately 5 ml of the crude solution was injected onto the column over the course of 2 minutes at a flow rate of 15 ml/minutes after which a linear gradient is employed from 80% A/20% B to 75% A/25% B over the next 5 minutes followed by a slower linear gradient from 75% A/25% B to 62% A/38% B over the next 22 minutes. Once the desired fraction was collected, the solution was rotovapped to remove acetonitrile and lyophilized to obtain pure conjugate whose identity was verified by LC-MS (HT Laboratories, San Diego, Calif.). The final product (95% pure by HPLC) was found to have the desired MW of 6744 g/mol (LC-MS), representing a total of 2.0 AEM molecules conjugated per insulin, with greater than 85% of the conjugate molecules conjugated at the Lys-B29 site (as determined by N-terminal sequencing).

Example 68

Long Acting I-17 Conjugates

In this example, we set out to determine the time action and glucose-responsive PK profile of long-acting formulations of conjugates constructed from Compound Z9A of Example 64. The conjugate for this example was synthesized according to the methods described in Example 67. The following long-acting formulation was used for this conjugate:

| Component | Variable | Volume (ml) |
|---|---|---|
| I-17 conjugate solution at 2.7 mg/ml | unmodified insulin = 16.7% | 1.000 |
| 250 mM HEPES buffered saline | NaCl concentration = 1.5M | 0.111 |
| Zinc acetate solution | Zinc concentration = 4.6 mg/ml | 0.124 |
| Cresol solution in water | 3% v/v | 0.159 |
| pH 7.2 Protamine solution in 25 mM HEPES buffered saline | Protamine concentration = 12.5 mg/ml | 4 × 0.194 aliquots |

Figure 44:
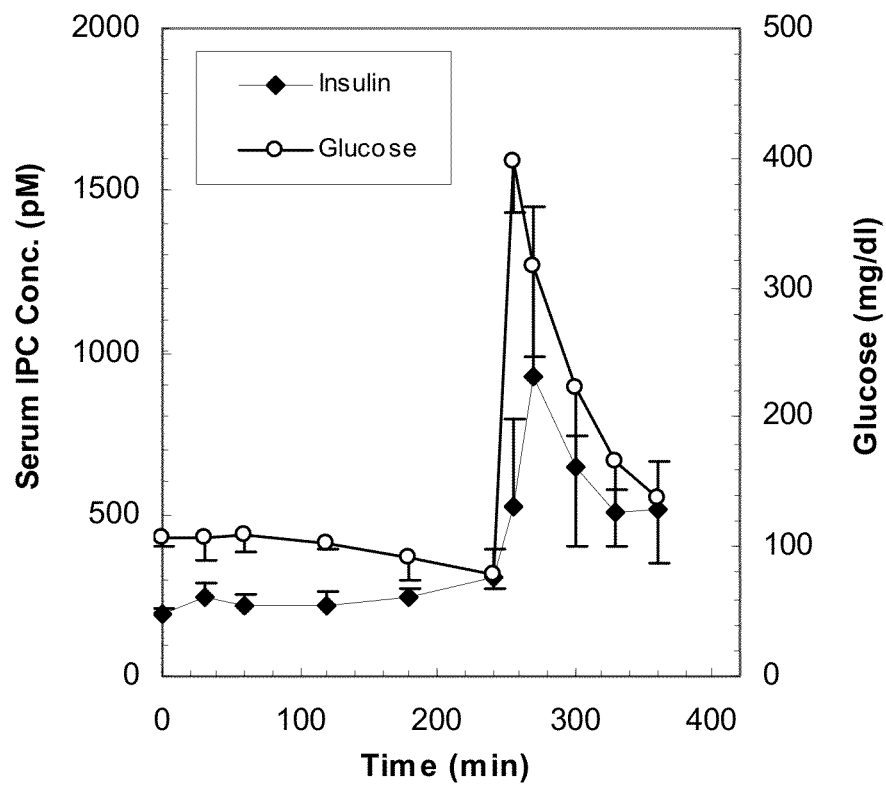
FIG. 44: Plot of serum insulin (♦) and blood glucose (○) levels following subcutaneous injection in non-diabetic, male SD rats (n=3 per dose) at time 0 with a long-acting conjugate I-17 formulation prepared according to Example 67 followed by IP injection of glucose (4 g/kg) at 240 minutes.

The four hour IP glucose injection (4 g/kg) experiments were performed by dosing 15 U/kg (body weight in grams/1.87=microliters of injection volume) of the formulation described above. As shown in FIG. 44, the conjugate exhibits a protracted absorption profile with a significant increase in measured serum insulin concentration following the 4 hour glucose injection.

Example 69

Conjugates prepared from 2-aminoethyl alpha-L-fucopyranoside and 2-aminoethyl N-acetyl-beta-D-glucosamine and evaluation The data from Example 42 demonstrates the ability of L-fucose to inhibit the presumed lectin pathway that leads to the increased PK profile of exemplary conjugates. It is also known that beta-linked N-acetyl glucosamine may also inhibit the pathways for which mannose and fucose are inhibitors (e.g. see Haurum et al. in *Biochem. J.* 293:873-878, 1993). This example describes how insulin conjugates such as the ones described above may be synthesized using 2-aminoethyl alpha-L-fucopyranoside or 2-aminoethyl N-acetyl-beta-D-glucosamine ligands. 2-aminoethyl alpha-L-fucopyranoside (MW=207 g/mol) is prepared according to the method of Ni et al. in *Bioconjugate Chem.* 14:232-238, 2003. 2-aminoethyl N-acetyl-beta-D-glucosamine (MW=264 g/mol) is synthesized according to the method of Cai et al. in *Organic Letters* 7:4021-4024, 2005. Either one of these ligands may be readily substituted for the amino-functionalized sugar ligands in any of the conjugate synthesis methods described above in Examples 11-13, 15, 17-27, and 29-31.

The PK of the resulting conjugates are tested in vivo for a-MM, L-fucose, or glucose-induced increases in PK/PD profiles following subcutaneous injection in rats according to the methods described in Example 42. The conjugates can also be formulated as sustained release formulations according to the methods in Examples 50-55 and subsequently evaluated for their protracted and glucose-responsive pharmacokinetics according to the 4 hour IP glucose injection protocol outlined in those same examples. Alternative methods of sustaining the release of these conjugates may also be employed such as those described in Examples 61-63.

Example 70

Exemplary Conjugate of Formula (VIb-3)

In certain embodiments the present disclosure provides a conjugate of formula (VIb-3):

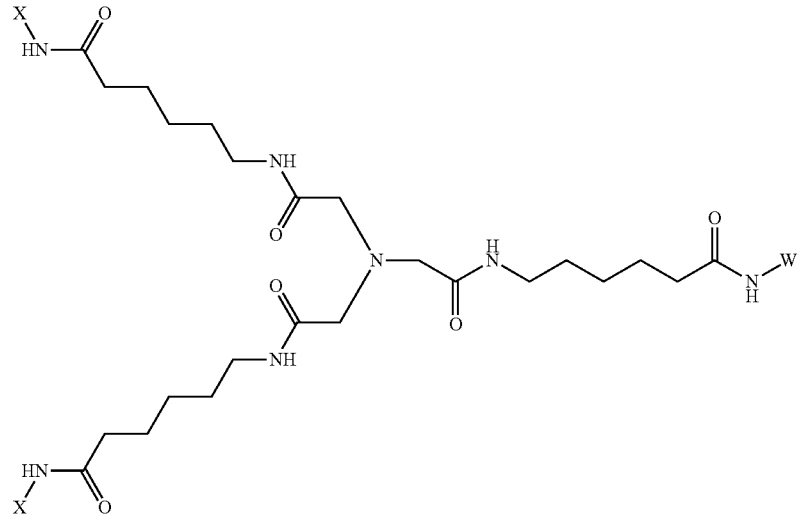

wherein:
W is an insulin molecule; and
each occurrence of —X is

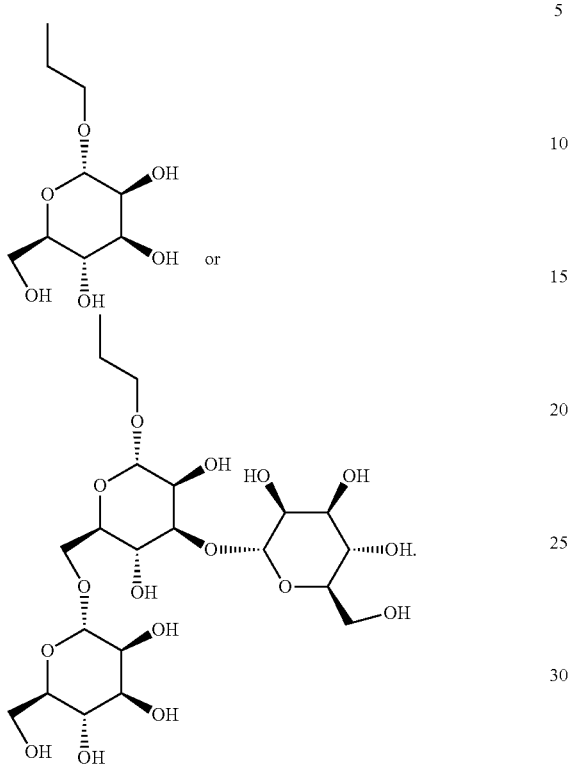

In certain embodiments, the insulin molecule is selected from the group consisting of human insulin, porcine insulin, and bovine insulin. In certain embodiments, the insulin molecule is insulin glargine or insulin detemir. In certain embodiments, the insulin molecule includes three disulfide bridges.

Example 71

Exemplary Conjugate I-6

In certain embodiments the present disclosure provides conjugate I-6:

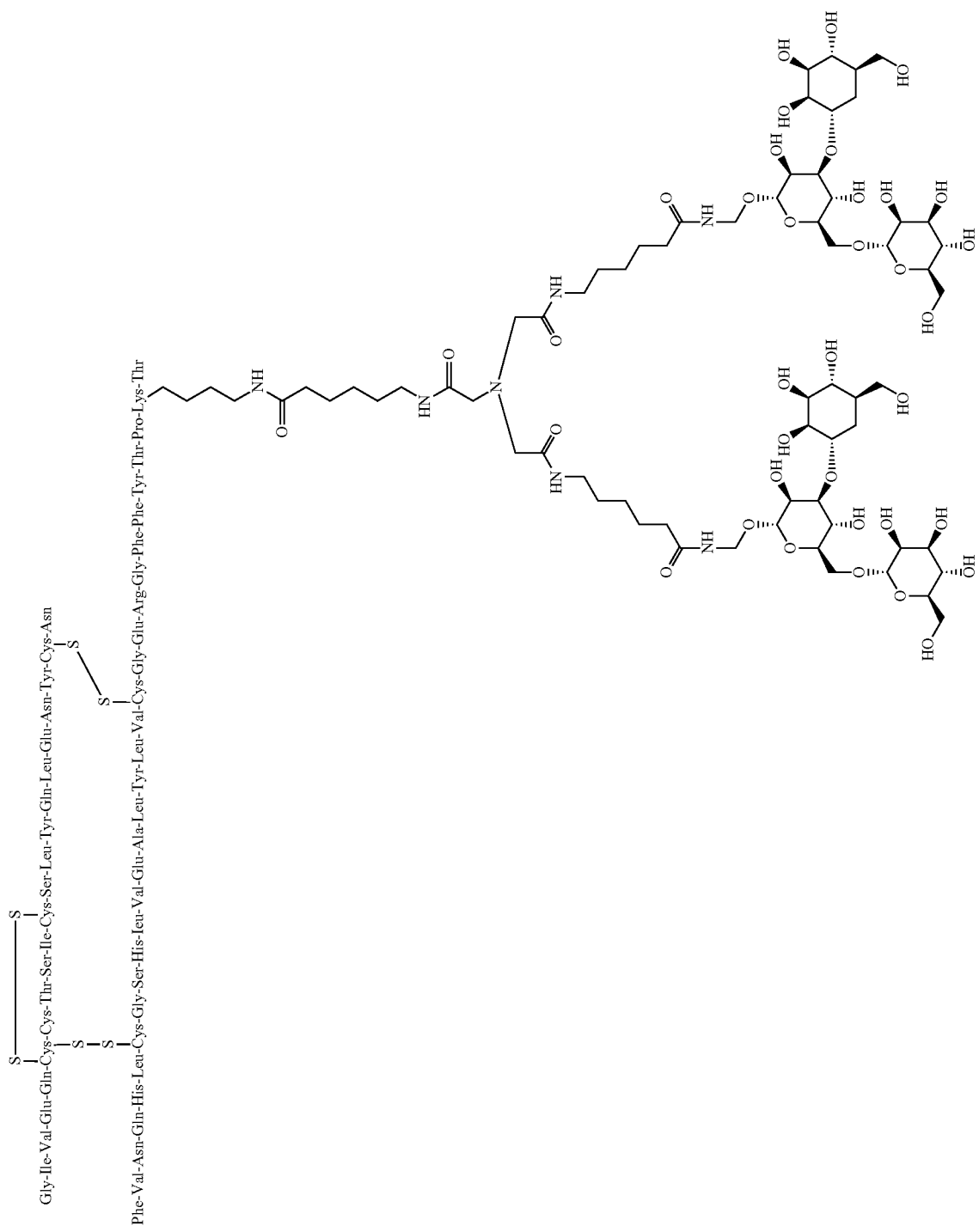

Example 72

Exemplary Conjugate of Formula (VIc-2)

In certain embodiments the present disclosure provides a conjugate of formula (VIc-2):

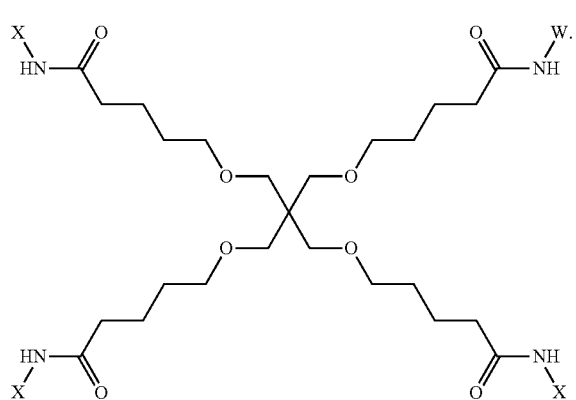

wherein:
W is an insulin molecule; and
each occurrence of —X is

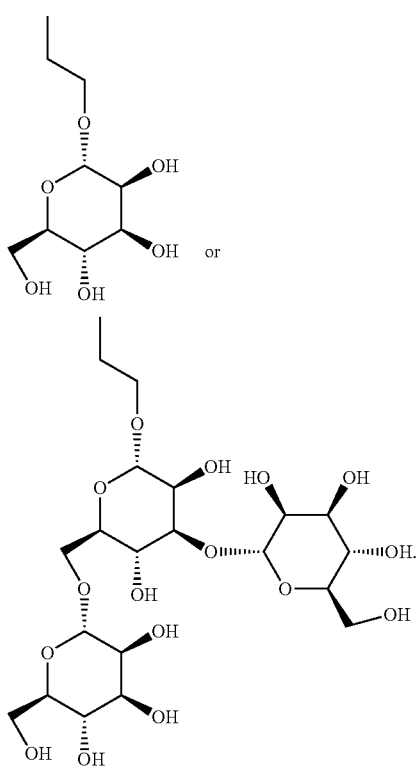

In certain embodiments, the insulin molecule is selected from the group consisting of human insulin, porcine insulin, and bovine insulin. In certain embodiments, the insulin molecule is insulin glargine or insulin detemir. In certain embodiments, the insulin molecule includes three disulfide bridges.

Example 73

Exemplary Conjugate of Formula (VId-1)

In certain embodiments the present disclosure provides a conjugate of formula (VId-1):

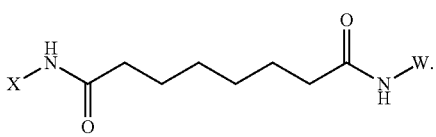

wherein:
W is an insulin molecule; and
—X is

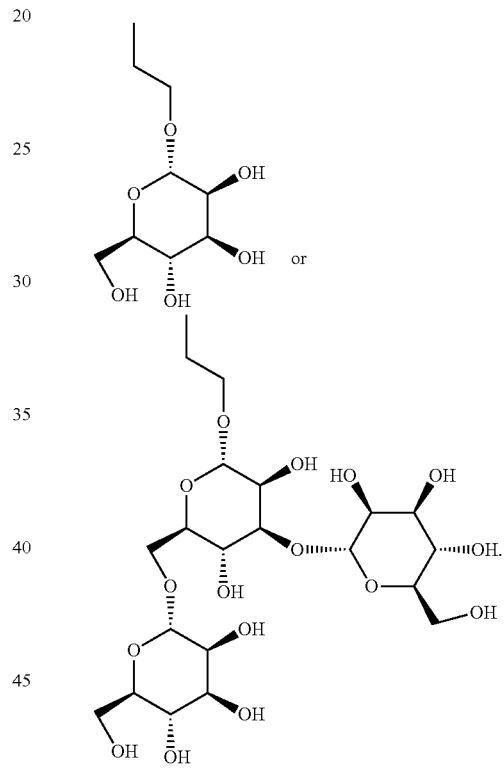

In certain embodiments, the insulin molecule is selected from the group consisting of human insulin, porcine insulin, and bovine insulin. In certain embodiments, the insulin molecule is insulin glargine or insulin detemir. In certain embodiments, the insulin molecule includes three disulfide bridges.

Example 74

Exemplary Formulations

In certain embodiments the present disclosure provides sustained release formulations that comprise a conjugate, wherein the formulation comprises protamine and zinc. It is to be understood that the present disclosure encompasses sustained release formulations with any one of the conjugates described herein (e.g., without limitation, any one of the conjugates of FIG. 45, 49, 55, 60, 61, or 62).

In certain embodiments, the formulation includes from about 1 to about 5 mg protamine/mg conjugate; and from about 0.1 to about 0.25 mg zinc/mg conjugate.

In certain embodiments, the formulation includes protamine and zinc in a ratio (w/w) in the range of about 40:1 to about 10:1.

In certain embodiments, the formulation further comprises an amount of unconjugated insulin molecule. In certain embodiments, the formulation comprises a molar ratio of conjugated insulin molecule to unconjugated insulin molecule in the range of about 25:1 to about 2:1.

In certain embodiments, the formulation further comprises an antimicrobial preservative. In certain embodiments, the antimicrobial preservative is m-cresol. In certain embodiments, the formulation comprises from about 0.15 to about 0.35% v/v m-cresol.

In certain embodiments, the formulation further comprises an isotonic agent. In certain embodiments, the isotonic agent is glycerol. In certain embodiments, the isotonic agent is NaCl. In certain embodiments, the formulation comprises from about 0.1 to about 0.2 M NaCl.

In certain embodiments, the formulation comprises:
protamine and zinc in a ratio (w/w) in the range of about 40:1 to about 10:1;
a molar ratio of conjugated insulin molecule to unconjugated insulin molecule in the range of about 25:1 to about 2:1;
about 0.15 to about 0.35% v/v m-cresol; and
glycerol or from about 0.1 to about 0.2 M NaCl.

In certain embodiments, the formulation comprises:
about 3.6 mg protamine/mg conjugate; and
about 0.2 mg zinc/mg conjugate.

In certain embodiments, the formulation comprises:
about 3.6 mg protamine/mg conjugate;
about 0.2 mg zinc/mg conjugate; and
a molar ratio of conjugated insulin molecule to unconjugated insulin molecule of about 5:1.

In certain embodiments, the formulation comprises:
about 3.6 mg protamine/mg conjugate;
about 0.2 mg zinc/mg conjugate;
a molar ratio of conjugated insulin molecule to unconjugated insulin molecule of about 5:1; and
about 0.2% v/v m-cresol.

In certain embodiments, the formulation comprises:
about 3.6 mg protamine/mg conjugate;
about 0.2 mg zinc/mg conjugate;
a molar ratio of conjugated insulin molecule to unconjugated insulin molecule of about 5:1;
about 0.2% v/v m-cresol; and
glycerol or about 0.15 M NaCl.

Example 75

Insulin Conjugation with Multivalent Activated Esters in Organic Solvent (Drug Added First) to Give A1-Substituted Insulin Conjugates—General Procedure Step 1

Insulin is dissolved in a 66:37 vol:vol mixture of 100 mM sodium carbonate buffer (pH 11) and acetonitrile at a concentration of 14.7 mM. Separately, a monofunctional protecting group-activated ester (e.g., BOC-NHS) is dissolved at 467 mM in acetonitrile. Once the insulin is dissolved, small aliquots of the monofunctional protecting group-activated ester (e.g., BOC-NHS) are added to the insulin solution. The pH is monitored throughout the process and is maintained between 10.2-11.0 through the addition of 0.1M sodium hydroxide. The reaction is monitored by reverse-phase HPLC. Aliquots of the monofunctional protecting group-activated ester are added until the HPLC chromatogram shows that all of the unmodified insulin has been reacted and that a substantial portion of the reaction mixture has been converted to B29-protected insulin. Typically the protecting group will be more hydrophobic in nature and, once reacted onto the insulin, will elute at an HPLC retention time that is longer than the unmodified insulin.

Step 2

Separately, a framework containing N-terminal activated esters is dissolved at 174 mM in 1.267 ml of anhydrous DMSO followed by the addition of 100 µl (excess) of triethylamine (TEA). The solution is stirred rapidly for 10 minutes at room temperature. In another vial, a 370 mM solution of ligand is prepared in an appropriate volume of dry DMSO. Once dissolved, enough solution is added to provide a number of reactive equivalents equal to three times the number of initial activated ester groups, N, minus one. For example, if there are N=3 initial activated ester groups per framework, then $(3\times(3-1)\times60$ mM/370 mM$)=0.973$ ml of ligand solution are added. If there are N=4 initial activated ester groups per framework, then $(3\times(4-1)\times60$ mM/370 mM$)=1.46$ ml of ligand solution are added, and so on. After the ligand solution is added, the solution is stirred for one more hour at room temperature to ensure complete reaction.

Step 3

Once the insulin has been sufficiently reacted with protecting group as described in Step 1, and after sufficient reaction has occurred between the framework and ligand in Step 2, the framework-ligand solution from Step 2 is added dropwise to the insulin solution in aliquots. The resulting reaction is monitored by HPLC. Aliquots are added until the B29-protected insulin is fully reacted to give the desired B29-protected, A1-framework/ligand, insulin-conjugate. Since the ligand-framework is often more hydrophilic than the insulin, the appearance of the desired product is signaled by a distinct shift to shorter HPLC retention times as compared to the B29-insulin (from Step 1). Once the desired level of reaction has been achieved, the reaction solution is superdiluted by 10× into a 20 mM pH 5.0 HEPES buffered saline solution containing 0.150 M NaCl followed by pH adjustment with dilute HCl to a final pH of 8.0. The aqueous solution is first purified by size exclusion using an appropriate solid phase for the desired separation of conjugated and unconjugated materials. The solution passing through the column void volume is then concentrated using an appropriately sized ultrafiltration membrane to approximately 10 ml. This solution is further purified to obtain the desired product using preparative reverse phase HPLC on a Waters C8, 7 um, 19×150 mm column. Buffer A is deionized water containing 0.1% TFA and Buffer B is acetonitrile containing 0.1% TFA. Before purification, the column is equilibrated at 15 ml/minutes with a 80% A/20% B mobile phase using a Waters DeltaPrep 600 system. Approximately 5 ml of the crude solution is injected onto the column over the course of 2 minutes at a flow rate of 15 ml/minutes after which a linear gradient is employed from 80% A/20% B to 75% A/25% B over the next 5 minutes followed by a slower linear gradient from 75% A/25% B to 62% A/38% B over the next 22 minutes. The retention time of the desired peak will vary depending on the insulin, framework, and ligand used. Once collected, the solution is rotovapped to remove acetonitrile and lyophilized to obtain pure mono-protected insulin-conjugate.

Step 4

In all cases the protecting group is then removed from the insulin-conjugate. In cases where a BOC protecting group is used in Step 1, the BOC groups are removed by dissolving the lyophilized powder obtained according to Step 3 in 90% TFA/10% anisole for one hour at 4 C followed by 10× superdilution in 25 mM HEPES pH 8.2 buffer containing 0.150M NaCl. (If a protecting group other than BOC is present on the amine-bearing drug, then the appropriate deprotection conditions are employed instead of TFA/anisole. A listing of protection agents and deprotection conditions may be found in *Protecting Groups in Organic Synthesis*, T. W. Greene and P. G. M. Wuts, $3^{rd}$ edition, John Wiley & Sons, 1999, as described in the Definitions section.) The pH was adjusted to between 7.0 and 8.0 using NaOH solution after which the material is passed through a Biogel P2 column to remove anisole, BOC and other low MW byproducts of deprotection, as well as any other contaminating salts. The deprotected, purified aqueous conjugate solution was then concentrated using Amicon 3K membranes (Millipore, Billerica, Mass.) to approximately 66 U of insulin/ml (based on A280 measurements) and stored at 4 C until needed. The identity of the final conjugate is verified by LC-MS (HT Laboratories, San Diego, Calif.). The A1 site of conjugation is confirmed by N-terminal sequencing (Western Analytical, St. Louis, Mo.), which reveals >95% of the Phe-B1-chain terminus present and <5% of the $Gly^{A1}$-chain terminus present due to the substitution of $Gly^{A1}$ with the ligand-containing framework.

One of ordinary skill in the art will appreciate that other amine-functionalized drugs can be conjugated to ligand-containing frameworks using analogous procedures to that described in Example 75. One of ordinary skill in the art will also appreciate that Example 75 is relevant not only to wild-type insulin, but also to insulin mutants as described herein.

The following insulin-conjugates were prepared according to the procedure in Example 75 using BOC-NHS as the protecting reagent.

| Conjugate | Framework | Framework MW | Ligand | AE-sugar MW | Purity (HPLC) | MW (LC-MS) | Sugar/Insulin |
|---|---|---|---|---|---|---|---|
| I-13: TSAT-C6-AEM-2 (A1) | TSAT-C6 | 822 | AEM | 223 | 97% | 6730 | 2.0 |
| I-12: TSAT-C6-AETM-2 (A1) | TSAT-C6 | 822 | AETM | 547 | 97% | 7378 | 2.0 |
| I-15: TSPE-AEM-3 (A1) | TSPE | 813 | AEM | 223 | 98% | 6829 | 3.0 |
| I-14: TSPE-AETM-3 (A1) | TSPE | 813 | AETM | 547 | 94% | 7802 | 3.0 |

The following insulin-conjugates can be prepared according to the procedure in Example 75. In some embodiments, the insulin-conjugates are prepared using BOC-NHS as the protecting reagent.

| Conjugate | Framework | Framework MW | Ligand | AE-sugar MW | MW (LC-MS) (expected) | Sugar/Insulin (expected) |
|---|---|---|---|---|---|---|
| DSS-AEM-1 (A1) | DSS | 368 | AEM | 223 | 6169 | 1.0 |
| DSS-AEBM-1 (A1) | DSS | 368 | AEBM | 385 | 6331 | 1.0 |
| DSS-AETM-1 (A1) | DSS | 368 | AETM | 547 | 6493 | 1.0 |
| TSAT-C6-AEBM-2 (A1) | TSAT-C6 | 822 | AEBM | 385 | 7054 | 2.0 |
| TSPE-AEBM-3 (A1) | TSPE | 813 | AEBM | 385 | 7314 | 3.0 |

Example 76

Insulin Conjugation with Multivalent Activated Esters in Organic Solvent (Drug Added First) to Give A1,B29-Substituted Insulin Conjugates—General Procedure Step 1

A framework containing N-terminal activated esters is dissolved at 147 mM in 2.5 ml of anhydrous DMSO followed by the addition of 1.0 mL (excess) of triethylamine (TEA). The solution is stirred rapidly for 10 minutes at room temperature. In another vial, a 272 mM solution of ligand is prepared in an appropriate volume of dry DMSO. Once dissolved, enough solution is added to provide a number of reactive equivalents equal to three times the number of initial activated ester groups, N, minus one. For example, if there are N=3 initial activated ester groups per framework, then (3×(3−1)×60 mM/370 mM)=0.973 ml of ligand solution are added. If there are N=4 initial activated ester groups per framework, then (3×(4−1)×60 mM/370 mM)=1.46 ml of ligand solution are added, and so on. After the ligand solution is added, the solution is stirred for one more hour at room temperature to ensure complete reaction.

Step 2

Insulin is dissolved in 1.5 mL of 100 mM sodium carbonate buffer (pH 11) at a concentration of 17.2 mM. Solution pH is maintained at ~11 by addition of 0.1 M NaOH as needed. Once the insulin is dissolved, small aliquots of the framework-ligand solution are added to the insulin solution. The pH is monitored throughout the process and is maintained between 10.2-11.0 through the addition of 0.1M sodium hydroxide. The reaction is monitored by reverse-phase HPLC. Aliquots of framework-ligand solution are added until the HPLC chromatogram shows that substantially all of the unmodified insulin has been reacted and that a substantial portion of the reaction mixture has been converted to a small portion of mono-reacted insulin/framework/ligand conjugate and the majority product is di-reacted insulin/framework/ligand conjugate. Typically the framework-ligand construct will be more hydrophilic than the unmodified insulin, causing the mono and di-reacted amine-bearing drug products to elute at HPLC retention times shorter than that of the unmodified insulin. Likewise, the HPLC peak of the desired product, the disubstituted insulin-conjugate, will appear at a retention time that is shorter than that of the mono-substituted insulin-conjugate.

Step 3

Once the insulin has been sufficiently reacted with framework ligand as described in Step 2, the solution is then super-diluted by 10× into a 20 mM pH 5.0 HEPES buffered saline solution containing 0.150 M NaCl followed by pH adjustment with dilute HCl to a final pH of 8.0. The aqueous solution is first purified by size exclusion using an appropriate solid phase for the desired separation of conjugated and unconjugated materials. The solution passing through the column void volume is then concentrated using an appropriately sized ultrafiltration membrane to approximately 10 ml. This solution is further purified to obtain the desired product using preparative reverse phase HPLC on a Waters C8, 7 um, 19×150 mm column. Buffer A is deionized water containing 0.1% TFA and Buffer B is acetonitrile containing 0.1% TFA. Before purification, the column is equilibrated at 15 ml/minutes with a 80% A/20% B mobile phase using a Waters DeltraPrep 600 system. Approximately 5 ml of the crude solution is injected onto the column over the course of 2 minutes at a flow rate of 15 ml/minutes after which a linear gradient is employed from 80% A/20% B to 75% A/25% B over the next 5 minutes followed by a slower linear gradient from 75% A/25% B to 62% A/38% B over the next 22 minutes. The retention time of the desired peak will vary depending on the insulin, framework, and ligand used. Once collected, the solution is rotovapped to remove acetonitrile and lyophilized to obtain pure conjugate. The identity of the final conjugate is verified by LC-MS (HT Laboratories, San Diego, Calif.). The A1, B29 sites of conjugation are confirmed by N-terminal sequencing (Western Analytical, St. Louis, Mo.), which reveals >95% of the Phe-B1-chain terminus present and <5% of the Gly$^{A1}$-chain terminus present due to the substitution of Gly$^{A1}$ with the ligand-containing framework.

One of ordinary skill in the art will appreciate that other amine-functionalized drugs can be conjugated to ligand-containing frameworks using analogous procedures to that described in Example 76. One of ordinary skill in the art will also appreciate that Example 76 is relevant not only to wild-type insulin, but also to insulin mutants as described herein.

The following insulin-conjugates were prepared according to the procedure Example 76.

| Conjugate | Framework | Framework MW | Ligand | AE-sugar MW | Purity (HPLC) | MW (LC-MS) | Sugar/Insulin |
|---|---|---|---|---|---|---|---|
| II-4: DSS-Di-sub-AEM-1 (A1, B29) | DSS | 368 | AEM | 223 | 92% | 6531 | 2.0 |
| II-3: DSS-Di-sub-AETM-1 (A1, B29) | DSS | 368 | AETM | 547 | 94% | 7179 | 2.0 |
| II-1: TSAT-C6-Di-sub-AEM-2 (A1, B29) | TSAT-C6 | 822 | AEM | 223 | 97% | 7653 | 4.0 |
| II-2: TSAT-C6-Di-sub-AETM-2 (A1, B29) | TSAT-C6 | 822 | AETM | 547 | 97% | 8949 | 4.0 |

The following insulin-conjugates can be prepared according to the procedure in Example 76.

| Conjugate | Framework | Framework MW | Ligand | AE-sugar MW | MW (LC-MS) | Sugar/Insulin |
|---|---|---|---|---|---|---|
| DSS-Di-sub-AEBM-1 (A1, B29) | DSS | 368 | AEBM | 385 | 6855 | 2.0 |
| TSAT-C6-Di-sub-AEBM-2 (A1, B29) | TSAT-C6 | 822 | AEBM | 385 | 8301 | 4.0 |
| TSPE-Di-sub-AEM-3 (A1, B29) | TSPE | 813 | AEM | 223 | 7852 | 6.0 |
| TSPE-Di-sub-AEBM-3 (A1, B29) | TSPE | 813 | AEBM | 385 | 8824 | 6.0 |
| TSPE-Di-sub-AETM-3 (A1, B29) | TSPE | 813 | AETM | 547 | 9796 | 6.0 |

Example 77

Insulin Conjugation with Multivalent Activated Esters in Organic Solvent (Drug Added First) to Give A1,B1-Substituted Insulin Conjugates Step 1

A framework containing N-terminal activated esters is dissolved at 147 mM in 2.5 ml of anhydrous DMSO followed by the addition of 1.0 mL (excess) of triethylamine (TEA). The solution is stirred rapidly for 10 minutes at room temperature. In another vial, a 272 mM solution of ligand is prepared in an appropriate volume of dry DMSO. Once dissolved, enough solution is added to provide a number of reactive equivalents equal to three times the number of initial activated ester groups, N, minus one. For example, if there are N=3 initial activated ester groups per framework, then (3×(3−1)×60 mM/370 mM)=0.973 ml of ligand solution are added. If there are N=4 initial activated ester groups per framework, then (3×(4−1)×60 mM/370 mM)=1.46 ml of ligand solution are added, and so on. After the ligand solution is added, the solution is stirred for one more hour at room temperature to ensure complete reaction.

Step 2

An insulin containing three reactive amine groups each with a distinguishable pKa (e.g., in the case of wild-type insulin, pKa Gly$^{A1}$=8.0, Phe$^{B1}$=6.7, Lys$^{\epsilon B29}$=11.2; see Mei et al., *Pharm. Res.* 16:1680-1686, 1999) that has been previously mono-protected at the highest pKa amine group (e.g., Lys$^{B29}$) with a monofunctional protecting group-activated ester (e.g., BOC-NHS) is dissolved in 1.5 mL of DMSO at a concentration of 17.2 mM. Once the B29-BOC-insulin is dissolved, small aliquots of the framework-ligand solution are added to the B29-BOC-insulin solution. The reaction is monitored by reverse-phase HPLC. Aliquots of framework-ligand solution are added until the HPLC chromatogram shows that substantially all of the B29-BOC-insulin has been reacted and that a substantial portion of the reaction mixture has been converted to a small portion of mono-reacted B29-BOC-insulin/framework/ligand conjugate and the majority product is di-reacted B29-BOC-insulin/framework/ligand conjugate. Typically the framework-ligand construct will be more hydrophilic than the B29-BOC-insulin, causing the mono-conjugated and di-conjugated B29-BOC-insulin-conjugates to elute at HPLC retention times shorter than that of the unmodified B29-BOC-insulin. Likewise, the HPLC peak for the desired product, the disubstituted B29-BOC-insulin-conjugate, will appear at a retention time that is shorter than that of the mono-substituted B29-BOC-insulin-conjugate.

Step 3

Once the B29-BOC-insulin has been sufficiently reacted with ligand-containing framework as described in Step 2, the solution is then superdiluted by 10× into a 20 mM pH 5.0 HEPES buffered saline solution containing 0.150 M NaCl followed by pH adjustment with dilute HCl to a final pH of 8.0. The aqueous solution is first purified by size exclusion using an appropriate solid phase for the desired separation of conjugated and unconjugated materials. The solution passing through the column void volume is then concentrated using an appropriately sized ultrafiltration membrane to approximately 10 ml. This solution is further purified to obtain the desired product using preparative reverse phase HPLC on a Waters C8, 7 um, 19×150 mm column. Buffer A is deionized water containing 0.1% TFA and Buffer B is acetonitrile containing 0.1% TFA. Before purification, the column is equilibrated at 15 ml/minutes with a 80% A/20% B mobile phase using a Waters DeltaPrep 600 system. Approximately 5 ml of the crude solution is injected onto the column over the course of 2 minutes at a flow rate of 15 ml/minutes after which a linear gradient is employed from 80% A/20% B to 75% A/25% B over the next 5 minutes followed by a slower linear gradient from 75% A/25% B to 62% A/38% B over the next 22 minutes. The retention time of the desired peak will vary depending on the insulin, framework, and ligand used. Once collected, the solution is rotovapped to remove acetonitrile and lyophilized to obtain pure conjugate.

Step 4

In all cases the protecting group is then removed from the conjugate. In cases where a BOC protecting group is used in Step 1, the BOC groups are removed by dissolving the lyophilized powder obtained according to Step 3 in 90% TFA/10% anisole for one hour at 4 C followed by 10× superdilution in 25 mM HEPES pH 8.2 buffer containing 0.150M NaCl. (If a protecting group other than BOC is present on the amine-bearing drug, then the appropriate deprotection conditions are employed instead of TFA/anisole. A listing of protection agents and deprotection conditions may be found in *Protecting Groups in Organic Synthesis*, T. W. Greene and P. G. M. Wuts, $3^{rd}$ edition, John Wiley & Sons, 1999, as described in the Definitions section.) The pH was adjusted to between 7.0 and 8.0 using NaOH solution after which the material is passed through a Biogel P2 column to remove anisole, BOC and other low MW byproducts of deprotection, as well as any other contaminating salts. The deprotected, purified aqueous conjugate solution was then concentrated using Amicon 3K membranes (Millipore, Billerica, Mass.) to approximately 66 U of insulin/ml (based on A280 measurements) and stored at 4 C until needed. The identity of the final conjugate is verified by LC-MS (HT Laboratories, San Diego, Calif.). The A1, B1 sites of conjugation are confirmed by N-terminal sequencing (Western Analytical, St. Louis, Mo.), which reveals essentially no Phe-B1-chain terminus present and no Gly-A1-chain terminus present due to the substitution at both termini with the ligand-containing framework.

One of ordinary skill in the art will appreciate that other amine-functionalized drugs can be conjugated to ligand-containing frameworks using analogous procedures to that described in Example 77. One of ordinary skill in the art will also appreciate that Example 77 is relevant not only to wild-type insulin, but also to insulin mutants as described herein.

Conjugate II-5 was prepared according to the procedure in Example 77 using BOC-NHS as the protecting reagent.

| Conjugate | Framework | Framework MW | Ligand | AE-sugar MW | Purity (HPLC) | MW (LC-MS) | Sugar/Insulin |
|---|---|---|---|---|---|---|---|
| II-5: TSAT-C6-Di-sub-AETM-2 (A1, B1) | TSAT-C6 | 822 | AETM | 547 | 97% | 8949 | 4.0 |

The following insulin-conjugates can be prepared according to the procedure in Example 77.

| Identity | Framework | Framework MW | Ligand | AE-sugar MW | MW (LC-MS) (expected) | Sugar/Insulin (expected) |
|---|---|---|---|---|---|---|
| DSS-Di-sub-AEM-1 (A1, B1) | DSS | 368 | AEM | 223 | 6531 | 2.0 |
| DSS-Di-sub-AEBM-1 (A1, B1) | DSS | 368 | AEBM | 385 | 6855 | 2.0 |
| DSS-Di-sub-AETM-1 (A1, B1) | DSS | 368 | AETM | 547 | 7179 | 2.0 |
| TSAT-C6-Di-sub-AEM-2 (A1, B1) | TSAT-C6 | 822 | AEM | 223 | 7653 | 4.0 |
| TSAT-C6-Di-sub-AEBM-2 (A1, B1) | TSAT-C6 | 822 | AEBM | 385 | 8301 | 4.0 |
| TSAT-C6-Di-sub-AETM-2 (A1, B1) | TSAT-C6 | 822 | AETM | 547 | 8949 | 4.0 |
| TSPE-Di-sub-AEM-3 (A1, B1) | TSPE | 813 | AEM | 223 | 7852 | 6.0 |
| TSPE-Di-sub-AEBM-3 (A1, B1) | TSPE | 813 | AEBM | 385 | 8824 | 6.0 |
| TSPE-Di-sub-AETM-3 (A1, B1) | TSPE | 813 | AETM | 547 | 9796 | 6.0 |

Example 78

Insulin Conjugation with Multivalent Activated Esters in Organic Solvent (Drug Added First) to Give B1,B29-Substituted Insulin Conjugates Step 1

A framework containing N-terminal activated esters is dissolved at 147 mM in 2.5 ml of anhydrous DMSO. No base is added, in contrast with previous examples. The solution is stirred rapidly for 10 minutes at room temperature. In another vial, a 272 mM solution of ligand is prepared in an appropriate volume of dry DMSO. Once dissolved, enough solution is added to provide a number of reactive equivalents equal to three times the number of initial activated ester groups, N, minus one. For example, if there are N=3 initial activated ester groups per framework, then (3×(3−1)×60 mM/370 mM)=0.973 ml of ligand solution are added. If there are N=4 initial activated ester groups per framework, then (3×(4−1)×60 mM/370 mM)=1.46 ml of ligand solution are added, and so on. After the ligand solution is added, the solution is stirred for one more hour at room temperature to ensure complete reaction.

Step 2

An insulin containing three reactive amine groups each with a distinguishable pKa (e.g., in the case of wild-type insulin, pKa $Gly^{A1}$=8.0, $Phe^{B1}$=6.7, $Lys^{\epsilon B29}$=11.2; see Mei et al., *Pharm. Res.* 16:1680-1686, 1999) that has been previously mono-protected at the amine group with the intermediate pKa (e.g., $Gly^{A1}$ for wild-type insulin) with a monofunctional protecting group-activated ester (e.g., BOC-NHS) is dissolved in 1.5 mL of DMSO at a concentration of 17.2 mM. (A1-BOC-insulin can be prepared using the procedure in Example 8 but reacting with fewer equivalents of the BOC reagent in order to yield a distribution of A1,B29-diBOC-insulin, A1-BOC-insulin, and B29-BOC-insulin products. A1-BOC-insulin can be isolated by RP-HPLC and confirmed by N-terminal sequencing.) Once the A1-BOC-insulin is dissolved, small aliquots of the framework-ligand solution are added to the A1-BOC-insulin solution. The reaction is monitored by reverse-phase HPLC. Aliquots of framework-ligand solution are added until the HPLC chromatogram shows that substantially all of the unmodified A1-BOC-insulin has been reacted and that a substantial portion of the reaction mixture has been converted to a small portion of mono-conjugated A1-BOC-insulin/framework/ligand conjugate and the majority product is di-conjugated A1-BOC-insulin/framework/ligand conjugate. Typically the framework-ligand construct will be more hydrophilic than the A1-BOC-insulin, causing the mono and di-substituted A1-BOC-insulin-conjugates to elute at HPLC retention times shorter than that of the unmodified A1-BOC-insulin. Likewise, the HPLC peak of the desired product, the di-substituted A1-BOC-insulin-conjugate, will appear at a retention time that is shorter than that of the mono-substituted A1-BOC-insulin-conjugate.

Step 3

Once the A1-BOC-insulin has been sufficiently reacted with framework ligand as described in Step 2, the solution is then superdiluted by 10× into a 20 mM pH 5.0 HEPES buffered saline solution containing 0.150 M NaCl followed by pH adjustment with dilute HCl to a final pH of 8.0. The aqueous solution is first purified by size exclusion using an appropriate solid phase for the desired separation of conjugated and unconjugated materials. The solution passing through the column void volume is then concentrated using an appropriately sized ultrafiltration membrane to approximately 10 ml. This solution is further purified to obtain the desired product using preparative reverse phase HPLC on a Waters C8, 7 um, 19×150 mm column. Buffer A is deionized water containing 0.1% TFA and Buffer B is acetonitrile containing 0.1% TFA. Before purification, the column is equilibrated at 15 ml/minutes with a 80% A/20% B mobile phase using a Waters DeltraPrep 600 system. Approximately 5 ml of the crude solution is injected onto the column over the course of 2 minutes at a flow rate of 15 ml/minutes after which a linear gradient is employed from 80% A/20% B to 75% A/25% B over the next 5 minutes followed by a slower linear gradient from 75% A/25% B to 62% A/38% B over the next 22 minutes. The retention time of the desired peak will vary depending on the drug, framework, and ligand used. Once collected, the solution is rotovapped to remove acetonitrile and lyophilized to obtain pure conjugate.

Step 4

In all cases the protecting group is then removed from the conjugate. In cases where a BOC protecting group is used in Step 1, the BOC groups are removed by dissolving the lyophilized powder obtained according to Step 3 in 90% TFA/10% anisole for one hour at 4 C. If a protecting group other than BOC is present on the amine-bearing drug, then the appropriate deprotection conditions are employed instead of TFA/anisole. A listing of protection agents and deprotection conditions may be found in *Protecting Groups in Organic Synthesis*, T. W. Greene and P. G. M. Wuts, 3$^{rd}$ edition, John Wiley & Sons, 1999, as described in the Definitions section. The deprotection step is followed by 10× superdilution in 25 mM HEPES pH 8.2 buffer containing 0.150M NaCl. The pH is adjusted to between 7.0 and 8.0 using NaOH solution after which the material is passed through a Biogel P2 column to remove anisole, BOC and other low MW byproducts of deprotection, as well as any other contaminating salts. The deprotected, purified aqueous conjugate solution is then concentrated using Amicon 3K membranes (Millipore, Billerica, Mass.) to approximately 66 U of insulin/ml (based on A280 measurements) and stored at 4 C until needed. The identity of the final conjugate is verified by LC-MS (HT Laboratories, San Diego, Calif.). The B1 site of conjugation is confirmed by N-terminal sequencing (Western Analytical, St. Louis, Mo.), which reveals >95% of the Gly-A1-chain terminus present and <5% of the Phe-B1-chain terminus present due to the substitution of Phe-B 1 with the ligand-containing framework.

One of ordinary skill in the art will appreciate that other amine-functionalized drugs can be conjugated to ligand-containing frameworks using analogous procedures to that described in Example 78. One of ordinary skill in the art will also appreciate that Example 78 is relevant not only to wild-type insulin, but also to insulin mutants as described herein.

The following insulin-conjugates can be prepared according to the procedure in Example 78.

| Conjugate | Framework | Framework MW | Ligand | AE-sugar MW | MW (LC-MS) (expected) | Sugar/Insulin (expected) |
|---|---|---|---|---|---|---|
| II-7: DSS-Di-sub-AETM-1 (B1, B29) | DSS | 368 | AETM | 547 | 7179 | 2.0 |
| II-6: TSAT-C6-Di-sub-AETM-2 (B1, B29) | TSAT-C6 | 822 | AETM | 547 | 8949 | 4.0 |
| DSS-Di-sub-AEM-1 (B1, B29) | DSS | 368 | AEM | 223 | 6531 | 2.0 |
| DSS-Di-sub-AEBM-1 (B1, B29) | DSS | 368 | AEBM | 385 | 6855 | 2.0 |
| TSAT-C6-Di-sub-AEM-2 (B1, B29) | TSAT-C6 | 822 | AEM | 223 | 7653 | 4.0 |
| TSAT-C6-Di-sub-AEBM-2 (B1, B29) | TSAT-C6 | 822 | AEBM | 385 | 8301 | 4.0 |
| TSPE-Di-sub-AEM-3 (B1, B29) | TSPE | 813 | AEM | 223 | 7852 | 6.0 |
| TSPE-Di-sub-AEBM-3 (B1, B29) | TSPE | 813 | AEBM | 385 | 8824 | 6.0 |
| TSPE-Di-sub-AETM-3 (B1, B29) | TSPE | 813 | AETM | 547 | 9796 | 6.0 |

Example 79

In Vivo Half Life/Elimination Rate Comparison

In order to determine the rate at which the I-6 conjugate was cleared from serum in vivo in the presence or absence of inhibitory sugars such as glucose or a-MM, the following experiment was conducted. In each case the soluble conjugate (or RHI as a control) was dosed at 0.4 mg conjugate/kg body weight into dual jugular vein cannulated male Sprague-Dawley rats (Taconic, JV/JV, 350-400 g, n=3).

To determine the elimination rate in the presence of elevated glucose levels, one hour before the start of the experiment one rat cannula was connected to a syringe infusion pump containing a sterile 50% w/v glucose solution. The pump infusion rate was adjusted by the experimenter to ensure that the blood glucose levels in the animal remained above 300 mg/dL at all times during the experiment. Blood glucose was measured using commercially available test strips (Precision Xtra, Abbott Laboratories, Abbott Park, Ill.). In a typical experiment, it was found that the infusion pump rate required to keep the animals above 300 mg/dL was typically greater than 85 uL/min. A blood sample was taken at t=0 min, after which a sterile conjugate solution or control insulin was injected intravenously via the second rat cannula, followed immediately by a chase solution of heparin-saline to ensure that all of the conjugate dose was administered into the animal. After an additional flush of the cannula line with heparin-saline, the second cannula was used to collect blood samples at t=1, 2, 4, 8, 15, 30, 60, 90, 120, and 180 minutes post-dose.

To determine the elimination rate in the presence of a-MM, one hour before the start of the experiment one rat cannula was connected to a syringe infusion pump containing a sterile 25% w/v a-MM solution. The pump infusion rate was adjusted by the experimenter, but was typically set at 85 uL/min. A blood sample was taken at t=0 min, after which a sterile conjugate solution or control insulin was injected intravenously via the second rat cannula, followed immediately by a chase solution of heparin-saline to ensure that all of the conjugate dose was administered into the animal. After an additional flush of the cannula line with heparin-saline, the second cannula was used to collect blood samples at t=1, 2, 4, 8, 15, 30, 60, 90, 120, and 180 minutes post-dose.

Throughout the experiment, blood glucose was measured using commercially available test strips (Precision Xtra, Abbott Laboratories, Abbott Park, Ill.). Blood from each timepoint was centrifuged at 4 C to collect the serum, and serum insulin or serum conjugate concentrations were subsequently measured with a commercially available ELISA kit (Iso-Insulin ELISA, Mercodia, Uppsala, Sweden). Insulin or conjugate serum concentration vs. time data was best fit with the sum of two independent decaying exponentials ($C(t)=a \exp(-k_a t)+b \exp(-k_b t)$) according to the two-compartment model, where $t\frac{1}{2}(a)=(\ln 2)/k_a$ and $t\frac{1}{2}(b)=(\ln 2)/k_b$. Results are shown in FIG. 46. The left panel demonstrates the significantly higher (>5×) elimination rate for the I-6 conjugate versus RHI in the absence of a-MM or glucose. The right panel shows that the elimination rate decreases somewhat (~50%) in the presence of glucose (G400 infusion) and quite substantially (~400%) in the presence of a-MM (a-MM infusion).

Example 80

Glucose-Responsive PK for I-6 i.v. Infusion

In this example, the i.v. elimination rate experiment described in Example 79 was modified from a single i.v. bolus of 0.4 mg conjugate/kg body weight to a continuous i.v. infusion. The goal of the experiment was to maintain a constant input rate of conjugate (or RHI as a control) for six hours with an i.p. injection of glucose administered at the four hour time point to determine the resulting effect on serum conjugate (or RHI) concentration. Dual jugular vein cannulated male Sprague-Dawley rats (Taconic, JV/JV, 350-400 g, n=3) were used in each experiment such that one jugular vein line was used for conjugate or RHI infusion and the other for blood collection.

For RHI, a 50 mU/ml solution was sterile filtered through a 0.2 um filtration membrane and infused at 0.07 ml/min to provide a constant input rate of 3.5 mU/min for the entire six hour experiment. A blood sample was taken at t=0 min, after which the constant i.v. infusion was initiated. The second cannula was used to collect blood samples at t=30, 60, 120, 180 and 240 min. At t=240 min, a 4 g/kg dose of glucose was administered via i.p. injection followed by blood collection at t=255, 270, 300, 330 and 360 min.

For the I-6 conjugate, a 150 mU/ml solution was sterile filtered through a 0.2 m filtration membrane and infused at 0.10 ml/min to provide a constant input rate of 15 mU/min for the entire six hour experiment. A blood sample was taken at t=0 min, after which the constant i.v. infusion was initiated. The second cannula was used to collect blood samples at t=30, 60, 120, 180 and 240 min. At t=240 min, a 1, 2, or 4 g/kg dose of glucose was administered via i.p. injection followed by blood collection at t=255, 270, 300, 330 and 360 min.

Throughout the experiments, blood glucose was measured using commercially available test strips (Precision Xtra, Abbott Laboratories, Abbott Park, Ill.). Blood from each timepoint was centrifuged at 4 C to collect the serum, and serum insulin or serum conjugate concentrations were subsequently measured with a commercially available ELISA kit (Iso-Insulin ELISA, Mercodia, Uppsala, Sweden).

Figure 47:
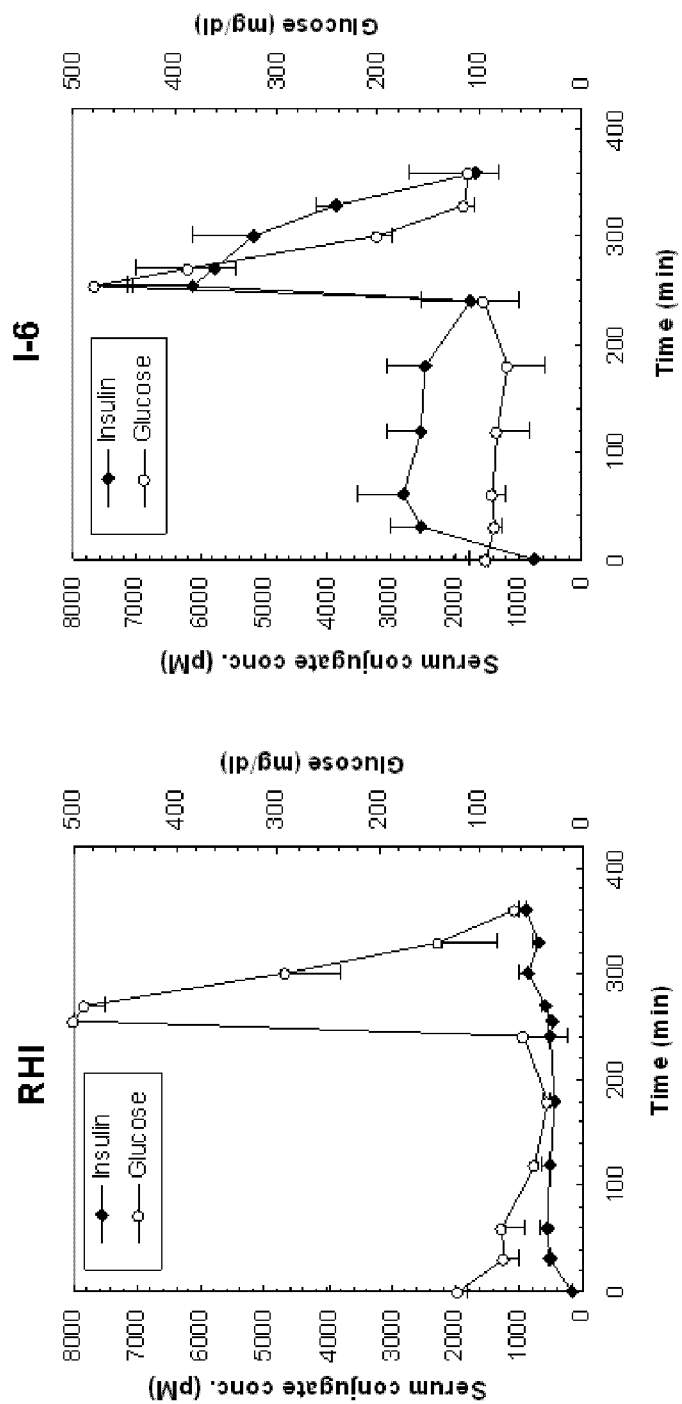
FIG. 47: The first two panels show plots of serum insulin (♦) and blood glucose (○) levels following constant intravenous (i.v.) infusion of RHI (3.5 mU/min) or I-6 (15 mU/min) in non-diabetic, male SD rats (n=3). IP injection of glucose (4 g/kg) was given at 240 minutes. The next three panels compare plots of serum insulin (♦) and blood glucose (○) levels following constant intravenous (i.v.) infusion of RHI (3.5 mU/min) or I-6 (15 mU/min) in non-diabetic, male SD rats (n=3) when an IP injection of glucose (4, 2, or 1 g/kg) was given at 240 minutes.
Figure 47:
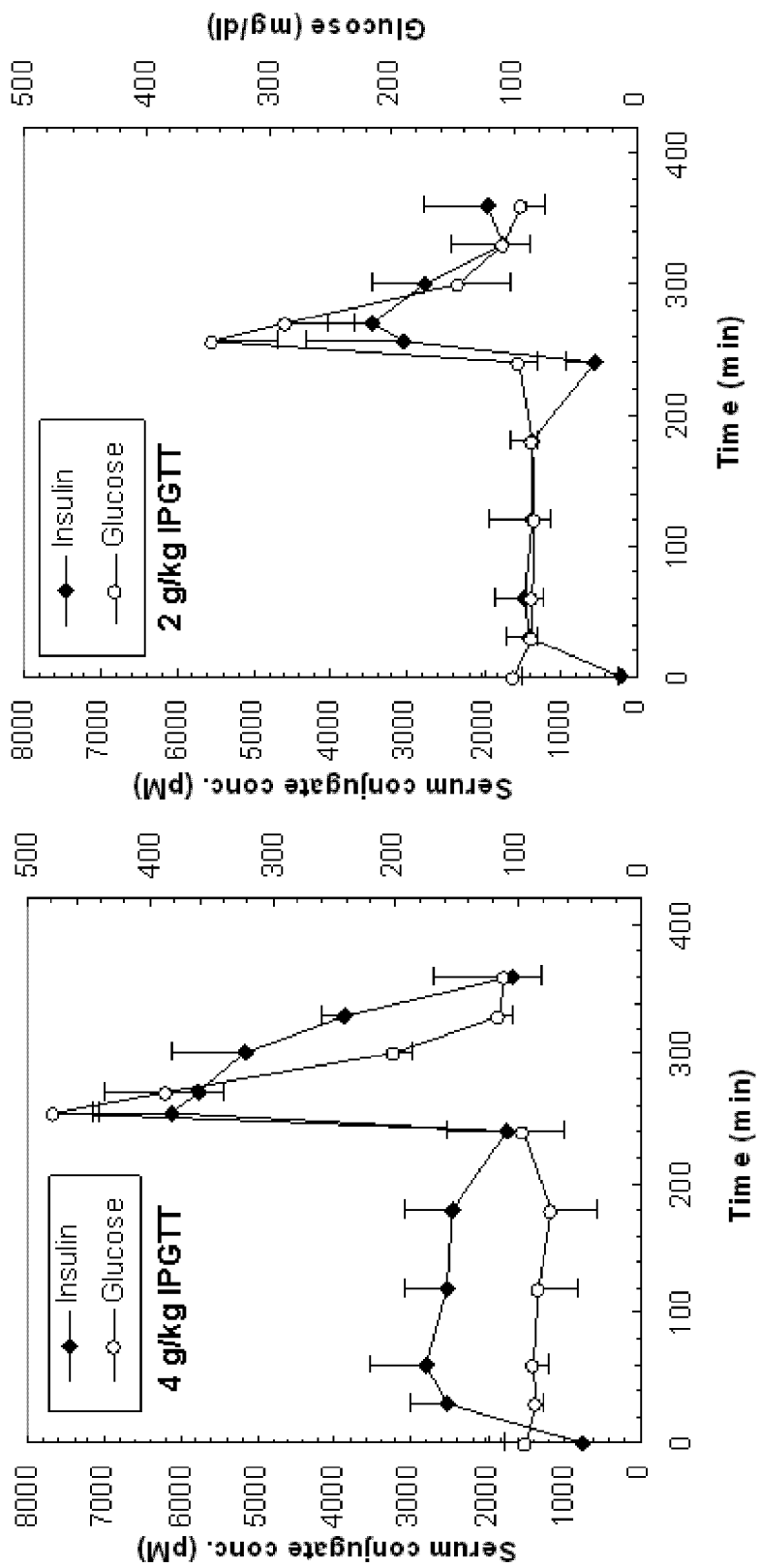
Figure 47:
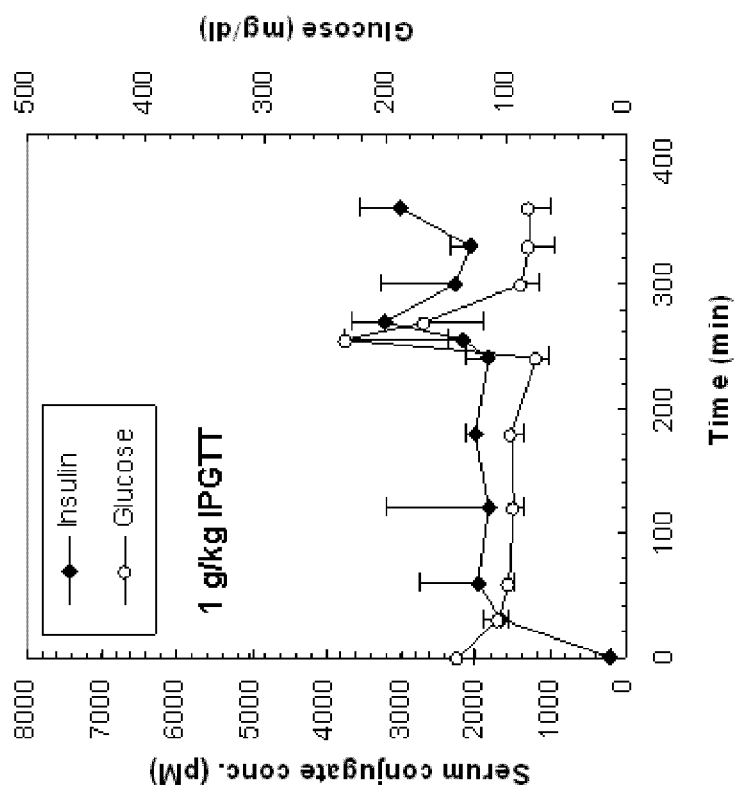

The first two panels of FIG. 47 compare the blood glucose and serum insulin/conjugate concentration profiles for a 3.5 mU/min infusion of RHI and 15 mU/min infusion of I-6 before and after a 4 g/kg i.p. glucose injection. RHI infusion causes significant hypoglycemia prior to glucose injection compared to the I-6 infusion. Following the i.p. glucose injection, the measured serum insulin concentration of I-6 immediately increases by over 300% as the blood glucose concentration increases followed by a rapid return to baseline levels as the glucose concentration decreases. On the other hand, there is no significant change in measured serum insulin concentration for RHI after i.p. glucose injection under the same experimental conditions. The next three panels of FIG. 47 show that the extent to which the measured insulin concentration increases during i.p. glucose injection is directly related to the dose of glucose administered and the resulting blood glucose levels. For example, only a 50% peak to baseline change in serum insulin concentration is observed for the 1 g/kg glucose injection versus the 300% peak to baseline change observed for the 4 g/kg dose.

Example 81

In Vivo Elimination Rate for Insulin-Conjugates with and without Sugar

In order to determine the rate at which the I-9 conjugate was cleared from serum in vivo in the presence or absence of inhibitory sugars such as glucose or a-MM, the following experiment was conducted. In each case the soluble conjugate (or RHI as a control) was dosed at 0.4 mg conjugate/kg body weight into dual jugular vein cannulated male Sprague-Dawley rats (Taconic, JV/JV, 350-400 g, n=3).

To determine the elimination rate in the presence of elevated glucose levels, one hour before the start of the experiment one rat cannula was connected to a syringe infusion pump containing a sterile 50% w/v glucose solution. The pump infusion rate was adjusted by the experimenter to ensure that the blood glucose levels in the animal remained above 300 mg/dL at all times during the experiment. Blood glucose was measured using commercially available test strips (Precision Xtra, Abbott Laboratories, Abbott Park, Ill.). In a typical experiment, it was found that the infusion pump rate required to keep the animals above 300 mg/dL was typically greater than 85 L/min. A blood sample was taken at t=0 min, after which a sterile conjugate solution or control insulin was injected intravenously via the second rat cannula, followed immediately by a chase solution of heparin-saline to ensure that all of the conjugate dose was administered into the animal. After an additional flush of the cannula line with heparin-saline, the second cannula was used to collect blood samples at t=1, 2, 4, 8, 15, 30, 60, 90, 120, and 180 minutes post-dose.

To determine the elimination rate in the presence of a-MM, one hour before the start of the experiment one rat cannula was connected to a syringe infusion pump containing a sterile 25% w/v a-MM solution. The pump infusion rate was adjusted by the experimenter, but was typically set at 85 uL/min. A blood sample was taken at t=0 min, after which a sterile conjugate solution or control insulin was injected intravenously via the second rat cannula, followed immediately by a chase solution of heparin-saline to ensure that all of the conjugate dose was administered into the animal. After an additional flush of the cannula line with heparin-saline, the second cannula was used to collect blood samples at t=1, 2, 4, 8, 15, 30, 60, 90, 120, and 180 minutes post-dose.

Figure 48:
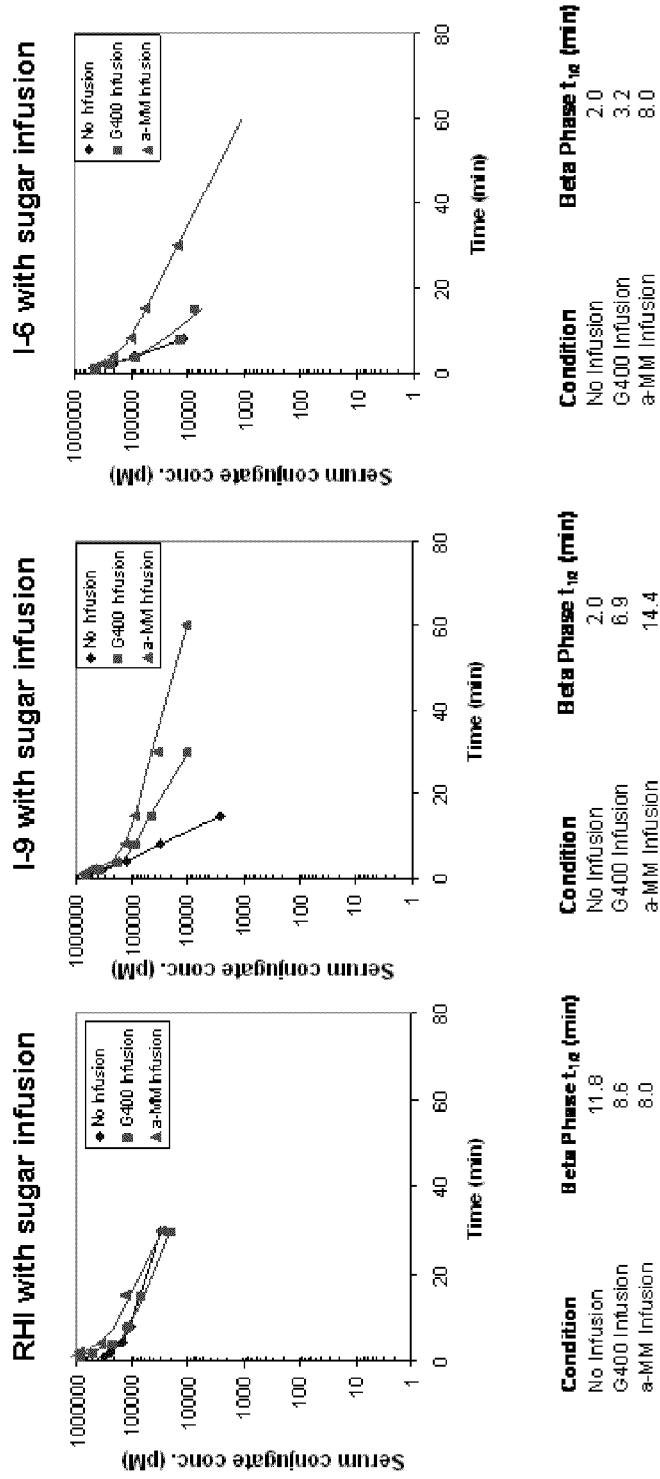
FIG. 48: Plots of serum insulin concentration as a function of time following injection of conjugates with and without glucose or α-methyl mannose. Rats were infused i.v. with sugar solution at t=−60 min and throughout study. Each conjugate was injected at 10 U/kg i.v. at time 0, and serum conjugate concentrations were measured.

Throughout the experiment, blood glucose was measured using commercially available test strips (Precision Xtra, Abbott Laboratories, Abbott Park, Ill.). Blood from each timepoint was centrifuged at 4 C to collect the serum, and serum insulin or serum conjugate concentrations were subsequently measured with a commercially available ELISA kit (Iso-Insulin ELISA, Mercodia, Uppsala, Sweden). Insulin or conjugate serum concentration vs. time data was best fit with the sum of two independent decaying exponentials (C(t)=a exp(-$k_a$t)+b exp(-$k_b$t)) according to the two-compartment model, where t½(a)=(ln 2)/$k_a$ and t½(b)=(ln 2)/$k_b$. The first panel of FIG. 48 shows that the elimination rate of unmodified insulin is not affected in the presence of sugars (glucose G400 or a-MM). For the sake of comparison, the last panel of FIG. 48 showing conjugate I-6 with sugar infusion is replotted from the Example 79 results. The middle panel of FIG. 48 showing conjugate I-9 with sugar infusion shows a much more pronounced decrease in elimination rate (~350% vs. ~50%) in the presence of glucose (G400 infusion) versus the I-6 conjugate. Conjugate I-9 also demonstrates a more significant decrease in elimination rate (~700% vs. ~400%) in the presence of a-MM (a-MM infusion) versus the I-6 conjugate.

Example 82

Mechanism Verification and Glucose-Responsive Performance in Miniature Swine

In order to determine whether the glucose-responsive insulin-conjugate results that are described above could be extended to other species beyond rats, we focused on exploring the sugar-dependent in vivo elimination rate in human-representative, non-diabetic, male miniature swine (Yucatan strain), also called "minipigs" herein. A subset of insulin-conjugates summarized in FIG. 49 were tested to initially determine the effects of sugar affinity and multivalency on sugar-dependent elimination rates. The conjugates are shown in FIG. 45 as I-7, I-6, I-11, and II-2. All conjugates used in this study were synthesized according to the general methods described in Example 20. To produce the A1,B29-disubstituted AETM-2 insulin-conjugate II-2, approximately ten times the amount of multivalent active ester framework and AETM ligand per insulin molecule was used compared to the B29-monosubstituted AETM-2 insulin-conjugate (I-6) synthesis.

In each experiment, the insulin-conjugate was dosed i.v. at 0.1 U/kg into non-diabetic, dual-vascular access ported minipigs and blood was collected at frequent time intervals post-injection. To determine the serum elimination rate in the presence of glucose, a sterile 50% w/v glucose solution was infused i.v. into one port using a syringe pump one hour prior to administering the insulin-conjugate, and the rate was adjusted throughout the entire experiment to ensure that the blood glucose levels in the animal remained at or near 400 mg/dl (typically 80-150 ml/h). To determine the serum elimination rate in the presence of a-MM, the glucose solution was replaced with a sterile 25% w/v a-MM solution and the pump infusion rate held constant throughout the experiment at 80 ml/h. In each case, the resulting insulin-conjugate concentration vs. time data was fit with the sum of two independent decaying exponentials (C(t)=α exp(-$k_\alpha$t)+β exp(-$k_\beta$t)) according to the two-compartment model.

Figure 51:
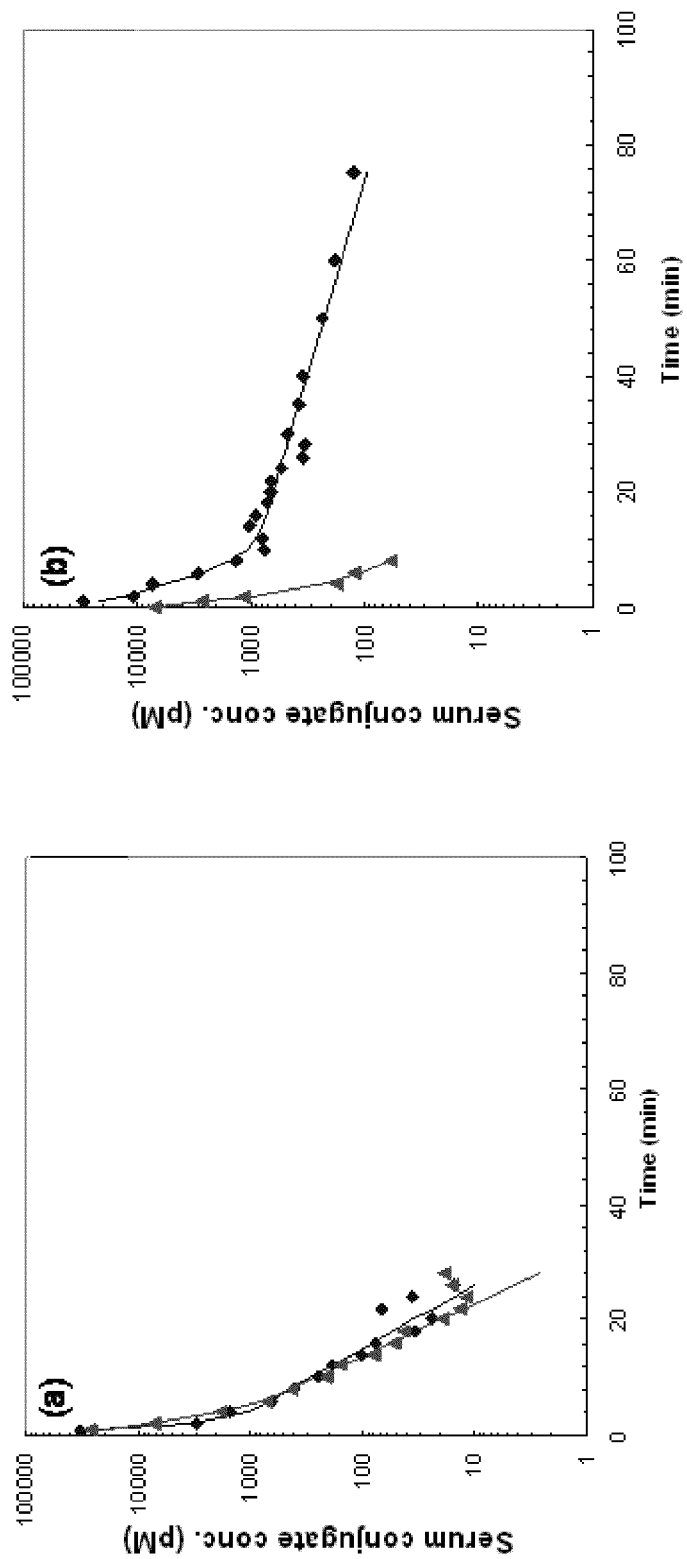
FIG. 51: Plots of serum concentrations of (a) recombinant human insulin (RHI) and (b) Di-Sub-AETM-2 insulin conjugate II-2 following a 0.1 U/kg intravenous (i.v.) injection into non-diabetic male Yucatan minipigs equipped with dual vascular access ports (n=3 per study). In each experiment, the animals were infused with (♦) i.v. alpha methyl mannose (a-MM) solution (25% w/v infused at constant rate of 80 ml/h) or (▲) no solution. Data are plotted as the average values fit with a curve derived from the two-compartment, bi-exponential model.

At 400 mg/dl the high levels of endogenous glucose-induced porcine insulin crossreacted with our insulin-conjugate immunoassay. As such, the PK results from the glucose infusion experiments required subtraction of values obtained from a porcine insulin-only assay leading to a particularly "noisy" set of data. Since a-MM does not induce endogenous porcine insulin secretion, data from the a-MM infusion studies were used as our primary indicator of sugar-responsive changes in insulin-conjugate half-life. Interestingly, in the pigs, the AETM-2 insulin-conjugate (I-6) showed only a modest 1.7× increase in $t_{1/2}$ in the presence of a-MM compared to a 4.0× increase in the rats (FIG. 56). However, in the pigs, the A1,B29-di-substituted AETM-2 insulin-conjugate (II-2) demonstrated an almost 10-fold increase in t½ in the presence of a-MM (FIGS. 50 and 51). Tabular results for other conjugates are shown in FIG. 57.

The area over the glucose lowering curve for the i.v. dose of di-substituted AETM-2 insulin-conjugate (II-2) in the presence of a-MM was approximately 2.6× higher than in the absence of sugar (FIG. 52). FIG. 59 compares the differences in bioactivity between RHI, I-6, and II-2 (di-substituted AETM-2 insulin-conjugate), and II-3. All three of the insulin-conjugates contain the high affinity AETM sugar ligands. In this selected set of insulin-conjugates, there is no correlation between sugar-dependent half-life and bioactivity.

Conjugate II-2 was injected sub-Q as a soluble solution at doses of 0.25, 0.50, and 1.00 U/kg in both non-diabetic, normoglycemic and alloxan-diabetic, hyperglycemic minipigs to determine its ability to lower glucose in diabetics without causing hypoglycemia in non-diabetic animals. The insulin-conjugate demonstrated a significant dose-dependent reduction in blood glucose levels in the diabetics with absolutely no hypoglycemia or signs of glucose-lowering in the non-diabetics (FIG. 53). In comparison, RHI injected at 0.063 and 0.125 U/kg caused significant glucose-lowering in the diabetic animals with noticeable hypoglycemia and significant glucose-lowering and hypoglycemia in the non-diabetic animals (FIG. 54). Based on these preliminary results, a single injection of approximately 0.5 U/kg of soluble insulin-conjugate II-2 provided hypoglycemia-free glucose control for 6-8 hours in diabetic minipigs. Serum elimination rates of sub-Q injected II-2 were determined in diabetic and normal minipigs (FIG. 58). Similar PK profiles were observed between diabetics and normals for all doses.

Taken together, these early results demonstrate that an endogenous lectin-based mechanism exists in the minipigs that can be exploited through selection of sugar affinity and multivalency. It appears that insulin-conjugates with higher affinities and multivalencies provide improved hypoglycemia-free glycemic control in minipigs as compared to rats.

Example 83

Optimization Studies in Miniature Swine

Figure 49:
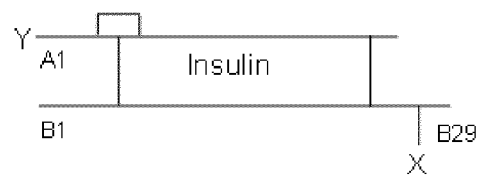
FIG. 49: Composition of insulin conjugates tested in non-diabetic minipig sugar-dependent elimination half-life studies. As described in the Examples, these conjugates were each prepared with recombinant wild-type human insulin (see FIG. 63 for the structure of wild-type human insulin). The schematic in FIG. 49 is therefore primarily intended to represent a wild-type human insulin. As discussed herein, it is to be understood that the present disclosure also encompasses inter alia versions of these and other conjugates that include an insulin molecule other than wild-type human insulin.

Based on the stark difference in performance of II-2 versus the other conjugates in FIG. 49, it is desirable to separate and quantify the effect of insulin conjugation site (A1 vs. B29) from the effects of sugar affinity and valency. Using similar conjugation techniques as were used to produce the insulin-conjugates in FIG. 49, we therefore have synthesized the array of insulin-conjugates listed in FIG. 55 (shown in FIG. 45 as I-12, I-13, I-14, I-15, II-1, II-3, and II-4), as well as the control compounds shown in FIG. 60. All the di-substituted conjugates to be used in this study were synthesized according to the general methods described in Example 20. To produce the A1, B29-disubstituted insulin-conjugates, approximately ten times the amount of multivalent active ester framework and sugar affinity ligand per insulin molecule was used compared to the B29-monosubstituted insulin-conjugate synthesis. The A1-only substituted materials were also prepared according to the general methods described Example 20. However, in this case B29-mono-BOC protected insulin isolated from a BOC protection synthesis described in Example 8 using half the number of equivalents of di-tert-butyl-dicarbonate was used. Once purified, the BOC groups were removed from the conjugate using a TFA/anisole method described in Example 12.

In general, the sugar-responsive half-lives and glucose-lowering effects of each of these insulin-conjugates were determined as follows. As described above, each insulin-conjugate was dosed i.v. at 0.1 U/kg into non-diabetic, dual-vascular access ported minipigs and blood was collected at frequent time intervals post-injection. To determine the serum elimination rate in the presence of a-MM, a sterile 25% w/v a-MM solution was infused i.v. into one port using a syringe pump (80 ml/h) one hour prior to administering the insulin-conjugate, and the rate was held constant throughout the entire experiment. In each case, the resulting insulin-conjugate concentration vs. time data was fit with the sum of two independent decaying exponentials ($C(t) = \alpha \exp(-k_\alpha t) + \beta \exp(-k_\beta t)$) according to the two-compartment model. Comparison of the $\beta$-phase elimination rates with and without a-MM infusion was used to identify suitable conjugates.

FIG. 61 shows a comparison of glucose levels when various insulin-conjugates were injected i.v. into minipigs. Conjugate I-12 (A1 substitution with AETM-2) was slightly more effective in lowering glucose than conjugate I-6 (B29 substitution with AETM-2). Substitution of conjugate I-6 at the A1 position with polyethylene oxide to give conjugate C3 reduced overall bioactivity but did not increase the a-MM induced bioactivity. Substitution of conjugate I-6 at the A1 position with another TSAT-C6-AETM-2 scaffold to give conjugate II-2 reduced overall bioactivity but increased the a-MM induced bioactivity.

FIG. 62 shows a comparison of glucose levels when various A1,B29 di-substituted insulin-conjugates were injected i.v. into minipigs. A1,B29 di-substitution of insulin with acetyl (conjugate C7) or PEO (conjugate C4) groups did not substantially reduce overall bioactivity. Furthermore, the C7 and C4 conjugates did not display distinguishable a-MM-induced bioactivity effects. Conjugate II-3 had substantially reduced bioactivity versus conjugates C7 and C4, but its bioactivity was virtually restored in the presence of a-MM.

Other Embodiments

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

We claim:

1. A conjugate comprising an insulin molecule conjugated to one or more ligands wherein at least one ligand comprises aminoethylfucose (AEF); wherein the conjugate is characterized in that, when the conjugate is administered to a mammal in the absence of an exogenous multivalent saccharide-binding molecule, at least one pharmacokinetic or pharmacodynamic property of the conjugate is sensitive to serum concentration of a saccharide.

2. The conjugate of claim 1, wherein the saccharide comprises glucose or alpha-methyl mannose.

3. The conjugate of claim 1, wherein the conjugate further comprises the insulin molecule conjugated via the A1 amino acid residue, via the B1 amino acid residue, via the epsilon-amino group of $Lys^{B29}$, via the epsilon-amino group of $Lys^{B28}$, or via the epsilon-amino group of $Lys^{B3}$.

4. The conjugate of claim 1, wherein the conjugate further comprises an insulin molecule that is truncated.

5. The conjugate of claim 1, wherein the conjugate includes two or more separate ligands wherein at least one ligand comprises aminoethylfucose (AEF).

6. The conjugate claim 1, wherein the conjugate has the general formula (II):

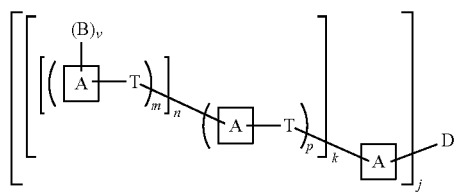

II wherein:
each occurrence of

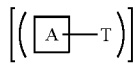

represents a potential branch within the conjugate;
each occurrence of

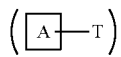

represents a potential repeat within a branch of the conjugate;
each occurrence of A is independently a covalent bond, a carbon atom, a heteroatom, or an optionally substituted group selected from the group consisting of acyl, aliphatic, heteroaliphatic, aryl, heteroaryl, and heterocyclic;
each occurrence of T is independently a covalent bond or a bivalent, straight or branched, saturated or unsaturated, optionally substituted $C_{1-30}$ hydrocarbon chain wherein one or more methylene units of T are optionally and independently replaced by —O—, —S—, —N(R)—, —C(O)—, —C(O)O—, —OC(O)—, —N(R)C(O)—, —C(O)N(R)—, —S(O)—, —S(O)$_2$—, —N(R)SO$_2$—, —SO$_2$N(R)—, a heterocyclic group, an aryl group, or a heteroaryl group;
each occurrence of R is independently hydrogen, a suitable protecting group, or an acyl moiety, arylalkyl moiety, aliphatic moiety, aryl moiety, heteroaryl moiety, or heteroaliphatic moiety;
—B is -T-$L^B$-X;
each occurrence of X is independently a ligand and wherein at least one ligand comprises aminoethylfucose (AEF);
each occurrence of $L^B$ is independently a covalent bond or a group derived from the covalent conjugation of a T with an X;
-D is -T-$L^D$-W;
each occurrence of W is independently an insulin molecule;
each occurrence of $L^D$ is independently a covalent bond or a group derived from the covalent conjugation of a T with a W;
k is an integer from 1 to 12, inclusive;
j is an integer from 1 to 4, inclusive;
each occurrence of p is independently an integer from 1 to 5, inclusive; and
each occurrence of n is independently an integer from 0 to 5, inclusive; and
each occurrence of m is independently an integer from 1 to 5, inclusive; and
each occurrence of v is independently an integer from 0 to 5, inclusive, with the proviso that within each k-branch at least one occurrence of n is ≥1 and at least one occurrence of v is ≥1.

7. The conjugate of claim 6, wherein the conjugate comprises the formula (VIa):

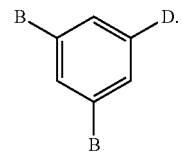

VIa

8. The conjugate of claim 7, wherein the conjugate comprises the formula:

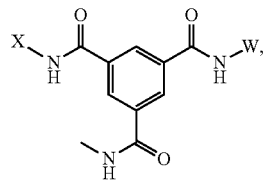

VIa-1

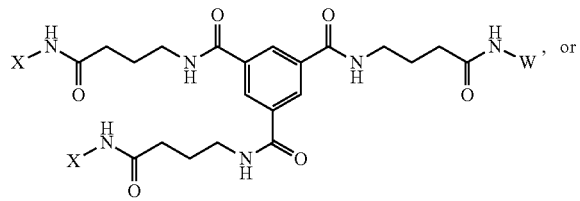

VIa-2

, or

-continued
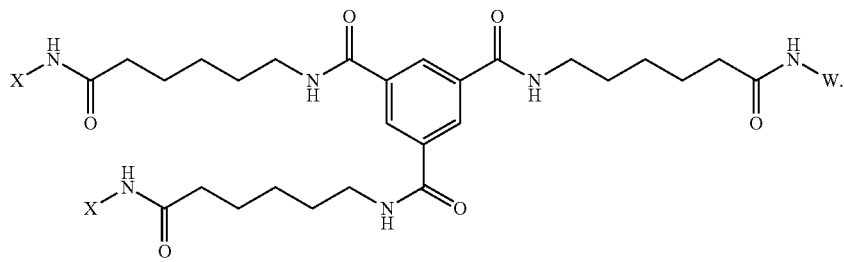
9. The conjugate of claim 6, wherein the conjugate comprises the formula (VIb):
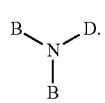
10. The conjugate of claim 9, wherein the conjugate comprises the formula:
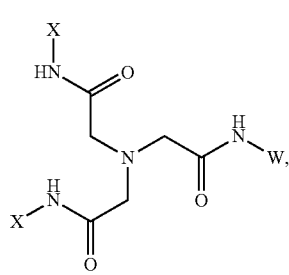
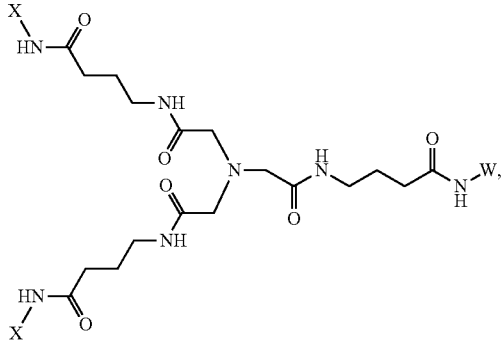
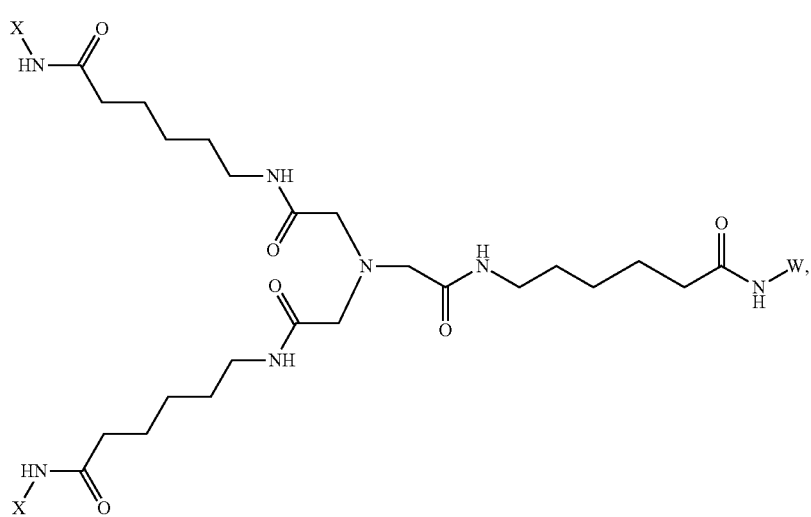

-continued
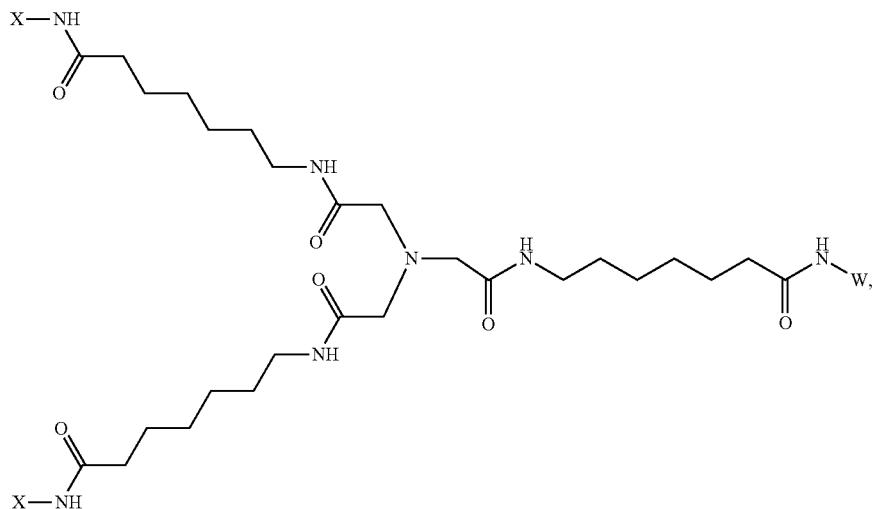
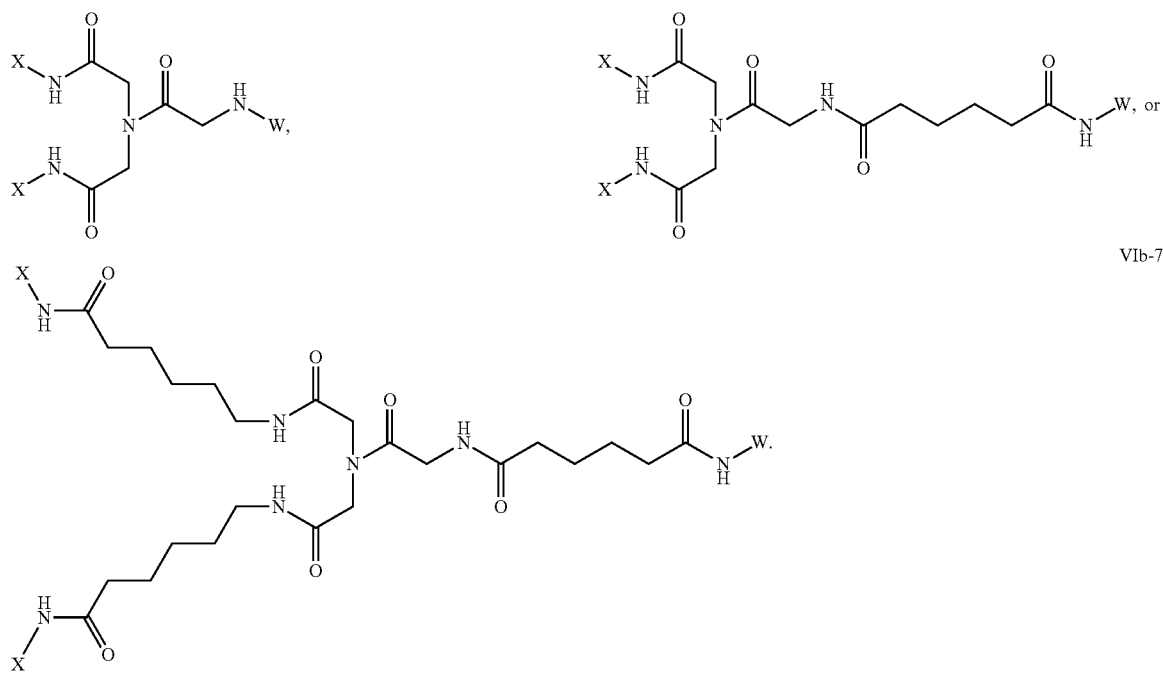
11. The conjugate of claim 6, wherein the conjugate comprises the formula:
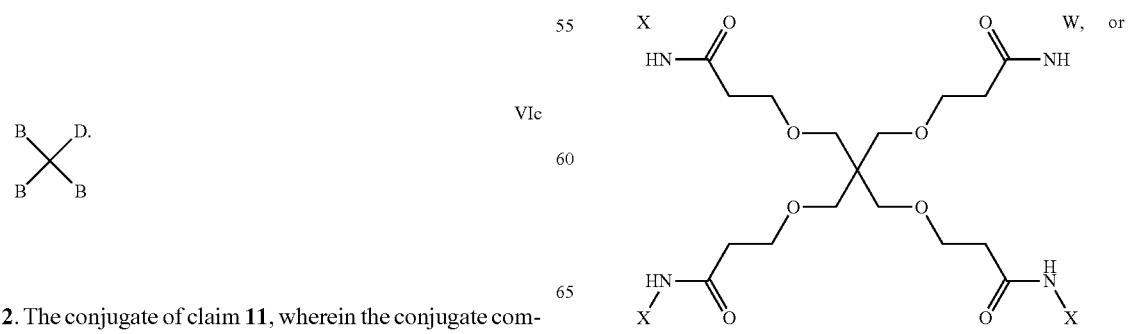
12. The conjugate of claim 11, wherein the conjugate comprises the formula:

-continued

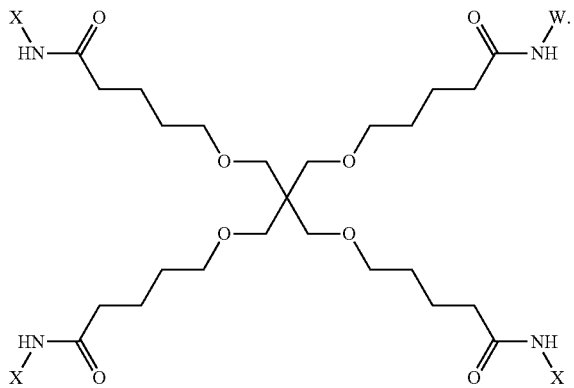

VIc-2

13. A sustained release formulation comprising the conjugate of claim 1.

14. The formulation of claim 13, wherein the formulation comprises protamine and zinc.

15. A pump delivery system comprising a conjugate of claim 1, wherein the pump delivery system operates by infusing the conjugate into a mammal.

16. A method of treating hyperglycemia comprising administering a formulation of claim 14 to a mammalian patient in need thereof.

17. A method comprising administering a conjugate of claim 1 to a mammalian patient in need thereof.

18. The conjugate of claim 1, wherein the conjugate further comprises a fatty acid.

19. The conjugate of claim 1, wherein the conjugate further comprises a fatty acid moiety of general formula:

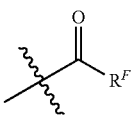

wherein RF is hydrogen or a $C_{1-30}$ alkyl group, in some embodiments, RF is a $C_{1-20}$ alkyl group, a $C_{3-19}$ alkyl group, a $C_{5-18}$ alkyl group, a $C_{6-17}$ alkyl group, a $C_{8-16}$ alkyl group, a $C_{10-15}$ alkyl group, or a $C_{12-14}$ alkyl group.

20. The conjugate of claim 19, wherein the fatty acid is selected from myristic acid (C14), pentadecylic acid (C15), palmitic acid (C16), heptadecylic acid (C17), and stearic acid (C18).

* * * * *

```
                        SEQUENCE LISTING

<160> NUMBER OF SEQ ID NOS: 2

<210> SEQ ID NO 1
<211> LENGTH: 21
<212> TYPE: PRT
<213> ORGANISM: Homo sapiens

<400> SEQUENCE: 1

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 2
<211> LENGTH: 30
<212> TYPE: PRT
<213> ORGANISM: Homo sapiens

<400> SEQUENCE: 2

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30
```